(12) United States Patent
Moussa

(10) Patent No.: US 9,474,753 B2
(45) Date of Patent: Oct. 25, 2016

(54) TREATING NEURAL DISEASE WITH TYROSINE KINASE INHIBITORS

(71) Applicant: Georgetown University, Washington, DC (US)

(72) Inventor: Charbel Moussa, Germantown, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 14/398,379

(22) PCT Filed: May 2, 2013

(86) PCT No.: PCT/US2013/039283
§ 371 (c)(1),
(2) Date: Oct. 31, 2014

(87) PCT Pub. No.: WO2013/166295
PCT Pub. Date: Nov. 7, 2013

(65) Prior Publication Data
US 2015/0087653 A1  Mar. 26, 2015

Related U.S. Application Data

(60) Provisional application No. 61/641,441, filed on May 2, 2012, provisional application No. 61/771,515, filed on Mar. 1, 2013.

(51) Int. Cl.
*A61K 31/506* (2006.01)
*A61K 31/496* (2006.01)
*A61K 45/06* (2006.01)

(52) U.S. Cl.
CPC .......... *A61K 31/506* (2013.01); *A61K 31/496* (2013.01); *A61K 45/06* (2013.01)

(58) Field of Classification Search
CPC .................... A61K 31/506; A61K 31/496
USPC .................................................. 514/253.06
See application file for complete search history.

(56) References Cited

U.S. PATENT DOCUMENTS

| | | | |
|---|---|---|---|
| 7,595,306 B2 * | 9/2009 | Bumcrot ............ | C12N 15/113 435/325 |
| 7,687,512 B2 | 3/2010 | Bilbe | |
| 9,061,029 B2 | 6/2015 | Gallagher et al. | |
| 2004/0038673 A1 * | 2/2004 | Dunn .................. | H04M 3/436 455/417 |
| 2005/0222091 A1 * | 10/2005 | Moussy ............... | A61K 31/00 514/114 |
| 2008/0103107 A1 | 5/2008 | Ward et al. | |
| 2009/0149485 A1 | 6/2009 | Vituduki Narayana et al. | |
| 2012/0083003 A1 | 4/2012 | Johnston et al. | |
| 2014/0350037 A1 | 11/2014 | Szczudlo et al. | |
| 2015/0087653 A1 | 3/2015 | Moussa | |
| 2015/0104467 A1 | 4/2015 | Constantin | |

FOREIGN PATENT DOCUMENTS

| | | |
|---|---|---|
| WO | 9938498 | 8/1999 |
| WO | 2009147009 | 5/2009 |
| WO | 2010/017541 A2 | 2/2010 |
| WO | 2011/097581 A2 | 8/2011 |
| WO | 2013166295 | 11/2013 |

OTHER PUBLICATIONS

Karuppagounder et al. Nilotinib, a cAb1 inhibitor, protects dopaminergic neurons from MPTP induced neurotoxicity. Neuroscience 2011 program#/Poster 883.02/Y1 abstract.*
Parkinson's Disease: Excess of Special Protein Identified as Key to Symptoms and Possible New Target for Treatment with Widely Used Anti-Cancer Drug, <http://www.hopkinsmedicine.org/news/media/releases/parkinsons_disease_excess_of_special_protein_identified_as_key_to_symptoms_and_possible_new_target_for_treatment_with_widely_used_anti_cancer_drug>, Sep. 30, 2013.
San Antonio researchers hope leukemia drug could treat Parkinson's, <http://www.kens5.com/home/Leukemia-drug-may-help-treat-Parkinsons-disease-113295119.html>, Nov. 8, 2013.
Avraham, et al., Phosphorylation of Parkin by the cyclin-dependent kinase 5 at the linker region modulates its ubiquitin-ligase activity and aggregation. J. Biol. Chem. 282:12842-12850 (2007).
Alvarez et al., Activation of the neuronal c-Abl tyrosine kinase by amyloid-beta-peptide and reactive oxygen species, Neurobiol Dis., 17 (2), Nov. 2004, pp. 326-336.
Bazzu, et al., alpha-Synuclein- and MPTP-generated rodent models of Parkinson's disease and the study of extracellular striatal dopamine dynamics: a microdialysis approach. CNS Neurol Disord Drug Targets Aug. 9, 2010, p. 482.
Bellodi et al., Targeting Autophagy Potentiates Tyrosine Kinase Inhibitor-Induced Cell Death in Philadelphia Chromosome-positive Cells, including Primary CML Stem Cells, J. Clin. Invest., 119, 2009, pp. 1109-1123.
Benner et al., Nitrated alpha-synuclein immunity accelerates degeneration of nigral dopaminergic neurons, PLoS One, 3, Jan. 2008, p. e1376.
Bjorkoy et al., p62/SQSTM1 forms protein aggregates degraded by autophagy and has a protective effect on huntingtin-induced cell death, J Cell Biol., 171, 2005, pp. 603-614.
Boland et al., Autophagy induction and autophagosome clearance in neurons: relationship to autophagic pathology in Alzheimer's disease, The Journal of Neuroscience, 28, 2008, pp. 6926-6937.
Braak et al., Staging of Alzheimer's disease-related neurofibrillary changes, Neurobiol Aging, 16, 1995, pp. 271-278.

(Continued)

*Primary Examiner* — Jennifer M Kim

(74) *Attorney, Agent, or Firm* — Kilpatrick Townsend & Stockton, LLP

(57) ABSTRACT

Provided herein are methods of treating or preventing a neurodegenerative disease, a myodegenerative disease or a prion disease in a subject comprising administering a tyrosine kinase inhibitor.

8 Claims, 98 Drawing Sheets

(56) References Cited

OTHER PUBLICATIONS

Burns et al., Parkin promotes intracellular Abeta1-42 clearance, Hum. Mol. Genet., 18, 2009, pp. 3206-3216.

Cancino et al., c-Abl tyrosine kinase modulates tau pathology and Cdk5 phosphorylation in AD transgenic mice, Neurobiology of Aging (2009), doi:10.1016/j.neurobiolaging.2009.09.007.

Cancino et al., STI571 prevents apoptosis, tau phosphorylation and behavioural impairments induced by Alzheimer's beta-amyloid deposits, Brain, 131, 2008, pp. 2425-2442.

Chabrol et al., X-linked myopathy with excessive autophagy: a clinicopathological study of five new families, Neuromuscular Disorders, vol. 11, Issue 4, May 2001, pp. 376-388.

Chen et al., Parkin Mono-ubiquitinates Bcl-2 and Regulates Autophagy, J Biol Chem., 285, Dec. 3, 2010, pp. 38214-38223.

Chu, Autophagic stress in neuronal injury and disease. J Neuropathol Exp Neurol 65, May 2006, p. 423.

Clark, et al., *Drosophila* pink1 is required for mitochondrial function and interacts genetically with parkin. Nature, 441:1162-1166 (2006).

Cook, et al., A beta(1-42) is generated in the endoplasmic reticulum/intermediate compartment of NT2N cells. Nat Med 3, 1997, pp. 1021-1023.

Cookson, et al., RING finger 1 mutations in Parkin produce altered localization of the protein. Hum. Mol. Genet., 12:2957-2965 (2003).

Cookson et al., Parkinson's disease: insights from pathways, Hum Mol Genet., 19, 2010, pp. R21-R27.

Cuervo et al., "Impaired degradation of mutant alpha-synuclein by chaperone-mediated autophagy", Science, vol. 305 No. 5688, Aug. 27, 2004, pp. 1292-1295.

D'Andrea, et al., Evidence that neurones accumulating amyloid can undergo lysis to form amyloid plaques in Alzheimer's disease. Histopathology 38, 2001, pp. 120-134.

Davis, et al., Early-onset and robust cerebral microvascular accumulation of amyloid beta-protein in transgenic mice expressing low levels of a vasculotropic Dutch/Iowa mutant form of amyloid beta-protein precursor. J Biol Chem 279, 2004, pp. 20296-20306.

De Duve et al., Functions of Lysosomes, Annual Review of Physiology, vol. 28, 1966, pp. 435-492.

Deremer, et al., Nilotinib: a second-generation tyrosine kinase inhibitor for the treatment of chronic myelogenous leukemia. Clin Ther 30, Nov. 2008, pp. 1956-1975.

Derkinderen et al., Tyrosine 394 is phosphorylated in Alzheimer's paired helical filament tau and in fetal tau with c-Abl as the candidate tyrosine kinase, J Neurosci., 25 (28), Jul. 13, 2005, pp. 6584-6893.

D'Hooge, et al., Applications of the Morris water maze in the study of learning and memory. Brain Res Brain Res Rev 36, 2001, pp. 60-90.

Ding et al., Histone deacetylase 6 interacts with the microtubule-associated protein tau, J Neurochem., 106, Sep. 2008, pp. 2119-2130.

Dunn, Jr., Autophagy and related mechanisms of lysosome-mediated protein degradation, Trends in cell biology, vol. 4, 1994, pp. 139-143.

Durcan, et al., Mutant ataxin-3 promotes the autophagic degradation of parkin. Autophagy, 7:233-234 (2011).

Durcan, et al., The Machado-Joseph disease-associated mutant form of ataxin-3 regulates parkin ubiquitination and stability. Hum. Mol. Genet., 20:141-154 (2011).

Ertmer et al., The Anticancer Drug Imatinib Induces Cellular Autophagy, Leukemia, 21, 2007, pp. 936-942.

Eskelinen, Maturation of Autophagic Vacuoles in Mammalian Cells, Autophagy, 1, Apr. 1, 2005, pp. 1-10.

Gasser et al., Molecular pathogenesis of Parkinson disease: insights from genetic studies, Expert Rev Mol Med., 11, 2009, p. e22.

Geisler et al., PINK1/Parkin-mediated mitophagy is dependent on VDAC1 and p62/SQSTM1, Nat Cell Biol., 12 (2), Feb. 2010, pp. 119-131.

Giasson, et al., Neuronal alpha-synucleinopathy with severe movement disorder in mice expressing A53T human alpha-synuclein. Neuron 34, May 16, 2002, p. 521.

Goedert et al., Alpha-synuclein and neurodegenerative diseases, Nat Rev Neurosci., 2, 2001, pp. 492-501.

Goedert et al., Filamentous nerve cell inclusions in neurodegenerative diseases: tauopathies and alpha-synucleinopathies, Philos Trans R Soc Lond B Biol Sci., 354, 1999, pp. 1101-1118.

Gonzalez-Polo et al., The apoptosis/autophagy paradox: autophagic vacuolization before apoptotic death, Journal of cell science, 118, 2005, pp. 3091-3102.

Gordon et al., Prelysosomal convergence of autophagic and endocytic pathways, Biochemical and biophysical research communications, 151, Feb. 29, 1988, pp. 40-47.

Gordon et al., Tyrosine Kinase Inhibitors in the Treatment of Systemic Sclerosis: The Difficulty in Interpreting Proof-of-Concept Studies, Hindawi Publishing Corporation International Journal of Rheumatology, Article ID 842181, 2011, pp. 1-8.

Gouras, et al., Intraneuronal Abeta42 accumulation in human brain. Am J Pathol 156, 2000, pp. 15-20.

Greene, et al., Mitochondrial pathology and apoptotic muscle degeneration in *Drosophila* parkin mutants. Proc. Natl. Acad. Sci. USA, 100:4078-4083 (2003).

Greenfield, et al., Endoplasmic reticulum and trans-Golgi network generate distinct populations of Alzheimer beta-amyloid peptides. Proc Natl Acad Sci U S A 96, 1999, pp. 742-747.

Hampe, et al., Biochemical analysis of Parkinson's disease-causing variants of Parkin, an E3 ubiquitin-protein ligase with monoubiquitylation capacity. Hum. Mol. Genet., 15:2059-2075 (2006).

Hara et al., Suppression of basal autophagy in neural cells causes neurodegenerative disease in mice, Nature, 441, Jun. 15, 2006, pp. 885-889.

Hardy, et al., the amyloid hypothesis of Alzheimer's disease: progress and problems on the road to therapeutics. Science 297, 2002, pp. 353-356.

Hasegawa et al., Phosphorylated TDP-43 in Frontotemporal Lobar Degeneration and Amyotrophic Lateral Sclerosis, PubMed, PMID: 18546284, Jul. 2008.

Park, et al, Mitochondrial dysfunction in Drosophila PINK1 mutants is complemented by parkin., Nature, 441:1157-1161 (2006).

Park et al., Mitochondrial dysfunction and Parkinson's disease genes: insights from *Drosophila*, Dis Model Mech., 2 (7-8), Jul.-Aug. 2009, pp. 336-340.

Perez et al., Tau—an inhibitor of deacetylase HDAC6 function, J. Neurochem., 109, 2009, pp. 1756-1766.

Perucho, et al., The effects of parkin suppression on the behaviour, amyloid processing, and cell survival in APP mutant transgenic mice. Exp Neurol 221, 2010, pp. 54-67.

Pickford, et al, The autophagy-related protein beclin 1 shows reduced expression in early Alzheimer disease and regulates amyloid beta accumulation in mice. J Clin Invest 118, 2008, pp. 2190-2199.

Qiu, et al., c-Abl tyrosine kinase regulates cardiac growth and development. Proc Natl Acad Sci U S A 107, Jan. 19, 2010, p. 1136.

Ravikumar et al., Aggregate-prone proteins with polyglutamine and polyalanine expansions are degraded by autophagy, Hum Mol Genet., vol. 11 Issue 9, 2002, pp. 1107-1117.

Ravikumar et al., Inhibition of mTOR induces autophagy and reduces toxicity of polyglutamine expansions in fly and mouse models of Huntington disease, Nat Genet., 36, 2004, pp. 585-595.

Rebeck et al., Beta-amyloid1-42 gene transfer model exhibits intraneuronal amyloid, gliosis, tau phosphorylation, and neuronal loss, The Journal of Biological Chemistry, 285 (10), Mar. 5, 2010, pp. 7440-7446.

Recchia, et al., Generation of a alpha-synuclein-based rat model of Parkinson's disease. Neurobiol Dis 30, Apr. 2008, p. 8.

Reynolds et al., Nitrated alpha-synuclein and microglial neuroregulatory activities, J Neuroimmune Pharmacol. 3(2), Jun. 2008, pp. 59-74.

(56) References Cited

OTHER PUBLICATIONS

Rodríguez-Navarro et al., Parkin deletion causes cerebral and systemic amyloidosis in human mutated tau over-expressing mice. Hum Mol Genet 17, 2008, 3128-3143.
Rodríguez-Navarro et al., Trehalose ameliorates dopaminergic and tau pathology in parkin deleted/tau overexpressing mice through autophagy activation, Neurobiol Dis., 39 (3), Sep. 2010, pp. 423-438.
Rosen et al., Parkin reverses intracellular beta-amyloid accumulation and its negative effects on proteasome function, J Neurosci Res., 88, 2010, pp. 167-178.
Rubio de la Torre, et al., Combined kinase inhibition modulates parkin inactivation. Hum Mol Genet., 18:809-823 (2009).
Sabatini, mTOR and cancer: insights into a complex relationship, Nat Rev Cancer, Sep. 6, 2006, pp. 729-734.
Sarkar et al., Autophagic clearance of aggregate-prone proteins associated with neurodegeneration, Methods Enzymol., 453, 2009, pp. 83-110.
Sarkar et al., Small molecules enhance autophagy and reduce toxicity in Huntington's disease models, Nat Chem Biol., 3, 2007, pp. 331-338.
Schlatterer et al., c-Abl in Neurodegenerative Disease, J Mol Neurosci. 45(3), Nov. 2011, pp. 445-452.
Schlatterer et al., Neuronal c-Abl overexpression leads to neuronal loss and neuroinflammation in the mouse forebrain, J Alzheimers Dis., 25, 2011, pp. 119-133.
Schlossmacher et al., Parkinson's disease: assays for the ubiquitin ligase activity of neural Parkin, Methods Mol. Biol. 301, 2005, pp. 351-369.
Schwartzberg, et al., Mice homozygous for the ablml mutation show poor viability and depletion of selected B and T cell populations. Cell 65, Jun. 28, 1991, p. 1165.
Seglen, Regulation of autophagic protein degradation in isolated liver cells, in: Glaumann H, Ballard FJ, eds. Lysosomes: Their Role in Protein Breakdown. London: Academic Press, 1987, pp. 369-414.
Sha, et al., Phosphorylation of parkin by Parkinson disease-linked kinase PINK1 activates parkin E3 ligase function and NF-kappaB signaling. Hum Mol Genet. 19:352-363 (2010).
Shimura, Familial Parkinson disease gene product, parkin, is a ubiquitin-protein ligase, Nat Genet., 25, 2000, pp. 302-305.
Skorski, BCR-ABL1 kinase: hunting an elusive target with new weapons. Chem Biol 18, Nov. 23, 2011, pp. 1352-1353.
Skovronsky, et al., Detection of a novel intraneuronal pool of insoluble amyloid beta protein that accumulates with time in culture. J Cell Biol 141, 1998, pp. 1031-1039.
Spencer, et al., Beclin 1 gene transfer activates autophagy and ameliorates the neurodegenerative pathology in alpha-synuclein models of Parkinson's and Lewy body diseases. J Neurosci 29, Oct. 28, 2009, p. 13578.
Spillantini et al., alpha-Synuclein in filamentous inclusions of Lewy bodies from Parkinson's disease and dementia with lewy bodies, Proc Natl Acad Sci U S A, 95, May 26, 1998, pp. 6469-6473.
Spillantini et al., Alpha-synuclein in Lewy bodies, Nature, 388, 1997, pp. 839-840.
Spillantini et al., Filamentous alpha-synuclein inclusions link multiple system atrophy with Parkinson's disease and dementia with Lewy bodies, Neurosci Lett., 251, 1998, pp. 205-208.
Spillantini et al., the alpha-synucleinopathies: Parkinson's disease, dementia with Lewy bodies, and multiple system atrophy, Ann N Y Acad Sci., 920, 2000, pp. 16-27.
Staropoli, et al., Parkin is a component of an SCF-like ubiquitin ligase complex and protects postmitotic neurons from kainite excitotoxicity, Neuron, 37:735-749 (2003).
Stefanis, Expression of A53T mutant but not wild-type alpha-synuclein in PC12 cells induces alterations of the ubiquitin-dependent degradation system, loss of dopamine release, and autophagic cell death, J Neurosci., 21, Dec. 15, 2001, pp. 9549-9560.
Sutovsky et al., Ubiquitin tag for sperm mitochondria, Nature, 402(6760), Nov. 25, 1999, pp. 371-372.
Takeda et al., C-terminal alpha-synuclein immunoreactivity in structures other than Lewy bodies in neurodegenerative disorders, Acta Neuropathol., 99 (3), Mar. 2000, pp. 296-304.
Tan et al., Lysine 63-linked polyubiquitin potentially partners with p62 to promote the clearance of protein inclusions by autophagy, Autophagy, 4, 4(2):251-253 (2008).
Thiruchelvam, et al., Risk factors for dopaminergic neuron loss in human alpha-synuclein transgenic mice. Eur J Neurosci 19, Feb. 2004, p. 845.
Tremblay et al., Tau phosphorylated at tyrosine 394 is found in Alzheimer's disease tangles and can be a product of the Abl-related kinase, Arg. J Alzheimers Dis., 19 (2), 2010, pp. 721-733.
Trojanowski et al., Parkinson's disease and related alpha-synucleinopathies are brain amyloidoses, Ann N Y Acad Sci., 991, 2003, pp. 107-110.
Tybulewicz, et al., Neonatal lethality and lymphopenia in mice with a homozygous disruption of the c-abl proto-oncogene. Cell 65, Jun. 28, 1991, p. 1153.
Vives-Bauza et al., PINK1-dependent recruitment of Parkin to mitochondria in mitophagy, Proc Natl Acad Sci U S A, vol. 107, No. 1, Jan. 5, 2010, pp. 378-383.
Wakabayashi et al., NACP, a presynaptic protein, immunoreactivity in Lewy bodies in Parkinson's disease, Neurosci Lett., 239, 1997, pp. 45-48.
Wang et al., Nilotinib induced remission of central nervous system relapse of imatinib-resistant PH+ CML after allogeneic haematopoietic cell transplantation, Minimal residual disease, <http://registration.akm.ch/einsicht.php?XNABSTRACT_ID=105837&XNSPRACHE_ID=2&XNKONGRESS_ID=110&XNMASKEN_ID=900>, Mar. 22, 2010.
Wang et al., Regulation of cell death by the Abl tyrosine kinase, Oncogene, 19, 2000, pp. 5643-5650.
Webb et al., Alpha-Synuclein is degraded by both autophagy and the proteasome, J Biol Chem., vol. 278, No. 27, Jul. 4, 2003, pp. 25009-25013.
Wenzel, et al., UBCH7 reactivity profile reveals parkin and HHARI to be RING/HECT hybrids, Nature, 474:105-108 (2011).
Wild et al., Mitochondria get a Parkin' ticket, Nature Cell Biology, 12, 2010, pp. 104-106.
Wilson, et al., Intracellular APP processing and A beta production in Alzheimer disease. J Neuropathol Exp Neurol 58, 1999, pp. 787-794.
Winslow et al., Autophagy in neurodegeneration and development, Biochim Biophys Acta., 1782, 2008, pp. 723-729.
Winslow, D. C. Rubinsztein, The Parkinson disease protein alpha-synuclein inhibits autophagy. Autophagy 7, Apr. 2011, p. 429.
Winslow et al., alpha-Synuclein impairs macroautophagy: implications for Parkinson's disease. J Cell Biol 190, 190(6):1023-1037 Sep. 20, 2010.
Xilouri et al., Abberant alpha-synuclein confers toxicity to neurons in part through inhibition of chaperone-mediated autophagy, PLoS One, vol. 4, Issue 5, May 2009, p. e5515.
Xu, et al., Generation of Alzheimer beta-amyloid protein in the trans-Golgi network in the apparent absence of vesicle formation. Proc Natl Acad Sci U S A 94, 1997, pp. 3748-3752.
Yamamoto, et al., Phosphorylation and modulation of its E3 ubiquitin ligase activity, J Biol Chem, 280:3390-3399 (2005).
Yang et al., Induction of autophagy in neurite degeneration of mouse superior cervical ganglion neurons, Eur J Neurosci., 26, 2007, pp. 2979-2988.
International Application No. PCT/US2013/039283, International Search Report and Written Opinion mailed Aug. 22, 2013, 8 pages.
International Application No. PCT/US2013/039283, International Preliminary Report on Patentability mailed Nov. 13, 2014, 7 pages.
He et al., Gamma-secretase Activating Protein, a Therapeutic Target for Alzheimer's Disease, Nature, 467, Sep. 2, 2010, pp. 95-98.
He et al., Post-translational modifications of three members of the human MAP1LC3 family and detection of a novel type of modification for MAP1LC3B, The Journal of biological chemistry, 278, 2003, pp. 29278-29287.
He et al., Regulation mechanisms and signaling pathways of autophagy, Annu Rev Genet., 43, 2009, pp. 67-93.

(56) References Cited

OTHER PUBLICATIONS

Healy et al., Tau gene and Parkinson's disease: a case-control study and meta-analysis, J Neurol Neurosurg Psychiatry, 75, 2003, pp. 962-965.
Helgason et al., Kill One Bird with Two Stones: Potential Efficacy of Bcr-Abl and Autophagy Inhibition in CML, Blood, vol. 118, No. 8, Aug. 25, 2011, pp. 2035-2043.
Henn, et al., Pathogenic mutations inactivate parkin by distinct mechanisms. J. Neurochem., 92:114-122 (2005).
Herman et al., The ubiquitin ligase parkin modulates the execution of autophagy, Autophagy, vol. 7, Issue 8, 2011, pp. 919-921.
Huang et al., The itinerary of a vesicle component, Aut7p/Cvt5p, terminates in the yeast vacuole via the autophagy/Cvt pathways, The Journal of biological chemistry, 275, 2000, pp. 5845-5851.
Imam et al., Novel regulation of parkin function through c-Abl-mediated tyrosine phosphorylation: implications for Parkinson's disease, The Journal of Neuroscience, 31 (1), Jan. 5, 2011, pp. 157-163.
Iwata et al., HDAC6 and microtubules are required for autophagic degradation of aggregated huntingtin, J Biol Chem., 280, 2005, pp. 40282-40292.
Jing et al., Altered subcellular distribution of c-Abl in Alzheimer's disease, J Alzheimers Dis., 17, 2009, pp. 409-422.
Kanki et al., Atg32 is a mitochondrial protein that confers selectivity during mitophagy, Dev Cell, Jul. 2009, pp. 98-109.
Kantarjian, et al., Hematologic and cytogenetic responses to imatinib mesylate in chronic myelogenous leukemia. N Engl J Med 346, Feb. 28, 2002, p. 645.
Kawahara, et al., Alpha-Synuclein aggregates interfere with Parkin solubility and distribution: role in the pathogenesis of Parkinson disease. J. Biol. Chem., 283:6979-6987 (2008).
Kegel et al., Huntingtin expression stimulates endosomal-lysosomal activity endosome tubulation, and autophagy, The Journal of Neuroscience, 20(19), Oct. 1, 2000, pp. 7268-7278.
Khandelwal et al., Parkin mediates beclin-dependent autophagic clearance of defective mitochondria and ubiquitinated Abeta in AD models, Hum Mol Genet., 20, 2011, pp. 2091-2102.
Khandelwal et al., Parkinson-related parkin reduces alpha-Synuclein phosphorylation in a gene transfer model, Mol Neurodegener., 5, 2010, p. 47.
Khandelwal et al., Wild type and P301L mutant Tau promote neuro-inflammation and alpha-Synuclein accumulation in lentiviral gene delivery models, Mol Cell Neurosci., 49 (1), Jan. 2012, pp. 44-53.
Kim, et al., PINK1 controls mitochondrial localization of Parkin through direct phosphorylation., Biochem Biophys Res Commun., 377:975-980 (2008).
Kirik, et al., Parkinson-like neurodegeneration induced by targeted overexpression of alpha-synuclein in the . nigrostnatal system. J Neurosci 22, Apr. 1, 2002, p. 2780.
Kirkin et al., A role for ubiquitin in selective autophagy, Molecular Cell, 34, May 15, 2009, pp. 259-269.
Kitada et al., Mutations in the parkin gene cause autosomal recessive juvenile parkinsonism, Nature, 392, Apr. 9, 1998, pp. 605-608.
Ko et al., Phosphorylation by the c-Abl protein tyrosine kinase inhibits parkin's ubiquitination and protective function, Proc Natl Acad Sci U S A, vol. 107, No. 38, Sep. 21, 2010, pp. 16691-16696.
Koike et al., Participation of autophagy in storage of lysosomes in neurons from mouse models of neuronal ceroid-lipofuscinoses lipofuscinoses (Batten disease), The American journal of pathology, 167, 2005, pp. 1713-1728.
Komatsu et al., Loss of autophagy in the central nervous system causes neurodegeneration in mice, Nature, 441, 2006, pp. 880-884.
Kovacs et al., Accumulation of autophagosomes after inhibition of hepatocytic protein degradation by vinblastine, leupeptin or a lysosomotropic amine, Experimental cell research, 137, 1982, pp. 191-201.
Krakstad et al., Survival Signalling and Apoptosis Resistance in Glioblastomas: Opportunities for Targeted Therapeuticus, Molecular Cancer, Retrieved from the Internet: URL: http://www.molecular-cfncer.com/content/9/1/135, 2010, pp. 1-14.
Kuhn et al., Dopamine quinones activate microglia and induce a neurotoxic gene expression profile: relationship to methamphetamine-induced nerve ending damage, Ann N Y Acad Sci., 1074, 2006, pp. 31-41.
Li, et al., Mice deficient in Abl are osteoporotic and have defects in osteoblast maturation. Nat Genet 24, Mar. 2000, p. 304.
Li, et al., The role of intracellular amyloid beta in Alzheimer's disease. Prog Neurobiol 83, 2007, pp. 131-139.
Liu et al., Inhibitors of LRRK2 kinase attenuate neurodegeneration and Parkinson-like phenotypes in C. elegans and Drosophila Parkinson's disease models, Hum. Mol. Genet., Jul. 18, 2011 20(20):3933-3942.
Lonskaya, et al., Decreased parkin solubility is associated with impairment of autophagy in the nigrostriatum of sporadic Parkinson's disease, Neuroscience, Mar. 1, 2013, pp. 90-105.
Lonskaya, et al., Diminished Parkin Solubility and Co-Localization with Intraneuronal Amyloid-beta are Associated with Autophagic Defects in Alzheimer's Disease. J Alzheimers Dis.33(1):231-247, 2013.
Lucking et al., Association between early-onset Parkinson's disease and mutations in the parkin gene, N Engl J Med., 342, 2000, pp. 1560-1567.
Lundvig et al., Pathogenic effects of alpha-synuclein aggregation, Mol Brain Res., 134, 2005, pp. 3-17.
Mahon, et al., Evidence that resistance to nilotinib may be due to BCR-ABL, Pgp, or Src kinase overexpression. Cancer Res 68, Dec. 1, 2008, pp. 9809-9816.
Malkus, et al., Regional deficiencies in chaperone-mediated autophagy underlie alpha-synuclein aggregation and neurodegeneration. Neurobiol Dis 46, Jun. 2012, p. 732.
Martin et al., Association of single-nucleotide polymorphisms of the tau gene with late-onset Parkinson disease, JAMA, 286, 2001, pp. 2245-2250.
Martin-Villalba, et al., Therapeutic neutralization of CD95-ligand and TNF attenuates brain damage in stroke, Cell Death Differ., 8:679-686 (2001).
Martinez-Vicente et al., Dopamine-modified alpha-synuclein blocks chaperone-mediated autophagy, J Clin Invest., 118, 2008, pp. 777-788.
Marzella et al., Isolation of autophagic vacuoles from rat liver: morphological and biochemical characterization, J Cell Biol, 93,1982, pp. 144-154.
McCormack, et al., Alpha-synuclein suppression by targeted small interfering RNA in the primate substantia nigra. PLoS One 5, 2010, p. e12122.
Mizushima et al., Autophagy fights disease through cellular self-digestion, Nature, 451, 2008, pp. 1069-1075.
Mizushima et al., How to interpret LC3 immunoblotting, Autophagy, 3, 2007, pp. 542-545.
Mizushima et al., In vivo analysis of autophagy in response to nutrient starvation using transgenic mice expressing a fluorescent autophagosome marker, Molecular biology of the cell, Mar. 15, 2004, pp. 1101-1111.
Mizuno, et al., Parkin and Parkinson's disease. Curr Opin Neurol 14, 2001, pp. 477-482.
Morrison et al., A simple cell based assay to measure Parkin activity, J. Neurochem., 116(3), 2011, pp. 342-349.
Narendra et al., Parkin is recruited selectively to impaired mitochondria and promotes their autophagy, J Cell Biol., 183 (5), Nov. 24, 2008, pp. 795-803.
Narendra, et al., PINK1 is selectively stabilized on impaired mitochondria to activate Parkin, PLoS Biol., 8:e1000298 (2010).
Nixon et al., Extensive involvement of autophagy in Alzheimer disease: an immuno-electron microscopy study, J Neuropathol Exp Neurol., 64, 2005, pp. 113-122.
Nixon et al., Neurodegenerative lysosomal disorders: a continuum from development to late age, Autophagy, 4, Jul. 1, 2008, pp. 590-599.
Nixon et al., Autophagy failure in Alzheimer's disease—locating the primary defect. Neurobiol Dis 43, 2011, pp. 38-45.

(56) References Cited

OTHER PUBLICATIONS

Novak et al., Nix is a selective autophagy receptor for mitochondrial clearance, EMBO Rep., 11, 2010, pp. 45-51.
Oddo, et al., Amyloid deposition precedes tangle formation in a triple transgenic model of Alzheimer's disease. Neurobiol Aging 24, 2003, pp. 1063-1070.
Okamoto et al., Mitochondria-anchored receptor Atg32 mediates degradation of mitochondria via selective autophagy, Developmental Cell, vol. 17, Issue 1, Jul. 21, 2009, pp. 87-97.
Orvedahl et al., Image-based genome-wide siRNA screen identifies selective autophagy factors, Nature, 480(7375), Dec. 1, 2011, pp. 113-117.
Pan et al., The role of autophagy-lysosome pathway in neurodegeneration associated with Parkinson's disease, Brain, 131, 2008, pp. 1969-1978.
Partial supplementary European search report for European Application No. 13784480.9, mailed Mar. 23, 2016 (9 pages).
Yokoseki, et al, "TDP-43 mutation in familial amyothrophic lateral sclerosis", Annals of Neurology, 63(4): 538-542, Apr. 1, 2008.
Hebron et al., "Tyrosine kinase inhibition facilitates autophagic SNCA/α-synuclein", Autophagy, 9:8, 1249-1250, DOI: 10.4161/auto.25368, (2013).
Hebron et al., "Nilotinib reverses loss of dopamine neurons and improves motor behavior via autophagic degradation of α-synuclein in Parkinson's diesease models" Human Molecular Genetics, 22(16):3315-3328 (2013).
Hebron et al., "Two sides of the same coin: tyrosine kinase inhibition in cancer and neurodegeneration", Neural Regen Res., 10(11):1767-1769 (Nov. 2015).
Karuppagounder et al., "The c-Abl inhibitor, Nilotinib, protects dopaminergic neurons in a preclinical animal model of Parkinson's disease", Scientific Reports, 4:4874; DOI: 10.1038/sprep04874, (May 2, 2014).
Lonskaya et al., "Tyrosine kinase inhibition increases functional parkin-Beclin-1 interaction and enhances amyloid clearance and cognitive performance", EMBO Molecular Medicine, 5:1247-1262, (2013).
Lonskaya et al., "Nilotinib-induced autophagic changes increase endogenous parkin level and ubiquitination, leading to amyloid clearence", J Mol Med (Berl), 92(4):373-386 (Apr. 2014).
Lonskaya et al., "Nilotinib and bosutinib modulate pre-plaque alternations of blood immune markers and neuro-inflammation in Alzheimer's disease models", Neuroscience, 304:316-327, (Sep. 24, 2015).
Moussa et al., "Cancer Drug Improved Cognition and Motor Skills in Small Parkinson's Clinical Trial", Georgetown University Medical Center, Chicago, (Oct. 17, 2015).
"Nilotinib in Cognitively Impaired Parkinson Disease Patients", ClinicalTrials.gov Identifier: NCT02281474, Georgetown University, (Dec. 15, 2015).
Tanabe et al., "A novel tyrosine kinase inhibitor AMN107 (nilotinib) normalizes striatal motor behaviors in a mouse model of Parkinson's disease" Frontiers in Cellular Neuroscience, 8(50):1-9 (Feb. 2014).
Walton, "A Cancer Drug may help treat Alzheimer's and other forms of Dementia", Forbes, Pharma & Healthcare, May 10, 2013, www.forbes.com.

* cited by examiner

A

B

A

B

A.

B.

G

TREATING NEURAL DISEASE WITH TYROSINE KINASE INHIBITORS

This application claims the benefit of U.S. Provisional Application No. 61/641,441, filed May 2, 2012, and U.S. Provisional Application No. 61/771,515, filed Mar. 1, 2013, both of which are hereby incorporated herein in their entireties.

STATEMENT REGARDING FEDERALLY FUNDED RESEARCH

This invention was made with government support under grant number AG30378 awarded by the National Institutes of Health. The government has certain rights in the invention.

BACKGROUND

Neurodegenerative diseases include genetic and sporadic disorders associated with progressive nervous system dysfunction. It has been estimated that one of four Americans will develop a neurodegenerative condition in their lifetimes. Generally, however, the underlying mechanisms causing the conditions are not well understood and few effective treatment options are available for preventing or treating neurodegenerative diseases. Similarly, treatment options for myodegenerative disease and prion disease are also limited.

SUMMARY

Provided herein is a method of treating or preventing a neurodegenerative disease, a myodegenerative disease or a prion disease in a subject, comprising selecting a subject with a neurodegenerative disease of the central nervous system, a myodegenerative disease or a prion disease or at risk for a neurodegenerative disease of the central nervous system, a myodegenerative disease or a prion disease and administering to the subject an effective amount of a tyrosine kinase inhibitor, wherein the tyrosine kinase inhibitor is not Gleevec, and wherein the tyrosine kinase inhibitor crosses the blood brain barrier.

Further provided is a method of inhibiting or preventing toxic protein aggregation in a neuron, a muscle cell or a glial cell comprising contacting the neuron, the muscle cell or the glial cell with an effective amount of a tyrosine kinase inhibitor, wherein the tyrosine kinase inhibitor is not Gleevec and wherein the tyrosine kinase inhibitor crosses the blood brain barrier.

Also provided is a method of rescuing a neuron from neurodegeneration, a muscle from myodegeneration or a glial cell from degeneration comprising contacting the neuron, the muscle cell or the glial cell with an effective amount of a tyrosine kinase inhibitor, wherein the tyrosine kinase inhibitor is not Gleevec and wherein the tyrosine kinase inhibitor crosses the blood brain barrier.

Further provided herein is a method of treating amyotrophic lateral sclerosis or frontotemporal dementia in a subject, comprising selecting a subject with amyotrophic lateral sclerosis or frontotemporal dementia, wherein the subject has a TDP-43 pathology, and administering to the subject an effective amount of a tyrosine kinase inhibitor, wherein the tyrosine kinase inhibitor is not Gleevec and wherein the tyrosine kinase inhibitor crosses the blood brain barrier.

Also provided is a method of promoting parkin activity in a subject, comprising selecting a subject with a disorder associated with decreased Parkin activity and administering to the subject an effective amount of a small molecule that increase parkin activity, wherein the small molecule is not Gleevec.

Further provided is a method of treating or preventing a neurodegenerative disease in a subject, comprising selecting a subject with a neurodegenerative disease or at risk for a neurodegenerative disease, determining that the subject has a decreased level of parkin activity relative to a control, and administering to the subject an effective amount of a small molecule that increases parkin activity, wherein the small molecule is not Gleevec.

The details of one or more embodiments of the invention are set forth in the accompanying drawings and the description below. Other features, objects, and advantages of the invention will be apparent from the description and drawings, and from the claims.

Wild type or parkin−/− mice were injected with lentiviral Aβ$_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and human specific ELISA was performed to determine protein contents. Aβ$_{1-42}$ accumulates in AV-10 in lentivirus injected brains but drug treatment enhances autophagic clearance via deposition of Aβ$_{1-42}$ in AV-20 and lysosome. N=5 animals per treatment.

Figure 21:
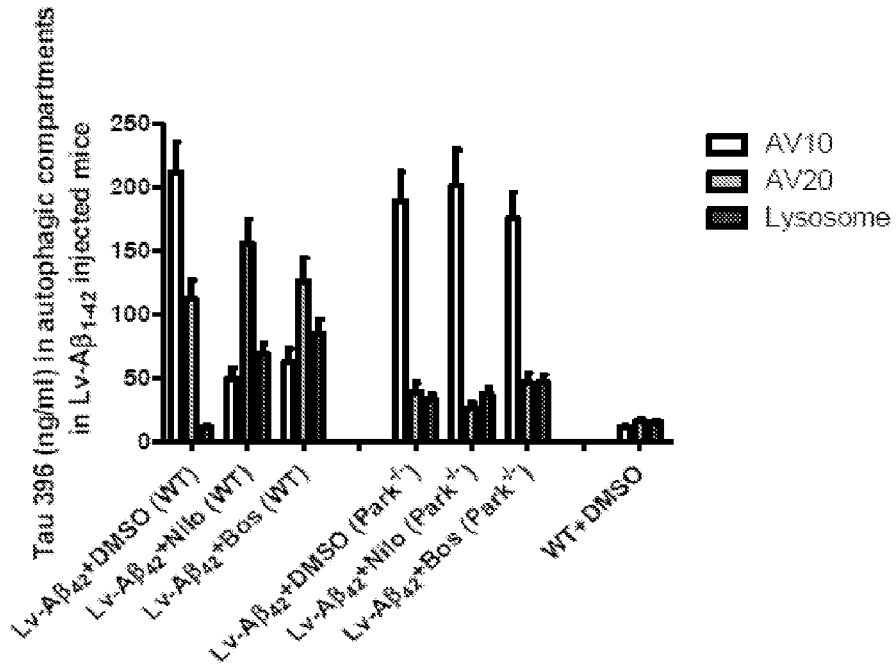

FIG. 21 shows that P-Tau at serine 396 accumulates in AV-10 in lentivirus injected brains but drug treatment enhances autophagic clearance via deposition of p-Tau in AV-20 and lysosome, where it is degraded. Histograms show p-Tau in subcellular fractions, including autophagic vacuole-10 (AV-10; phagophores+autophagosomes), AV-20 (autophagosomes) and lysosomes. Wild type or parkin−/− mice were injected with lentiviral Aβ$_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and mouse specific. ELISA was performed to determine protein contents. Autophagic clearance is parkin-dependent. N=5 animals per treatment.

Figure 22:
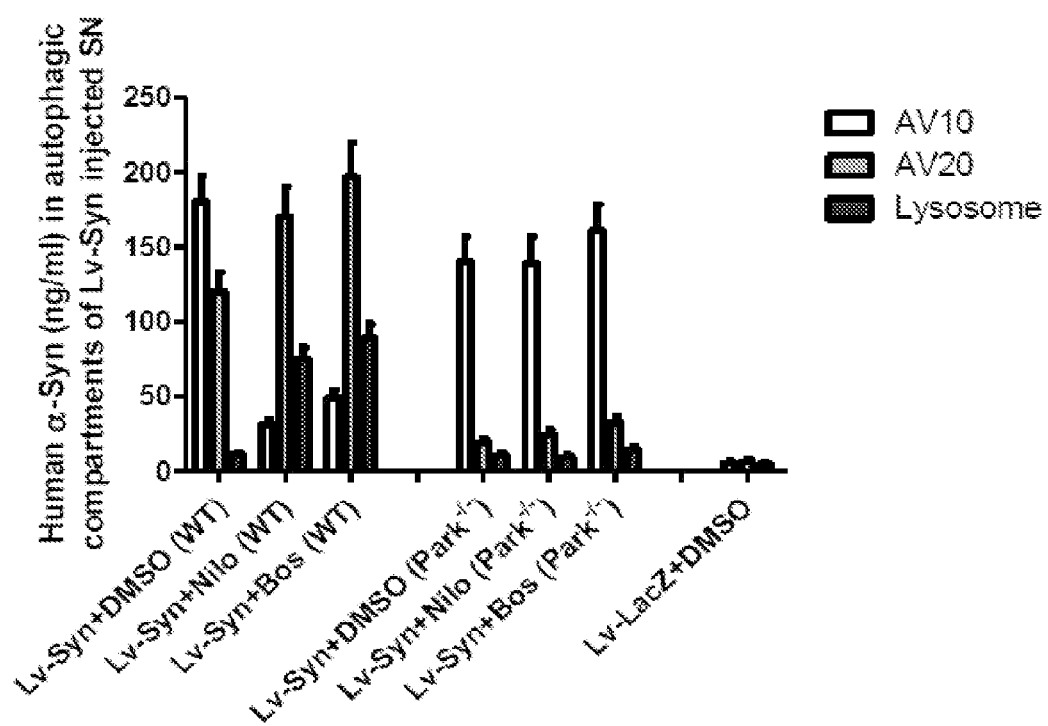

FIG. 22 shows that α-synuclein accumulates in AV-10 in lentivirus injected brains but drug treatment enhances autophagic clearance via deposition of α-synuclein in AV-20 and lysosome, which contains degradative enzymes. Histograms show α-synuclein in subcellular fractions, including autophagic vacuole-10 (AV-10; phagophores+autophagosomes), AV-20 (autophagosomes) and lysosomes. Wild type or parkin−/− mice were injected SN with lentiviral α-synuclein for 3 weeks and treated IP with 10 mg/kg Nilotinib or 5 mg/Kg Bosutinib or DMSO once a day for 3 (additional) consecutive weeks. SN tissues were fractionated to isolate AVs and human specific ELISA was performed to determine protein contents. Autophagic clearance is parkin-dependent. N=5 animals per treatment.

Figure 23:
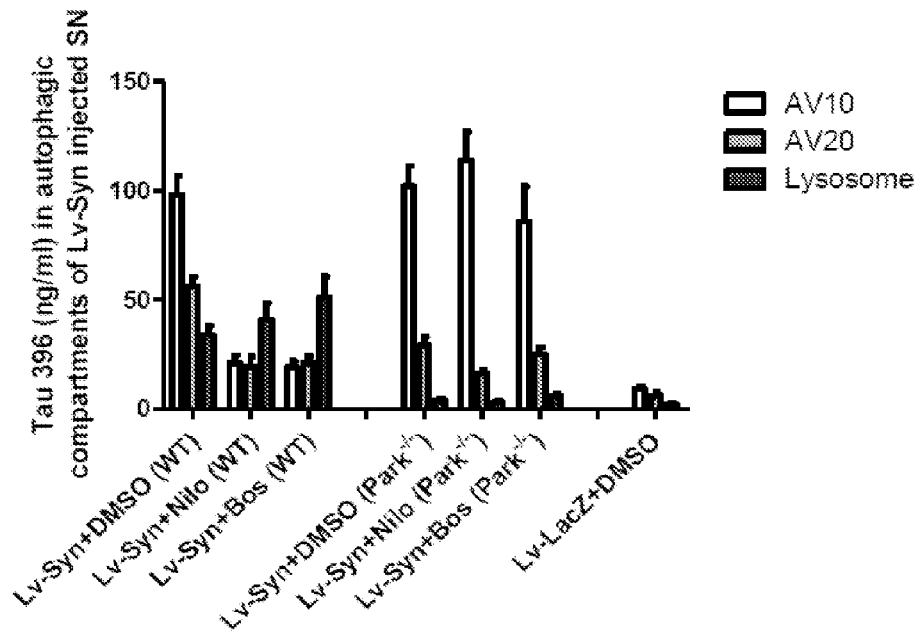

FIG. 23 shows that P-Tau accumulates in AV-10 in lentivirus injected brains but drug treatment enhances autophagic clearance via p-Tau deposition in AV-20 and lysosome, which contains degradative enzymes. Histograms show p-Tau at serine 396 in subcellular fractions, including autophagic vacuole-10 (AV-10; phagophores+autophagosomes), AV-20 (autophagosomes) and lysosomes. Wild type or parkin−/− mice were injected SN with lentiviral α-synuclein for 3 weeks and treated IP with 10 mg/kg Nilotinib or 5 mg/Kg Bosutinib or DMSO once a day for 3 (additional) consecutive weeks. SN tissues were fractionated to isolate AVs and mouse specific ELISA was performed to determine protein contents. Autophagic clearance is parkin-dependent. N=5 animals per treatment.

Figure 24:
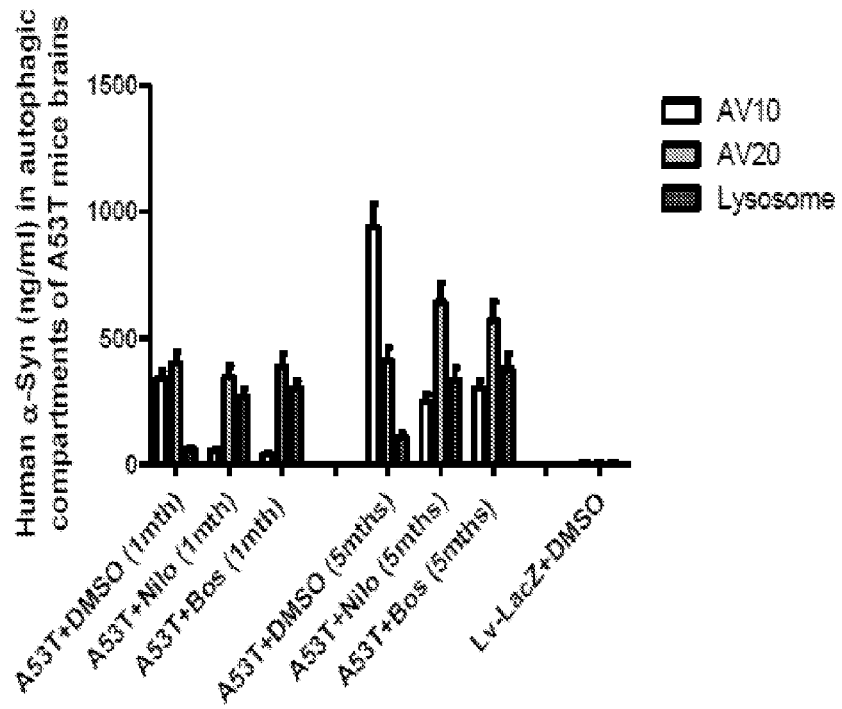

FIG. 24 shows that α-synuclein accumulates in AV-10 in A53T brains but drug treatment enhances autophagic clearance via α-synuclein deposition in AV-20 and lysosome. Histograms show α-synuclein in subcellular fractions, including autophagic vacuole-10 (AV-10; phagophores+autophagosomes), AV-20 (autophagosomes) and lysosomes, containing digestive enzymes. Transgenic A53T mice were injected IP with 10 mg/kg Nilotinib or 5 mg/Kg Bosutinib or DMSO once a day for 3 consecutive weeks. Brain tissues were fractionated to isolate AVs and human specific ELISA was performed to determine protein contents. N=5 animals per treatment.

Figure 25:
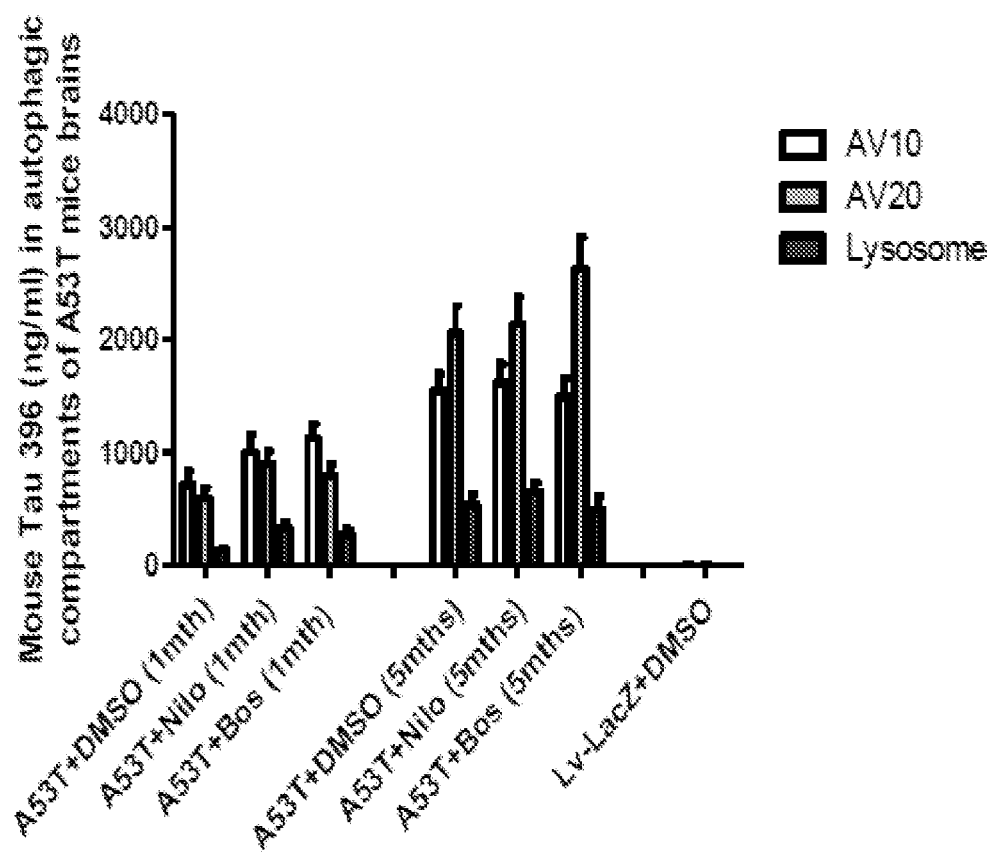

FIG. 25 shows that P-Tau accumulates in AV-10 in A53T brains but drug treatment enhances autophagic clearance via p-Tau deposition in AV-20 and lysosome. Histograms show p-Tau at Serine 396 in subcellular fractions, including autophagic vacuole-10 (AV-10; phagophores+autophagosomes), AV-20 (autophagosomes) and lysosomes, containing digestive enzymes. Transgenic A53T mice were injected IP with 10 mg/kg Nilotinib or 5 mg/Kg Bosutinib or DMSO once a day for 3 consecutive weeks. Brain tissues were fractionated to isolate AVs and mouse specific ELISA was performed to determine protein contents. N=5 animals per treatment.

Figure 26:
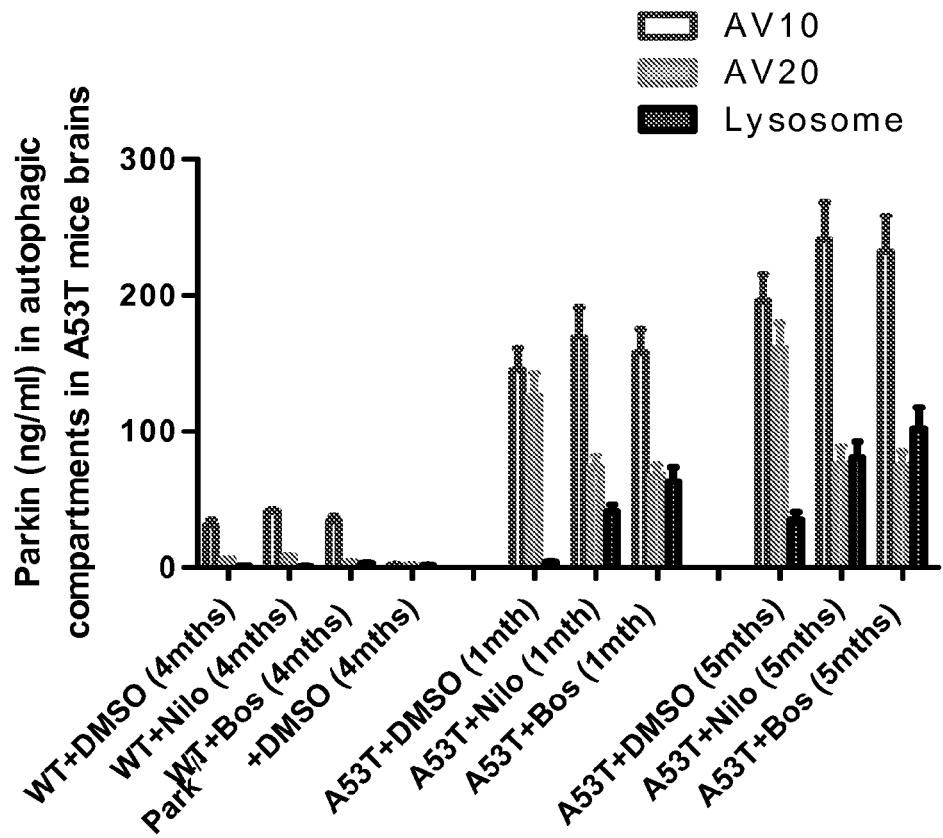

FIG. 26 shows that parkin accumulates in AV-10 in A53T brains but drug treatment enhances autophagic clearance via parkin deposition in AV-20 and lysosome. Histograms show parkin in subcellular fractions, including autophagic vacuole-10 (AV-10; phagophores+autophagosomes), AV-20 (autophagosomes) and lysosomes, containing digestive enzymes. Transgenic A53T mice were injected IP with 10 mg/kg Nilotinib or 5 mg/Kg Bosutinib or DMSO once a day for 3 consecutive weeks. Brain tissues were fractionated to isolate AVs and mouse specific ELISA was performed to determine protein contents. N=5 animals per treatment.

Figure 27:
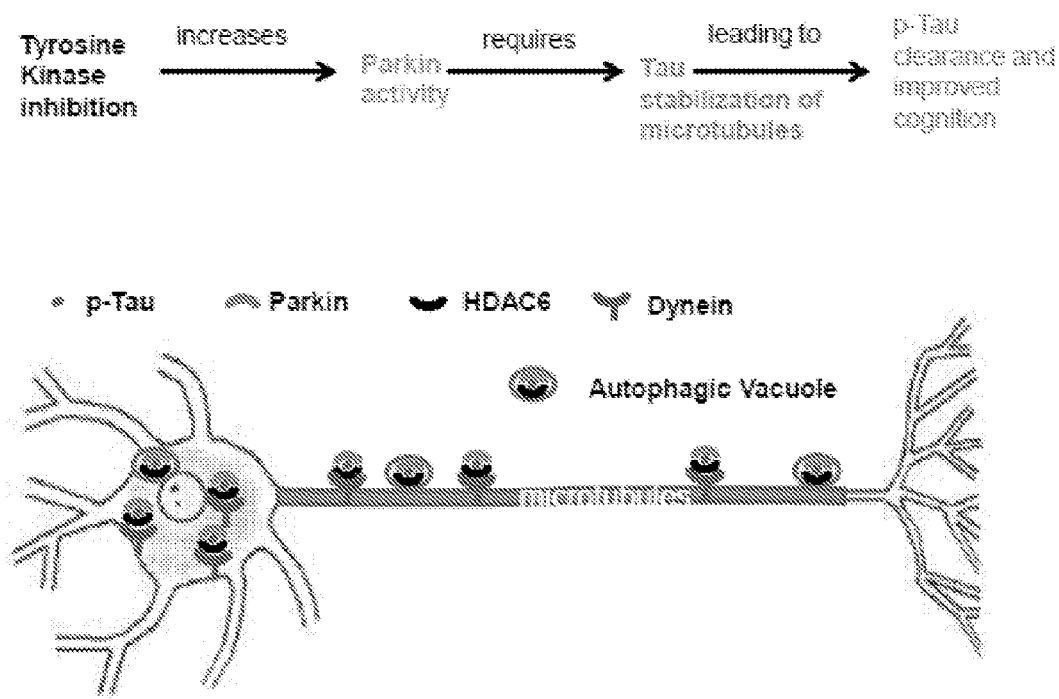

FIG. 27 is a diagram illustrating how Tyrosine kinase inhibition increases parkin activity and facilitates autophagic clearance of p-Tau. This process requires Tau stabilization of intact microtubules. Tyrosine kinase activation, p-Tau accumulation and impaired autophagy are recognized in neurodegeneration. Decreased parkin solubility and accumulation with intracellular Aβ and p-Tau in autophagic vacuoles in AD brains occurs, while exogenous parkin facilitates autophagic clearance in animal models.

Figure 28:
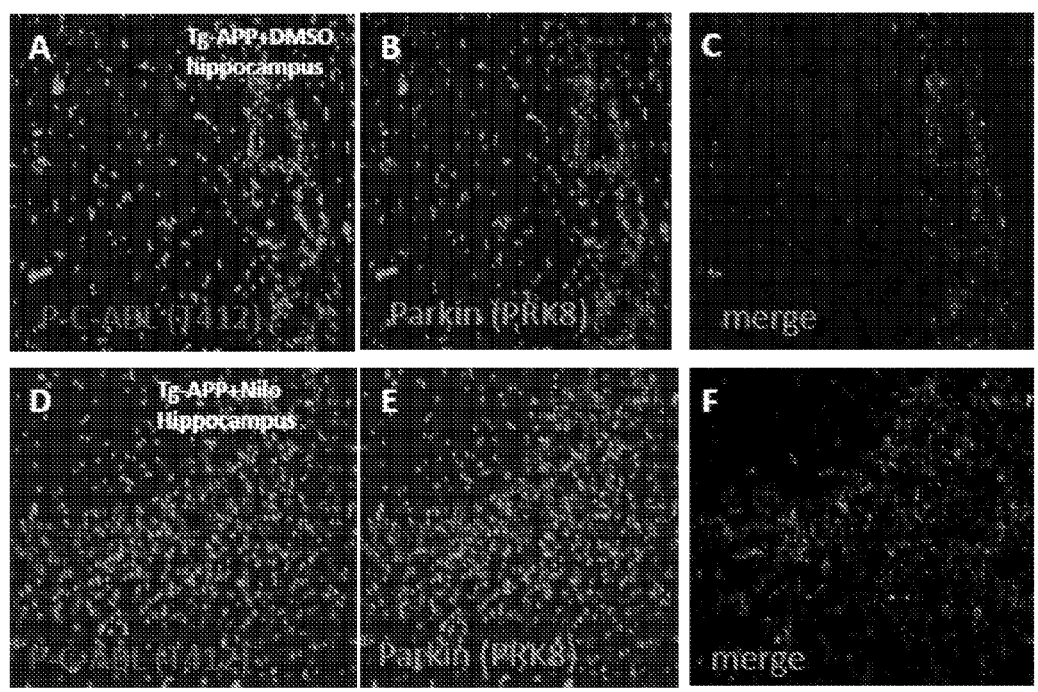

FIG. 28 shows A) phosphorylated c-Abl at tyrosine 412 (T412) and B) endogenous parkin expression merged in C) hippocampus of 6 month old C57BL/6 mice treated IP with DMSO daily for 3 weeks. FIG. 28 also shows D) decreased phosphorylated c-Abl at tyrosine 412 (T412) and E) increased endogenous parkin expression merged in F) hippocampus of 6 month old C57BL/6 mice treated IP with 5 mg/kg Bosutinib daily for 3 weeks.

Figure 29:
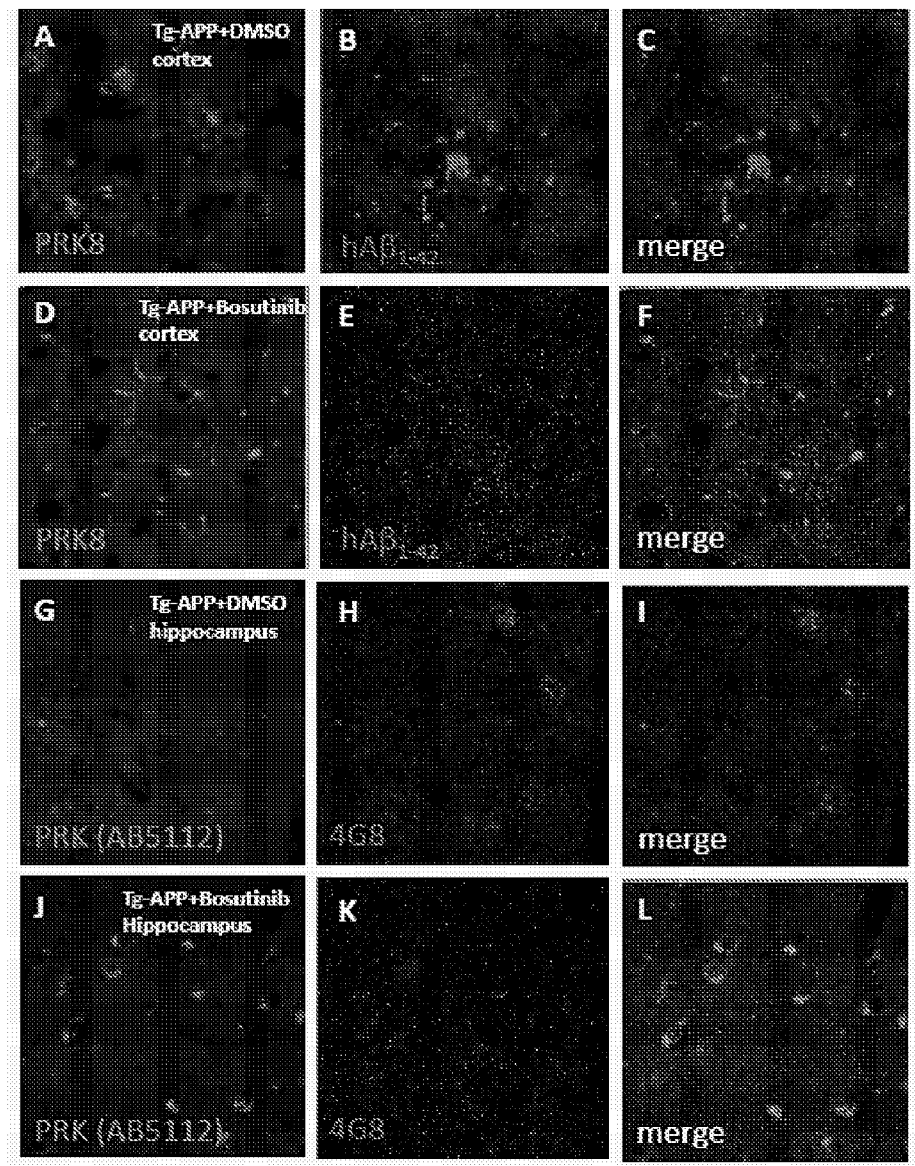

FIG. 29 shows A) parkin and B) Aβ expression merged in C) cortex of 6 month old Tg-APP mice treated with DMSO or 5 mg/kg Bosutinib (D-F) once a day for 3 weeks. Using a different combination of antibodies (see figure G-I showing expression of parkin (G) and Aβ (H) in the hippocampus of Tg-APP mice treated DMSO. J-H show the increase in parkin level in animals treated for 3 weeks once a day with Bosutinib (J) along with decreased plaque levels (K and L) in the hippocampus.

Figure 30:
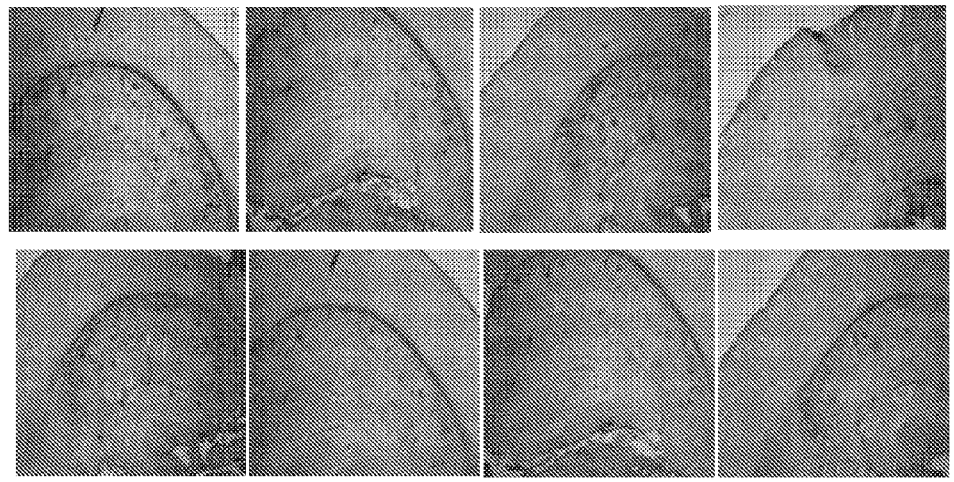

FIG. 30 shows plaque Aβ stained with 6E10 antibody and counterstained with DAB in the brain of Tg-APP animals treated IP with DMSO once a day for 3 weeks.

Figure 31:
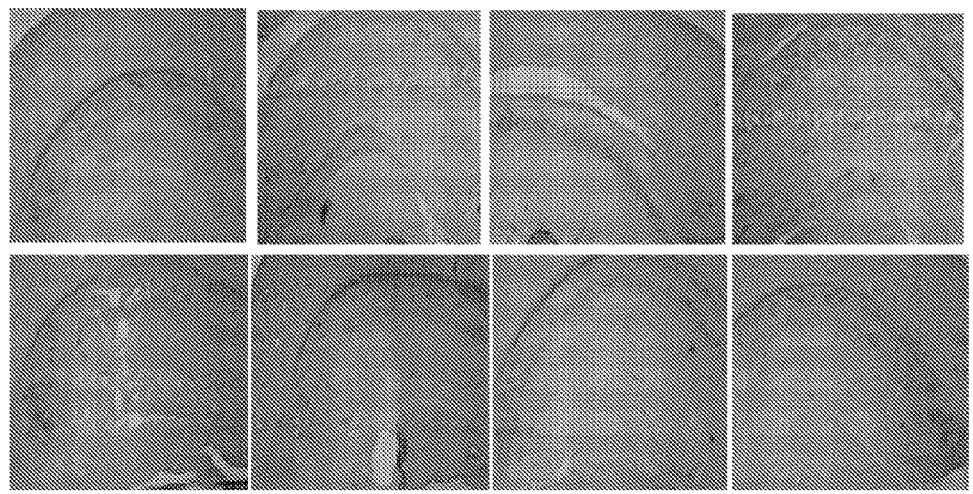

FIG. 31 shows plaque Aβ stained with 6E10 antibody and counterstained with DAB in the brain of Tg-APP animals treated IP with 5 mg/kg Bosutinib once a day for 3 weeks.

Figure 32:
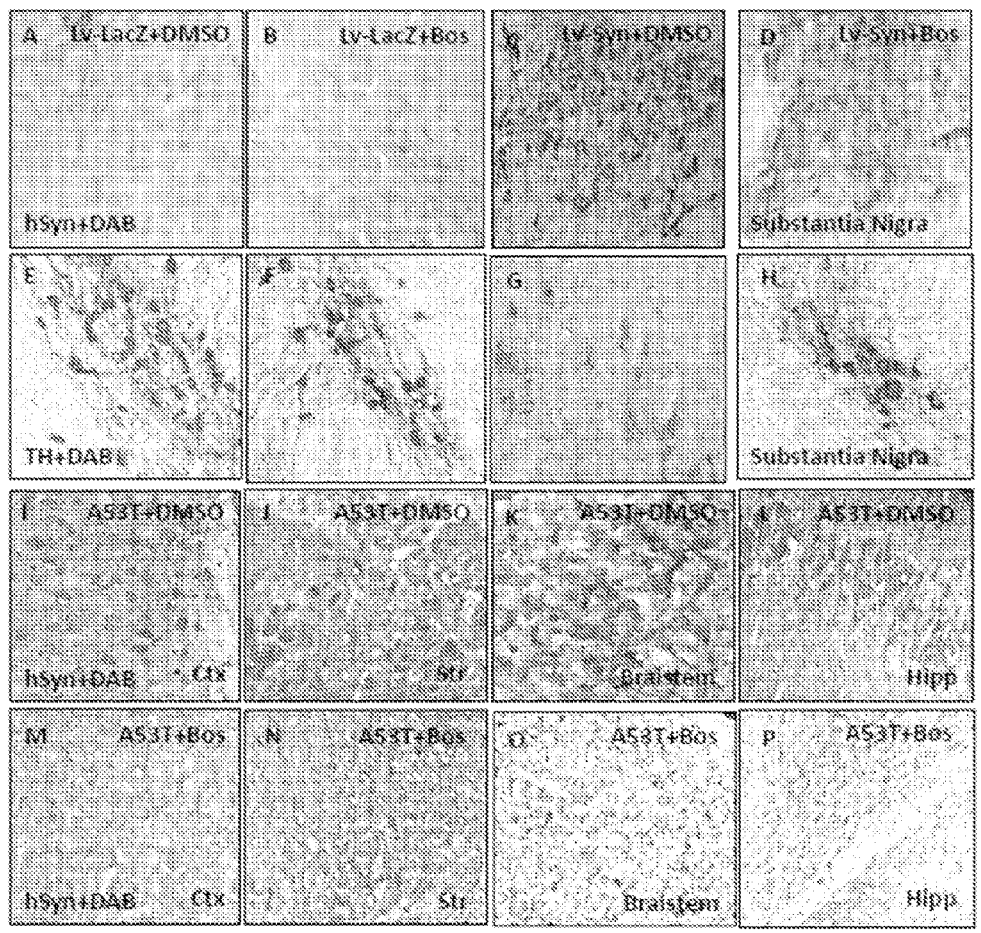

FIG. 32 shows that Bosutinib decreases α-synuclein levels in transgenic mice expressing A53T throughout the brain. A-D show human α-synuclein expression in lentiviral LacZ injected (for 3 weeks) substantia nigra with A) DMSO and B) 5 mg/kg Bosutinib once a day for 3 weeks. C and D show human α-synuclein expression in lentiviral α-synuclein injected (for 3 weeks) substantia nigra with C) DMSO and D) or Bosutinib once a day for 3 weeks. E-H show Tyrosine Hydroxylase (TH) expression in lentiviral LacZ injected (for 3 weeks) substantia nigra with E) DMSO and F) 5 mg/kg Bosutinib once a day for 3 weeks. G and H show TH expression in lentiviral α-synuclein injected (for 3 weeks) substantia nigra with G) DMSO and H) or Bosutinib once a day for 3 weeks. α-synuclein decreases TH neurons and Bosutinib rescues these cells. I-L show human α-synuclein expression in A53T mice in I) Cortex, J) Striatum, K)

Brainstem and L) Hippocampus treated with DMSO for 3 weeks. M-P show human α-synuclein expression in A53T mice in M) cortex, N) striatum, O) brainstem and P) hippocampus treated with 5 mg/kg Bosutinib for 3 weeks.

Figure 33:
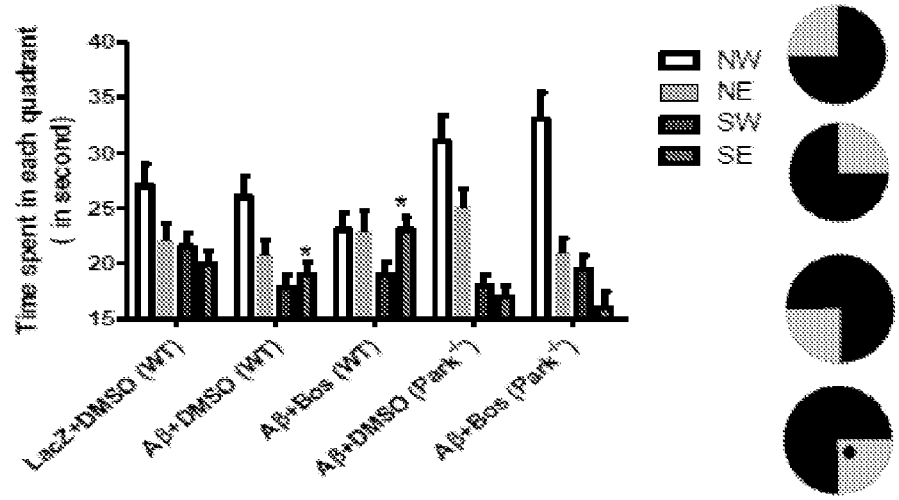
Figure 33:
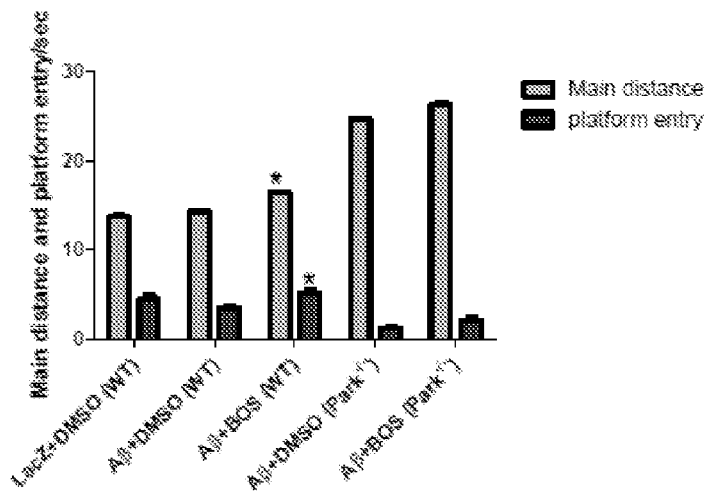

FIG. 33 provides graphs representing performance on a Morris water maze test (in seconds) showing that IP treatment with 5 mg/kg Bosutinib once daily for 3 weeks improved cognitive behavior in mice injected bilaterally with lentiviral $Aβ_{1-42}$ for 3 weeks prior to drug treatment. Bosutinib treated mice found the platform (A) but DMSO treated mice spent more time in NW area, where they were initially placed or the NE or SW without effectively finding the platform area. Bosutninb improved cognitive performance in a parkin-dependent manner as the parkin−/− mice did seemed not to learn much. B) shows that Bosutinib treated mice traveled less distance with less speed, but entered the platform area more than DMSO treated mice.

Figure 34:
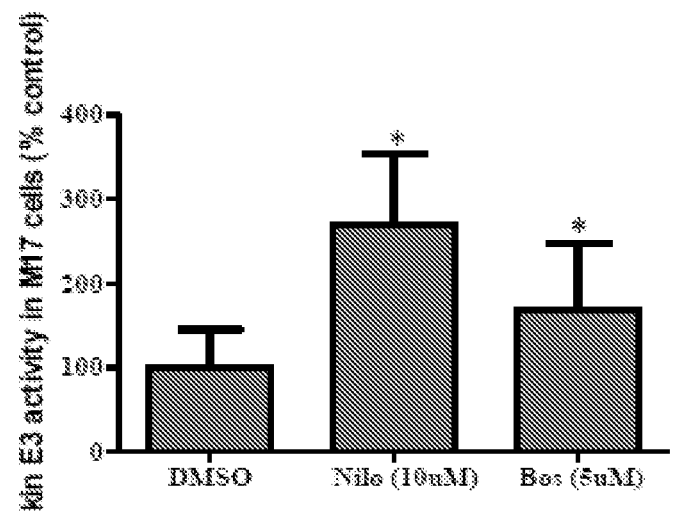
Figure 34:
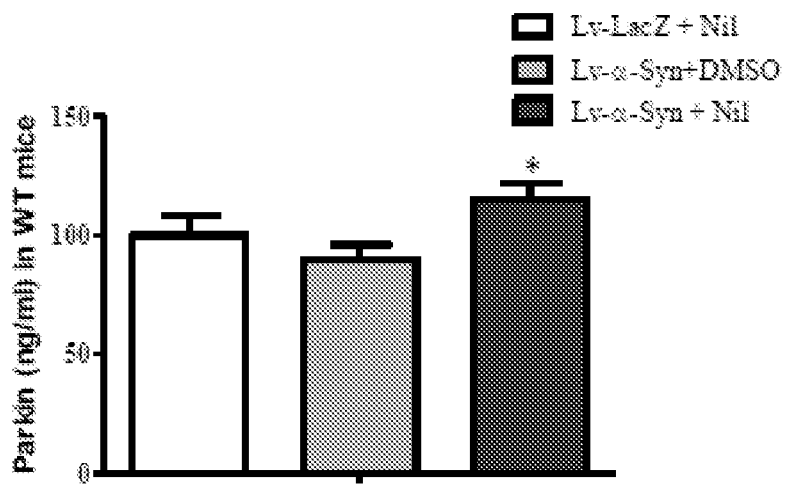

FIG. 34 shows that tyrosine kinase inhibitors increase parkin activity levels. A) shows ELISA levels of parkin activity in human M17 neuroblastoma cells treated with either 10 mg/kg Nilotinib or 5 mg/kg Bosutinib for 24 hrs. N=12. $P<0.05$.ANOVA, with Neuman Keuls multiple comparison. An asterisk indicates a significant difference as compared to DMSO. Bars are mean±SD. B) shows parkin levels (ELISA) in brain lysates of wild type mice injected with lentiviral α-synuclein for 3 weeks and then treated with 10 mg/kg Nilotinib once every two days for 3 weeks. N=10 animals. $P<0.05$.ANOVA, with Neuman Keuls multiple comparison. An asterisk indicates a significant difference as compared to DMSO. Bars are mean±SD.

Figure 35:
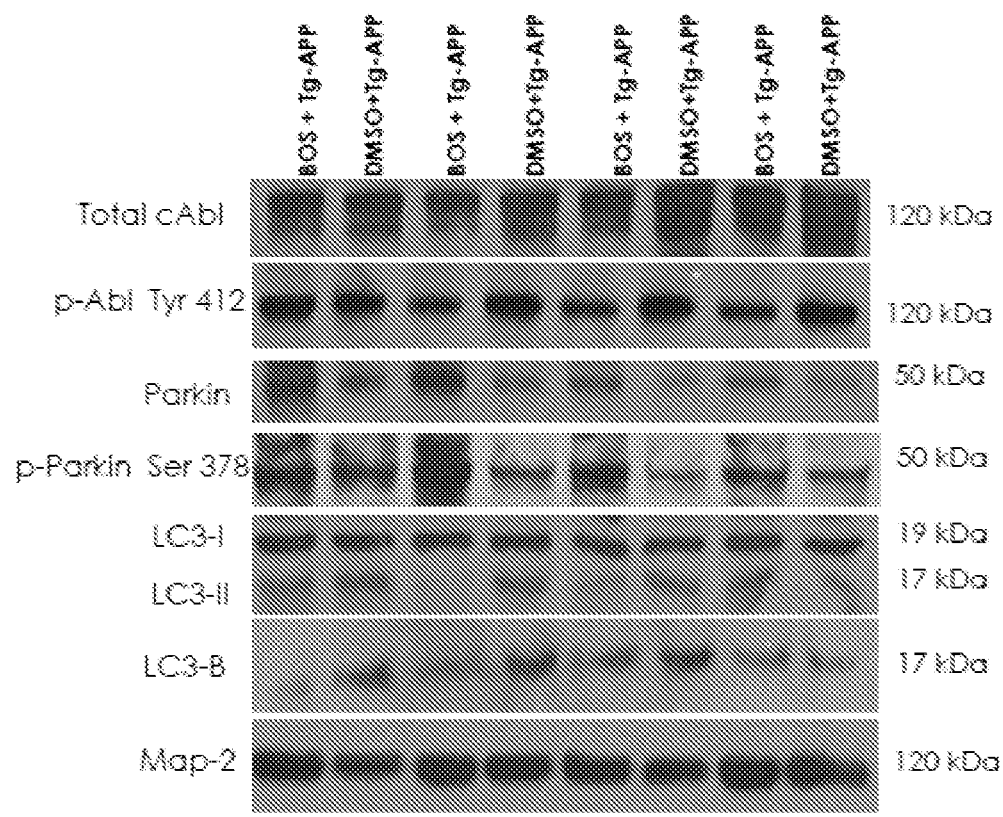

FIG. 35 is a Western blot analysis of brain lysates from Tg-APP mice treated with 5 mg/kg Bosutinib for 3 additional weeks. These blots show decreased levels of c-Abl, increased parkin and alteration of different molecular markers of autophagy, indicating that Aβ alters normal autophagy and Bosutinib boosts autophagy to clear $Aβ_{1-42}$.

Figure 36:
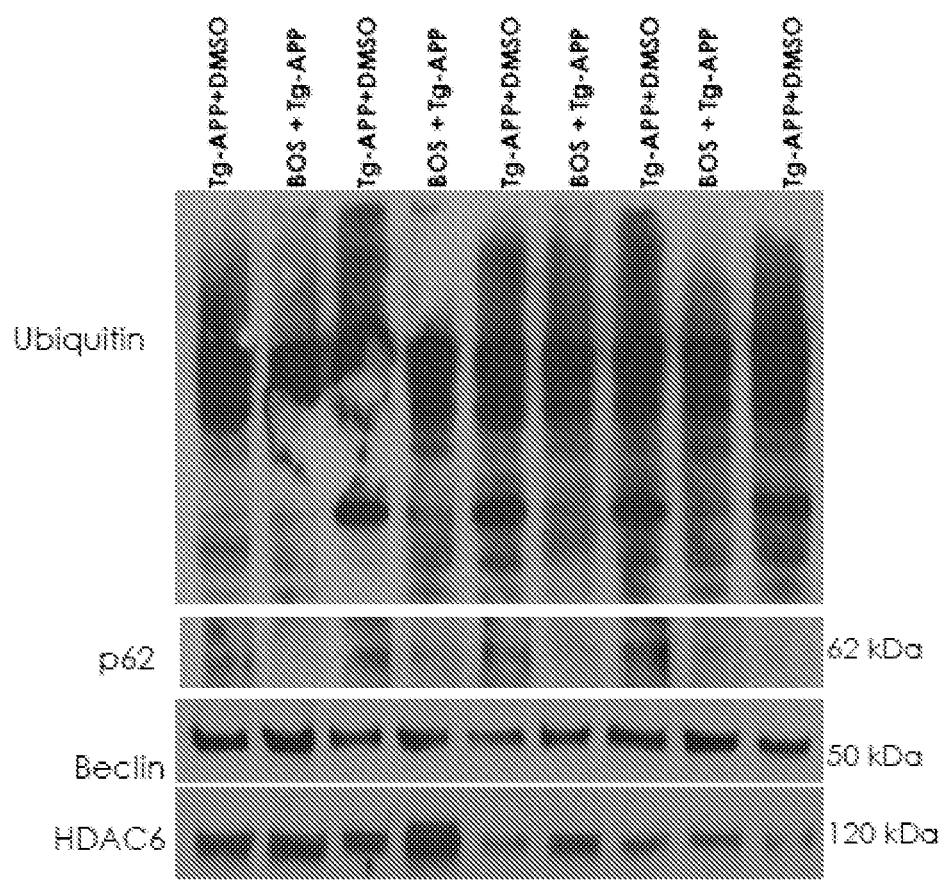

FIG. 36 is a Western blot analysis of brain lysates from Tg-APP mice treated with 5 mg/kg Bosutinib for 3 weeks. These blots show alterations in the levels of molecular markers of autophagy.

Figure 37:
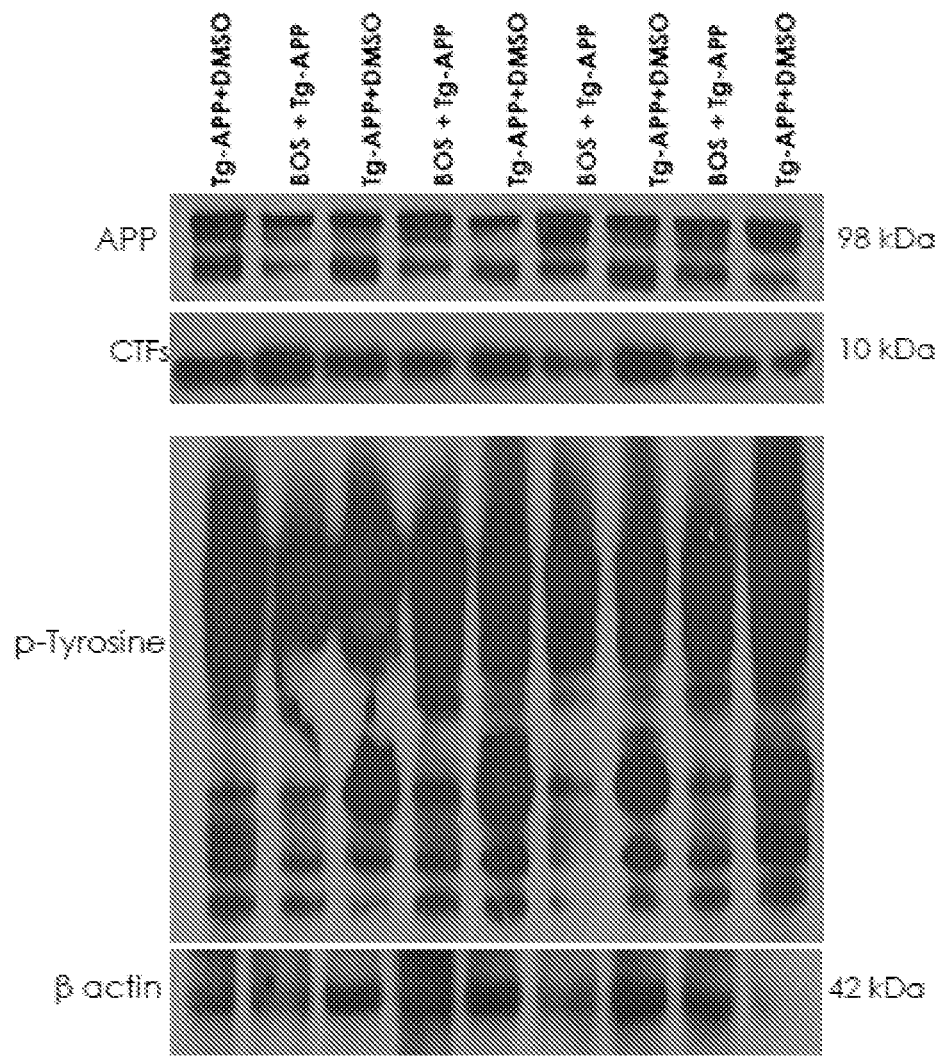

FIG. 37 is a Western blot analysis of brain lysates from Tg-APP mice treated with 5 mg/kg Bosutinib for 3 additional weeks. These blots show decreased levels of C-terminal fragments (CTFs) and phospho-tyrosine.

Figure 38:
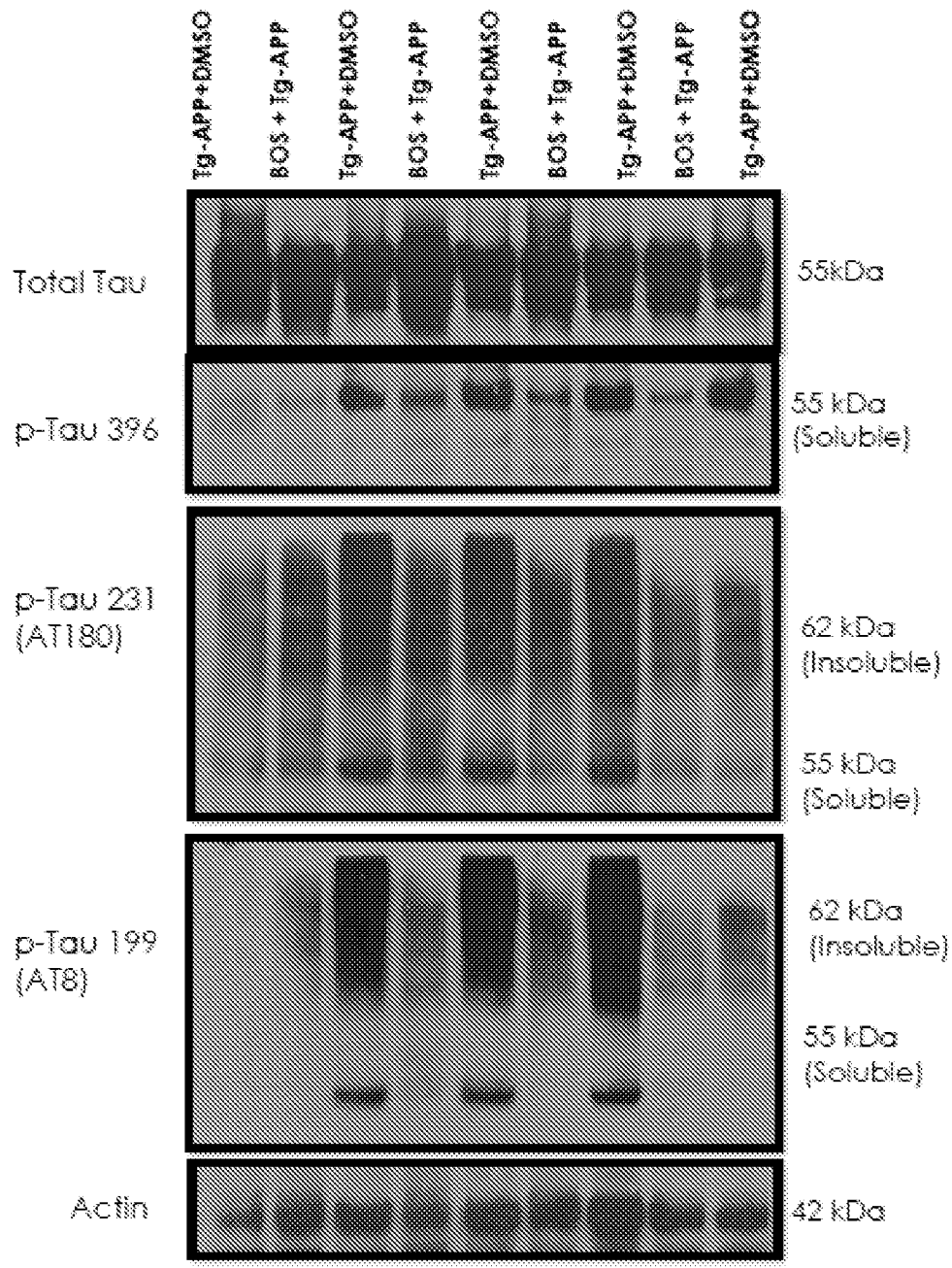

FIG. 38 is a Western blot analysis of brain lysates from Tg-APP mice treated with 5 mg/kg Bosutinib once a day for additional weeks. These blots show decreased levels of different Tau isotopes.

Figure 39:
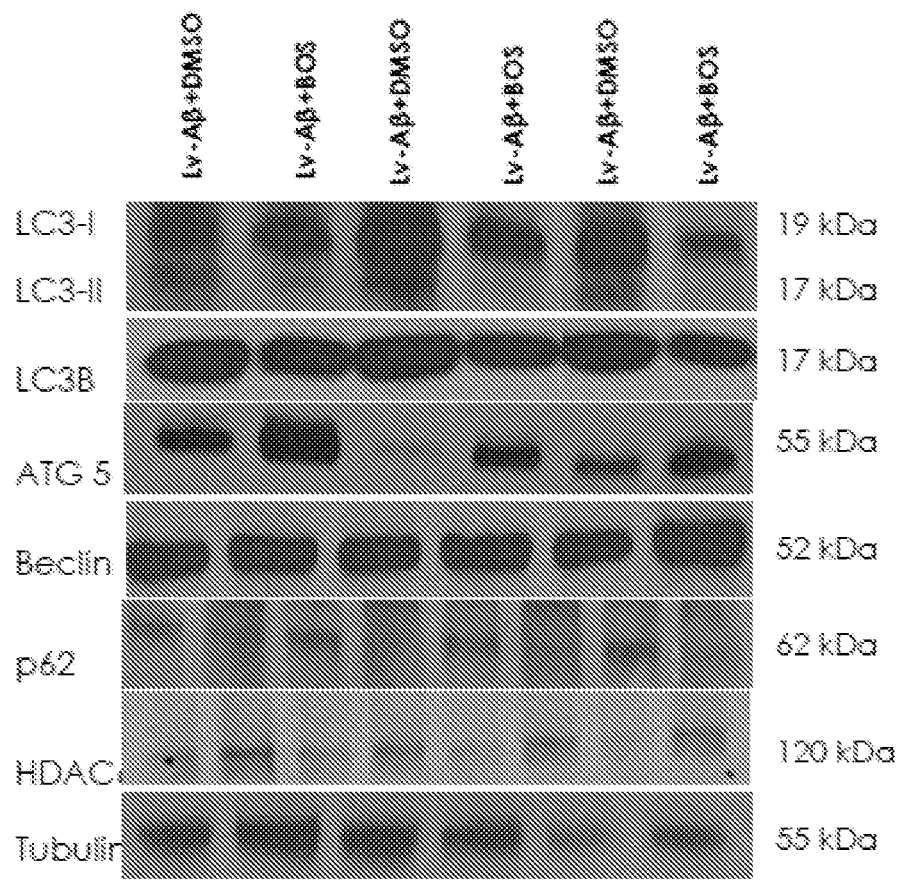

FIG. 39 is a Western blot analysis of brain lysates from wild type mice expressing lentiviral $Aβ_{1-42}$ (3 weeks) with and without Bosutinib (5 mg/kg) treatment for 3 additional weeks. These blots show levels of different molecular markers of autophagy, indicating that $Aβ_{1-42}$ alters normal autophagy and Bosutinib boosts autophagy to clear $Aβ_{1-42}$.

Figure 40:
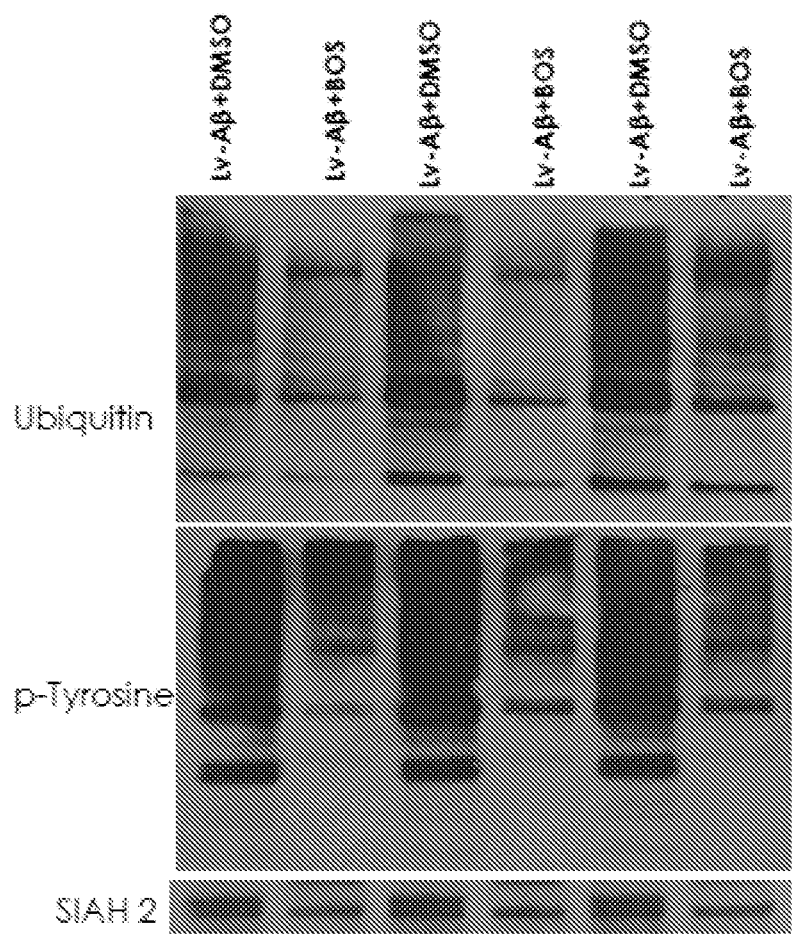

FIG. 40 is a Western blot analysis of brain lysates from wild type mice expressing lentiviral $Aβ_{1-42}$ (3 weeks) with and without Bosutinib treatment for 3 additional weeks. These blots show decreased levels of ubiquitin (top blot) and pan phospho-tyrosine (second blot) and SIAH2, suggesting that Bosutinib is a broad tyrosine kinase inhibitor.

Figure 41:
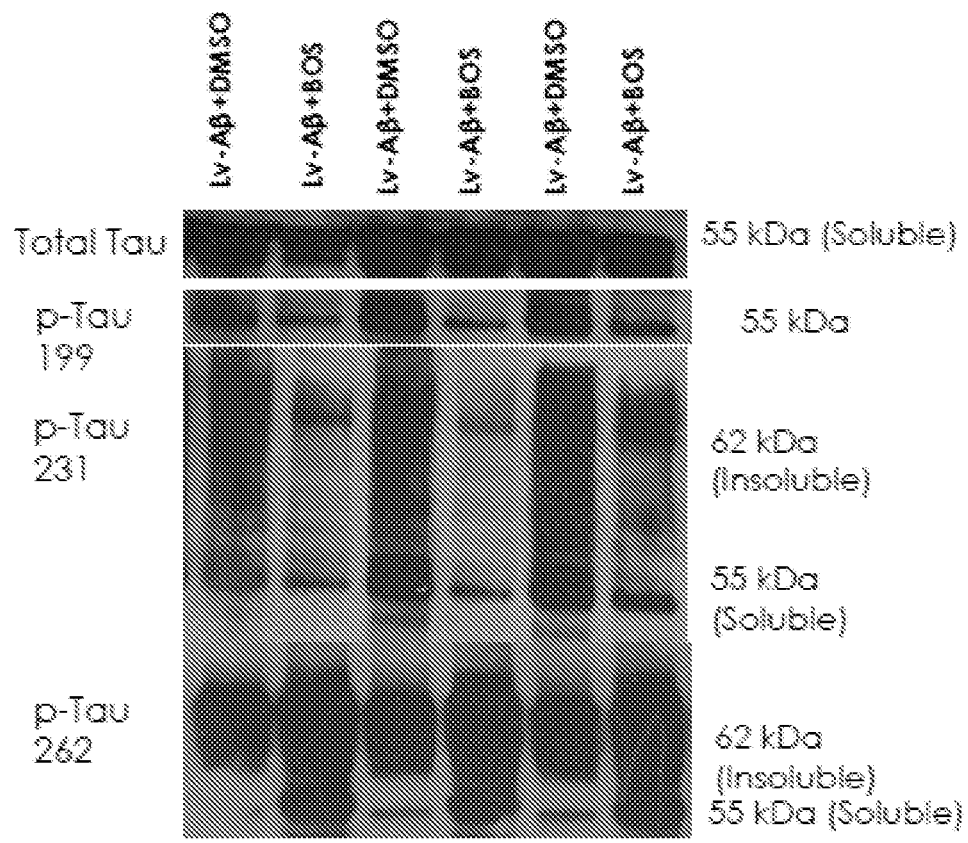

FIG. 41 is a Western blot analysis of brain lysates from wild type mice expressing lentiviral $Aβ_{1-42}$ (3 weeks) with and without Bosutinib treatment for 3 additional weeks. These blots show decreased levels of different Tau isotopes.

Figure 42:
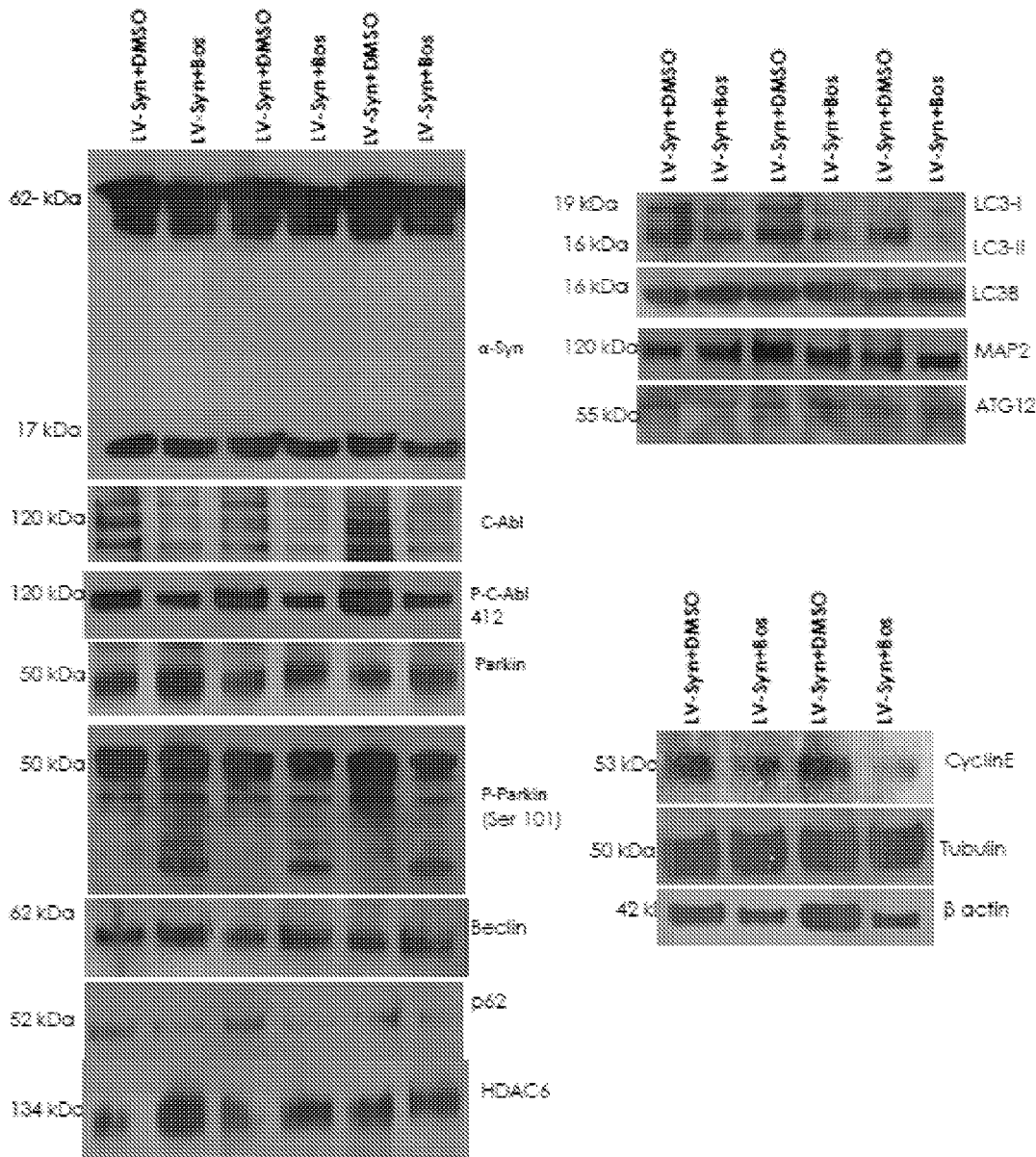

FIG. 42 is a Western blot analysis of brain lysates from wild type mice expressing lentiviral α-synuclein (3 weeks) with and without Bosutinib treatment for 3 additional weeks. Blots show in order increased α-synuclein in lentiviral synuclein injected animals, along with decreased c-Abl levels and phosphorylation, increased parkin levels and markers of autophagy, including P62, HDAC6, LC3 and ATG12 compared to loading controls tubulin and MAP2.

Figure 43:
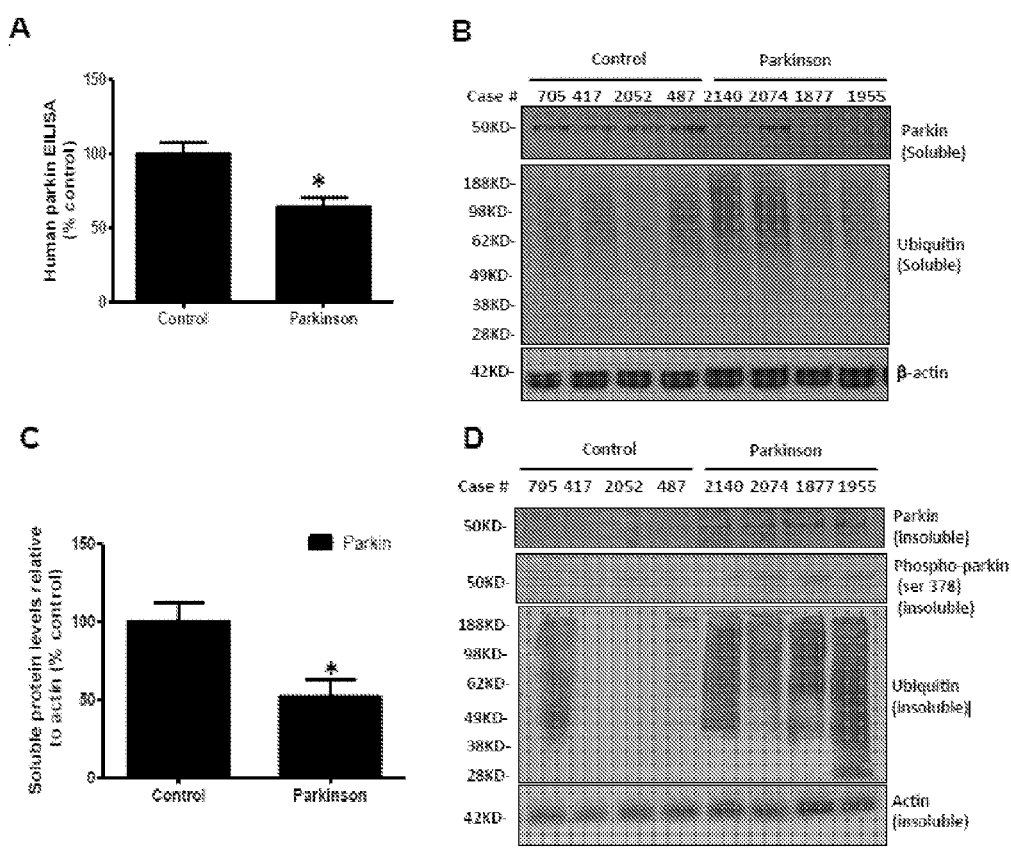
Figure 43:
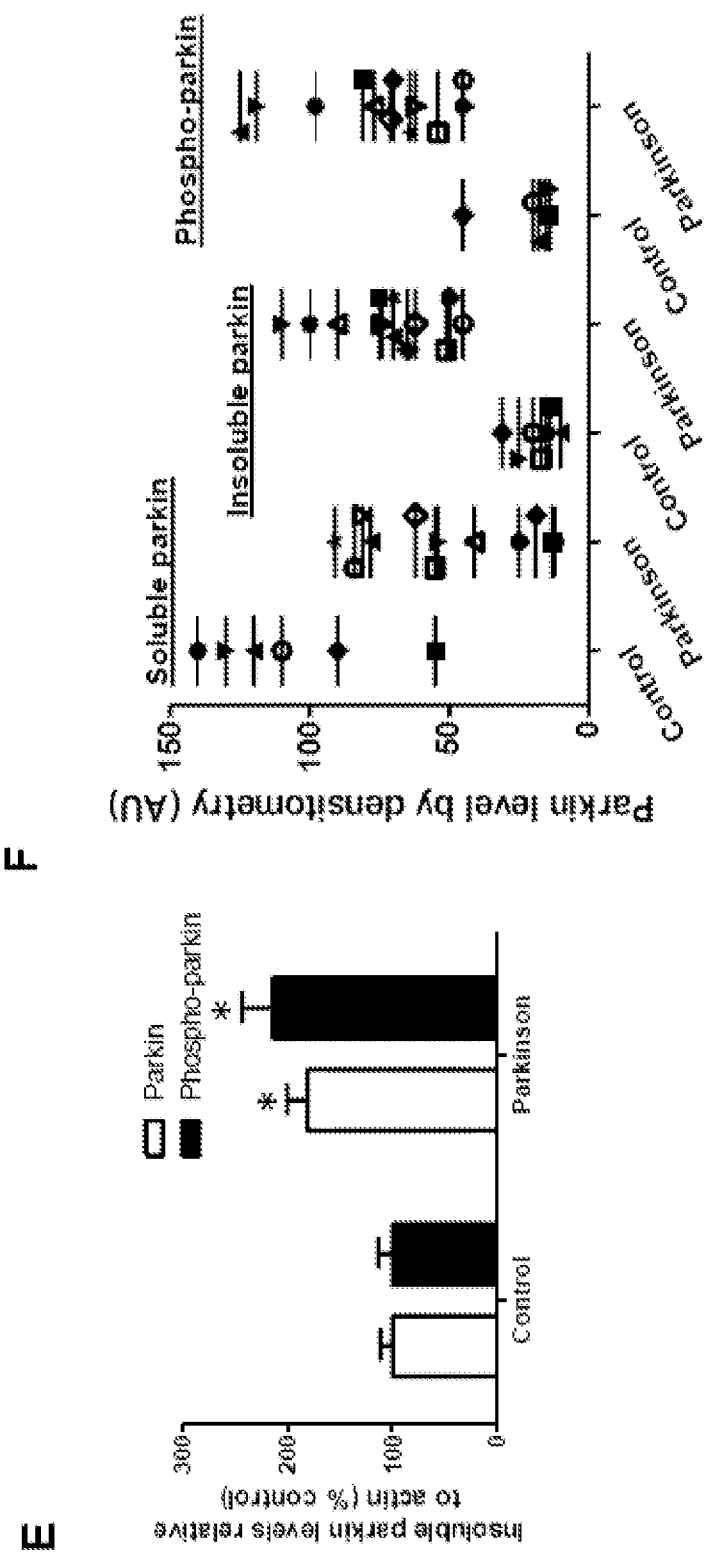

FIG. 43 shows that parkin is insoluble in post-mortem striatum of human PD patients. A) Histograms represent ELISA measurement of human parkin in the caudate of PD patients and control subjects. B) is a WB analysis on 4-12% SDS-NuPAGE gel of soluble human post-mortem striatal lysates in PD patients and control subjects, showing parkin (1st blot) and ubiquitinated proteins (2nd blot) compared to actin loading control. C) Histograms represent quantification of blots. D) is a WB analysis on 4-12% SDS NuPAGE gel showing the levels of insoluble parkin (1st blot), phospho-parkin (2nd blot), ubiquitinated proteins (3rd blot), and actin (4th blot). E) Histograms represent quantification of blots. Asterisks indicate a significant difference. F) Box plot represents individual samples of human PD patients and age-matched controls. Histograms are mean±SD expressed as % to control. ANOVA, Neumann Keuls with multiple comparison, or non-parametirc t-Test. $P<0.05$. N=12 PD patients and 7 control subjects.

Figure 44:
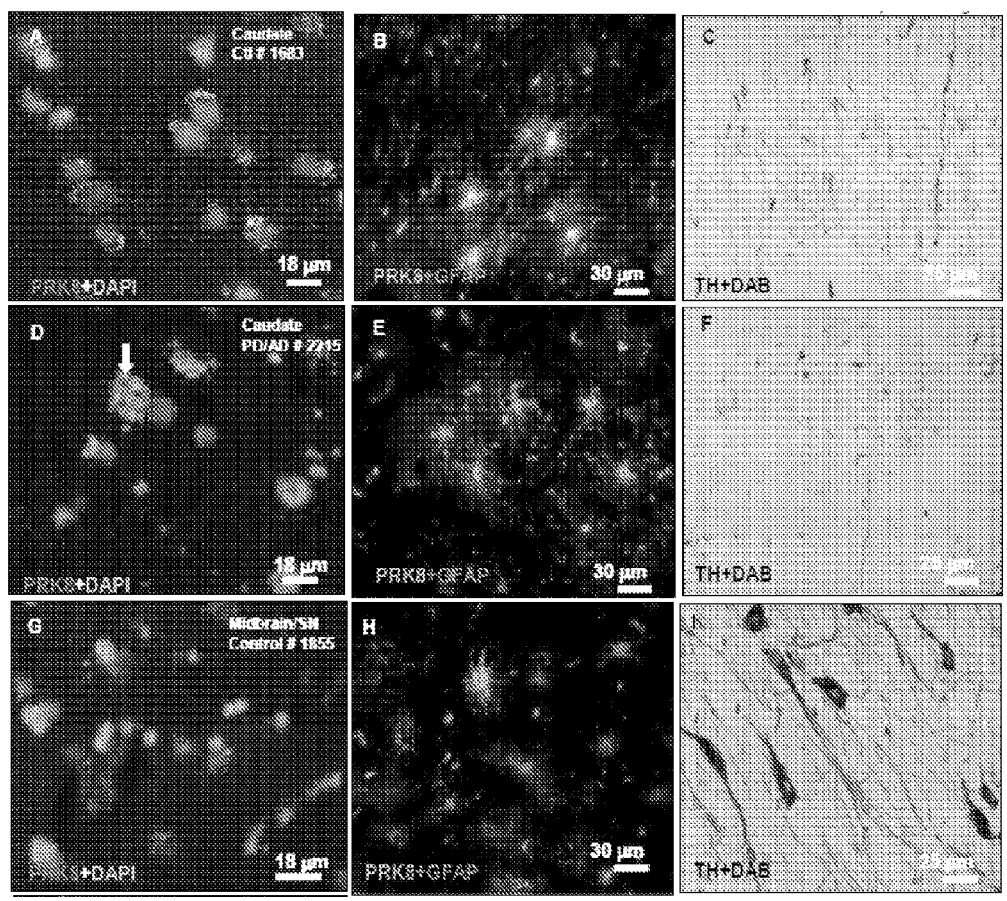
Figure 44:
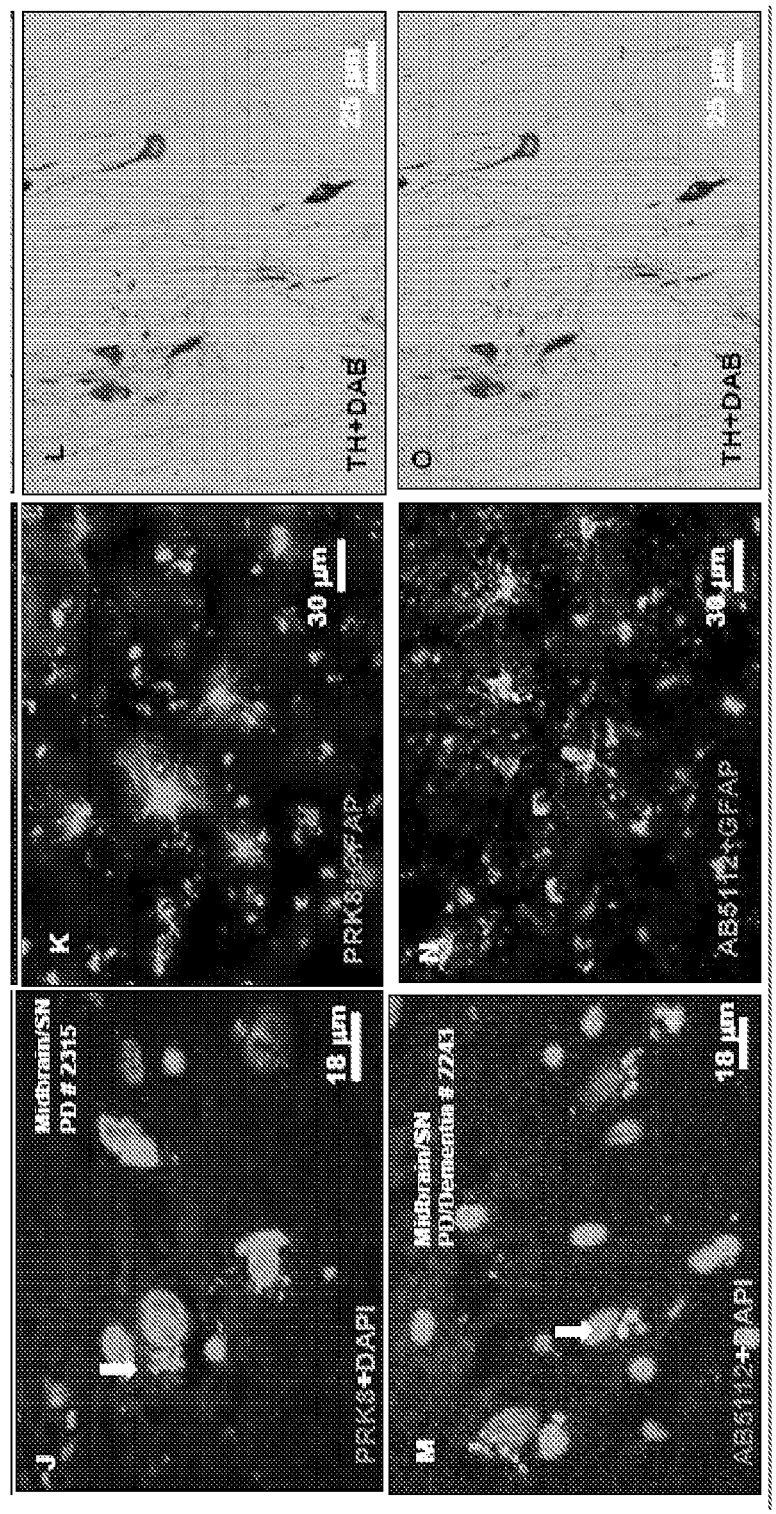

FIG. 44 shows immunostaining of human tissues with human and GFAP antibodies. Immunostaining of 20 μm thick paraffin embedded serially sectioned brains with A) human anti-parkin (PRK8) staining and counterstaining with nuclear marker DAPI showing cytosolic protein, B) co-staining with parkin and glial marker GFAP showing parkin expression in astrocytes, C) TH staining in the caudate of a control subject, D) parkin staining and counterstaining with nuclear marker DAPI showing cytosolic protein, E). co-staining with parkin and glial marker GFAP showing parkin expression in astrocytes, F). TH staining in the caudate of a PD/AD patient, G) parkin staining and counterstaining with DAPI showing cytosolic protein, H) co-staining with parkin and glial marker GFAP showing parkin expression in astrocytes, I) TH staining in the midbrain/SN of a control subject, J) parkin staining and counterstaining with DAPI showing cytosolic protein, K) co-staining with parkin and glial marker GFAP showing parkin expression in astrocytes, L) TH staining in the midbrain/SN of a PD patient. M). human anti-parkin (AB5112) staining and counterstaining with nuclear marker DAPI showing cytosolic protein, N) co-staining with parkin and glial marker GFAP showing parkin expression in astrocytes, O) TH staining in the caudate of a control subject.

Figure 45:
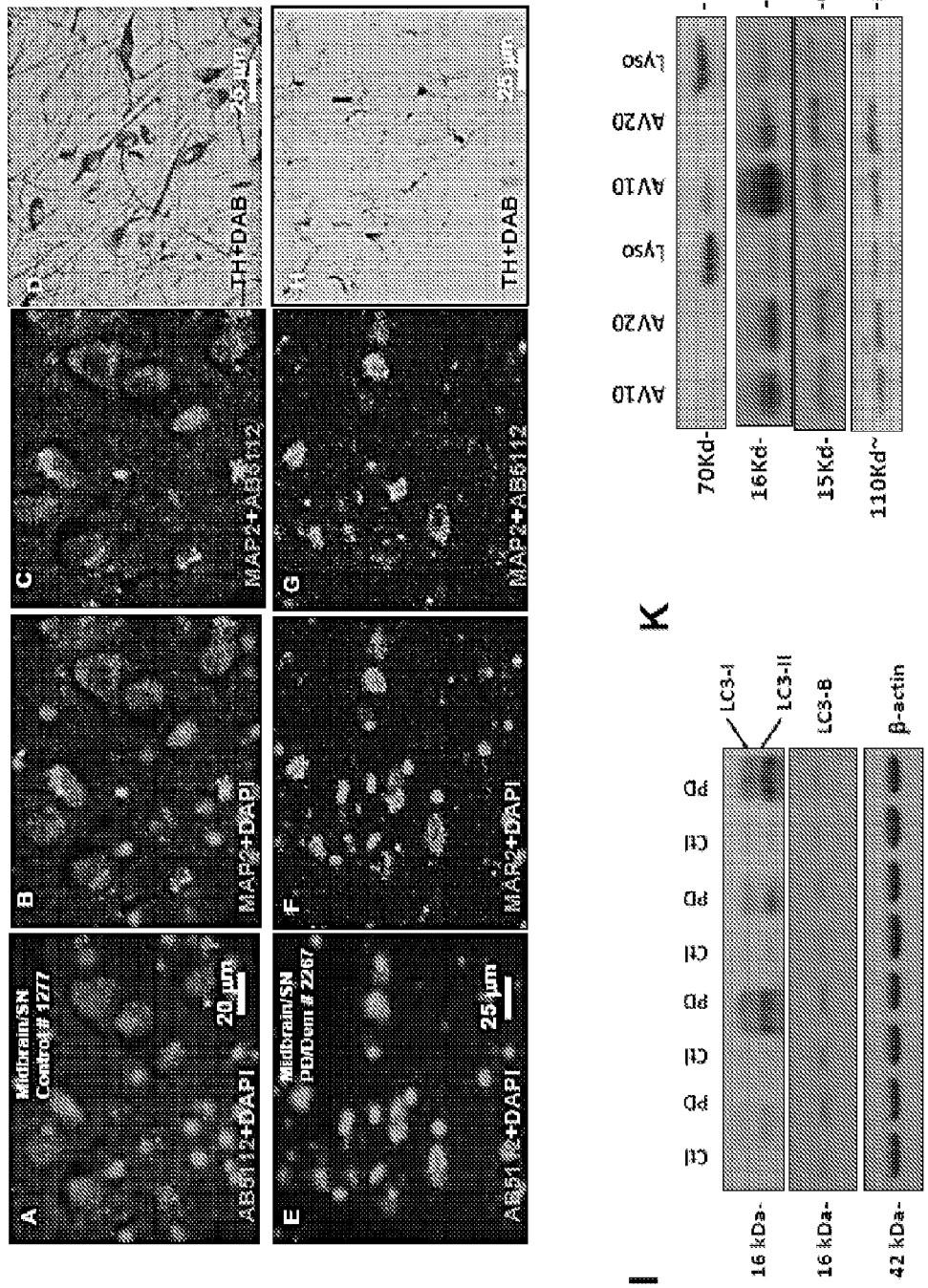
Figure 45:
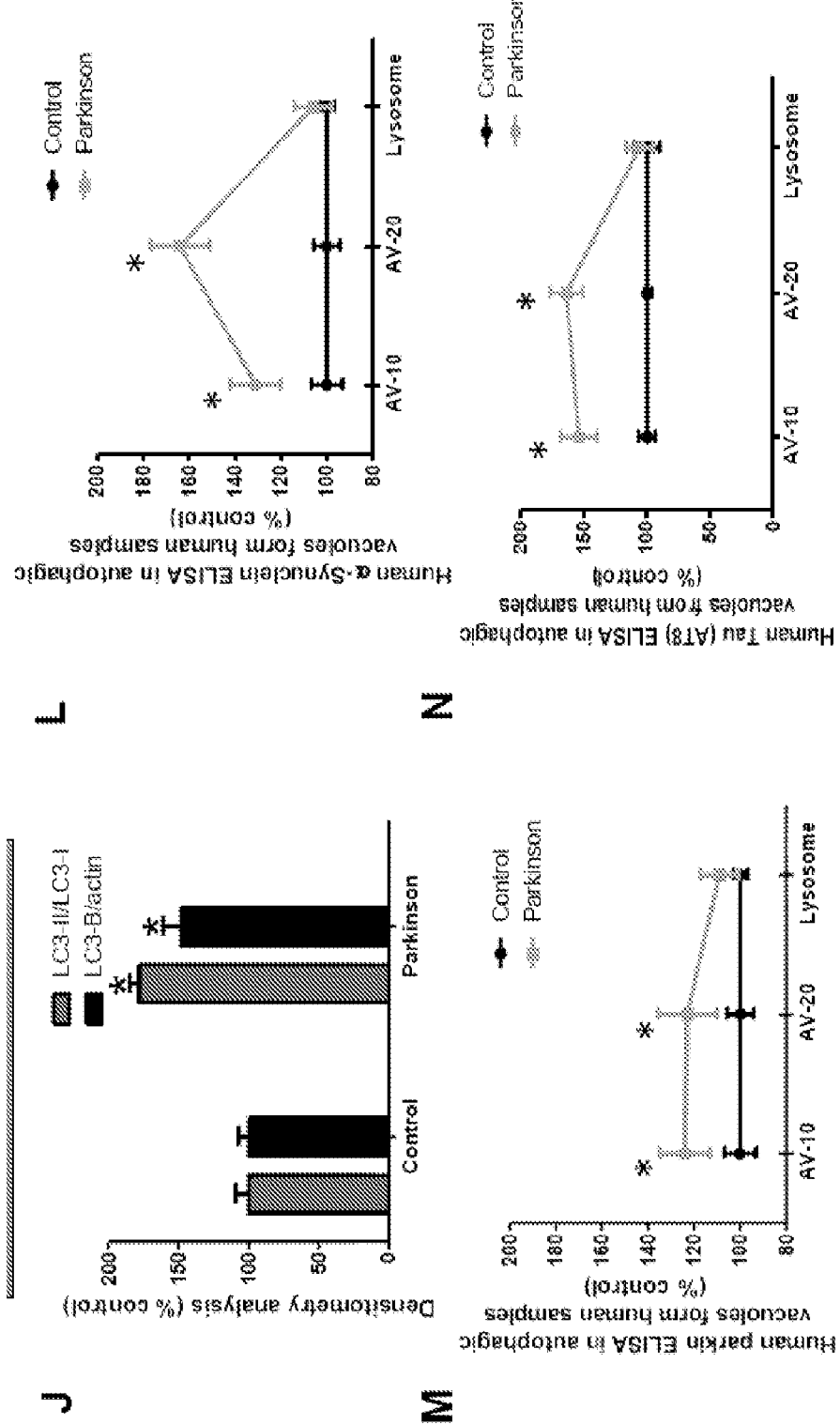

FIG. 45 shows subcellular fractionation in frozen human PD brain tissues. A) shows human anti-parkin (AB5112) staining and counterstaining with nuclear marker DAPI showing cytosolic protein. B) shows neuronal marker MAP-2 staining and DAPI and C) shows merged parkin and MAP-2 in stained serial sections. D) shows TH in the midbrain/SN of a control subject. E) shows human anti-parkin (AB5112) staining and counterstaining with nuclear marker DAPI showing cytosolic protein. F) shows neuronal marker MAP-2 staining and DAPI and G) shows merged parkin and MAP-2 in serial sections stained with H) TH in the midbrain/SN of a PD with Dementia patient. I) shows a WB analysis on 4-12% SDS NuPAGE gel of human striatal lysates showing expression of LC3-I and LC3-II (first panel), LC3-B (second panel) compared to actin loading control (bottom panel) J) shows histograms representing densitometry analysis of blots. K) shows a Western blot in subcellular extracts showing LC3-B in AV-10 and AV-20 and LAMP-3 in lysosomal fraction, as well as mitochondrial marker COX-IV and nuclear marker PARP-1. Graphs represent subcellular fractionation and ELISA measurement of L) human α-synuclein, M) human parkin and N) human p-Tau (AT8). Asterisks indicate significantly different to control. ANOVA, Neumann Keuls with multiple comparison, P<0.05. N=12 PD patients and 7 control subjects.

Figure 46:
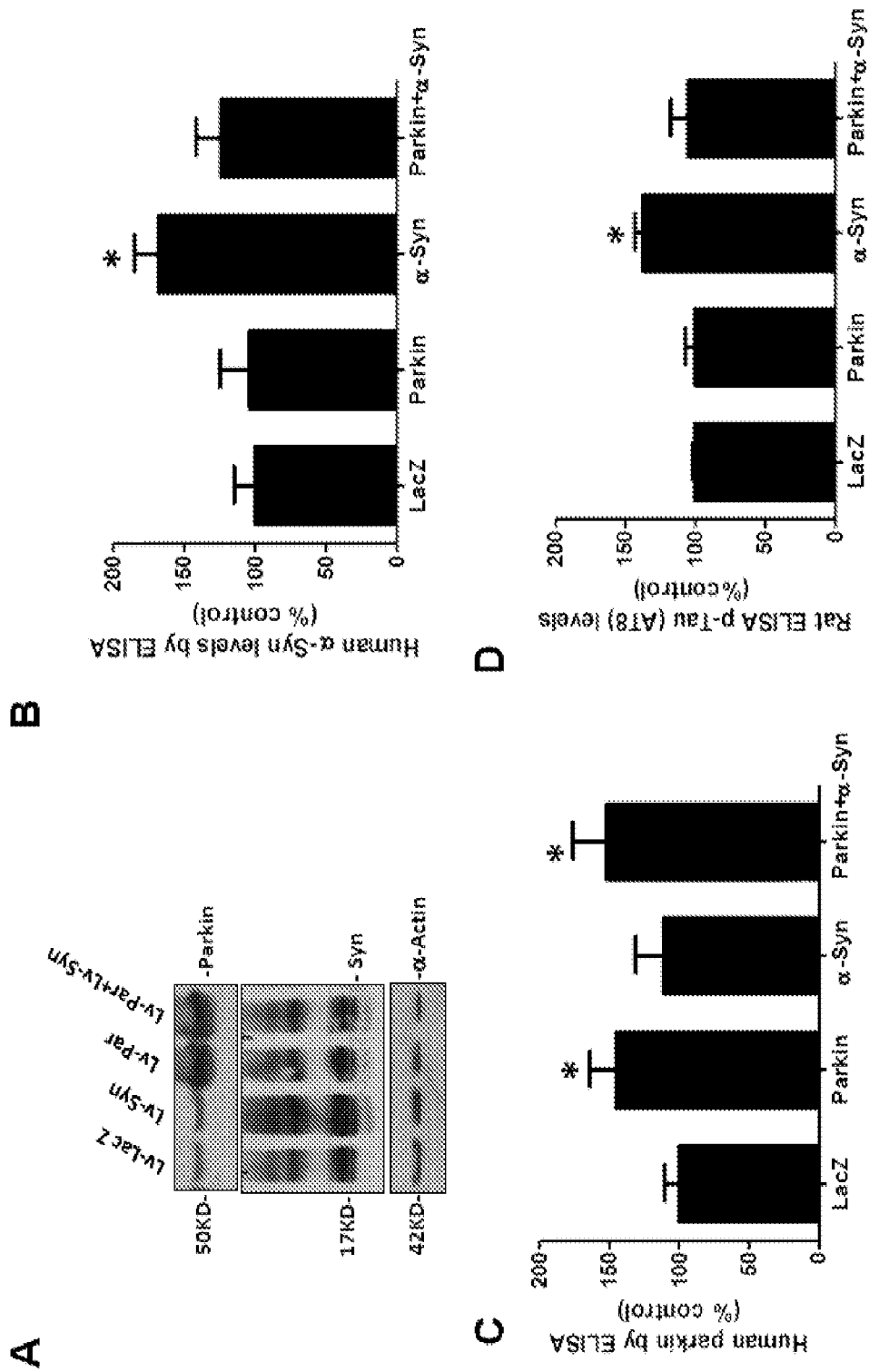
Figure 46:
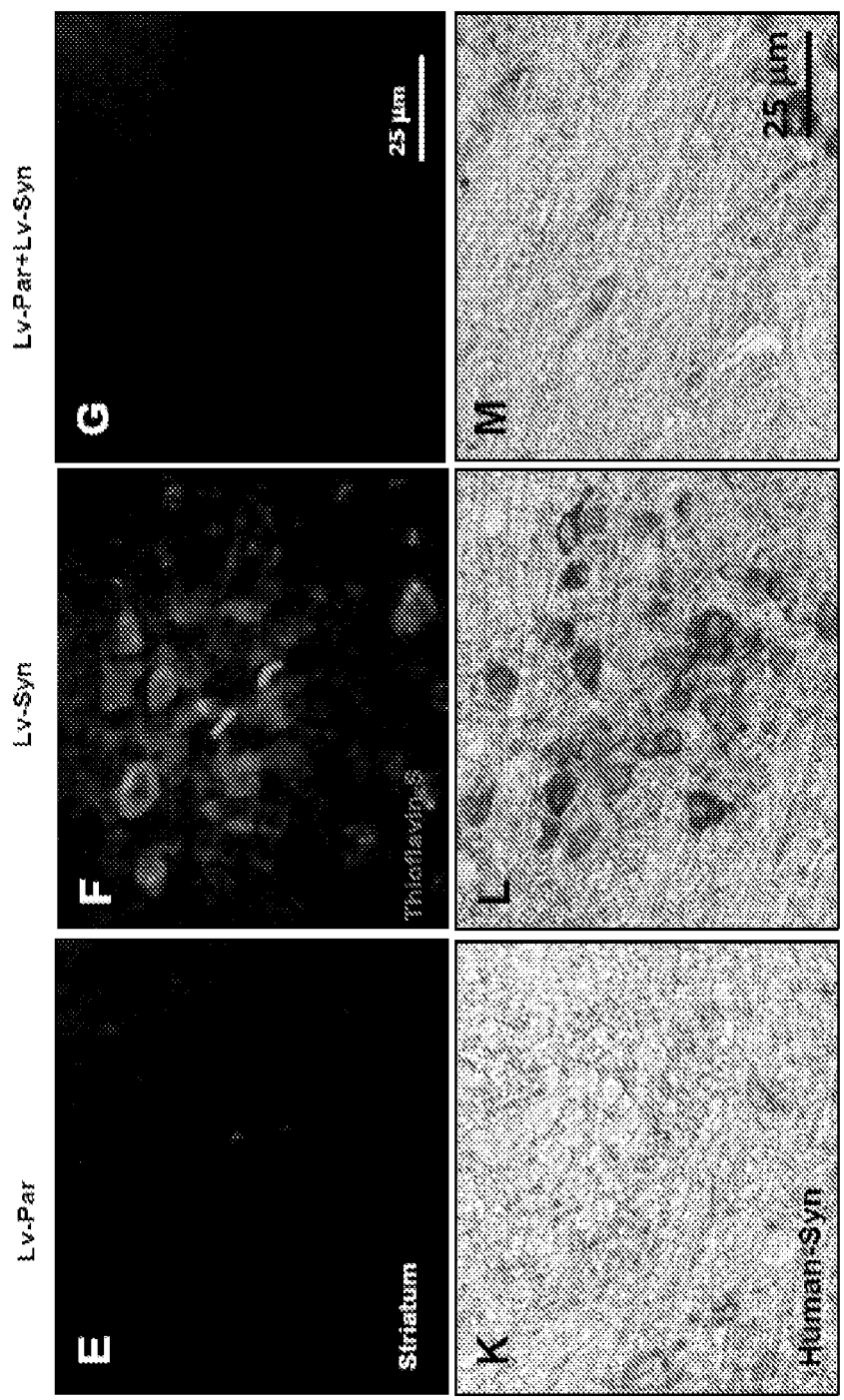

FIG. 46 shows lentiviral expression of α-synuclein leads to p-Tau and parkin activity reverses these effects. A) is a WB analysis on 4-12% SDS-NuPAGE gel of rat striatal extracts showing levels of parkin (top blot) and α-synuclein (middle blot) expression and actin levels (lower blot). B) shows histograms representing quantification of human α-synuclein levels by ELISA. C) shows histograms representing quantification of human parkin activity. D) is an ELISA measurement of rat p-Tau. Thioflavin-S staining of 20 µm striatal sections in lentiviral E) parkin, F) α-synuclein and G) parkin+α-synuclein injected brains. Human α-synuclein staining of 20 µm sections cut serially with the thioflavin-S sections is shown in for lentiviral K) parkin, L) α-synuclein and M) parkin+α-synuclein injected brains. Asterisks indicate significantly different. Histograms are mean±SD expressed as % control. ANOVA, Neumann Keuls with multiple comparison, P<0.05. N=8 animals per treatment for WB and ELISA, 8 for IHC.

Figure 47:
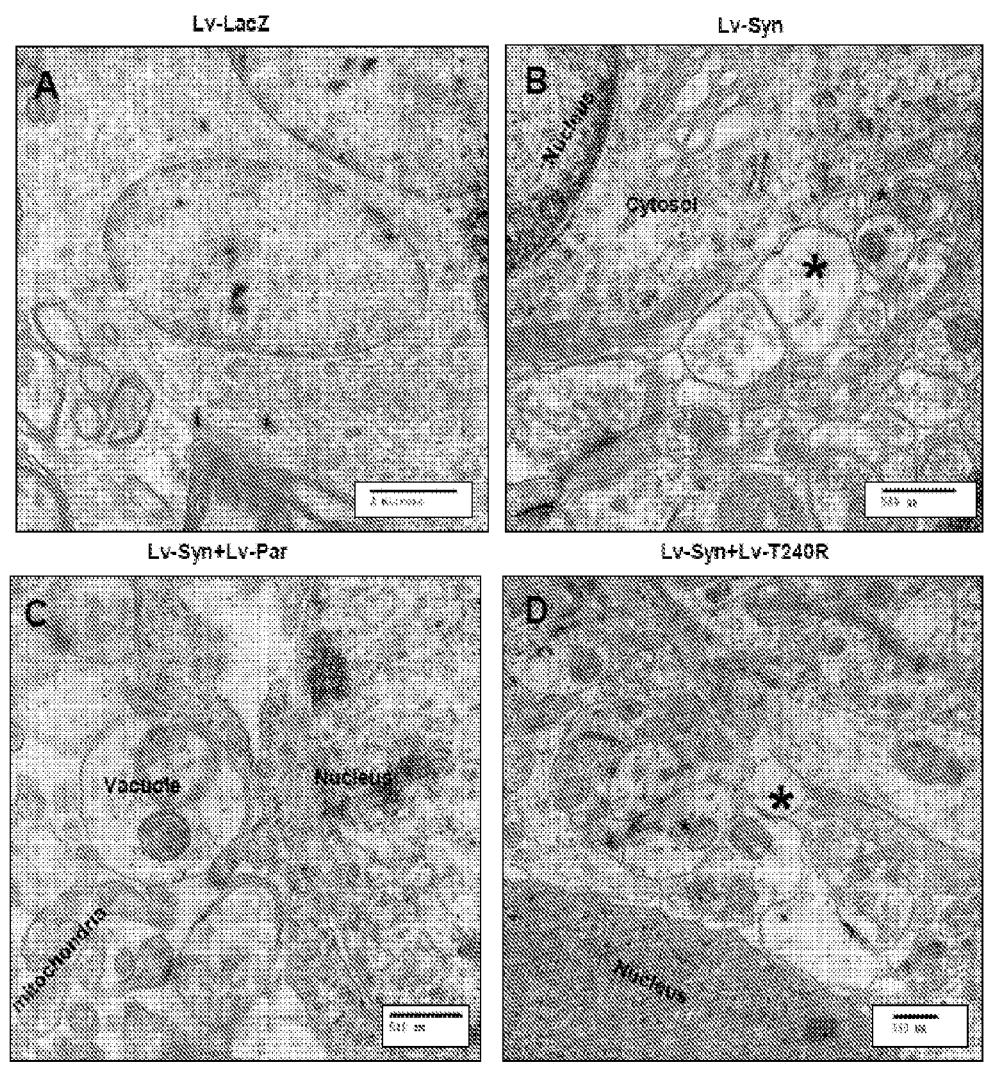
Figure 47:
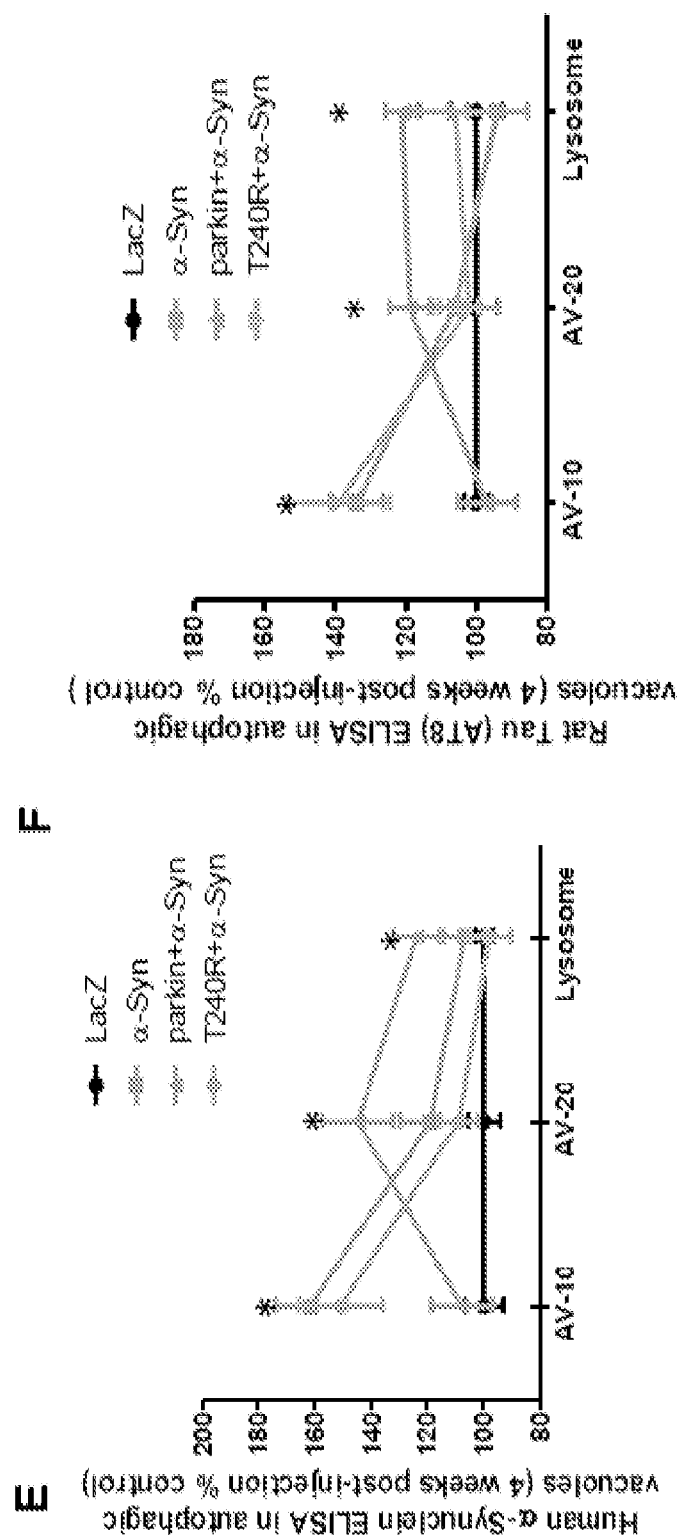

FIG. 47 shows that wild type, but not T240R, parkin reverses α-synuclein-induced accumulation of autophagosomes. Electron micrographs of striatal sections in rat brains injected with A) Lentiviral LacZ (Lv-LacZ) as control, B) Lentiviral α-synuclein (Lv-Syn), C) Lentiviral parkin+lentiviral-α-synuclein (Lv-Syn+Lv-Par), vacuoles contain debris and D) Lentiviral α-synuclein+lentiviral T240R (Lv-Syn+Lv-T240R). Asterisk indicates autophagic vacuoles. N=8. Graphs represent subcellular fractionation and ELISA measurement of E) α-synuclein and F) p-Tau in gene transfer animal models. ANOVA, Neumann Keuls with multiple comparison, P<0.05. N=5 animals per treatment for subcellular fractionation.

Figure 48:
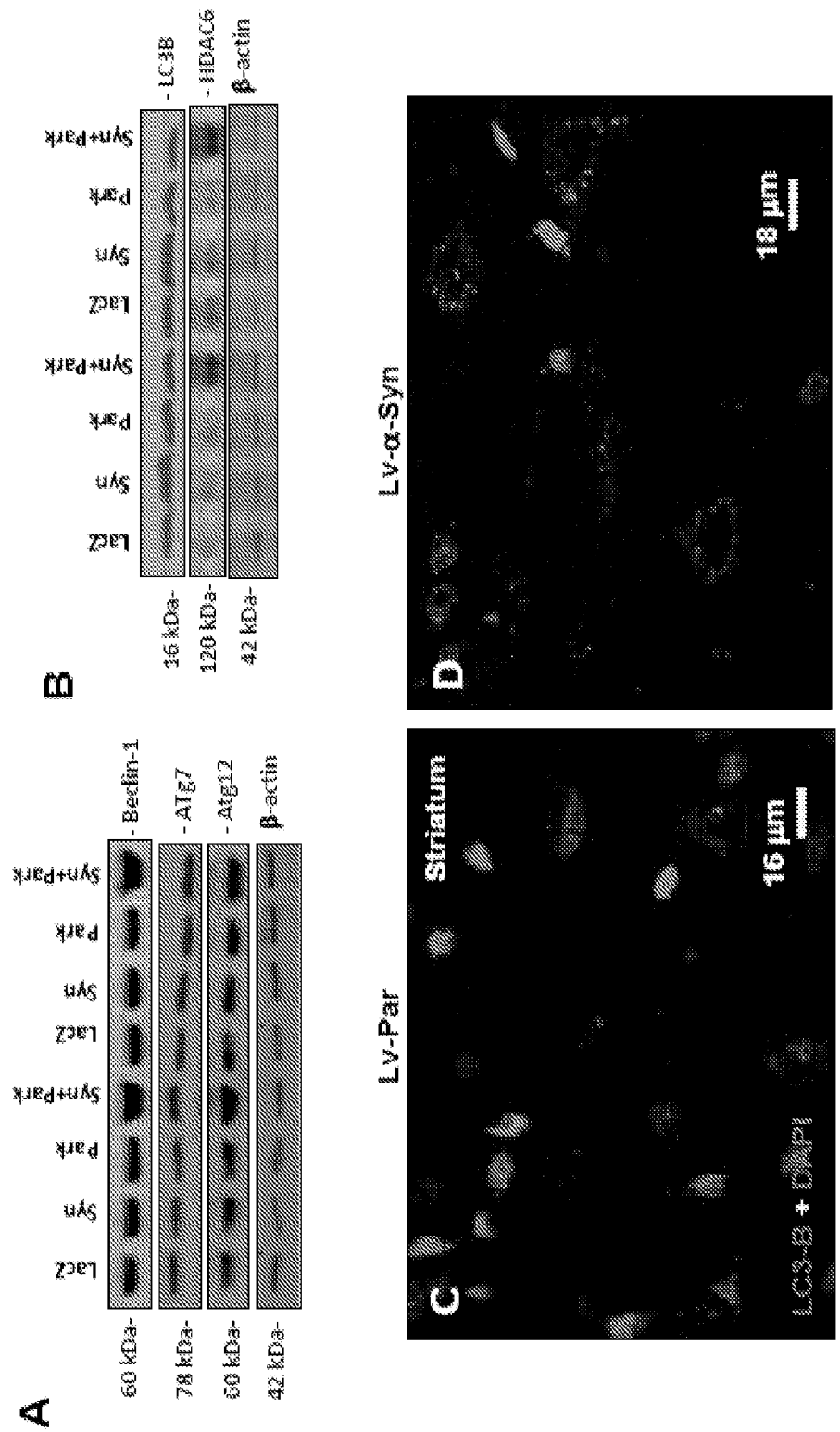
Figure 48:
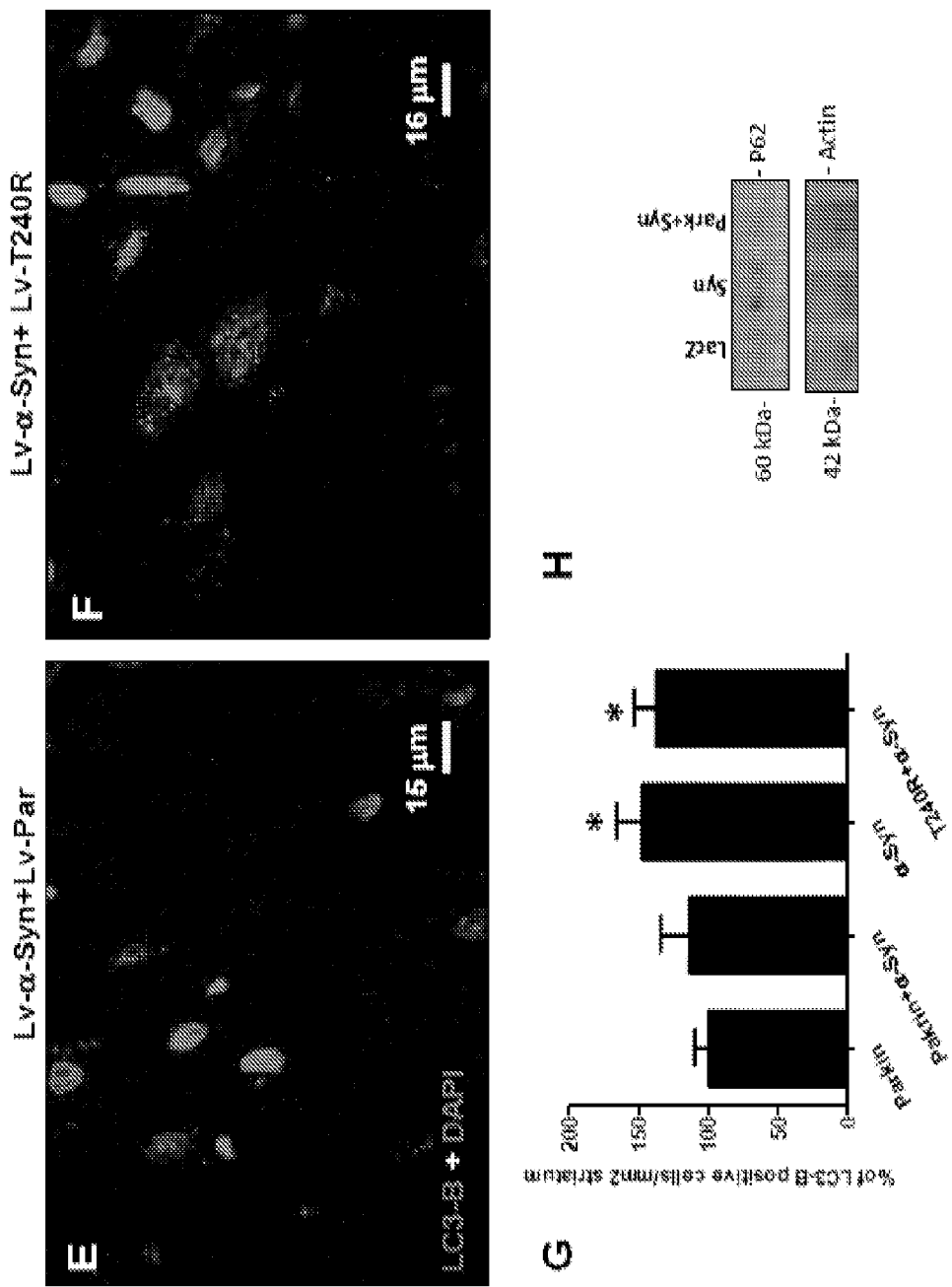

FIG. 48 shows that functional parkin, not mutant T240R reverses α-synuclein alteration of normal autophagy. A) shows a WB analysis on 4-12% SDS NuPAGE gel of rat striatal lysates showing expression of beclin (first panel), Atg7 (second panel) and Atg12 (third panel) compared to actin loading control (bottom panel) in animals injected with Lv-LacZ, Lv-Par, Lv-Syn and Lv-Par+Lv-Syn. B) shows a WB analysis of rat striatal brain lysates showing expression of LC3-B (first panel), and HDAC6 (second panel) compared to actin loading control (bottom panel) in animals injected with Lv-LacZ, Lv-Par, Lv-Syn and Lv-Par+Lv-Syn. Staining of 20 µm thick cortical brain sections injected with C) Lentiviral parkin (Lv-Par), D) Lentiviral α-synuclein (Lv-Syn) E) Lentiviral parkin+lentiviral α-synuclein (Lv-Par+Lv-Syn) and F) Lentiviral T240R+lentiviral α-synuclein (Lv-T240R+Lv-Syn) is shown. G) shows histograms representing stereological counting of LC3-B positive cells in the striatum. H) is a Western blot analysis on 4-12% SDS NuPAGE gel with P62 antibody. Asterisks indicate a significant difference. Histograms are mean±SD converted to % control. ANOVA, Neumann Keuls with multiple comparison, P<0.05. N=8 animals per treatment for WB and ELISA, 8 for IHC.

Figure 49:
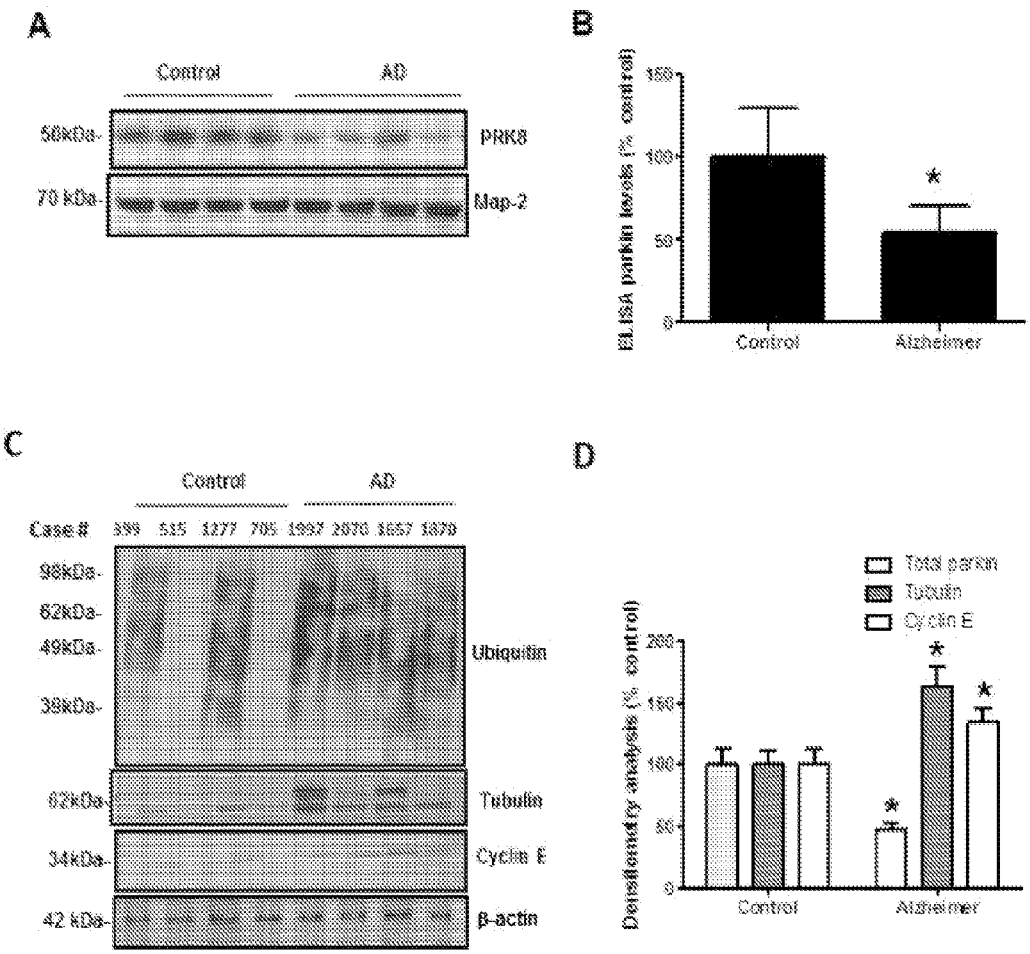
Figure 49:
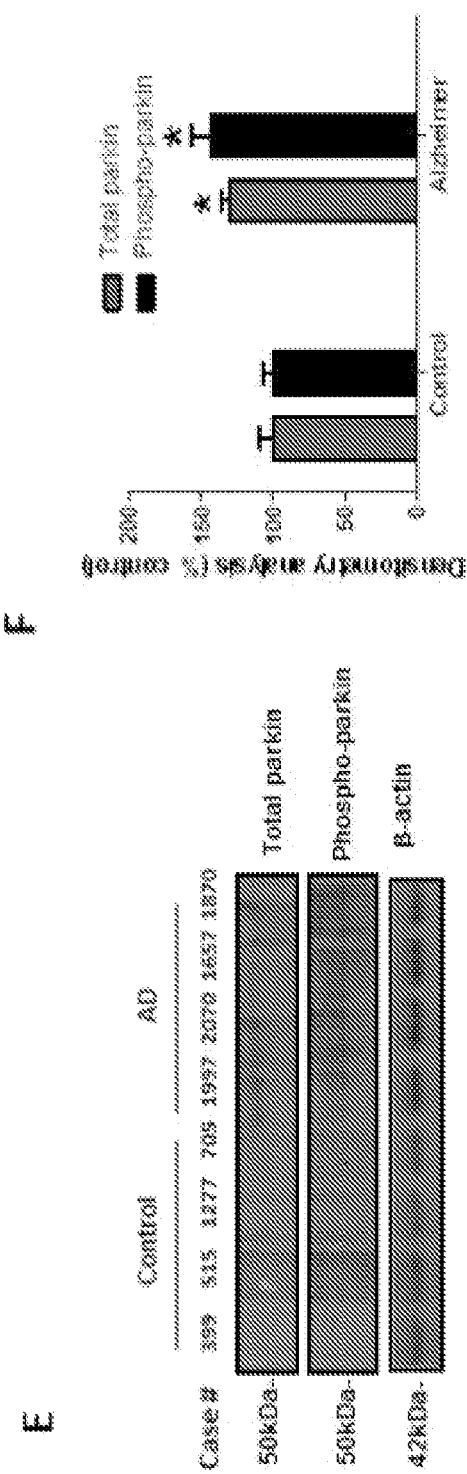

FIG. 49 shows that parkin is increased in AD brains. A) shows a WB analysis on 4-12% SDS-NuPAGE gel of human post-mortem cortical lysates in AD. B) shows histograms representing human parkin levels measured by ELISA. C) is a WB analysis on 4-12% SDS-NuPAGE gel showing expression level of parkin's possible targets for degradation, including ubiquitinated proteins (top blot), tubulin (2nd blot) and Cyclin E (3rd blot) and actin (4th blot). D) shows histograms representing blot quantification by densitometry. E) is a WB analysis on 4-12% SDS-NuPAGE gel showing insoluble proteins extracted in 4M urea, including total parkin (top blot) and phosphorylated parkin at Serine 378 (2nd blot) and actin (3rd blot). F) shows Histograms representing blot quantification by densitometry. Asterisks indicate a significant difference. Histograms are mean±SD expressed as % control. All bands were quantified relative to actin levels. ANOVA, Neumann Keuls with multiple comparison, P<0.05.

Figure 50:
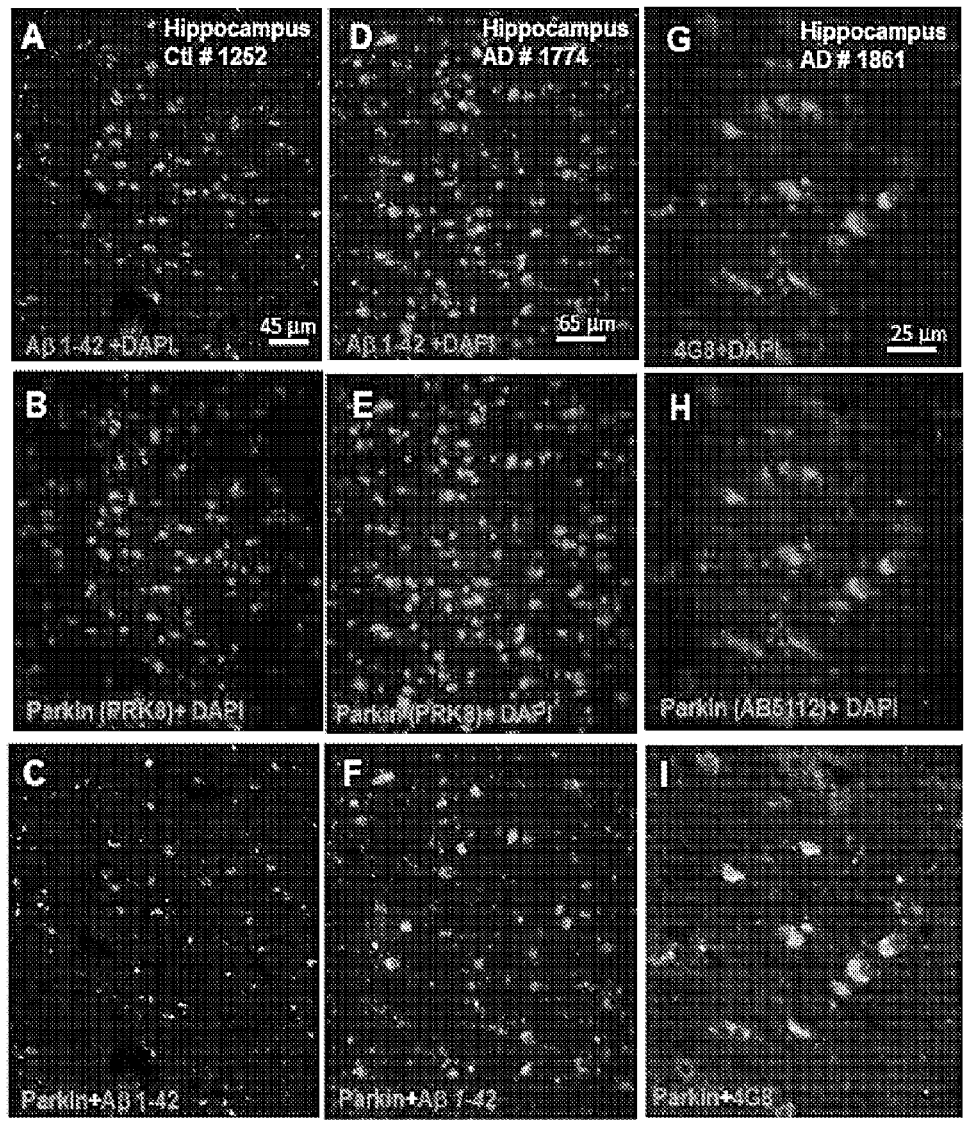

FIG. 50 shows increased intraneuronal $A\beta_{1-42}$ and parkin co-localization in the hippocampus of AD brains. IHC of paraffin embedded 30 µm thick sections of human hippocampus from control subject (case #1252) stained with A) Human anti-$A\mu_{1-42}$ antibody+DAPI and B) Anti-parkin antibody+DAPI are shown. C) is a merged figure showing co-staining of $A\beta_{1-42}$ and parkin. IHC of sections of hippocampus from AD patient (case #1774) stained with D) Human anti-$A\beta_{1-42}$ antibody+DAPI and E) Human anti-parkin antibody+DAPI are shown. F) is a merged figure showing co-staining of $A\beta_{1-42}$ and parkin. IHC of sections of hippocampus from AD patient (case #1861) stained with G) 4G8 anti-$A\beta_{1-42}$ antibody+DAPI and H) human anti-parkin antibody+DAPI are shown. and I) is a merged figure showing co-staining of (4G8) $A\beta_{1-42}$ and parkin.

Figure 51:
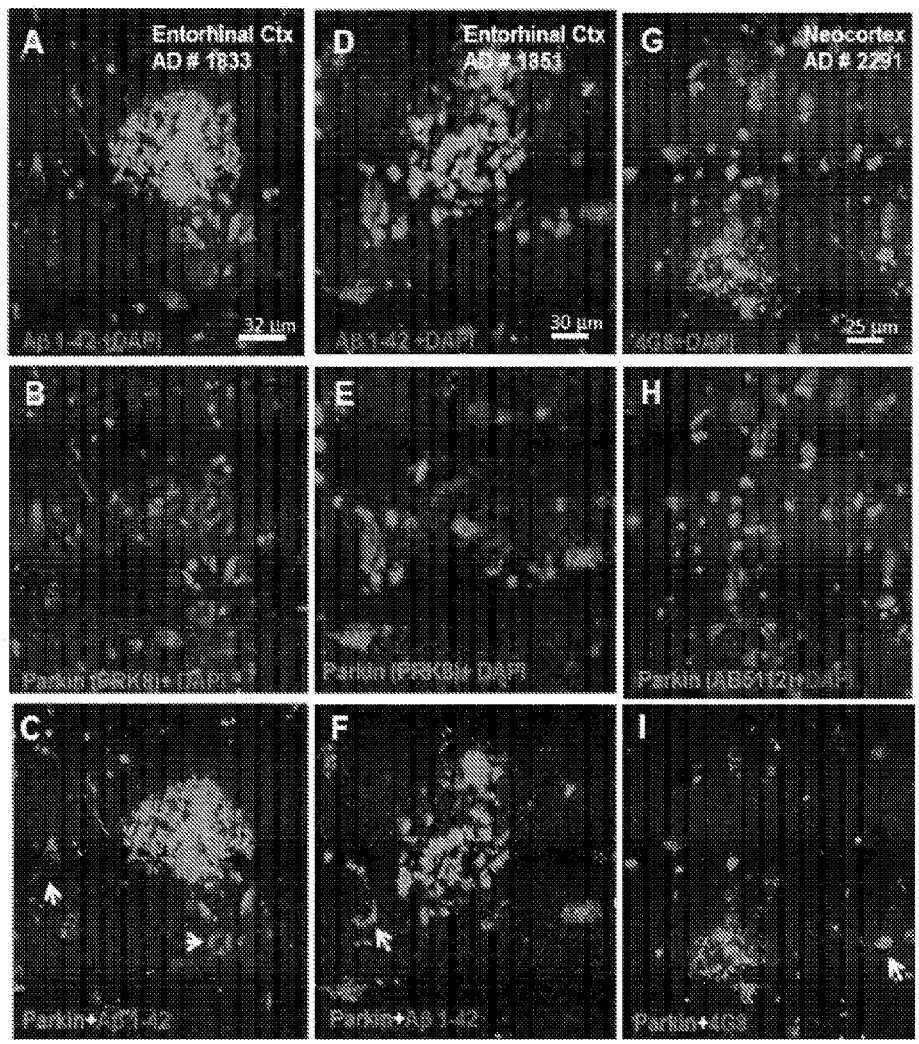

FIG. 51 shows that parkin co-localizes with intraneuronal $A\beta_{1-42}$ in the cortex of AD brains. IHC of paraffin embedded 30 µm thick sections of human entorhinal cortex from AD patient (case #1833) stained with A) human anti-$A\beta_{1-42}$ antibody+DAPI and B) anti-parkin antibody+DAPI are shown. C) is a merged figure showing co-staining of $A\beta_{1-42}$ and parkin. IHC of sections of human neocortex from AD patient (case #1851) stained with D) human anti-$A\beta_{1-42}$ antibody+DAPI and E) anti-parkin antibody+DAPI are shown. F) is a merged figure showing co-staining of $A\beta_{1-42}$ and parkin. IHC of sections of necortex from AD patient (case #1861) stained with G) 4G8 anti-$A\beta_{1-42}$ antibody+ DAPI and H) human anti-parkin antibody+DAPI are shown. I) is a merged figure showing co-staining of (4G8) $A\beta_{1-42}$ and parkin.

Figure 52:
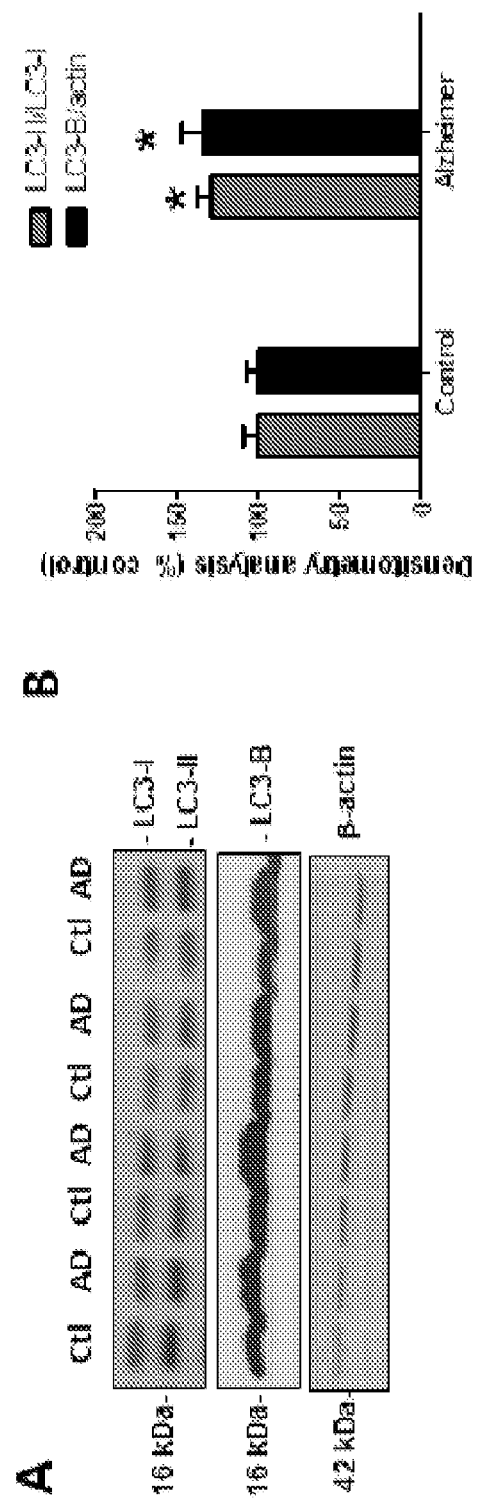
Figure 52:
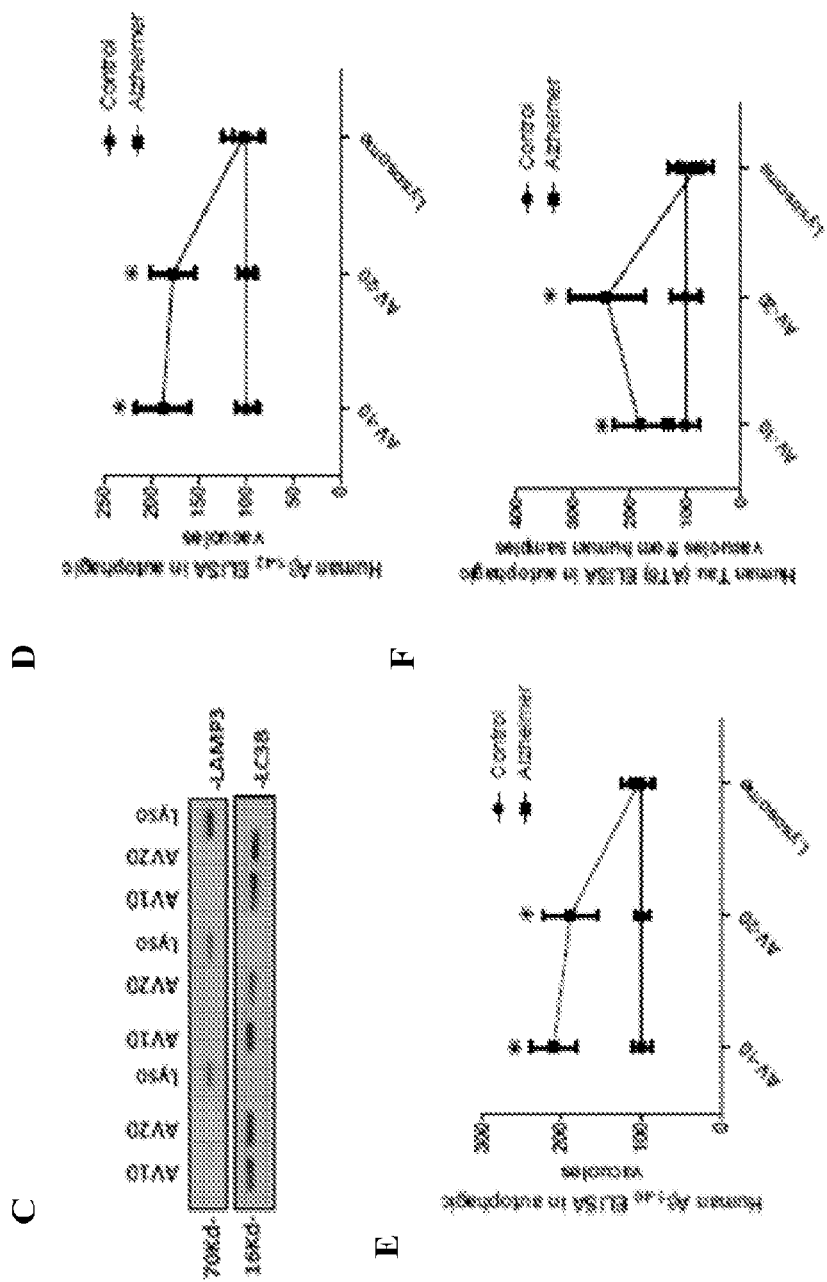
Figure 52:
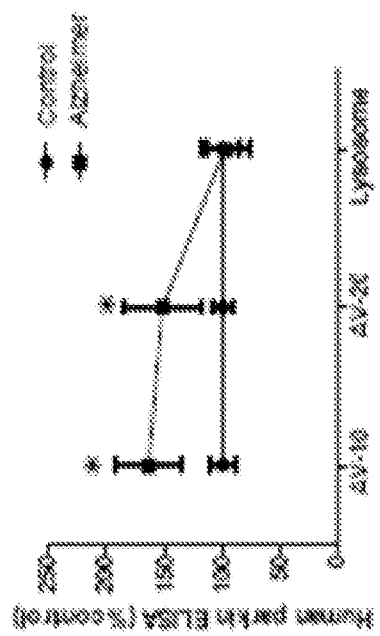

FIG. 52 shows that parkin, $A\beta_{1-42}$ and p-Tau accumulate in autophagic vacuoles of AD brains. A) is a WB analysis on 4-12% SDS-NuPAGE gel of human post-mortem cortical lysates in AD probed with anti-LC3 antibody showing LC3-I and LC3-II (1st blot) and LC3-B (2nd blot) and actin (3rd blot). B) shows histograms representing blot quantification by densitometry. C) is a WB analysis of Metrazimide-isolated fractions from frozen brain tissue showing lysosomal marker LAMP-3 in the floating fraction and detection of LC3-B in AV-10 and AV-20. Graphs represent ELISA measurement in autophagic vacuoles of human D) $A\beta_{1-42}$, E) $A\beta_{1-40}$, F) p-Tau (AT8) and G) parkin. Asterisks indicate a significant difference. Histograms are mean±SD expressed as control. All bands were quantified relative to actin levels. ANOVA, Neumann Keuls with multiple comparison, P<0.05.

Figure 53:
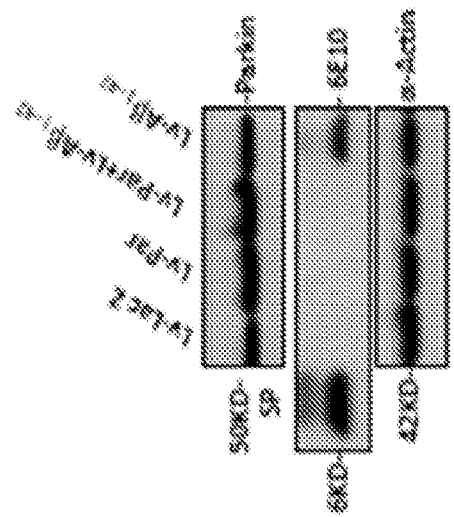
Figure 53:
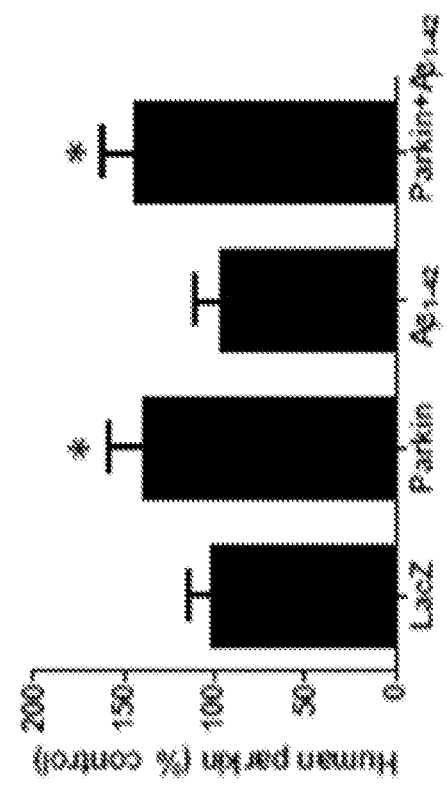
Figure 53:
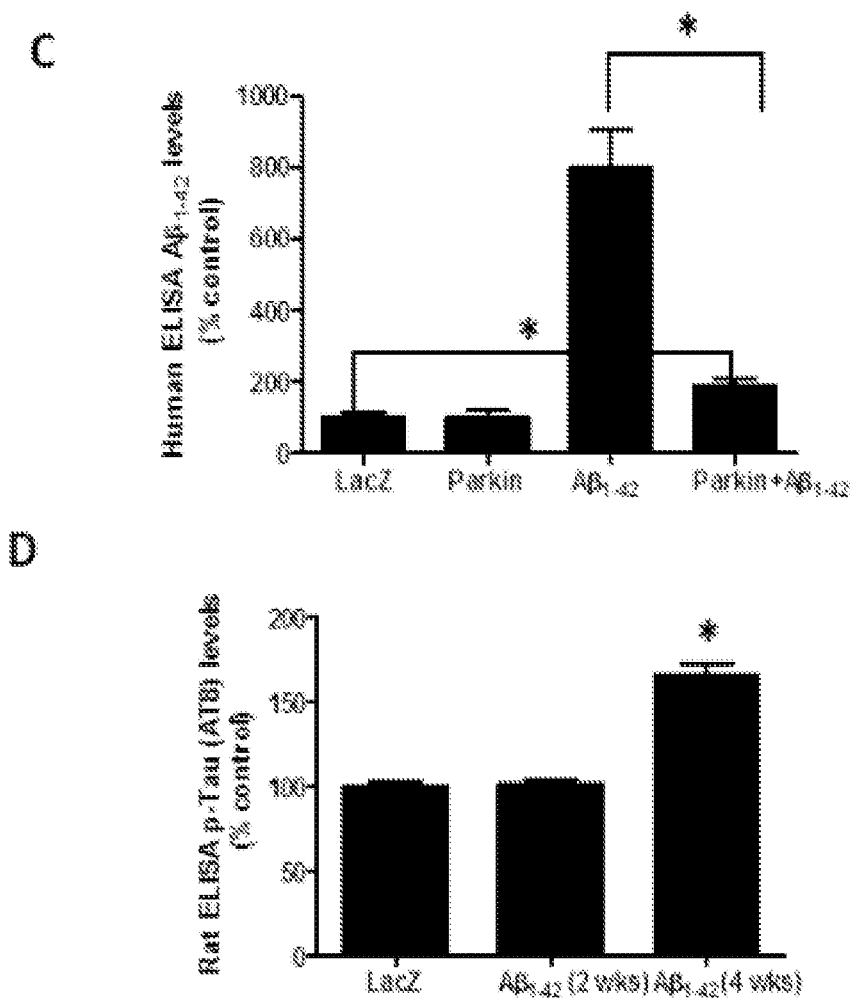
Figure 53:
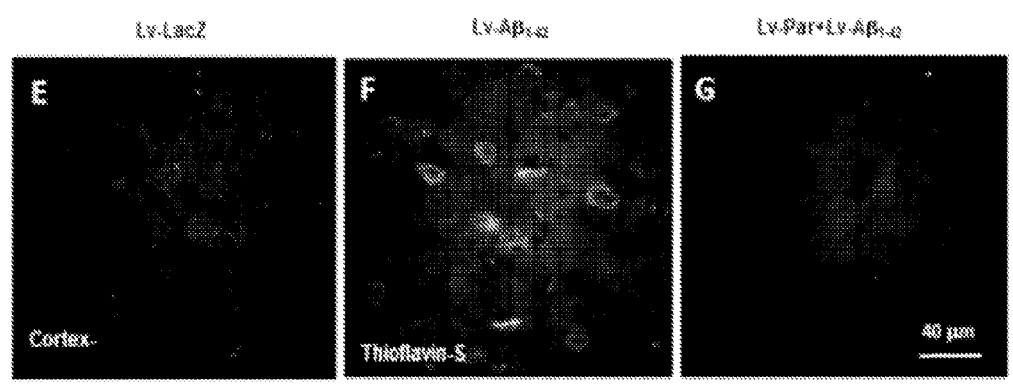

FIG. 53 shows that parkin decreases the level of lentiviral $A\beta_{1-42}$ and p-Tau in gene transfer animal models. A) is a WB analysis on 4-12% SDS NuPAGE gel showing the expression levels of parkin and $A\beta_{1-42}$, analyzed with a synthetic peptide as a molecular weight and antibody control. B) shows histograms represent quantification of human parkin by ELISA. C) shows a human $A\beta_{1-42}$ ELISA 2 weeks after lentiviral injection. D) shows ELISA measurement of rat p-Tau 2 and 4 weeks post-injection. Thioflavin-S staining of 20 µm cortical sections in lentiviral E) LacZ, F) $A\beta_{1-42}$ and G). parkin+$A\beta_{1-42}$ injected brains is also shown. Asterisks indicate a significant difference. Histograms are mean±SD expressed as % to control. All bands were quantified relative to actin levels. ANOVA, Neumann Keuls with multiple comparison, P<0.05. N=8 animals per treatment for WB and ELISA, 8 for IHC.

Figure 54:
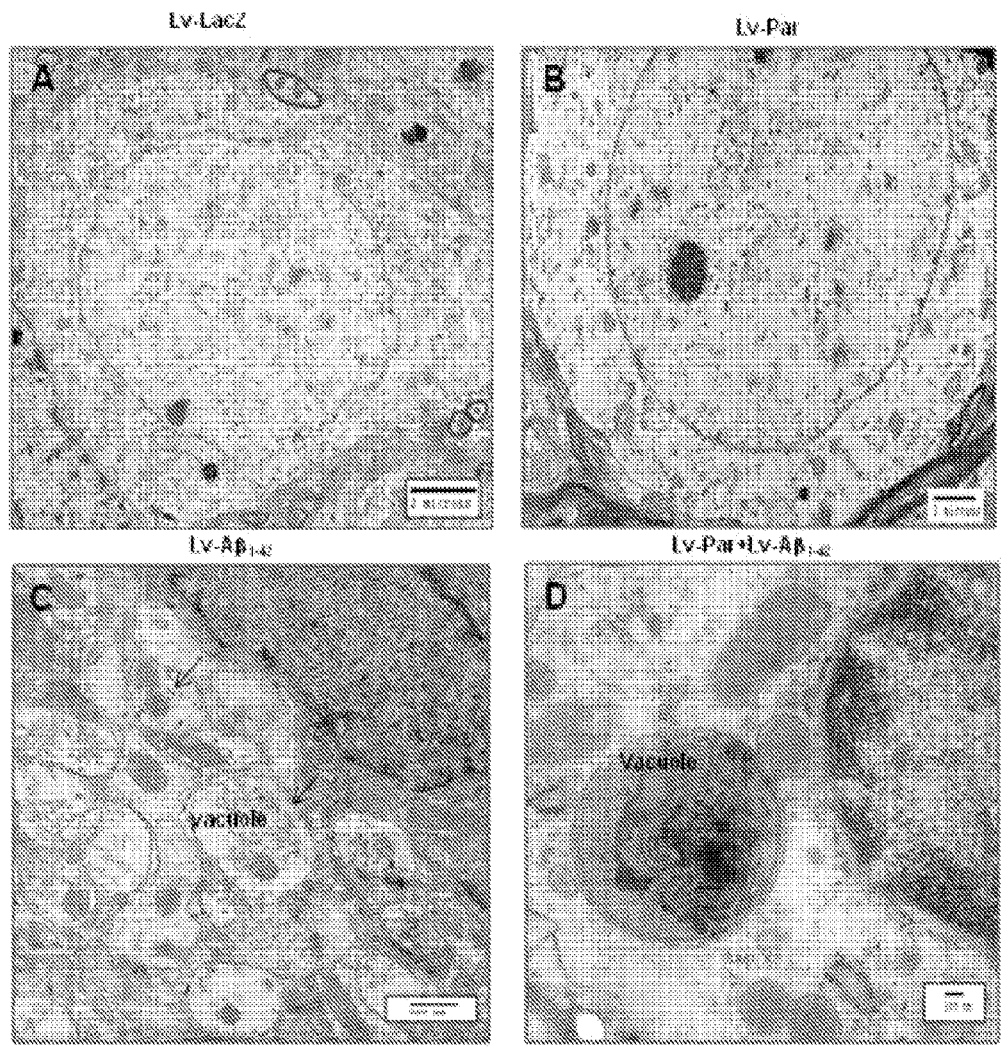
Figure 54:
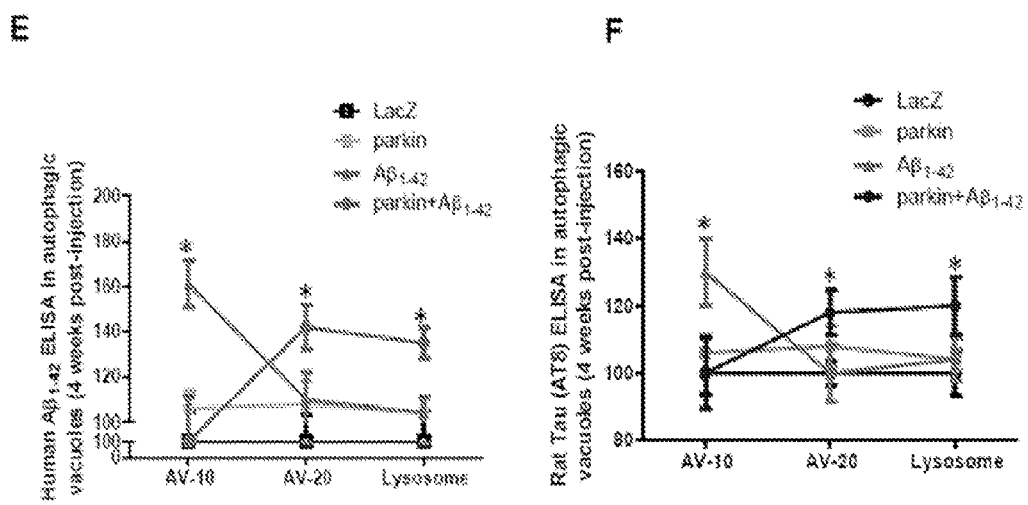

FIG. 54 shows that parkin clears $A\beta_{1-42}$-induced accumulation of autophagic vacuoles. Electron micrographs of cortical sections in rat brains injected with A) Lentiviral LacZ (Lv-LacZ) as control, B) lentiviral parkin (Lv-Par), C) lentiviral $AA\beta_{1-42}$ (Lv-A $A\beta_{1-42}$) (arrows indicate vacuoles) and D) lentiviral parkin+lentiviral A $A\beta_{1-42}$ (Lv-A $A\beta_{1-42}$+Lv-Par) (vacuole contains debris) are shown. N=8. Graphs represent subcellular fractionation (Blot) and ELISA measurement of E) $A\beta_{1-42}$ and F) p-Tau in gene transfer animal models. All bands were quantified relative to actin levels. ANOVA, Neumann Keuls with multiple comparison, P<0.05. N=5 animals per treatment for subcellular fractionation.

Figure 55:
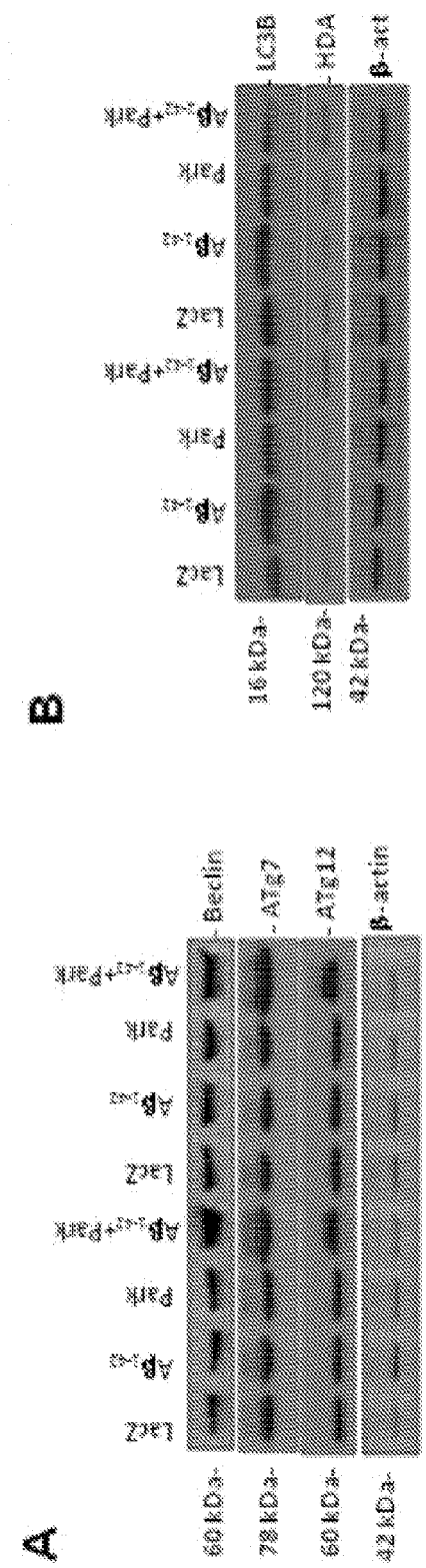
Figure 55:
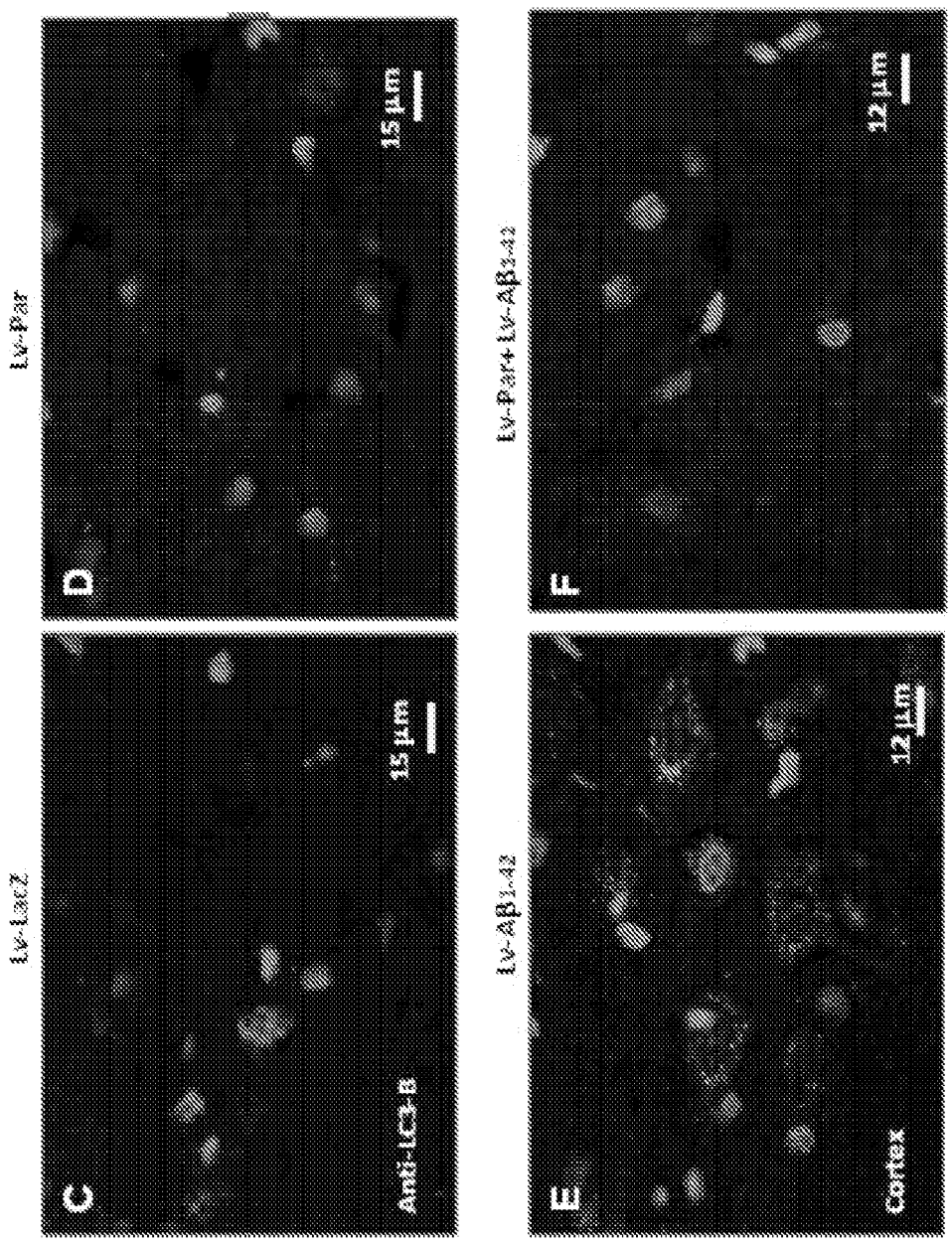
Figure 55:
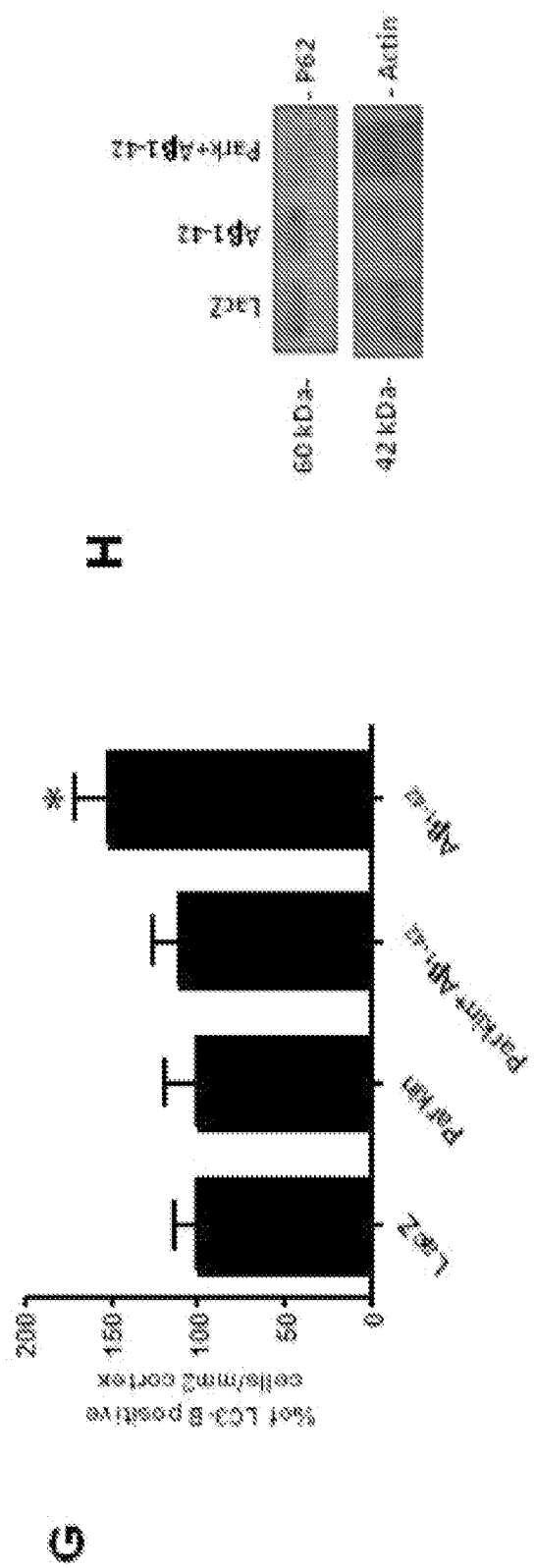

FIG. 55 shows that intracellular $A\beta_{1-42}$ impairs normal autophagy and parkin facilitates autophagic clearance. A) is lysis on 4-12% SDS NuPAGE gel of rat cortical lysates showing expression of beclin (first panel), Atg7 (second panel) and Atg12 (third panel) and actin loading control (bottom panel) in animals injected with Lv-LacZ, Lv-Par, Lv-$A\beta_{1-42}$ and Lv-Par+Lv-$A\beta_{1-42}$. B) is a WB analysis of rat cortical brain lysates showing expression of LC3-B (first panel), and HDAC6 (second panel) and actin loading control (bottom panel) in animals injected with Lv-LacZ, Lv-Par, Lv-$A\beta_{1-42}$ and Lv-Par+Lv-$A\beta_{1-42}$. Staining of 20 µm thick cortical brain sections injected with C) lentiviral LacZ (Lv-LacZ), D) lentiviral parkin (Lv-Par) E) lentiviral $A\beta_{1-42}$ (Lv-$A\beta_{1-42}$) and F) lentiviral parkin+lentiviral $A\beta_{1-42}$ (Lv-Par+Lv-$A\beta_{1-42}$) are shown. G) shows histograms representing stereological counting of LC3-B positive cells in the cortex. H) is a WB analysis of 4-12% SDS NuPAGE gel showing P62 levels. Asterisks indicate a significant difference. Histograms are mean±SD expressed as % control. All bands were quantified relative to actin levels. ANOVA, Neumann Keuls with multiple comparison, P<0.05. N=8 animals per treatment for WB and ELISA, 8 for IHC.

Figure 56:
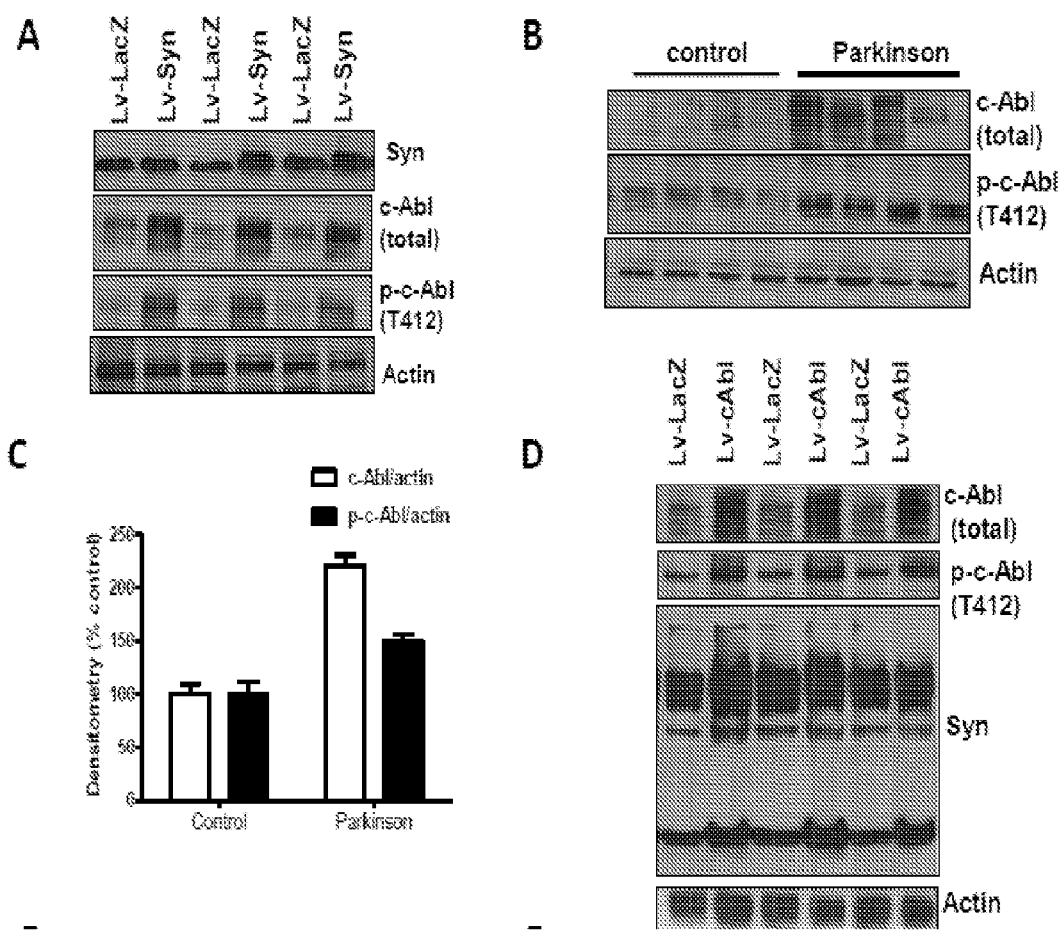
Figure 56:
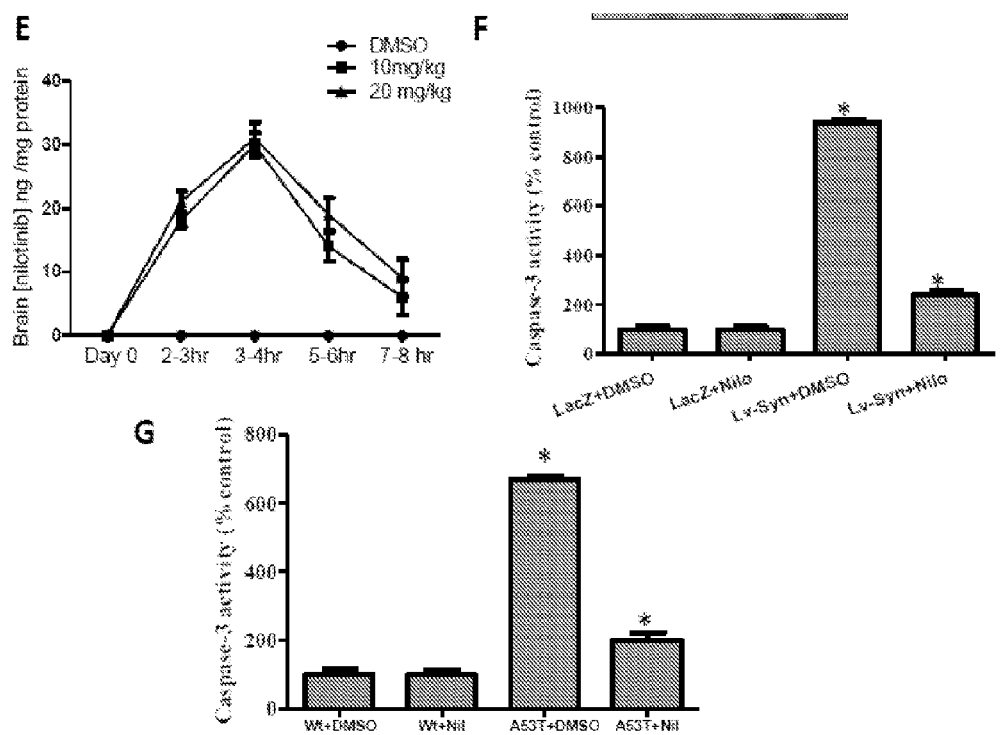

FIG. 56 shows that c-Abl activation is associated with accumulation of α-synuclein. A WB on 10% SDS-NuPAGE gel shows A) lentiviral α-synuclein expression (1st blot), total c-Abl (2nd blot) and tyrosine 412 (T412) phosphorylated c-Abl (3rd blot) and actin (N=9). B) shows total c-Abl (1st blot) T412 c-Abl (2nd blot) and actin in human post-mortem striatal extracts, N=9 PD and 7 controls, p<0.02, two-tailed t-test. C) shows densitometry of human WBs. D) is a WB on 4-12% SDS-NuPAGE gel that shows total c-Abl (1st blot) and tyrosine 412 (T412) phosphorylated c-Abl (2nd blot), and mouse α-synuclein expression (3rd blot) and actin (N=9). E) is a graph representing quantification of Mass Spec analysis of brain Nilotinib (N=5/time point). Graphs represent caspase-3 activity in F) lentiviral α-synuclein and LacZ injected mice (N=14) with and without Nilotinib, and G) 6-8 month old transgenic A53T mice (N=15) and wild type age-matched controls (N=64) with and without Nilotinib. *Significantly different, ANOVA, Neumann Keuls multiple comparison, p<0.05.

Figure 57:
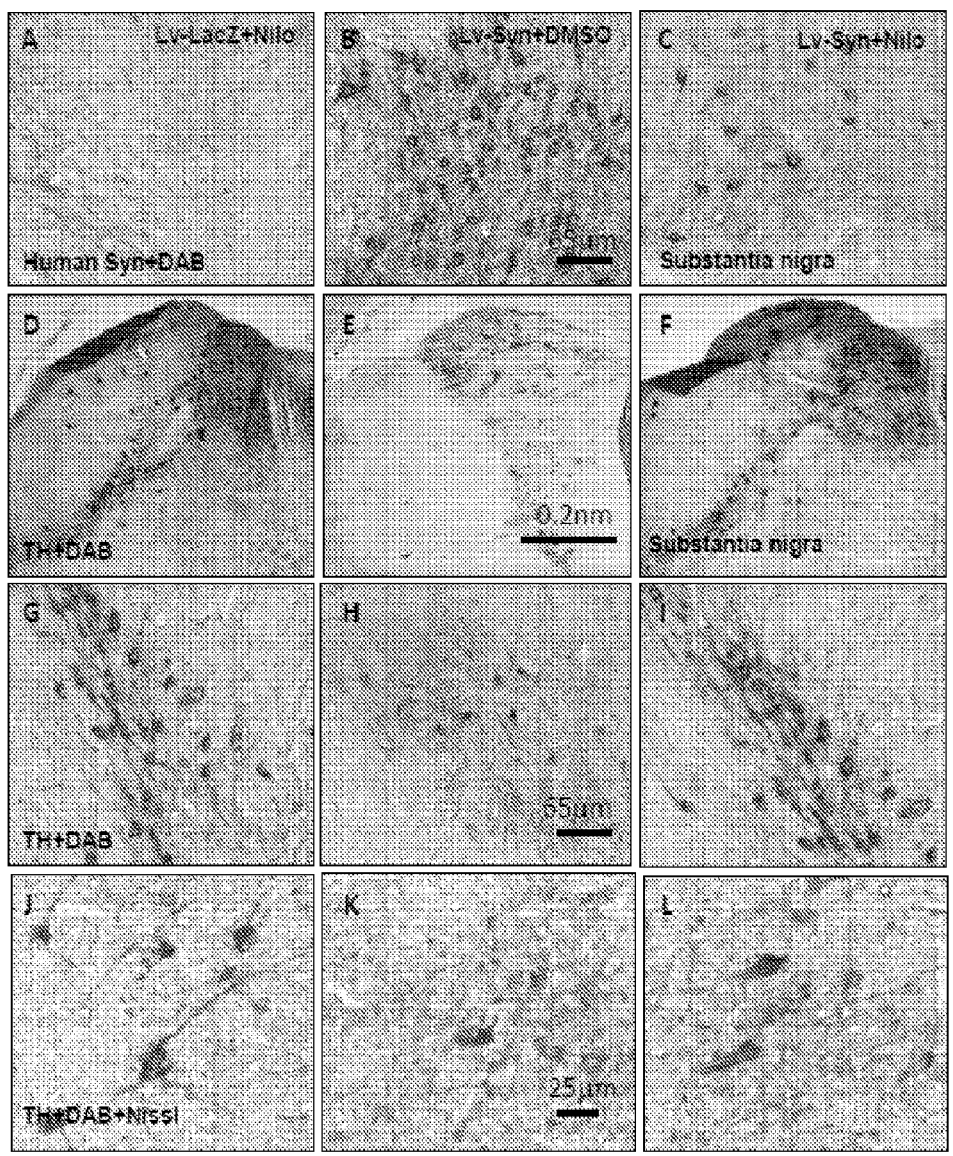

FIG. 57 shows that Nilotinib clears α-synuclein and protects SN Tyrosine hydroxylase (TH) neurons. Immunohistochemical staining of 20 µm thick brain sections show human α-synuclein in A) lentiviral injected LacZ+Nilotinib mice, B) mice injected with lentiviral α-synuclein into the SN and treated with DMSO and C) mice injected with lentiviral α-synuclein and treated with Nilotinib. Immunohistochemical staining of 20 µm thick brain sections show Tyrosine Hydroxylase in D) lentiviral injected LacZ+Nilotinib mice, G is higher magnification from a different animal and E) mice injected with lentiviral α-synuclein and treated with DMSO. H) is higher magnification from a different animal. F) shows mice injected with lentiviral α-synuclein and treated with Nilotinib. I) is higher magnification from a different animal. J) shows Nissl counter-stained cells in LacZ+Nilotinib, K). α-synuclein+DMSO and L). α-synuclein+Nilotinib.

Figure 58:
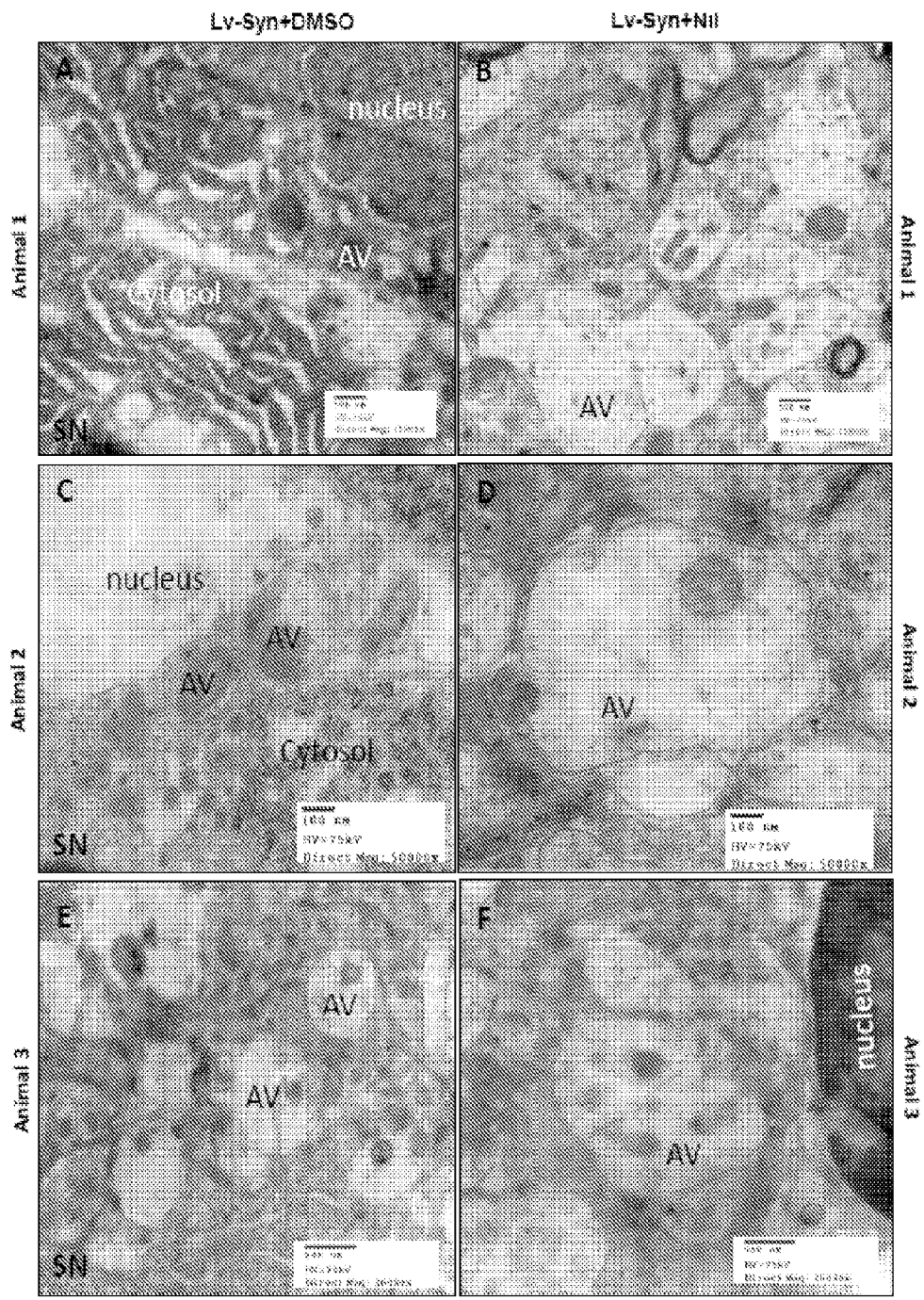

FIG. 58 shows that Nilotinib clears accumulation of autophagic vacuoles in SN of lentiviral α-synuclein mice. Transmission electron microscopy of SN neurons shows accumulation of cytosolic debris and autophagic vacuoles (AVs) in Lentiviral α-synuclein expressing mice with DMSO treatment (see FIGS. 58 A, C and E). FIGS. 58 B, D&F) show appearance of larger AVs in Nilotinib treated mice.

Figure 59:
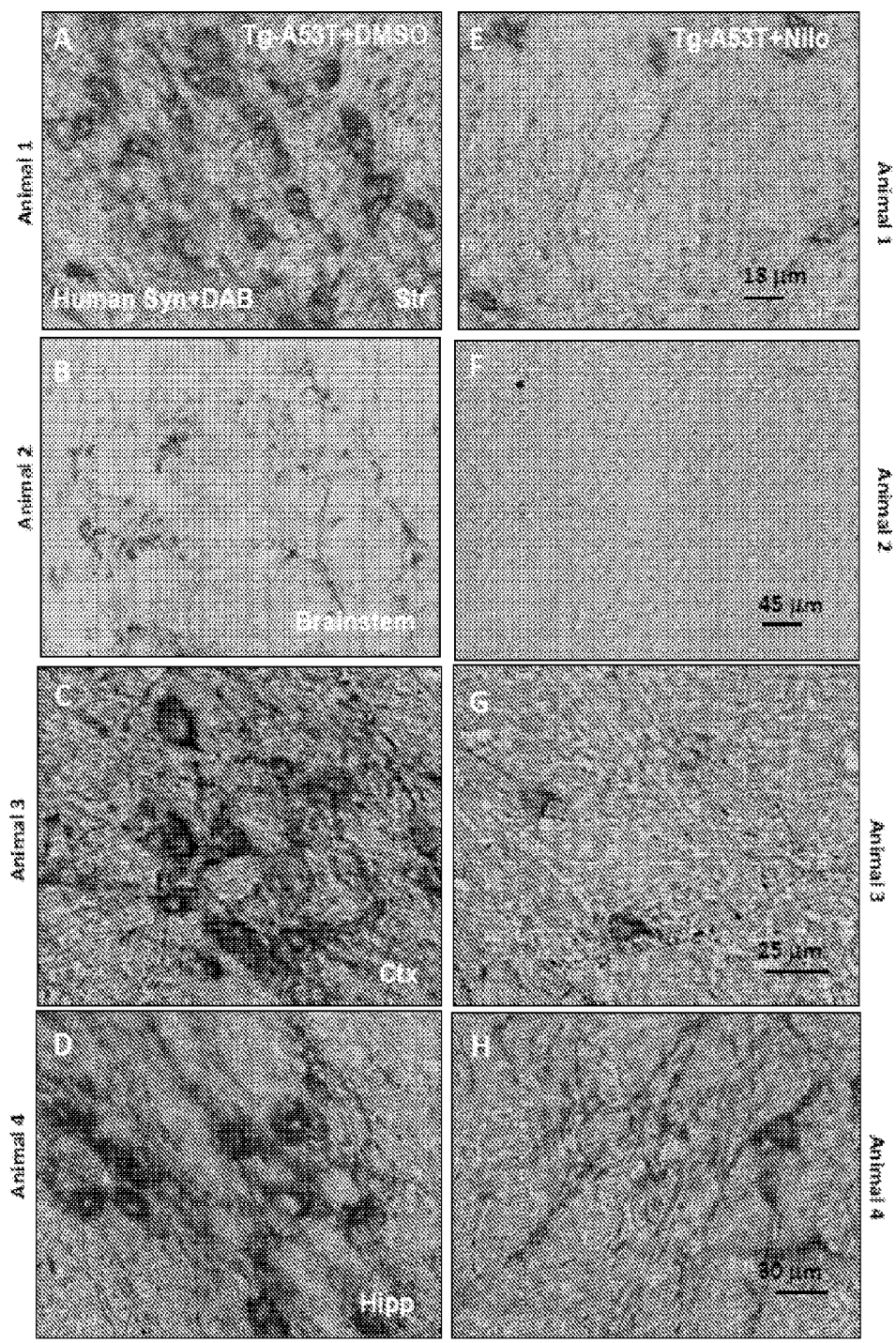

FIG. 59 shows that Nilotinib attenuates α-synuclein levels in A53T mice. Immunohistochemical staining of 20 µm thick brain sections shows abundant expression of human α-synuclein in 6-8 month old transgenic A53T mice treated with DMSO in the A) striatum, B) brainstem C) cortex and D) hippocampus of different animals. Daily IP injection of Nilotinib for 3 weeks shows decrease of human α-synuclein in the E) striatum, F) brainstem G) cortex and H) hippocampus.

Figure 60:
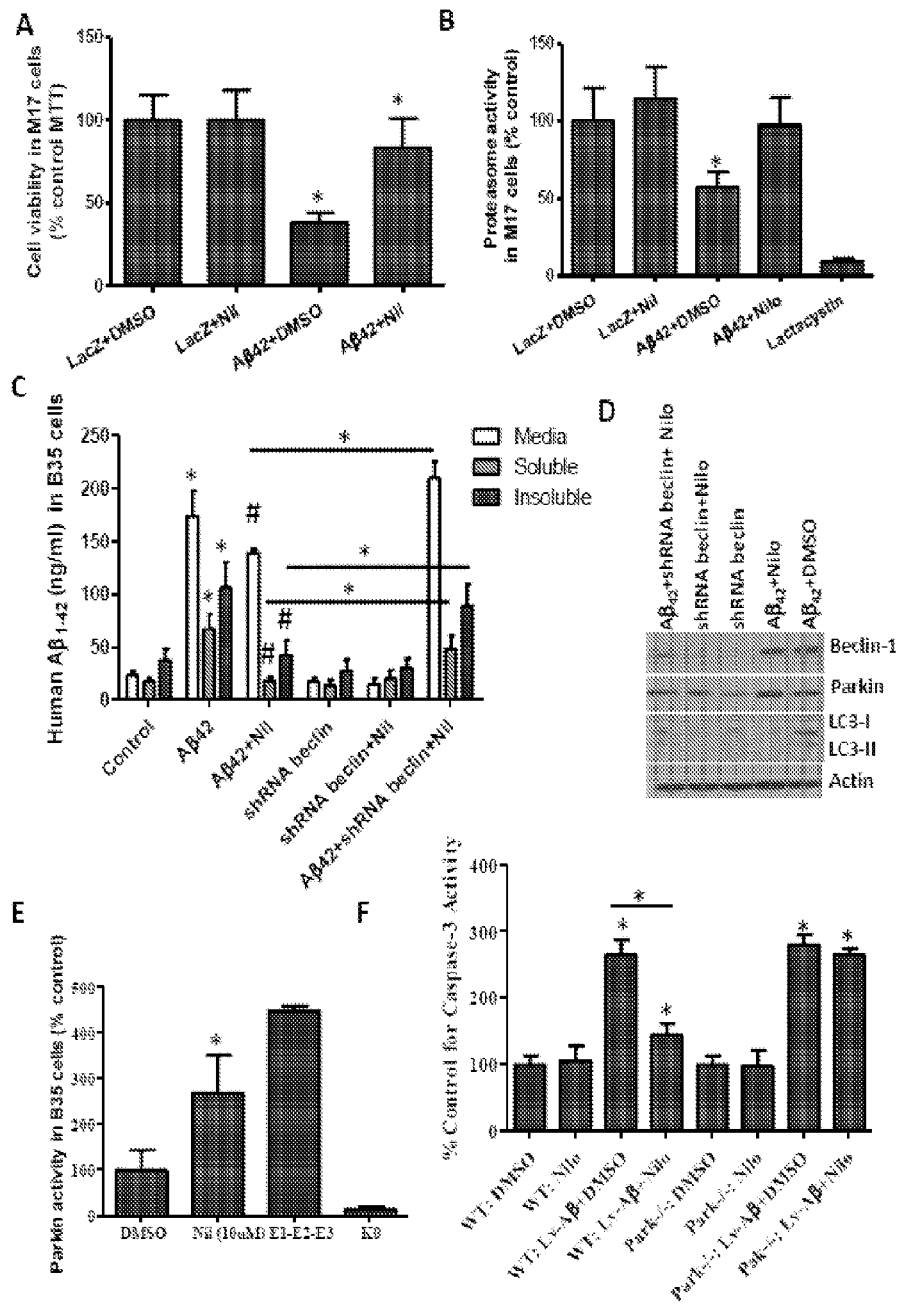

FIG. 60 shows that Nilotinib activates parkin and induces autophagic clearance. A) is a graph representing MTT-based cell viability in human M17 neuroblastoma cells (N=12) transfected with $A\beta_{1-42}$ (or LacZ) cDNA for 24 hr, and then treated with 10 µM Nilotinib for an additional 24 hr. B) is a graph representing proteasome activity via Chymotrypsin-like assays using 20 µM 20S proteasome inhibitor lactacystin as a specificity control in human neuroblastoma cells (N=12) with and without Nilotinib. C) is a Human $A\beta_{1-42}$ ELISA before and after Nilotinib treatment in B35 rat neuroblastoma cells (N=12) in media, soluble (STEN buffer) and insoluble (30% formic acid) lysates in the presence and absence of shRNA beclin-1. D) is a WB of soluble cell lysates (from C) showing beclin-1, parkin and LC3 levels with and without Nilotinib (N=12). E) is a graph represents parkin E3 ubiquitin ligase function in B35 neuroblastoma cells treated with DMSO or Nilotinib for 24 hr. Recombinant E1-E2-E3 (positive) or K0 (negative) were used as specificity controls. F) is a graph representing caspase-3 activity in 1 year old C57BL/6 (N=64) (wild type) or parkin−/− mice (N=16-19) injected with lentiviral $A\beta_{1-42}$ and treated (IP) with 10 mg/kg for 3 weeks. * Significantly different, ANOVA with Neumann Keuls multiple comparison, p<0.05.

Figure 61:
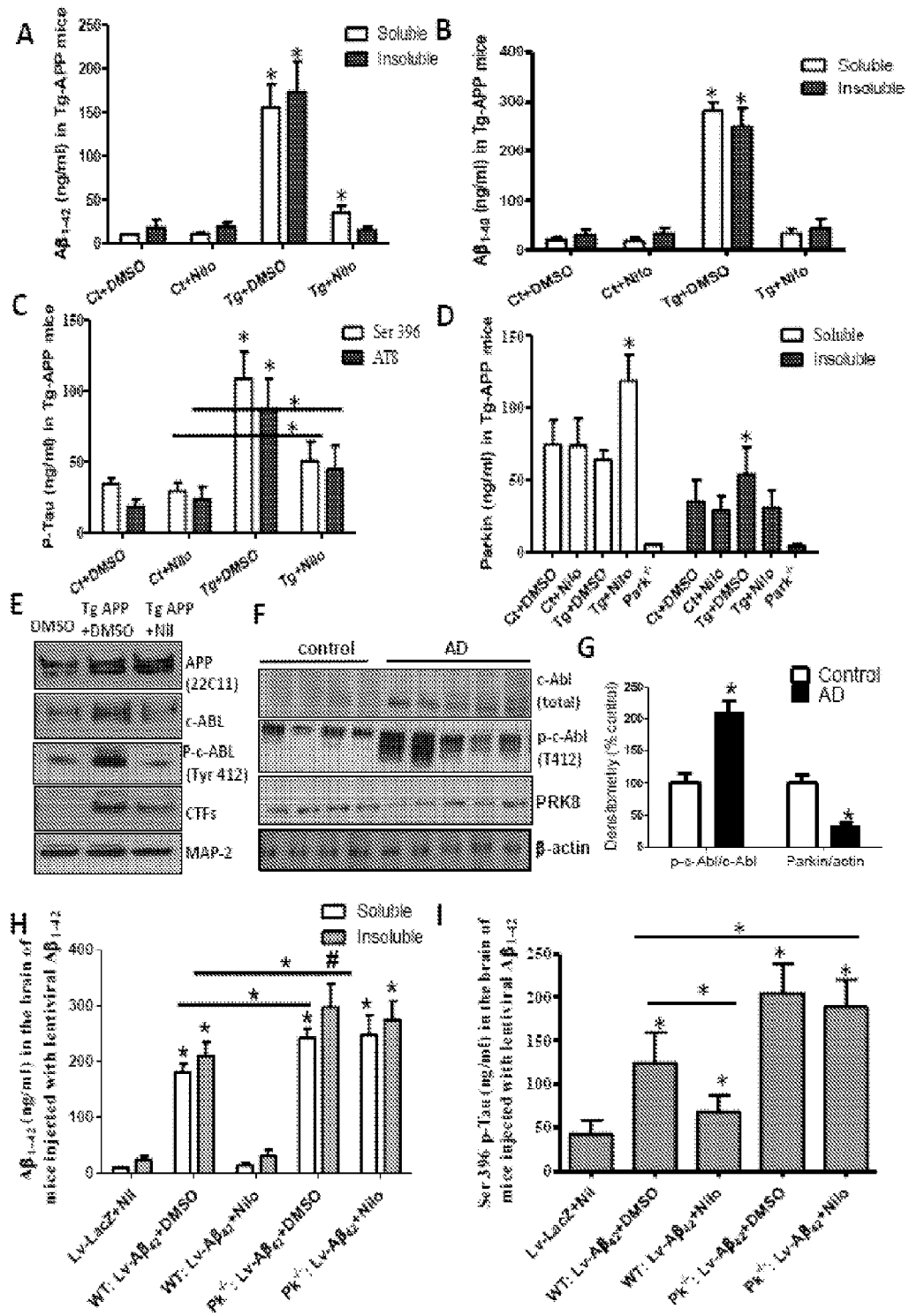

FIG. 61 shows that Nilotinib clearance of brain amyloid is associated with parkin activation. A graph represents ELISA levels of A) soluble and insoluble human $A\beta_{1-42}$ and B) ELISA levels of soluble and insoluble human Aβ1-40 in the brain of 8-12 months old Tg-APP mice (N=9) injected (IP) with 10 mg/kg once a day for 3 weeks. C) is a graph that represents ELISA levels of mouse p-Tau in the brain of 8-12 months old Tg-APP mice (N=9). D) is a graph tat represents ELISA levels of soluble and insoluble mouse parkin in the brain of 8-12 months old Tg-APP mice (N=9) injected (IP) with 10 mg/kg (daily for 3 weeks) and parkin−/− brain extracts as specificity control. E) is a WB analysis on 4-12% SDS Nu-PAGE gels of brain extracts from Tg-APP treated with Nilotinib or DMSO showing APP, c-Abl, p-c-AB1 and CTFs and MAP-2 as control (N=11). F) is a WB of post-mortem cortical extracts of AD patients (N=12 AD and 7 control) on 10% SDS Nu-PAGE and G) is a graph that represents densitometry and ratio of c-Abl and p-c-Abl and parkin. * Significantly different, non-parametric t-test, P<0.05. Also shown is a graph representing ELISA levels of H) soluble and insoluble human Aβ$_{1-42}$, and I) ELISA levels of mouse p-Tau in the brain of mice (N=9) injected (IP) with 10 mg/kg (3 weeks). * Significantly different, ANOVA with Neumann Keuls multiple comparison, p<0.05.

Figure 62:
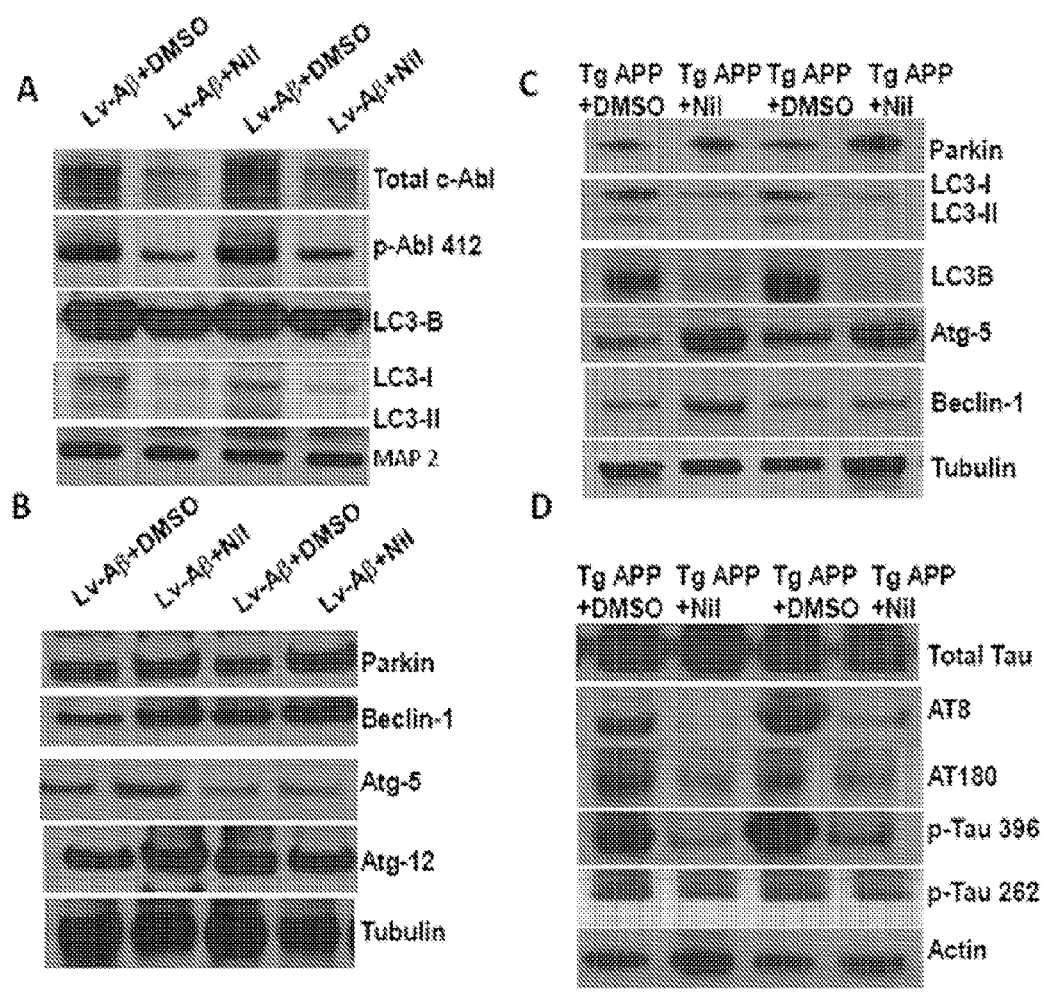
Figure 62:
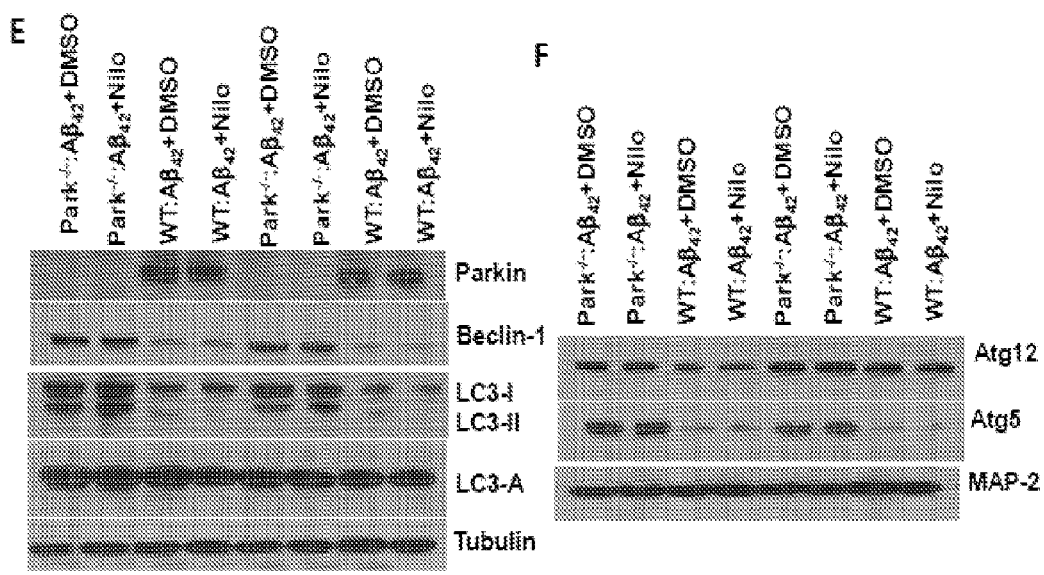

FIG. 62 shows that Nilotinib promotes autophagic clearance of amyloid. WB of brain extracts on 4-12% Nu-Page SDS gels are shown for A) in lentiviral Aβ$_{1-42}$ in wild type mice±Nilotinib showing, c-Abl, p-c-Abl, LC3-B and LC3 relative to MAP-2 and B) parkin, beclin-1, Atg-5 and 12 relative to tubulin (N=9). Western blot analysis of brain extracts on 10% Nu-Page SDS gels for C) Tg-APP±Nilotinib showing, parkin, LC3B, LC3, Atg-5 and beclin-1 relative to tubulin and D) total Tau, AT8, AT180, Ser 396 and Ser 262 relative to actin (N=12) are also provided. E) is a Western blot analysis of brain extracts on 4-12% Nu-Page SDS gels in lentiviral Aβ$_{1-42}$ in parkin−/− mice±Nilotinib showing, parkin, beclin-1, LC3 and LC3A relative to tubulin and F) is a Western blot analysis of Atg-5 and Atg12 relative to MAP-2 (N=7).).* Significantly different, ANOVA with Neumann Keuls multiple comparison, p<0.05.

Figure 63:
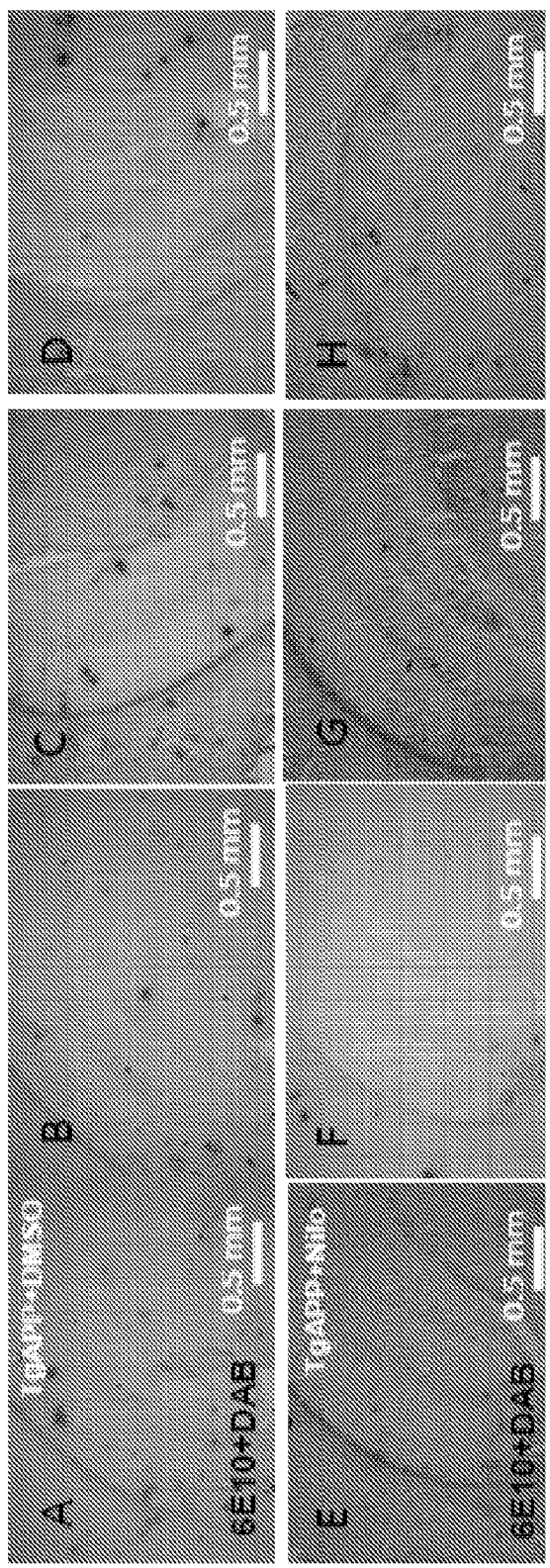
Figure 63:
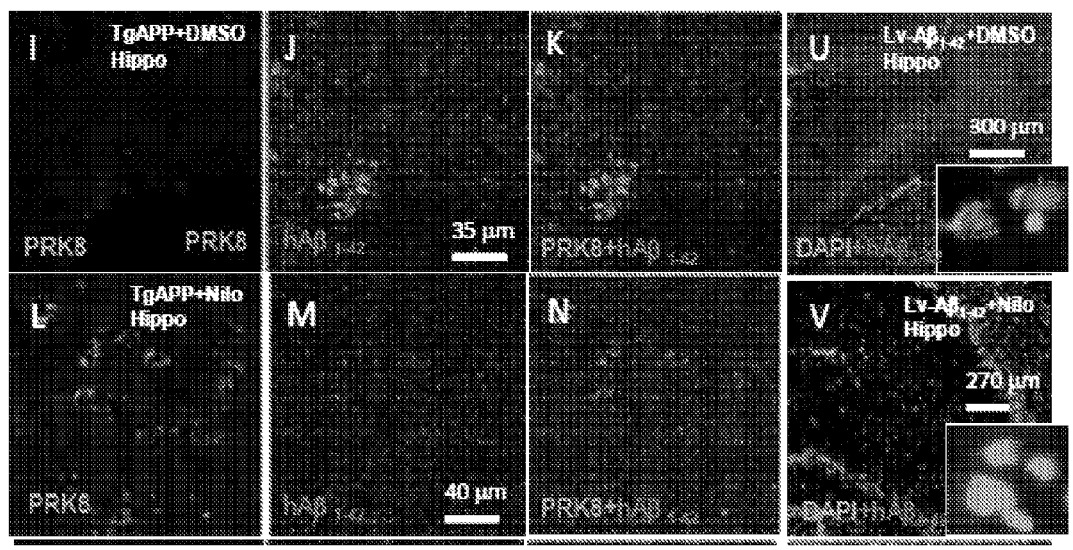
Figure 63:
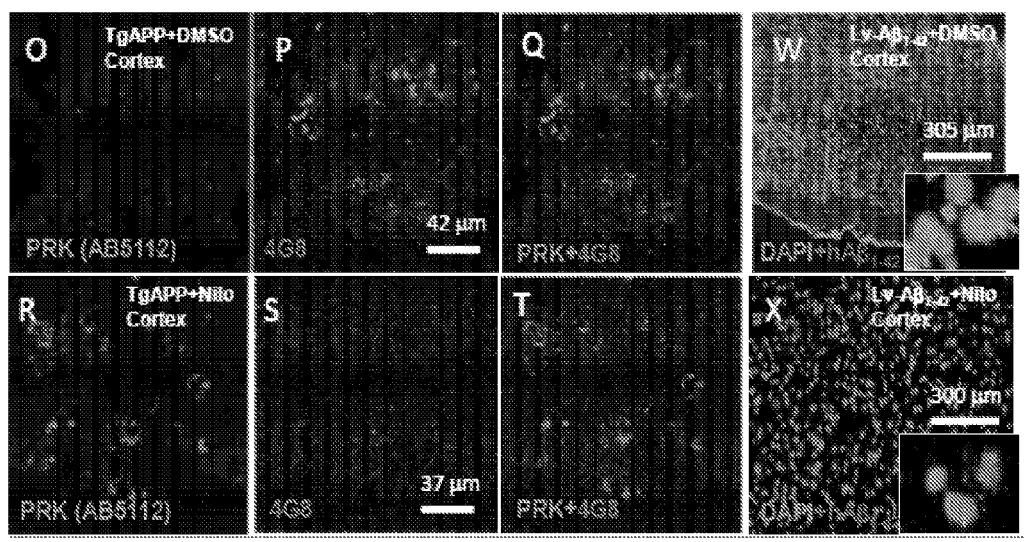

FIG. 63 shows that Nilotinib increases parkin level and decreases plaque load. Staining of 20 μm brain sections shows plaque formation within various brain regions in A-D) Tg-APP+DMSO and E-H) Nilotinib group after a 3-week treatment. Staining of 20 μm thick brain sections shows I) parkin and J) Aβ$_{1-42}$. K) is a merged figure in hippocampus of Tg-APP mice after 3 weeks of DMSO treatment. L) shows parkin, M) shows Aβ$_{1-42}$ and N) is a merged figure in hippocampus of Tg-APP mice after 3 weeks of Nilotinib treatment. O) shows parkin, P) shows Aβ$_{1-42}$ and Q) is amerged figure in the cortex of Tg-APP mice after 3 weeks of DMSO treatment. R) shows parkin, S) shows Aβ$_{1-42}$ and T) is amerged figure in cortex of Tg-APP mice after 3 weeks of Nilotinib treatment. Staining of 20 μm brain sections shows intracellular Aβ$_{1-42}$ within the U). hippocampus of lentiviral Aβ$_{1-42}$ injected mice, inset higher magnification, and V) Nilotinib clearance of intracellular Aβ$_{1-42}$ (inset is higher magnification). Staining of 20 μm brain sections shows intracellular Aβ$_{1-42}$ within the W) cortex of lentiviral Aβ$_{1-42}$ injected mice, inset higher magnification, and X) Nilotinib clearance of intracellular Aβ$_{1-42}$ (inset is higher magnification).

Figure 64:
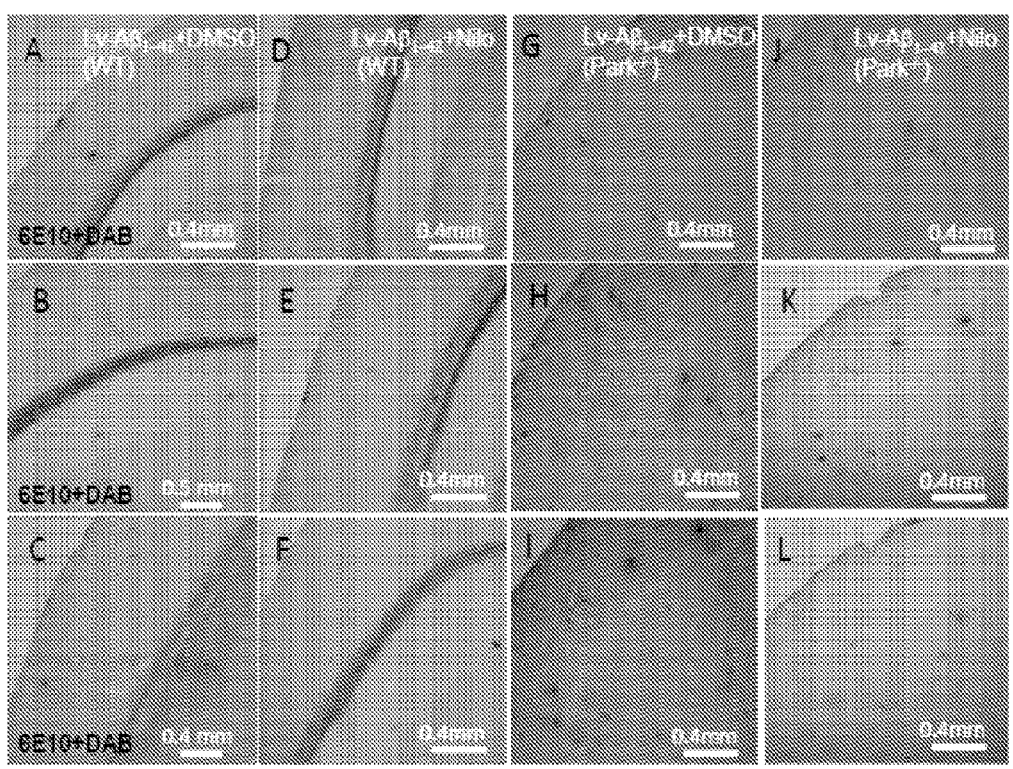
Figure 64:
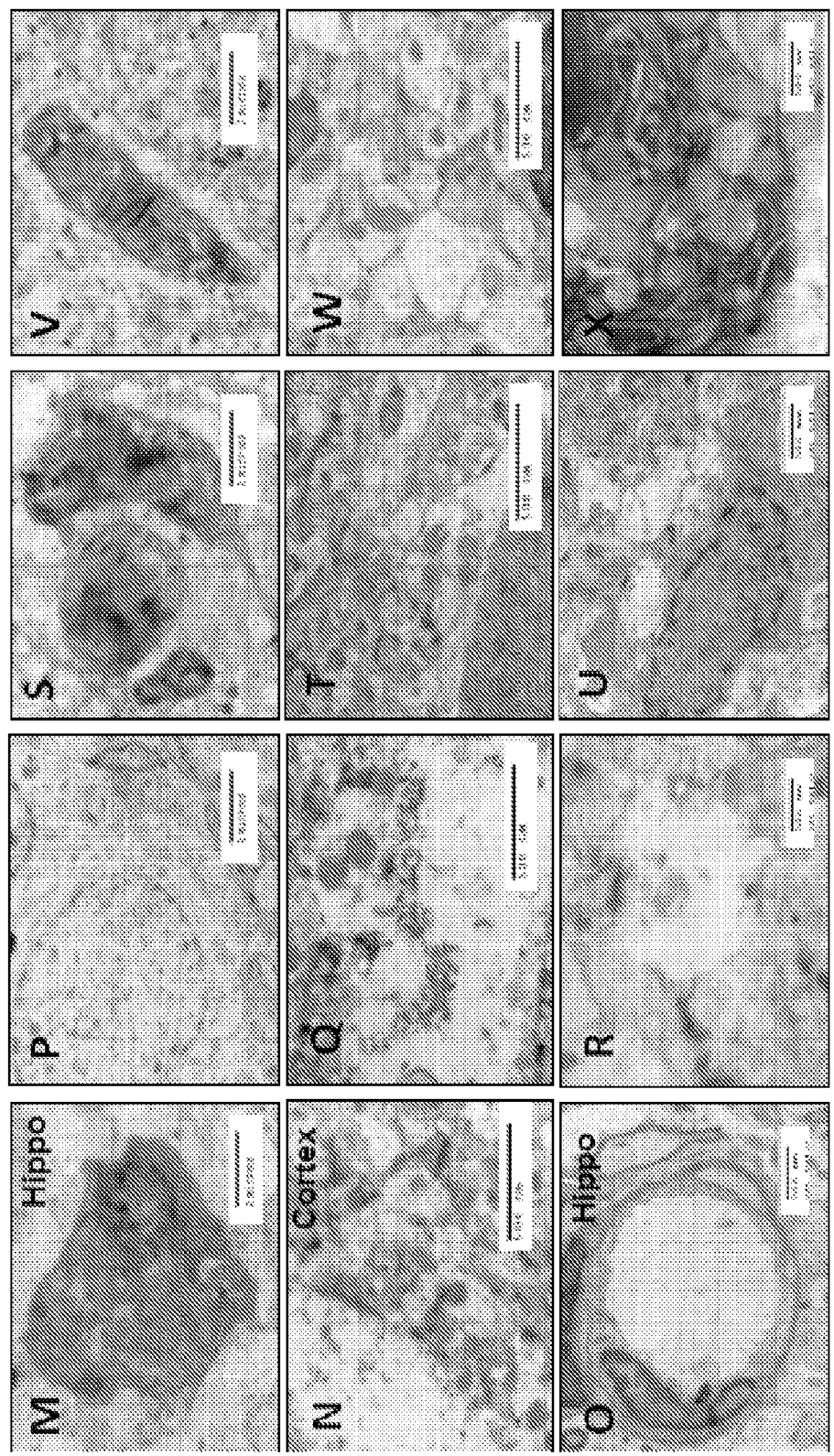

FIG. 64 shows that Nilotinib eliminates plaques in lentiviral Aβ$_{1-42}$ injected wild type but not parkin−/− mice. Staining of 20 μm brain sections shows plaque formation within various brain regions in different A-C) lentiviral Aβ$_{1-42}$+DMSO wild type mice and D-F) Nilotinib group after 3-week treatment. G-I) show lentiviral Aβ$_{1-42}$+DMSO in parkin−/− mice and J-L) show the Nilotinib group after 3-week treatment. Transmission electron microscopy shows autophagic defects in different lentiviral Aβ$_{1-42}$+DMSO wild type brains within M) hippocampus showing distrophic neurons, N) cortex showing accumulation of autophagic vacuoles, O) hippocampus showing enlarged lysosomes. Lentiviral Aβ$_{1-42}$+Nilotinib wild type brains within P) hippocampus, Q) cortex showing clearance of autophagic vacuoles, R) hippocampus. Lentiviral Aβ$_{1-42}$±Nilotinib in parkin−/− brains within S&V) hippocampus showing distrophic neurons, T&W) cortex showing accumulation of autophagic vacuoles and U&X), hippocampus showing accumulation of autophagic vacuoles, are also shown.

FIG. 65 shows that Nilotinib ameliorates cognition in a parkin-dependent manner. A) represents the results of a Morris water maze test after 4 days of training (trials) in lentiviral Aβ$_{1-42}$-injected±Nilotinib wild type (N=14) and parkin−/− (N=7) mice. B) shows graphs representing the total number of entry into platform area and distance travelled. C) represents the results of a Morris water maze test after 4 days of training (trials) in Tg-APP±Nilotinib (N=12) mice, including heat maps for each group showing overall performance. D) shows graphs representing total number of entry into platform area and distance travelled. E) represents the results of an object recognition test in Tg-APP±Nilotinib (N=12) and lentiviral Aβ$_{1-42}$-injected±Nilotinib in parkin−/− (N=7). The recognition index was calculated as (time exploring one of the objects/time exploring both objects)× 100 for acquisition session, and (time exploring new object/ time exploring both familiar and novel objects)×100 for the recognition session given 1.5 hrs later. * Significantly different, ANOVA with Neumann Keuls multiple comparison, P<0.05, Significant effect of Nilotinib on recognition in Tg-APP group, pairwise T-test p<0.001.

Figure 66:
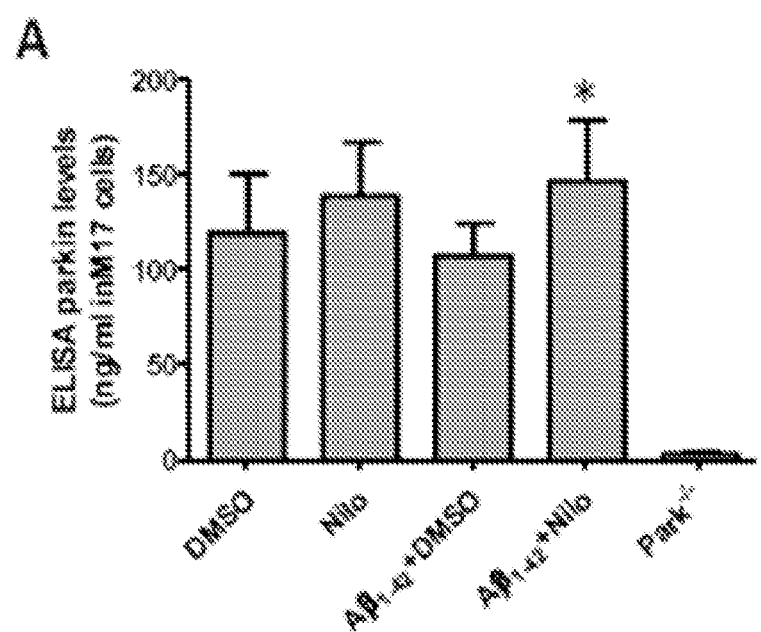

FIG. 66 shows that Nilotinib increases parkin level and crosses the blood brain barrier. Parkin levels by ELISA in wild type mice and lentiviral Aβ$_{1-42}$±Nilotinib using parkin−/− brain extracts as a specificity control (N=12) are shown.

Figure 67:
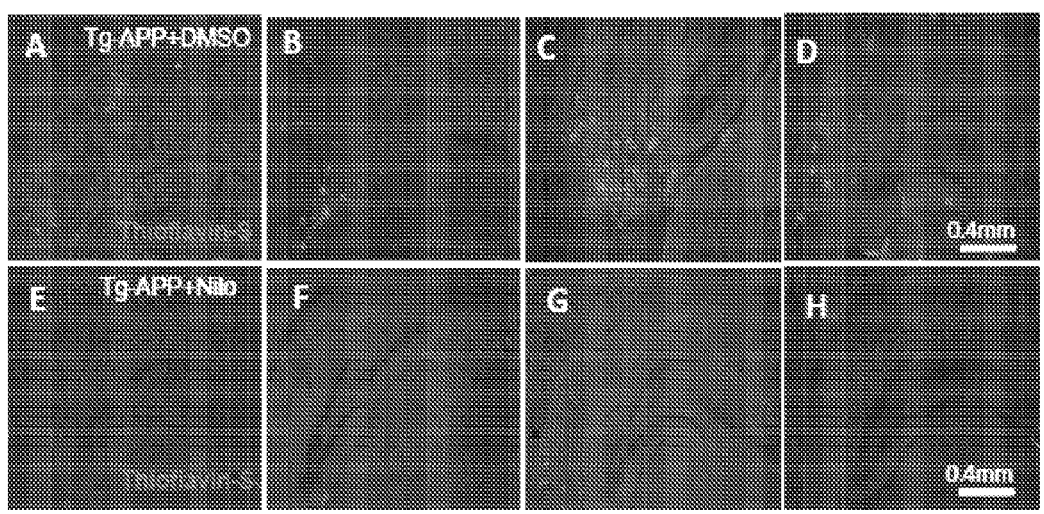

FIG. 67 shows that Nilotinib eliminates thioflavin-S staining Thioflavin staining of 20 μm brain sections shows plaque formation within various brain regions in different A-D) Tg-APP+DMSO and E-H) Nilotinib group after 3-week treatment.

Figure 68:
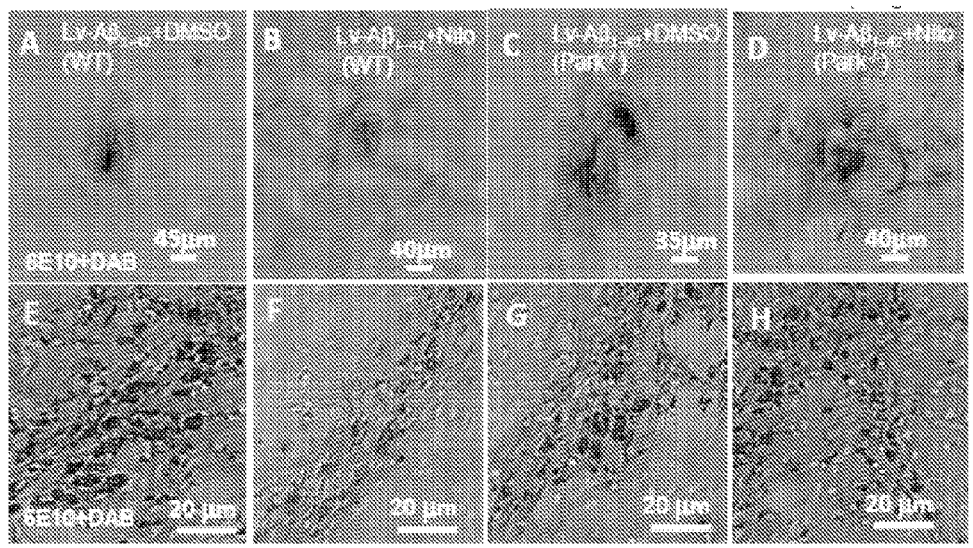
Figure 68:
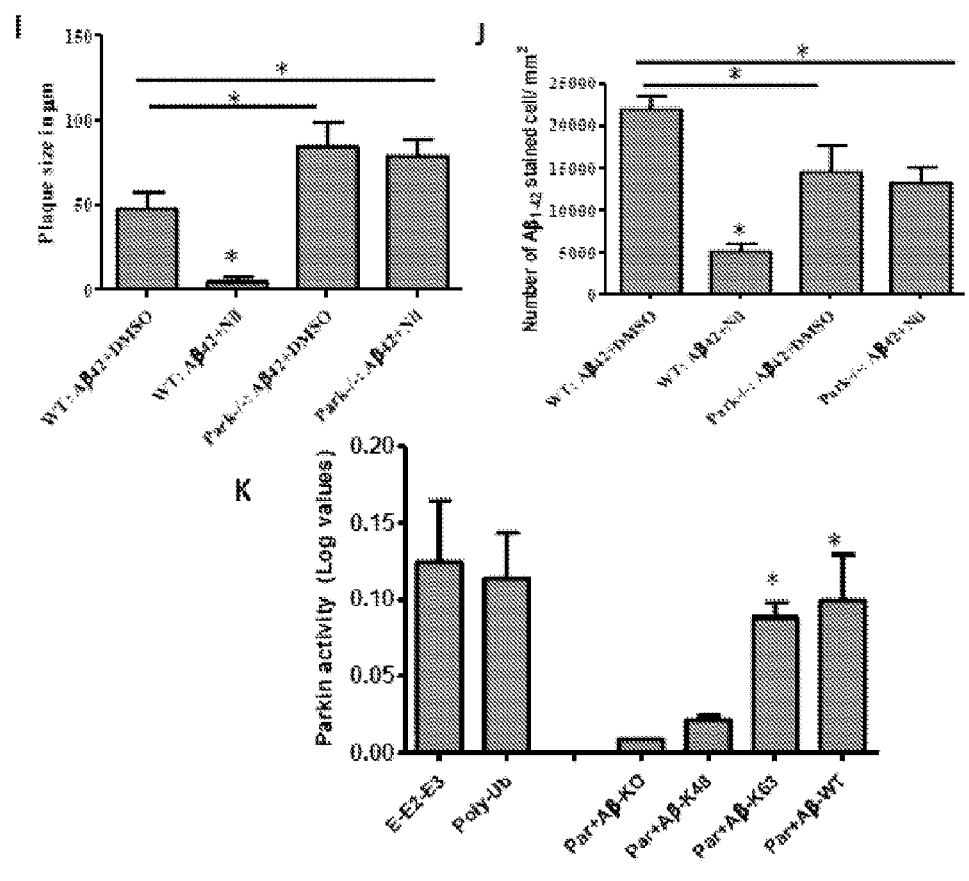

FIG. 68 shows that parkin ubiquitinates Aβ$_{1-42}$ to mediate its degradation. Staining of 20 μm thick sections shows formation of 6E10-positive plaques in Aβ$_{1-42}$ expressing group 6 weeks post-injection in A) Aβ$_{1-42}$ wild type mice+ DMSO, B) Aβ$_{1-42}$ wild type mice+Nilotinib, C) Aβ$_{1-42}$ parkin−/− mice+DMSO and D) Aβ$_{1-42}$ parkin−/− mice+ Nilotinib. Higher magnification showing 6E10 positive cells are provided in E) Aβ$_{1-42}$ wild type mice+DMSO, F) Aβ$_{1-42}$ wild type mice+Nilotinib, G) Aβ$_{1-42}$ parkin−/− mice+ DMSO, H) Aβ$_{1-42}$ parkin−/− mice+Nilotinib. I) shows a graph representing quantification of plaque size using image J to delineate boundaries around individual plaques using 15-25 plaques (2 plaques per animal) and J) shows stereological counting of Aβ$_{1-42}$ positive cells (N=12 animals). K) is a graph representing parkin activity (N=6). * Significantly different, ANOVA with Neumann Keuls multiple comparison, p<0.05.

Figure 69:
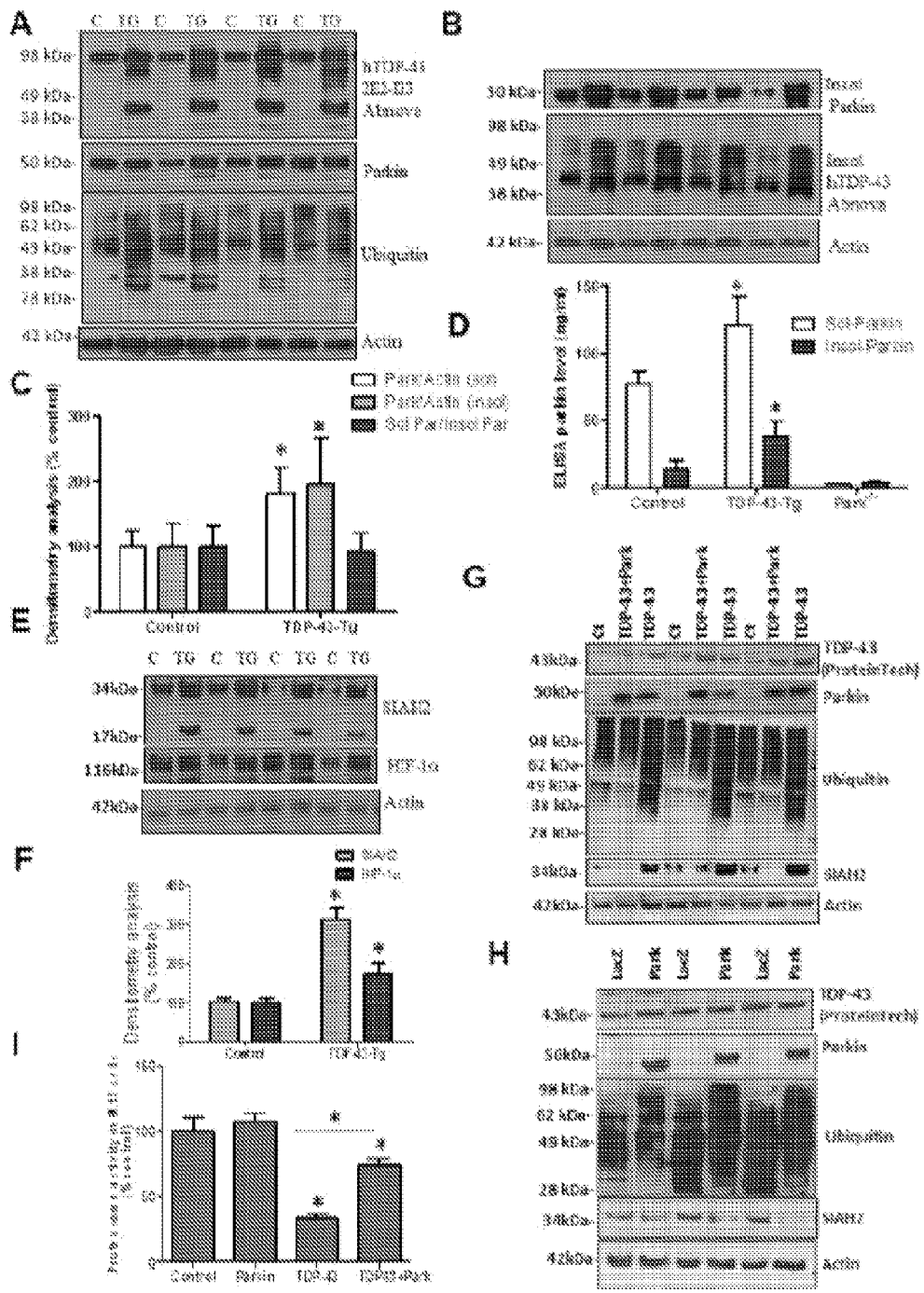

FIG. 69 shows that TDP-43 inhibits proteasome activity and alters parkin levels. Western blot analysis of soluble cortical brain lysates from different litters of mixed male and female TDP-43 transgenic mice and non-transgenic control littermates on 4-12% SDS NuPAGE gel are provided showing A) human TDP-43 levels probed with 2E2-D3 antibody (1st blot), total parkin (2nd blot), ubiquitin (3rd blot) and actin (4th blot) levels. B) shows that the pellet was resuspended in 4M urea to extract the insoluble protein fraction and Western blot was performed showing insoluble parkin (1st blot) and insoluble TDP-43 (2nd blot) compared to actin loading control (3rd blot). C) shows a densitometry analysis of A and B blots showing soluble and insoluble parkin protein levels normalized to actin and the ratio of soluble to insoluble parkin. D) shows an ELISA measurement of parkin level in soluble (STEN extracts) and insoluble (4M Urea) brain extracts compared to parkin−/− brain extracts as a specificity control. E) is a Western blot analysis of cortical brain lysates on ±-12% SDS NuPAGE gel showing soluble protein levels of the E3 ubiquitin ligase SIAH2 (1st blot) and its target protein HIF-1α (2nd blot) compared to actin loading control. F) shows densitometry analysis of blots in D normalized to actin control, N=4, ANOVA with Neumann Keuls, P<0.05. G) shows Western blot analysis of M17 cell lysates on 4-12% SDS NuPAGE gel showing human TDP-43 levels (1st blot), total parkin (2nd blot), ubiquitin (3rd blot) SIAH2 (4th blot) and actin levels (5th blot) in cells expressing TDP-43 and wild type parkin. H) is a Western blot analysis of M17 cell lysates on 4-12% SDS NuPAGE gel showing human TDP-43 levels (1st blot), total parkin (2nd blot), ubiquitin (3rd blot) SIAH2 (4th blot) and actin levels (5th blot) in cells expressing LacZ and wild type parkin. I) shows Histograms represent the chymotrypsin proteasome activity in M17 neuroblastoma cells. * Significantly different, ANOVA, Neumann Keuls, P<0.05, N=6 for cells.

Figure 70:
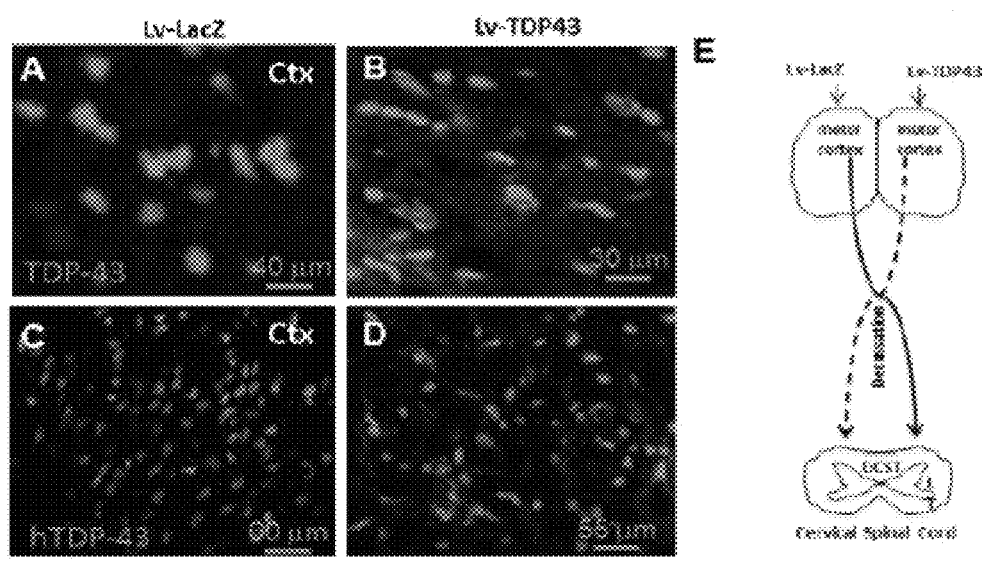
Figure 70:
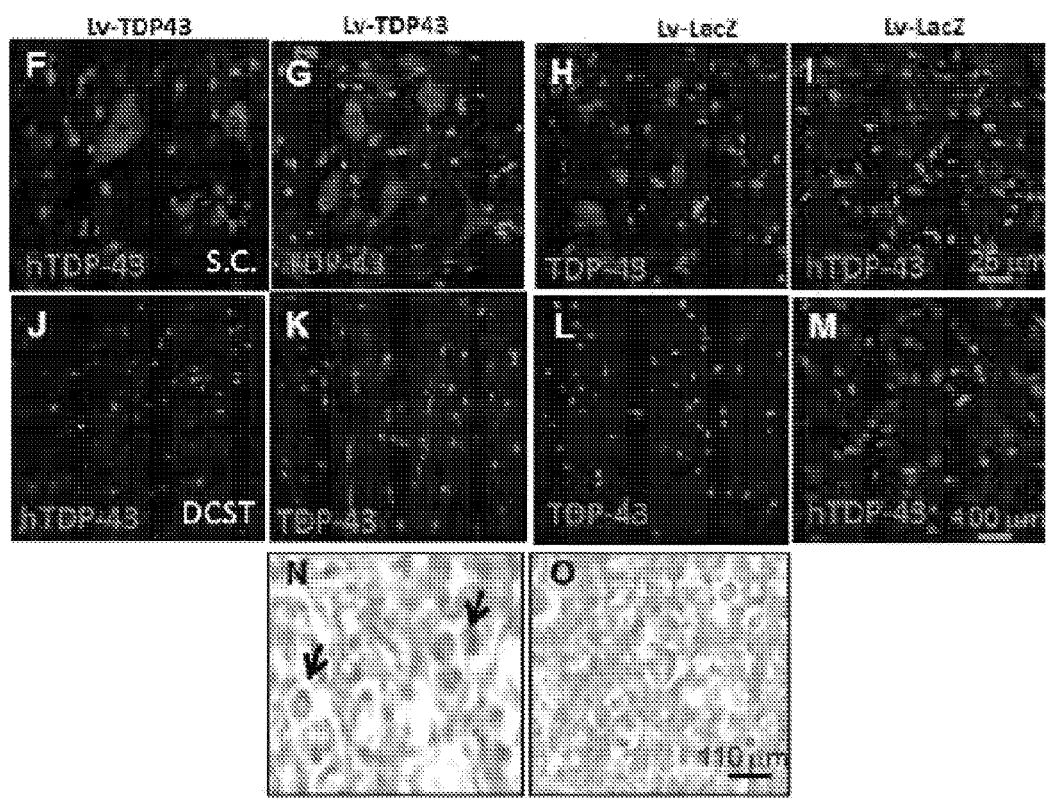

FIG. 70 shows that Lentiviral expression of TDP-43 in rat motor cortex results in detection of TDP-43 in preganglionic cervical spinal cord inter-neurons. Staining of 20 μm thick sections from rat brain injected with lentiviral TDP-43 in the right hemisphere and lentiviral LacZ in the left hemisphere showing A) neurons in rat motor cortex stained with anti-TDP-43 antibody that detects both human and rat TDP-43 and DAPI-stained nuclei in lentiviral LacZ-injected and B) TDP-43 injected hemisphere are shown. C) shows that neurons in rat motor cortex stained with anti-TDP-43 antibody that detects human TDP-43 and DAPI-stained nuclei in lentiviral LacZ-injected and D) TDP-43 injected hemisphere. E) is a schematic representation of injected motor cortex relative to contralateral spinal cord region and dorsocortical spinal tract (DCST). Staining of 20 μm thick sections showing pre-ganglionic cervical spinal cord inter-neurons stained with F). hTDP-43 mouse monoclonal antibody (Abnova) that recognizes human TDP-43 and G). Anti-TDP-43 rat polyclonal antibody (ProteinTech) that recognizes both human and rat, and DAPI-stained nuclei contralateral to lentiviral TDP-43-injected cortex and H (TDP-43) and I (hTDP-43) contralateral to LacZ injected hemisphere are shown. Staining of 20 μm thick sections showing fibers in DCST stained with J) mouse monoclonal hTDP-43 and DAPI and K) rabbit polyclonal anti-TDP-43 antibody DAPI contralateral to lentiviral TDP-43-injected cortex are also shown. L shows TDP-43 and M shows hTDP-43. TDP-43 staining and DAPI in DCST contralateral to LacZ injected hemisphere was also performed. N) shows toluidine blue stained DCST contralateral to lentiviral TDP-43-injected cortex compared to O) LacZ injected hemisphere. Lv: lentivirus.

Figure 71:
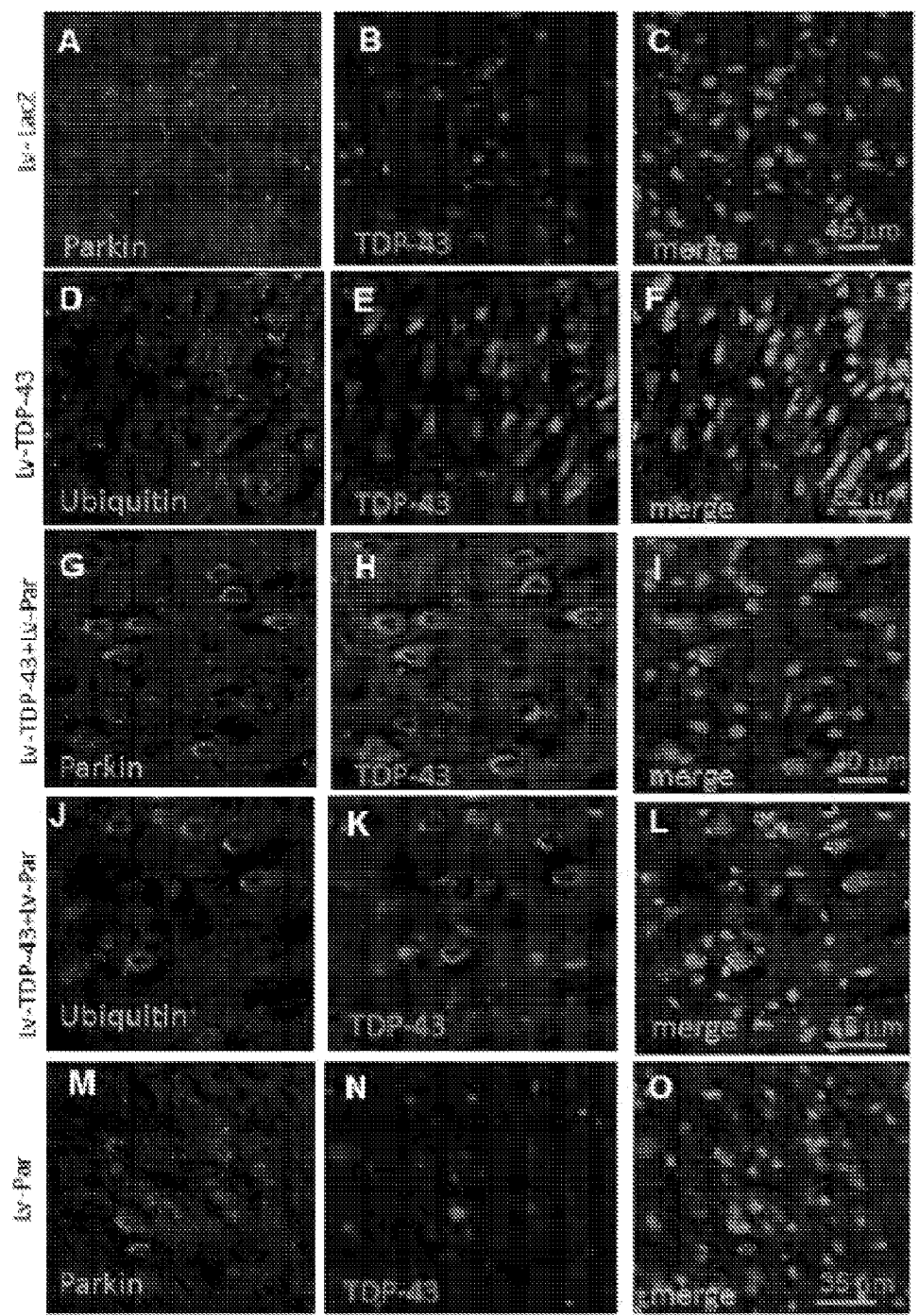

FIG. 71 shows that lentiviral parkin increases cytosolic co-localization of ubiquitin and TDP-43. Staining of 20 μm thick sections from rat brain injected with lentiviral TDP-43 in the right hemisphere and lentiviral LacZ in the left hemisphere shows A) neurons in rat motor cortex stained with mouse monoclonal (Millipore) anti-parkin, B) rabbit polyclonal anti-TDP-43 antibodies, C) parkin, TDP-43 and DAPI in lentiviral LacZ-injected hemisphere. D) shows neurons in rat motor cortex stained with mouse monoclonal anti-ubiquitin and E) rabbit polyclonal anti-TDP-43 antibodies. F) shows ubiquitin, TDP-43 and DAPI in lentiviral TDP-43-injected hemisphere. G) shows neurons in rat motor cortex stained with mouse monoclonal anti-parkin and H) rabbit polyclonal anti-TDP-43 antibodies. I) shows parkin, TDP-43 and DAPI in animals co-injected with lentiviral TDP-43 and parkin. J) shows neurons in rat motor cortex stained with mouse monoclonal anti-ubiquitin and K) rabbit polyclonal anti-TDP-43 antibodies. L) shows ubiquitin, TDP-43 and DAPI stained nuclei in animals co-injected with lentiviral TDP-43 and parkin. Neurons in rat motor cortex stained with M) mouse monoclonal anti-parkin antibodies, N) rabbit polyclonal anti-TDP-43 antibodies, and O) parkin, TDP-43 and DAPI stained nuclei in animals injected with lentiviral parkin alone are shown. Lv: lentiviral.

Figure 72:
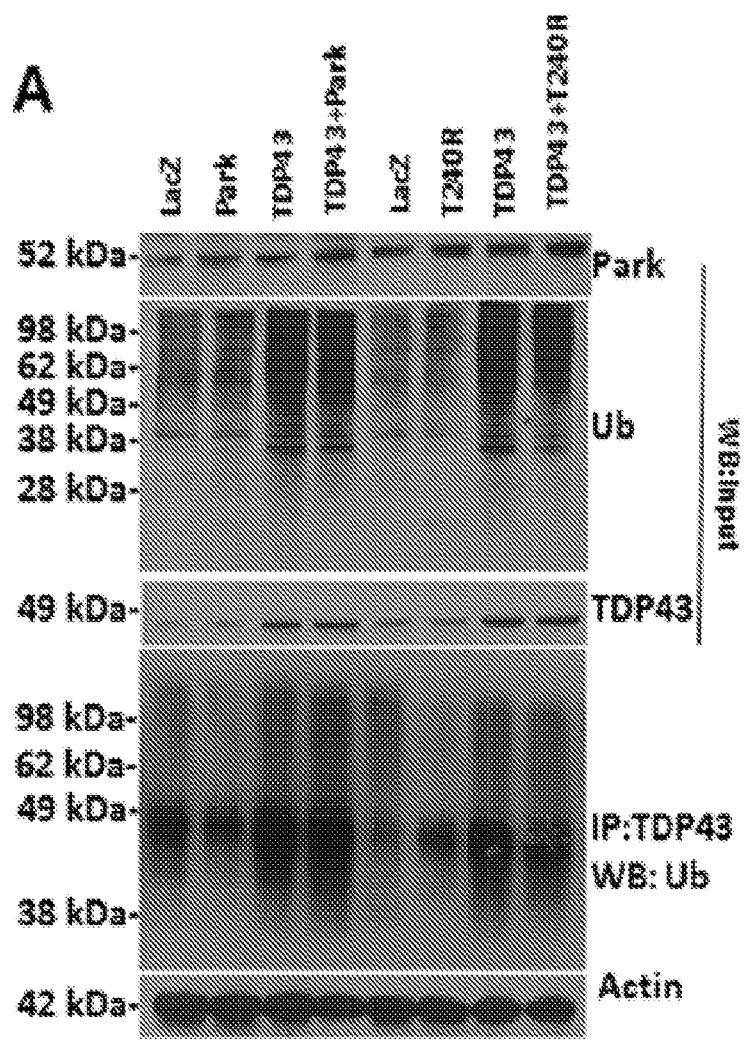
Figure 72:
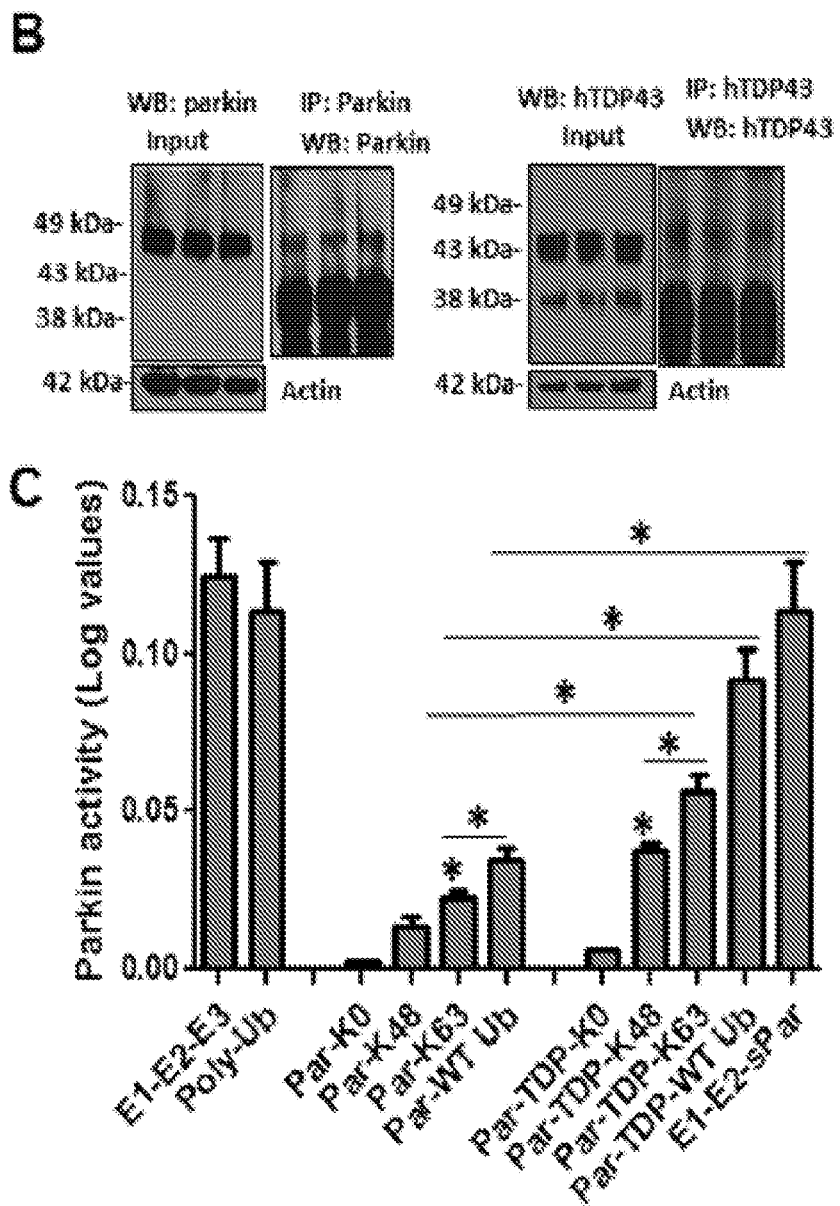
Figure 72:
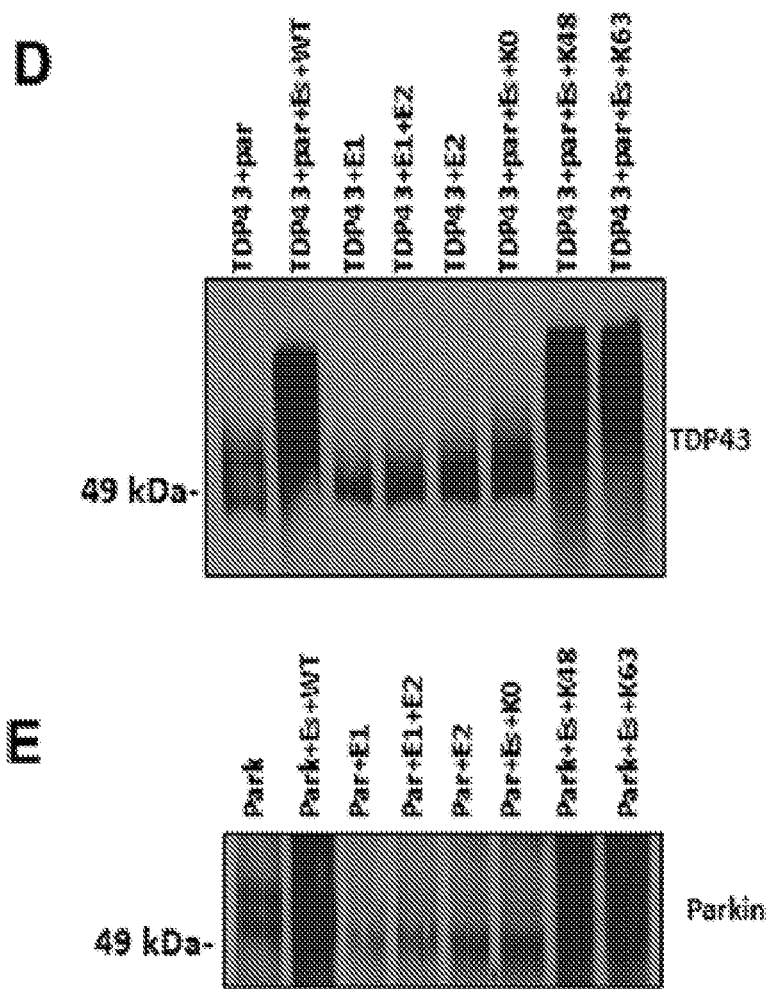
Figure 72:
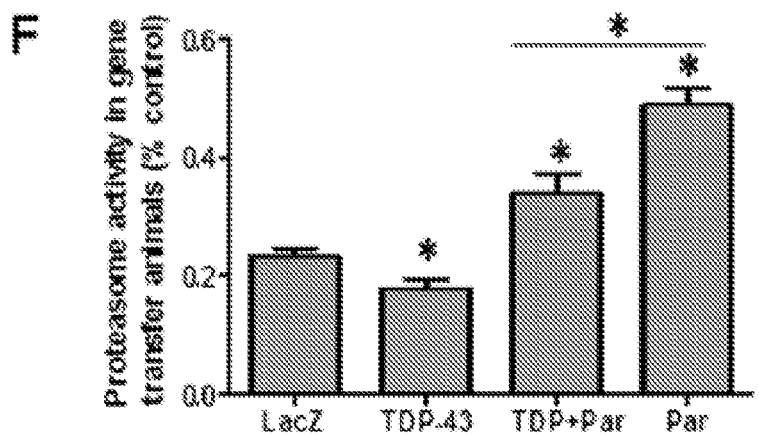
Figure 72:
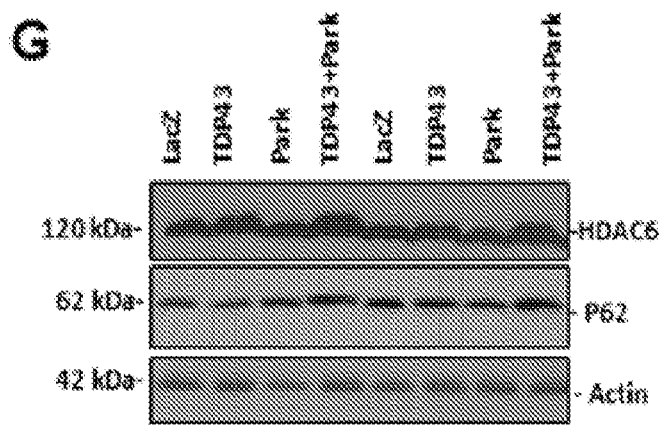
Figure 72:
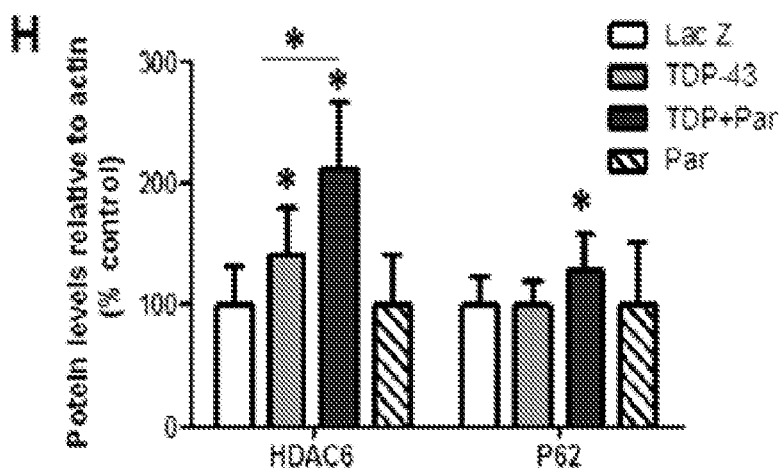

FIG. 72 shows that parkin mediates K48 and K63-linked ubiquitination of TDP-43. Western blot of input samples from cortical brain lysates analyzed on 4-12% SDS NuPAGE gel show A) parkin expression levels (1st blot), ubiquitin bound protein levels (2nd blot) and TDP-43 levels (3rd blot), compared to actin loading control in rat cortex injected with lentiviral LacZ, TDP-43, parkin, TDP-43+parkin and TDP-43+T240R mutant. A total of 100 mg cortical brain samples were immuno-precipitated using rabbit polyclonal anti-TDP-43 and probed (1:1000) with anti-ubiquitin antibody (4th blot) compared to actin loading control (5th blot) from input samples. B) shows a Western blot of input samples and immuno-precipitated parkin (top blot) and TDP-43 (bottom blot) from transgenic mice used to measure parkin E3 ubiquitin ligase activity. C) shows histograms representing parkin E3 ubiquitin ligase activity in the presence and absence of human TDP-43 immuno-precipitated from TDP-43 transgenic mice, compared to E3 ubiquitin ligase activity using recombinant parkin (sPar), poly-ubiquitin chain as control and a synthetic 1-E2-E3 control combination. N=8, P<0.05, ANOVA Neumann Keuls. D) is a WB analysis showing ubiquitinated TDP-43 in the presence of K48 and K63 and E) is a WB analysis showing ubiquitinated parkin at K48 and K63. F) shows histograms representing the chymotrypsin proteasome activity in fresh cortical brain lysates from rats injected with lentiviral LacZ, parkin, TDP-43 and TDP-43+parkin. * indicates a significant difference, ANOVA, Neumann Keuls, P<0.05, N=8. G). Western blot analysis of cortical brain lysates on 4-12% SDS NuPAGE gel showing HDAC6 (1st blot) and P62 levels (2nd blot) and actin control (3rd blot) are provided. H) is a densitometry analysis of blots in E from gene transfer animal models. * Indicates significantly different, ANOVA, Neumann Keuls, P<0.05, N=8.

Figure 73:
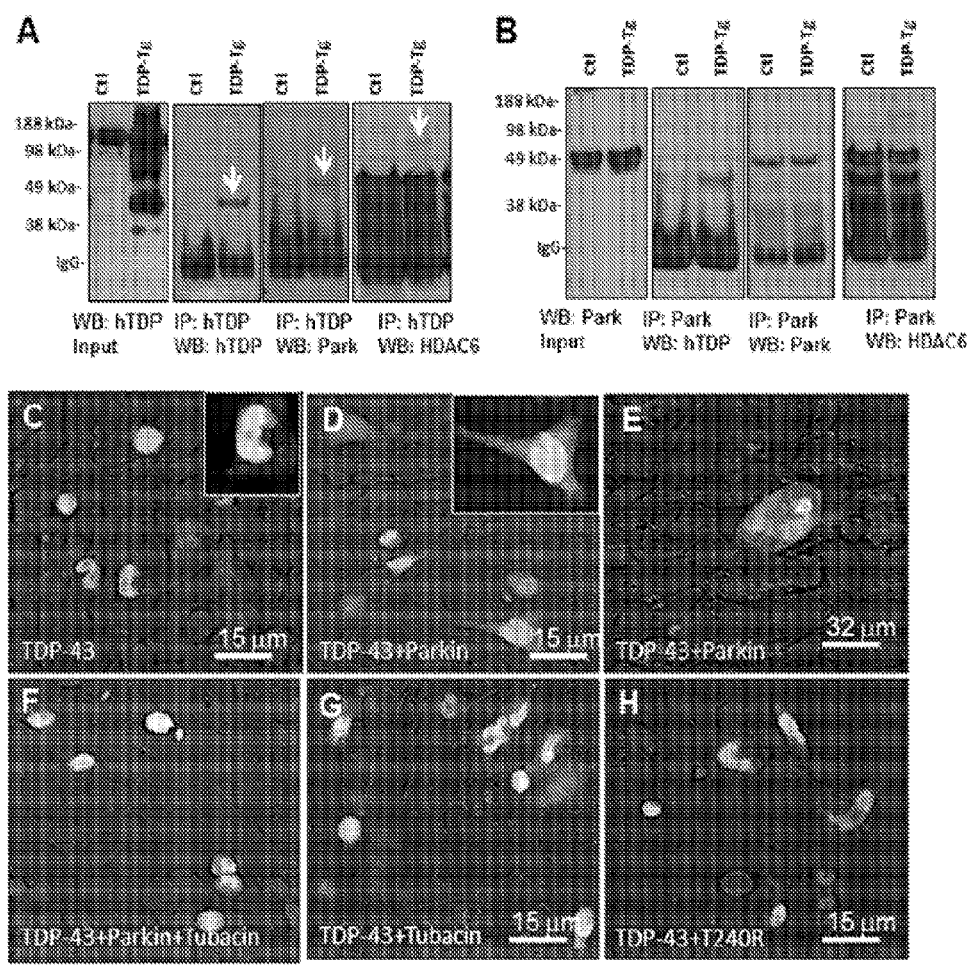
Figure 73:
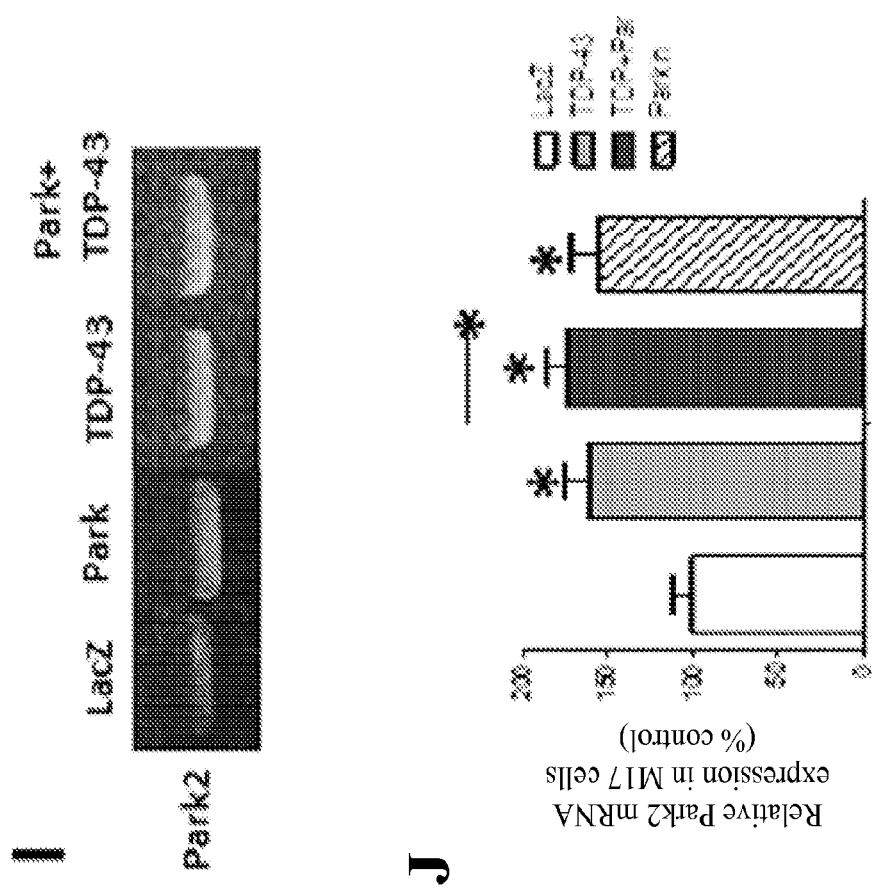
Figure 73:
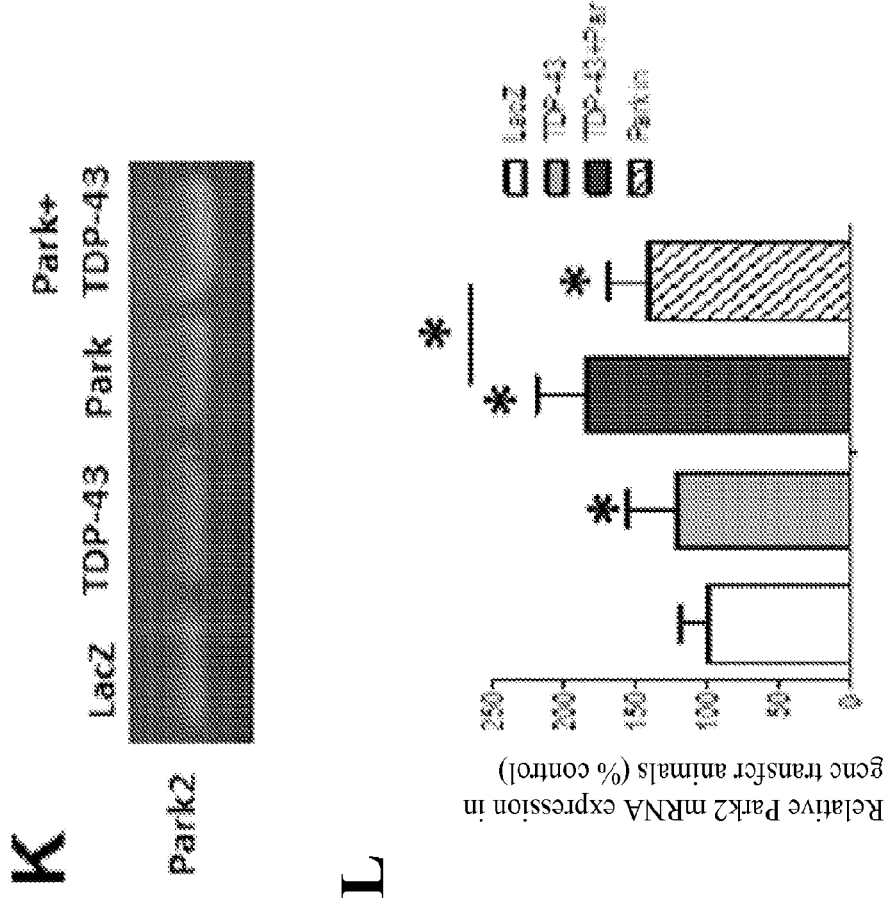
Figure 73:
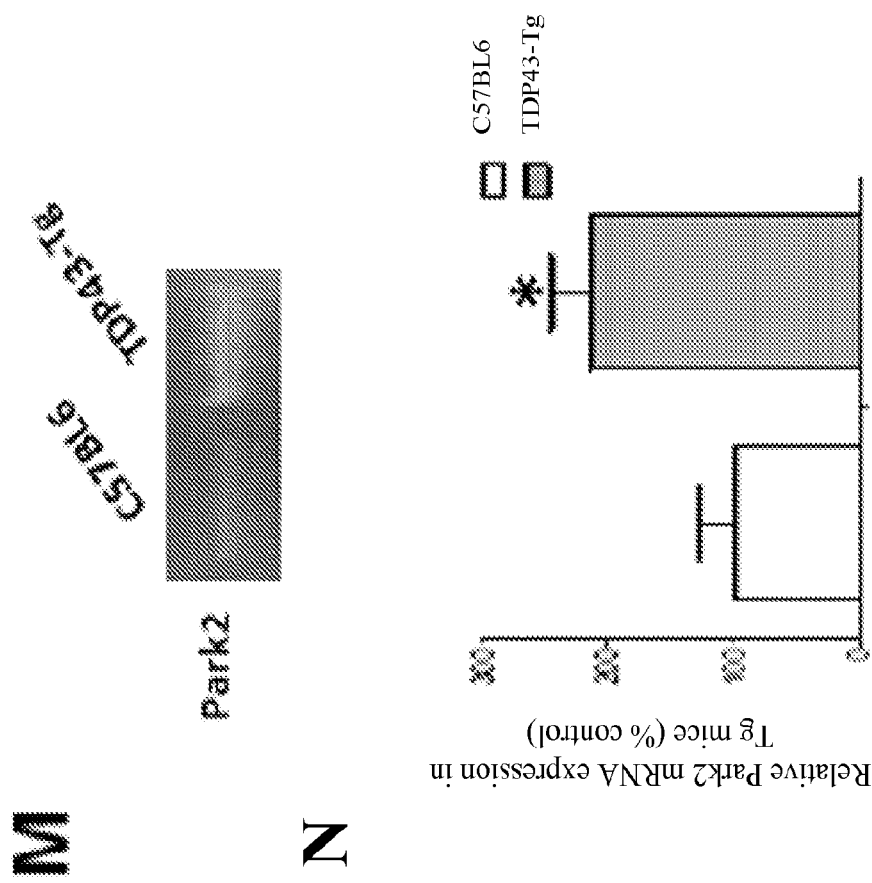

FIG. 73 shows that TDP-43 forms a multi-protein complex with parkin and HDAC6. Western blot of input samples from cortical brain lysates in transgenic A315T mice and control littermates analyzed on 4-12% SDS NuPAGE gel showing A) shows human TDP-43 expression levels (1st blot) and immuno-precipitation of TDP-43 showing TDP-43 (2nd blot), parkin (3rd blot) and HDAC6 (4th blot) forming a protein complex. B) represents the reverse immune-precipitation experiment, where Western blot of input samples from cortical brain lysates in transgenic A315T mice and control littermates analyzed on 4-12% SDS NuPAGE show parkin expression levels (1st blot) and immuno-precipitation of parkin showing TDP-43 (2nd blot), parkin (3rd blot) and HDAC6 (4th blot). GFP fluorescence and nuclear DAPI-staining in living human M17 neuroblastoma cells C) shows cells transfected with GFP-TDP-43 alone showing GFP fluorescence within the nucleus. D &E) show cells transfected with GFP-TDP-43 and parkin showing GFP fluorescence in cytosol and cellular processes. Inset in D shows higher magnification. F) shows cells transfected with GFP-TDP-43 and parkin treated with 5 μM HDAC6 inhibitor, tubacin for 24 hours showing GFP fluorescence within DAPI-stained nuclei. G). shows cells transfected with GFP-TDP-43 for 24 hours and treated with tubacin for an additional 24 hours. H) shows cells transfected with GFP-TDP-43 and T240R, showing lack of GFP fluorescence with parkin mutant. I) shows qRT-PCR showing Park2 mRNA in M17 cells transfected with LacZ TDP-43, parkin and TDP-43+parkin. J) shows quantification of qRT-PCR showing relative Park2 mRNA levels normalized to GADPH and expressed as % control. N=4, P<0.05, ANOVA, Neumann Keuls. K) shows qRT-PCR showing Park2 mRNA in rat cortex injected with LacZ (un-injected control), TDP-43, parkin and TDP-43+parkin. L) shows quantification of qRT-PCR showing relative Park2 mRNA levels normalized to GADPH and expressed as % control. N=4, P<0.05, ANOVA, Neumann Keuls. M) shows qRT-PCR showing Park2 mRNA in TDP43-Tg and control cortex. N) shows quantification of qRT-PCR showing relative Park2 mRNA levels normalized to GADPH and expressed as % control. N=3, P<0.05, ANOVA, Neumann Keuls.

Figure 74:

FIG. 74 is a schematic showing potential effects of parkin on TDP-43 localization.

Figure 75:
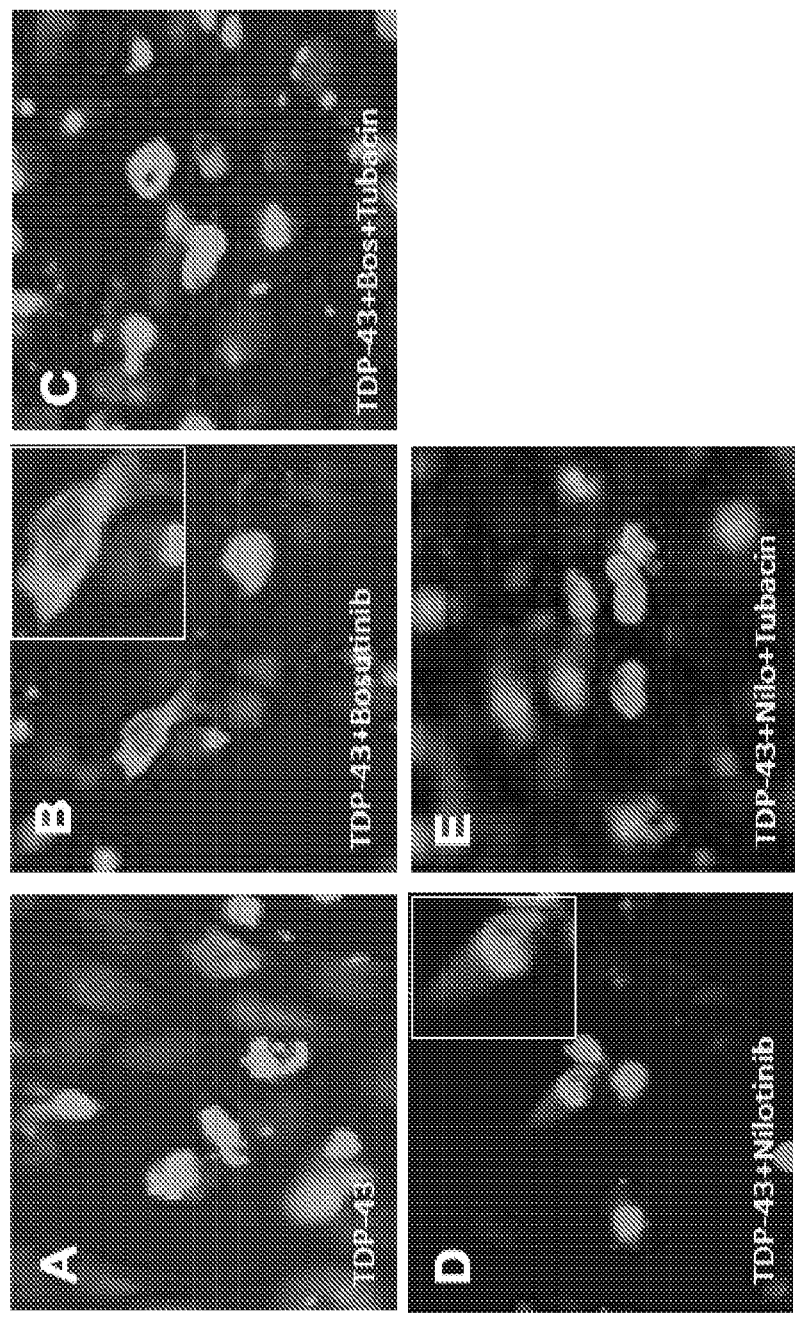

FIG. 75 shows the distribution of GFP-tagged TDP-43 in M17 cells transfected with 3 mg cDNA for 24 hrs and then treated with Nilotinib (10 mM) or Bosutinib (5 mM) and HDAC6 inhibitor Tubacin (5 mM) for additional 24 hrs. Inserts (B&D) represent higher magnification images showing translocation of GFP-tagged TDP-43 from nucleus (A) into the cytosol (B&D, and inserts), while tubacin impairs translocation (C&E).

DETAILED DESCRIPTION

Provided herein are methods of treating or preventing a neurodegenerative disease, a myodegenerative disease or a prion disease. Neurodegenerative diseases include amyotrophic lateral sclerosis, Alzheimer's disease, frontotemporal dementia, frontotemporal dementia with TDP-43, frontotemporal dementia linked to chromosome-17, Pick's disease, Parkinson's disease, Huntington's chorea, mild cognitive impairment, Lewy Body disease, multiple system atrophy, progressive supranuclear palsy, and cortico-basal degeneration in a subject. The methods include the use of tyrosine kinase inhibitors. The methods also include the use of tyrosine kinase inhibitors wherein the tyrosine kinase inhibitor is not Gleevec and wherein the tyrosine kinase inhibitor crosses the blood brain barrier. The methods also include the use of tyrosine kinase inhibitors, wherein the tyrosine kinase inhibitors are not c-Abl tyrosine kinase inhibitors or are not specific c-Abl inhibitors.

Provided herein is a method of treating or preventing a neurodegenerative disease in a subject, comprising selecting a subject with a neurodegenerative disease of the central nervous system, a myodegenerative disease or a prion disease or at risk for a neurodegenerative disease of the central nervous system, a myodegenerative disease or a prion disease and administering to the subject an effective amount of a tyrosine kinase inhibitor, as described throughout. Optionally, the tyrosine kinase inhibitor is not Gleevec and the tyrosine kinase inhibitor crosses the blood brain barrier. For example, the tyrosine kinase inhibitor is selected from the group consisting of nilotinib, bosutinib, and a combination thereof.

In the methods provided herein, neurodegenerative diseases of the central nervous system include, but are not limited to, Amyotrophic Lateral Sclerosis, Alzheimer's Disease, Parkinson's Disease, frontotemporal dementia, Huntington's Disease, Mild Cognitive Impairment, an α-Synucleinopathy, a Tauopathy or a pathology associated with intracellular accumulation of TDP-43.

In the methods provided herein, myodegenerative diseases include, but are not limited to, inclusion body myositis (IBM), spinal-bulbar muscular atrophy (SBMA), and motor neuron disease (MND).

In the methods provided herein, prion diseases or transmissible spongiform encephalopathies (TSEs) include, but are not limited to, Creutzfeldt-Jakob Disease (CJD), Variant Creutzfeldt-Jakob Disease (vCJD), Gerstmann-Straussler-Scheinker Syndrome, Fatal Familial Insomnia and Kuru in humans. Animal prion diseases include, but are not limited to, Scrapie, Bovine Spongiform Encephalopathy (BSE), Chronic Wasting Disease (CWD), Transmissible mink encephalopathy, Feline spongiform encephalopathy and Ungulate spongiform encephalopathy.

Examples of tyrosine kinase inhibitors include, but are not limited to, nilotinib, bosutinib, or a combination thereof. Nilotinib (or AMN-107), which is sold as TASIGNA® (Novartis, Basel Switzerland), and Bosutinib (or SKI-606) (Pfizer, New York, N.Y.) are Bcr-Abl tyrosine kinase inhibitors developed as alternatives to the Bcr-Abl tyrosine kinase inhibitor and CML treatment, Imatinib. Nilotinib is an Abelson kinase inhibitor (c-Abl kinase), whereas Bosutinib is a dual Src and c-Abl kinase inhibitor. These agents are cancer therapeutics that block cellular proliferation of cancer cells and are currently used primarily in the treatment of chronic myelogenous leukemia (CML).

In neurodegenerative disorders, normal autophagic flux is altered, resulting in the accumulation of autophagic vacuoles or autophagosomes. This is shown in the Examples where the accumulation of vacuoles is seen in human patients with decreased parkin solubility activity. Normal autophagy is a dynamic multi-step process that prevents protein accumulation via sequestration into autophagic vacuoles (autophagosomes). Subsequent fusion of the autophagosomes with lysosomes results in protein degradation. Interruption of this process results in accumulation of protein aggregates and neurodegeneration. Parkin is an E3 ligase involved in proteasomal and autophagic degradation via protein ubiquitination and autophagosome maturation.

Tyrosine kinase inhibition activates parkin-mediated clearance of aggregated proteins and/or activates ubiquitination. Activation of parkin by tyrosine kinase inhibitors up-regulates protein levels of beclin, thus facilitating autophagic clearance. For example, nilotinib, bosutinib, or a combination thereof activates parkin-mediated clearance of aggregated proteins and/or activates ubiquitination. Significantly, both nilotinib and bosutinib cross the blood brain barrier and promote parkin activity in the central nervous system. Parkin activity promotes autophagic clearance of amyloid beta and alpha-synuclein and causes protective mechanisms for parkin ubiquitination, for example, sequestration of TDP-43 associated with amyotrophic lateral sclerosis (ALS) and frontotemporal dementia. Furthermore, the tyrosine kinase inhibitors rescue brain cells from apoptotic death in neurodegenerative disease. In the case of ALS, the inhibitors increase ubiquitination of TDP-43 and translocate it from the nucleus, where it interacts deleteriously with mRNA and thousands of genes, to the cytosol where it is sequestered.

The method optionally includes selecting a subject with a neurodegenerative disease or at risk for developing a neurodegenerative disease. One of skill in the art knows how to diagnose a subject with or at risk of developing a neurodegenerative disease. For example, one or more of the follow tests can be used genetic test (e.g., identification of a mutation in TDP-43 gene) or familial analysis (e.g., family history), central nervous system imaging (e.g., magnetic resonance imaging and positron emission tomography), clinical or behavioral tests (e.g., assessments of muscle weakness, tremor, or memory), laboratory tests.

The method optionally further includes administering a second therapeutic agent to the subject. The second therapeutic agent is selected from the group consisting of levadopa, a dopamine agonist, an anticholinergic agent, a monoamine oxidase inhibitor, a COMT inhibitor, amantadine, rivastigmine, an NMDA antagonist, a cholinesterase inhibitor, riluzole, an anti-psychotic agent, an antidepressant, and tetrabenazine.

By way of example, provided herein is a method of treating amyotrophic lateral sclerosis or frontotemporal dementia in a subject. The method includes selecting a subject with amyotrophic lateral sclerosis or frontotemporal dementia, wherein the subject has a TDP-43 pathology, and administering to the subject an effective amount of the tyrosine kinase inhibitor. The TDP-43 pathology can be, for example, a TDP-43 mutation. For example, the tyrosine kinase inhibitor is a tyrosine kinase inhibitor that is not Gleevec and crosses the blood brain barrier. In another example, the tyrosine kinase inhibitor is selected from the group consisting of nilotinib, bosutinib, and a combination thereof. TDP-43 pathology occurs in ALS and frontotemporal dementia and an elevated level of TDP-43 in the cytoplasm has been noted in some cases of ALS and frontotemporal dementia. Mutations in the gene that encodes the TDP-43 protein (known as TARDBP) have been discovered in some individuals with ALS and frontotemporal dementia. Thus, mutated TDP-43 or mutations in TARDBP can serve as biomarkers for a subject at risk for ALS or frontotemporal dementia.

Also provided herein is a method of promoting parkin activity in a subject. The method includes selecting a subject with a disorder associated with decreased parkin activity and administering to the subject an effective amount of the tyrosine kinase inhibitor. For example, the tyrosine kinase inhibitor is a tyrosine kinase inhibitor that is not Gleevec and crosses the blood brain barrier. In another example, the tyrosine kinase inhibitor is selected from the group consisting of nilotinib, bosutinib, and a combination thereof.

Methods for measuring parkin activity are known in the art. See, for example, Schlossmacher and Shimura ("Parkinson's disease: assays for the ubiquitin ligase activity of neural Parkin," *Methods Mol. Biol.* 301: 351-69 (2005)); Morrison et al. ("A simple cell based assay to measure Parkin activity," *J. Neurochem.* 116(3): 342-9 (2011)) and Burns et al. (*Hum. Mol. Genet.* 18 3206-3216 (2009)).

Further provided is a method of treating or preventing a neurodegenerative disease in a subject, comprising selecting a subject with a neurodegenerative disease or at risk for a neurodegenerative disease, determining that the subject has a decreased level of parkin activity relative to a control, and administering to the subject an effective amount of a small molecule that increases parkin activity, wherein the small molecule is not Gleevec. For example, the small molecule can be a tyrosine kinase inhibitor, such as, for example, a tyrosine kinase inhibitor that crosses the blood brain barrier. The tyrosine kinase inhibitor can also be selected from the group consisting of nilotinib, bosutinib, and a combination thereof.

The term effective amount, as used throughout, is defined as any amount necessary to produce a desired physiologic response. The effective amount is generally less than the amount used in chemotherapeutic methods to treat cancer or leukemia, but is an amount sufficient to activate parkin. Thus, the dosage of the tyrosine kinase inhibitor in the present methods is optionally lower than a chemotherapeutic dosage of the inhibitor. For example, the dosage is optionally less than about 10 mg/kg and can be 8, 7, 6, 5, 4, 3, 2, or 1 mg/kg. One of skill in the art would adjust the dosage as described below based on specific characteristics of the inhibitor and the subject receiving it.

Furthermore, the duration of treatment can be longer in the present methods than the duration of chemotherapeutic treatment, for example cancer treatment. For example, administration to a subject with or at risk of developing a neurodegenerative disease could be at least daily (e.g., once, twice, three times per day) for weeks, months, or years so long as the effect is sustained and side effects are manageable.

There are several ways to activate parkin. Parkin immunoprecipitation and incubation with a series of activating and ligating enzymes (E and E2) and ATP result in parkin auto-ubiquitination, and confer activity to ubiquitinate targets like Abeta and TDP-43. So, in order to increase parkin activity, parkin expression must be increased. This can be achieved by viral introduction of parkin which leads to over-expression of the protein and increased activity. As shown in the Examples, this method repeatedly increases protein degradation via the proteasome and/or autophagy. Parkin can also be activated by administration of a tyrosine kinase, such as, for example, nilotinib or bosutinib, which leads to increased levels of parkin and increased activity.

Effective amounts and schedules for administering the tyrosine kinase inhibitor can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily.

The tyrosine kinase inhibitor is administered systemically and preferably orally.

Also provided herein is a method of inhibiting or preventing toxic protein aggregation in a neuron and/or rescuing a neuron from degeneration. The method includes contacting the neuron with an effective amount of a tyrosine kinase inhibitor. For example, the tyrosine kinase inhibitor is a tyrosine kinase inhibitor that is not Gleevec and crosses the blood brain barrier. In another example, the tyrosine kinase inhibitor is selected from the group consisting of nilotinib, bosutinib, and a combination thereof. The toxic protein aggregate optionally comprises one or more of an amyloidogenic protein, alpha-synuclein, tau, insoluble Parkin, TDP-43, a prion protein or toxic fragments thereof. By amyloidogenic protein is meant a peptide, polypeptide, or protein that has the ability to aggregate. An example of an amyloidogenic protein is β-amyloid.

The contacting is performed in vivo or in vitro. The in vivo method is useful in treating a subject with or at risk of developing toxic protein aggregates and comprises administering the tyrosine kinase inhibitor as described above. The in vitro method is useful for example in treating neural cells prior to transplantation. The tyrosine kinase inhibitor is generally added to a culture medium. Optionally, the target neurons are contacted with a second therapeutic agent as described above.

Also provided herein is a method of inhibiting or preventing toxic protein aggregation in a muscle cell and/or rescuing a muscle cell from degeneration. Further provided is a method of inhibiting or preventing toxic protein aggregation in a glial cell and/or rescuing a glial cell from degeneration. The method includes contacting the glial cell with an effective amount of a tyrosine kinase inhibitor. For example, the tyrosine kinase inhibitor is a tyrosine kinase inhibitor that is not Gleevec and crosses the blood brain barrier.

The disclosure also provides a pharmaceutical pack or kit comprising packaging and/or one or more containers filled with one or more of the ingredients of the pharmaceutical compositions. Instructions for use of the composition can also be included.

Provided herein is a pharmaceutical composition comprising an effective amount of the tyrosine kinase inhibitor in a pharmaceutically acceptable carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Depending on the intended mode of administration, the pharmaceutical composition can be in the form of solid, semi-solid, or liquid dosage forms, such as, for example, tablets, suppositories, pills, capsules, powders, liquids, aerosols, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or pharmaceutically acceptable salts or prodrugs thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or pharmaceutically acceptable salts or prodrugs thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Throughout, treat, treating, and treatment refer to a method of reducing or delaying one or more effects or symptoms of a neurodegenerative disease or disorder. The subject can be diagnosed with disease or disorder. Treatment can also refer to a method of reducing the underlying pathology rather than just the symptoms. The effect of the administration to the subject can have the effect of but is not limited to reducing one or more symptoms of the neurodegenerative disease or disorder, a reduction in the severity of the neurological disease or injury, the complete ablation of the neurological disease or injury, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As utilized herein, by prevent, preventing, or prevention is meant a method of precluding, delaying, averting, obviating, forestalling, stopping, or hindering the onset, incidence, severity, or recurrence of the neurodegenerative disease or disorder. For example, the disclosed method is considered to be a prevention if there is a reduction or delay in onset, incidence, severity, or recurrence of neurodegeneration or one or more symptoms of neurodegeneration (e.g., tremor, weakness, memory loss, rigidity, spasticity, atrophy) in a subject susceptible to neurodegeneration as compared to control subjects susceptible to neurodegeneration that did not receive an agent that activates parkin. The disclosed method is also considered to be a prevention if there is a reduction or delay in onset, incidence, severity, or recurrence of neurodegeneration or one or more symptoms of neurodegeneration in a subject susceptible to neurodegeneration after receiving an agent that promotes parkin activity as compared to the subject's progression prior to receiving treatment. Thus, the reduction or delay in onset, incidence, severity, or recurrence of neurodegeneration can be about a 10, 20, 30, 40, 50, 60, 70, 80, 90, 100%, or any amount of reduction in between.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. A number of embodiments have been described. Nevertheless, it will be understood that various modifications may be made. Accordingly, other embodiments are within the scope of the following claims.

EXAMPLES

Example 1

Figure 1:
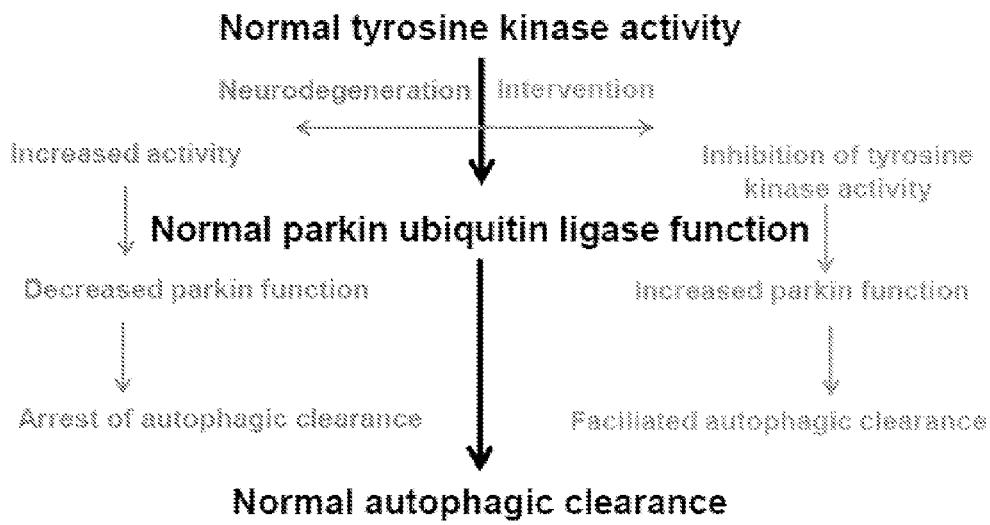
FIG. 1 is a diagram showing the cellular mechanisms associated with parkin activity in neurodegenerative conditions (left) and upon intervention with tyrosine kinase inhibitors (right). Intervention activates parkin activity to promote clearance of autophagic vacuoles.
Figure 2:
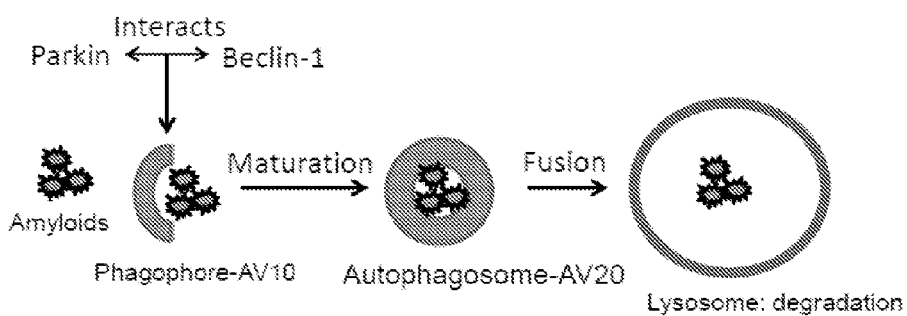
FIG. 2 is a diagram showing that amyloid accumulation leads to autophagic induction and sequestration in phagophores. In transgenic or amyloid expressing animals parkin interaction with beclin-1 is reduced, leading to decreased maturation of phagophore into autophagosomes and autophagic defects. Kinase inhibition activates parkin and increases its interaction with beclin-1, resulting in maturation of phagophores into phagosomes and clearance. Subcellular fractionation via metrazimide gradients to isolate the phagophore (AV-10), autophagosomes (AV-20) and the lysosomes was used to show how the cell handles amyloid accumulation and clearance.
Figure 3:
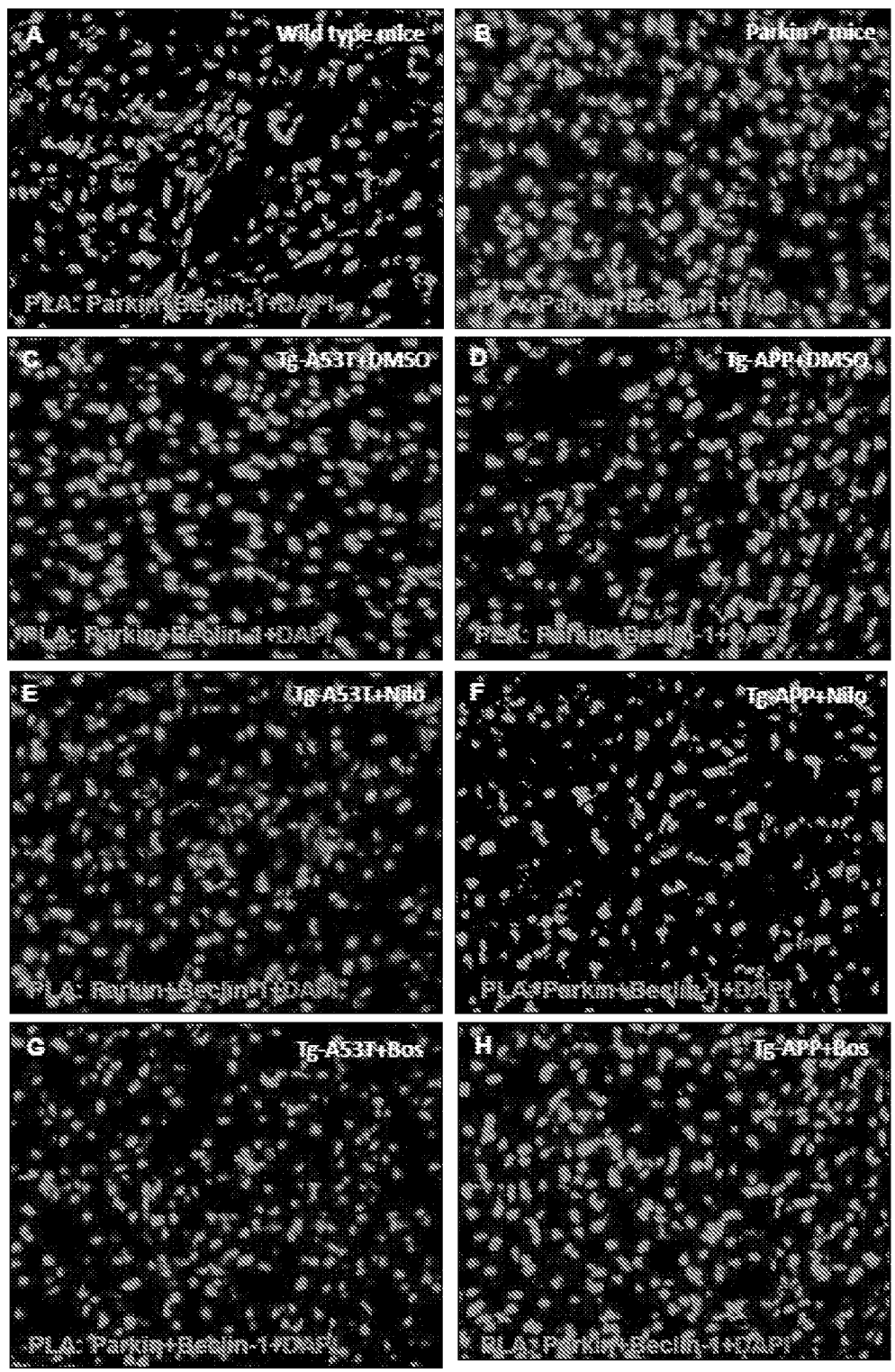
FIG. 3 shows that parkin interacts with beclin-1 in wild type but not parkin−/− mice: Proximity Ligation Assay (PLA) in situ on 20 mm thick brain sections showed parkin and beclin-1 interaction in A) C57BL/6 mice but not B) parkin−/− mice (control), indicating that parkin interacts with beclin-1. PLA in situ on 20 mm thick brain sections showed parkin and beclin-1 interaction in C) Tg-A53T and D) Tg-APP mice treated with DMSO, E) Tg-A53T and F) Tg-APP treated with 10 mg/kg nilotinib for 3 weeks, G) Tg-A53T and H) Tg-APP treated with 5 mg/kg bosutinib for 3 weeks.
Figure 4:
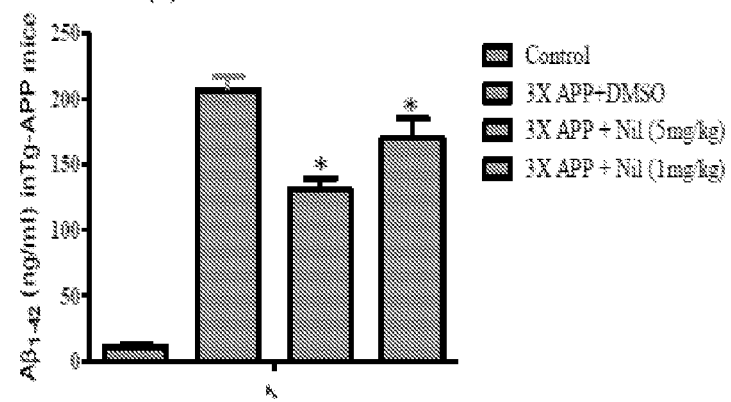
FIG. 4 is a graph representing ELISA levels of human $A\beta_{1-42}$ in brain lysates of triple mutant APP-AD mice (Tg-APP) treated with either 1 mg/kg or 5 mg/kg Nilotinib once every two days for 6 weeks. N=10 animals. P<0.05. ANOVA, with Neuman Keuls multiple comparison. An asterisk indicates a significant difference compared to DMSO. Bars are mean±SD.
Figure 5:
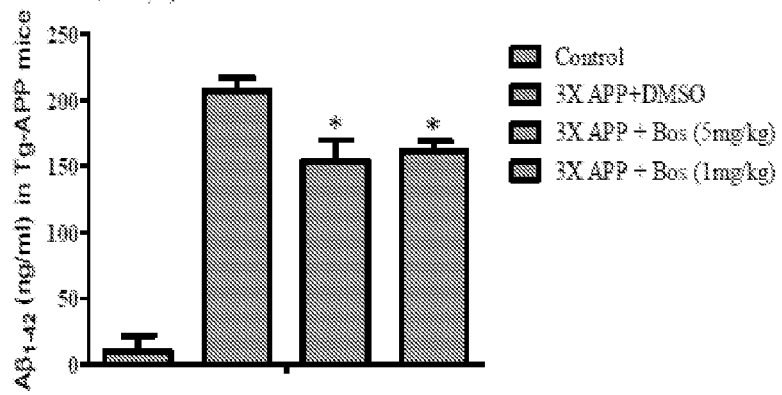
FIG. 5 is a graph representing ELISA levels of human $A\beta_{1-42}$ in brain lysates of triple mutant APP-AD mice (Tg-APP) treated with either 1 mg/kg or 5 mg/kg bosutinib once every two days for 6 weeks. N=10 animals. P<0.05. ANOVA With Neuman Keuls multiple comparison. An asterisk indicates a significant difference as compared to DMSO. Bars are mean±SD.
Figure 6:
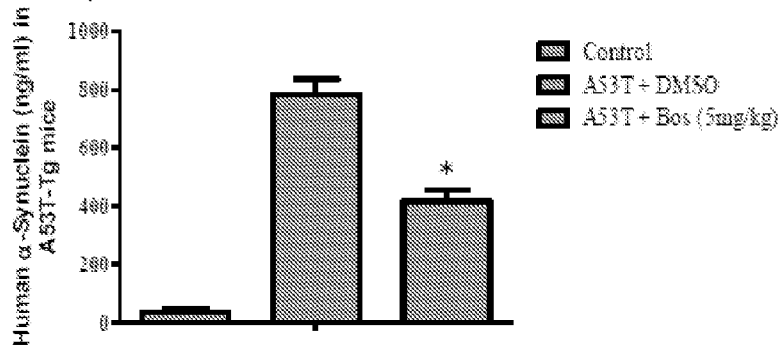
FIG. 6 is a graph representing ELISA levels of human α-synuclein in brain lysates of A53T mice (A53T-Tg) treated with 5 mg/kg Bosutinib once a day for 3 weeks. N=10 animals. P<0.05. ANOVA, with Neuman Keuls multiple comparison. An asterisk indicates a significant difference as compared to DMSO. Bars are mean±SD.
Figure 7:
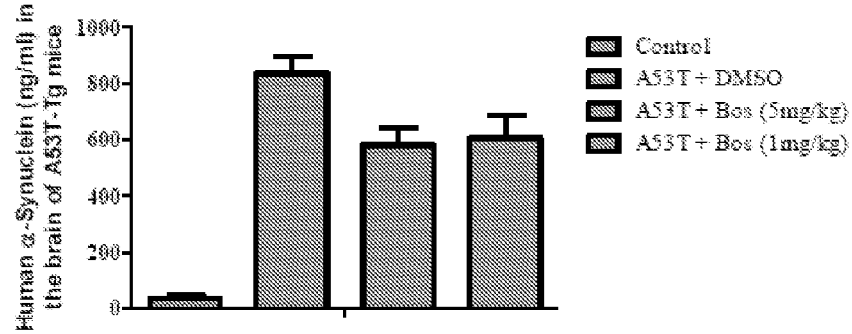
FIG. 7 is a graph representing ELISA levels of human α-synuclein in brain lysates of A53T mice (A53T-Tg) treated with either 1 mg/kg or 5 mg/kg Bosutinib once every 2 days for 6 weeks. N=10 animals. P<0.05. ANOVA, with Neuman Keuls multiple comparison. An asterisk indicates a significant difference as compared to DMSO. Bars are mean±SD.
Figure 8:
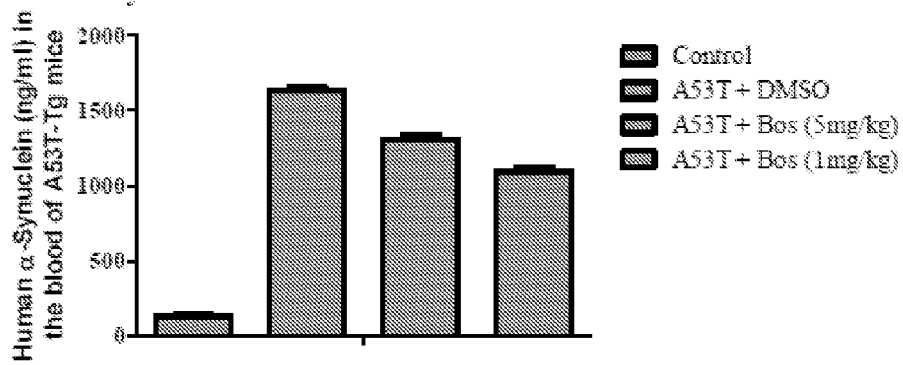
FIG. 8 is a graph representing ELISA levels of human α-synuclein in blood of A53T mice (A53T-Tg) treated with either 1 mg/kg or 5 mg/kg Bosutinib once every 2 days for 6 weeks. N=10 animals. P<0.05. ANOVA, with Neuman Keuls multiple comparison. An asterisk indicates a significant difference as compared to DMSO. Bars are mean±SD.
Figure 9:
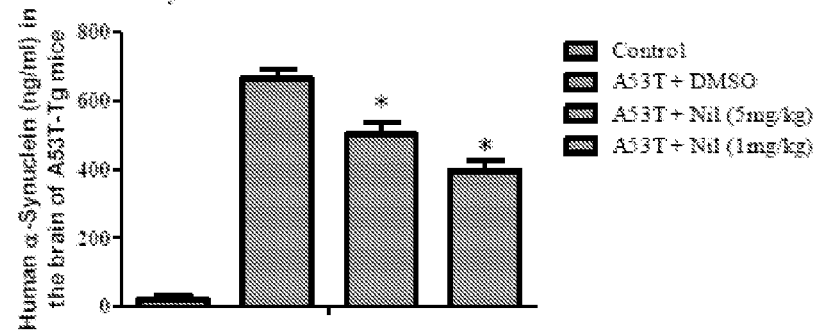
FIG. 9 is a graph representing ELISA levels of human α-synuclein in brain lysates of A53T mice (A53T-Tg) treated with either 1 mg/kg or 5 mg/kg Nilotinib once every second day for 6 weeks. N=10 animals. P<0.05. ANOVA, with Neuman Keuls multiple comparison. An asterisk indicates a significant difference as compared to DMSO. Bars are mean±SD.
Figure 10:
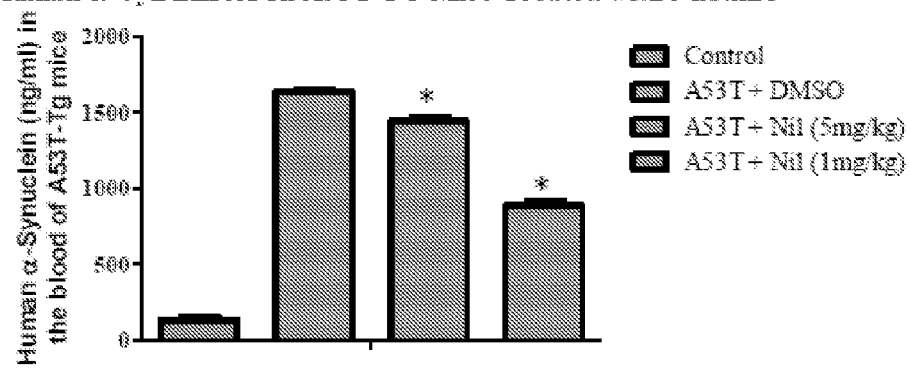
FIG. 10 is a graph representing ELISA levels of human α-synuclein in blood of A53T mice (A53T-Tg) treated with either 1 mg/kg or 5 mg/kg Nilotinib once every second day for 6 weeks. N=10 animals. P<0.05. ANOVA, with Neuman Keuls multiple comparison. An asterisk indicates a significant difference as compared to DMSO. Bars are mean±SD.
Figure 11:
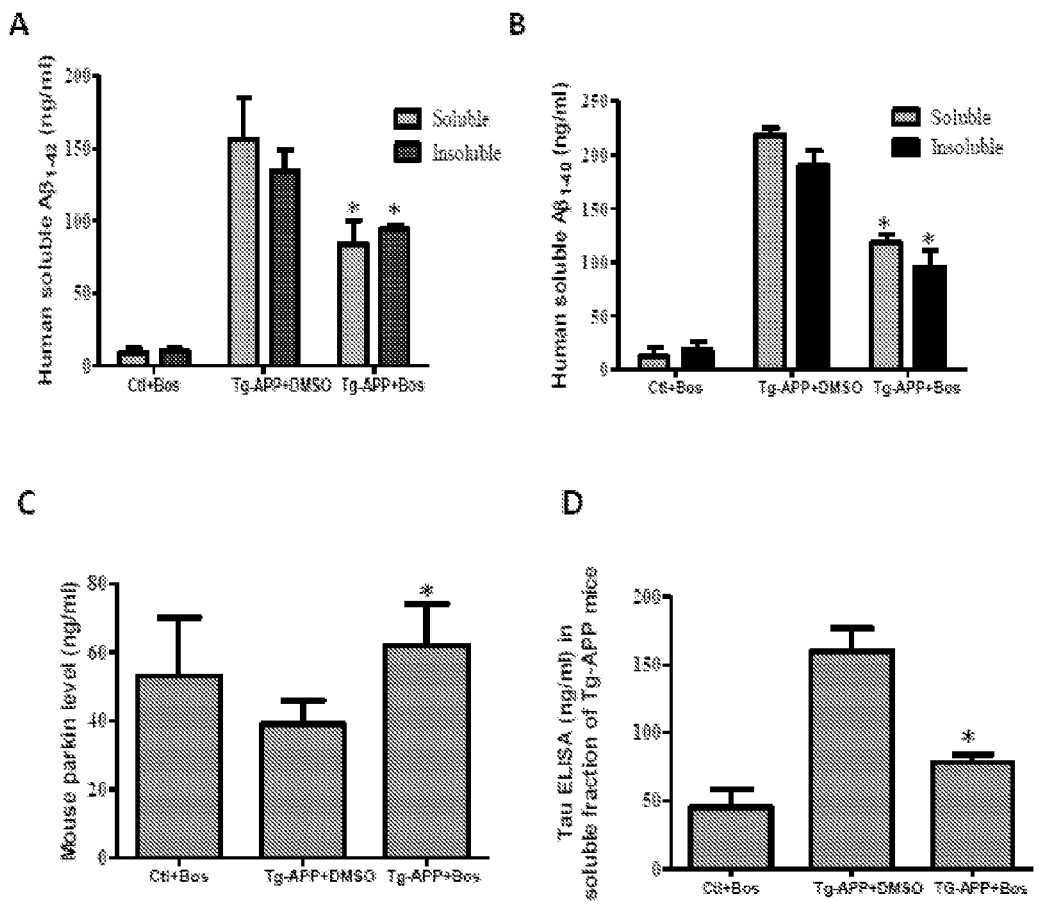
FIG. 11 shows A) a graph representing ELISA levels of human Aβ1-42, B) a graph representing human Aβ1-40 in brain lysates of triple mutant APP-AD mice (Tg-APP) treated with 5 mg/kg Bosutinib every day for 3 weeks, C) a graph representing ELISA levels of mouse parkin and D) a graph representing mouse phosphorylated Tau (Ser 396) in brain lysates of triple mutant APP-AD mice (Tg-APP) treated with 5 mg/kg Bosutinib every day for 3 weeks. N=10 animals. P<0.05. ANOVA With Neuman Keuls multiple comparison. An asterisk indicates a significant difference as compared to DMSO. Bars are mean±SD.

Methods for the animal experiments described herein are detailed in Examples 2-5. Cell culture experiments are referenced below and explained in Burns et al. (Human Molecular Genetics. 2009) and Rebeck et al. (*J. Biol. Chem.* 2010, 285:7440-7446). Additional details are provided in the brief description of the figures. Using these methods, cellular mechanisms (FIG. 1) associated with parkin activity in neurodegenerative conditions and upon intervention with tyrosine kinase inhibitors were studied. These studies revealed that tyrosine kinase inhibition activates parkin and increases its interaction with beclin-1, resulting in maturation of phagophores into phagosomes and clearance (FIG. 2). It was also shown that parkin interacts with beclin-1 in wild type, but not parkin−/− mice (FIG. 3). As shown in FIGS. 4-5, 3×APP mice treated with either Nilotinib or Bosutinib resulted in reduced $A\beta_{1-42}$ in the brain lysates of these mice as compared to treatment with DMSO. Also, as shown in FIGS. 6-8, treatment of A53T mice (A53T-Tg) with Bosutinib at different dosages and dosage schedules resulted in a decrease in human α-synuclein in the brain lystates of these mice, as compared to treatment with DMSO. Further, as shown in FIGS. 9-10, treatment of A53T mice (A53T-Tg) with Nilotinib at different dosages and dosage schedules resulted in a decrease in human α-synuclein in the brain lystates of these mice, as compared to treatment with DMSO. Decreases in human soluble $A\beta_{1-42}$ and human soluble $A\beta_{1-40}$ in the brain lysates of triple mutant APP-AD mice were also observed after treatment with Bosutinib (FIGS. 11A and B). Treatment with Bosutinib also resulted in increased parkin levels and decreased levels of phosphorylated Tau (FIGS. 11C and D).

In other experiments, M17 cells transfected with Tau cDNA were treated with Nilobinib and Tubacin (an HDAC6 inhibitor). Treatment with Nilotinib resulted in a decrease in human Tau, a decrease in human $A\beta_{1-42}$ and a decrease in α-synuclein as compared to transfected cells.

Figure 12:
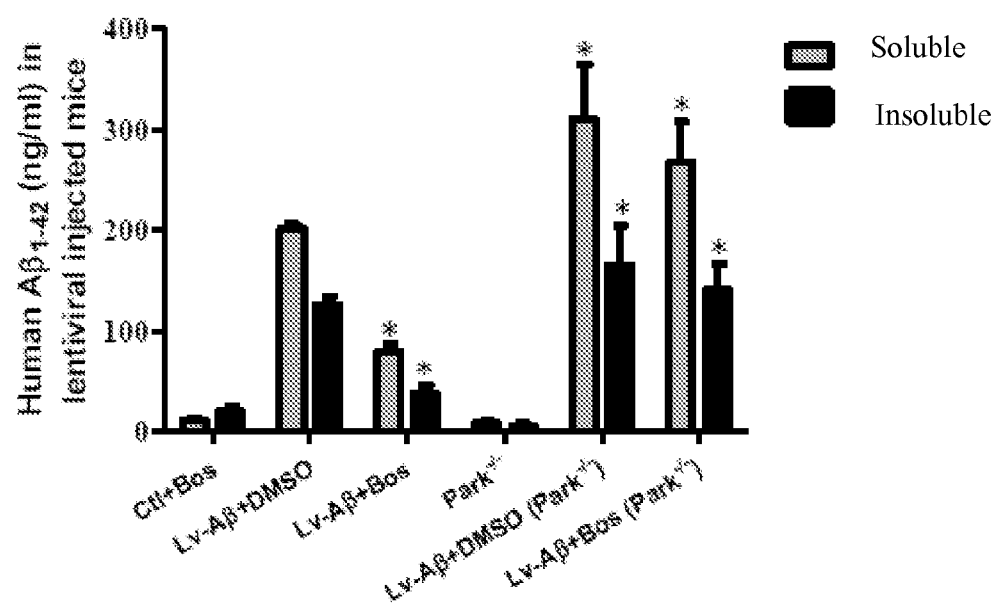
FIG. 12 is a graph representing ELISA levels of human $A\beta_{1-42}$ in brain lysates of lentiviral $A\beta_{1-42}$ injected mice (wild type and parkin-/- for 3 weeks and treated with 5 mg/kg Bosutinib every day for 3 additional weeks. N=10 animals. P<0.05. ANOVA with Neuman Keuls multiple comparison. An asterisk indicates a significant difference as compared to DMSO. Bars are mean±SD.

Treatment of lentiviral $A\beta_{1-42}$-injected mice with bosutinib also resulted in decreased levels of $A\beta_{1-42}$ in brain lysates (FIG. 12).

Figure 13:
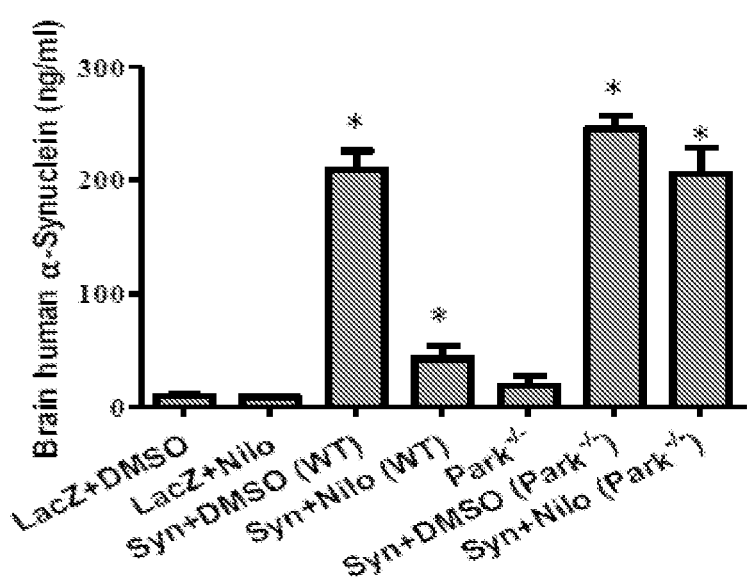
FIG. 13 shows that α-synuclein expression in the brain increases its blood level and tyrosine kinase inhibition reverses these effects in a parkin-dependent manner. Mice were injected stereotaxically (bilaterally) with lentiviral α-synuclein into the substantia nigra for 3 weeks. Then, half of the animals were injected with 10 mg/Kg nilotinib and the other half with DMSO. The effects of α-synuclein expression and tyrosine kinase inhibition on A) brain and B) blood levels of α-synuclein were compared. An asterisk indicates a significant difference as compared to DMSO. Bars are mean±SD.
Figure 13:
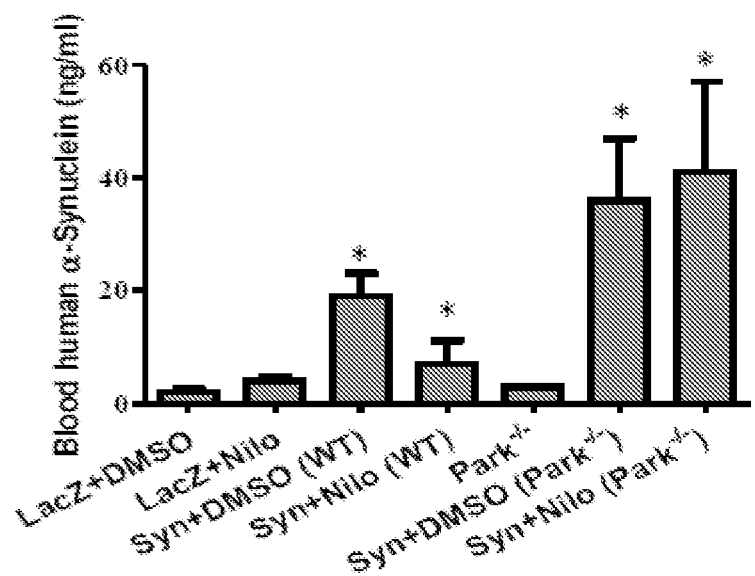

In another experiment, mice were injected stereotaxically (bilaterally) with lentiviral α-synuclein into the substantia nigra for 3 weeks. Then, half of the animals were injected with 10 mg/Kg nilotinib and the other half with DMSO. The effects of α-synuclein expression and tyrosine kinase inhibition on brain (FIG. 13A) and blood (FIG. 13B) levels of α-synuclein were compared. As shown in FIG. 13, α-synuclein expression in the brain increases its blood level and tyrosine kinase inhibition reverses these effects in a parkin-dependent manner.

Figure 14:
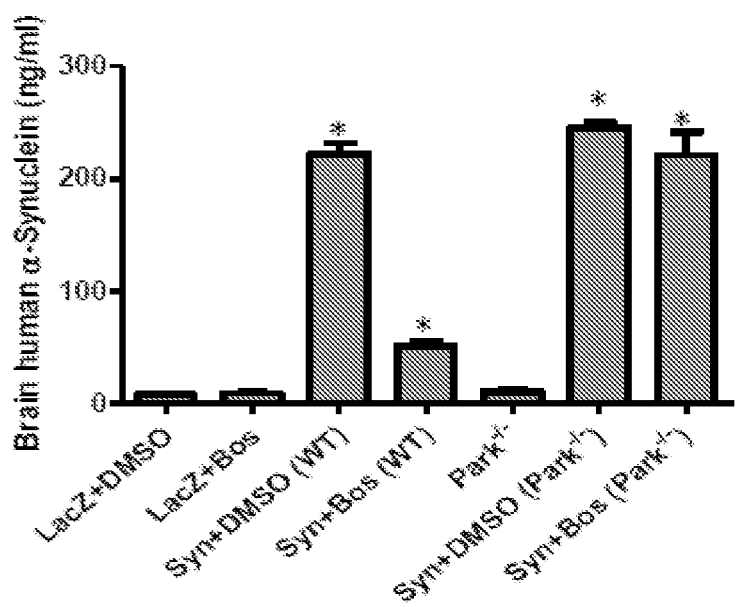
FIG. 14 shows that α-synuclein expression in the brain increases its blood level and tyrosine kinase inhibition reverses these effects in a parkin-dependent manner. Mice were injected stereotaxically (bilaterally) with lentiviral α-synuclein into the substantia nigra for 3 weeks. Then, half of the animals were injected with 5 mg/Kg bosutinib and the other half with DMSO. The effects of α-synuclein expression and tyrosine kinase inhibition on A) brain and B) blood levels of α-synuclein were compared. An asterisk indicates a significant difference as compared to DMSO. Bars are mean±SD.
Figure 14:
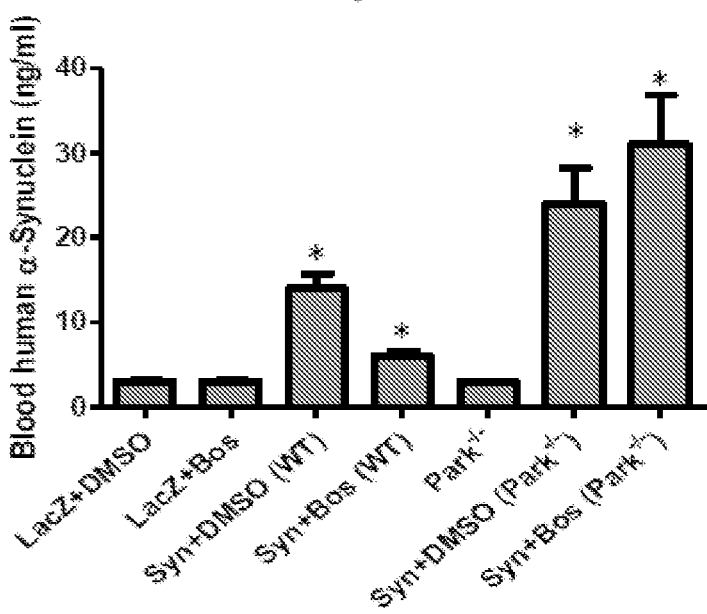

In another experiment, mice were injected stereotaxically (bilaterally) with lentiviral α-synuclein into the substantia nigra for 3 weeks. Then, half of the animals were injected with 5 mg/Kg Bosutinib and the other half with DMSO. The effects of α-synuclein expression and tyrosine kinase inhibition on brain (FIG. 14A) and blood (FIG. 14B) levels of α-synuclein were compared. As shown in FIG. 14, α-synuclein expression in the brain increases its blood level and tyrosine kinase inhibition reverses these effects in a parkin-dependent manner.

Figure 15:
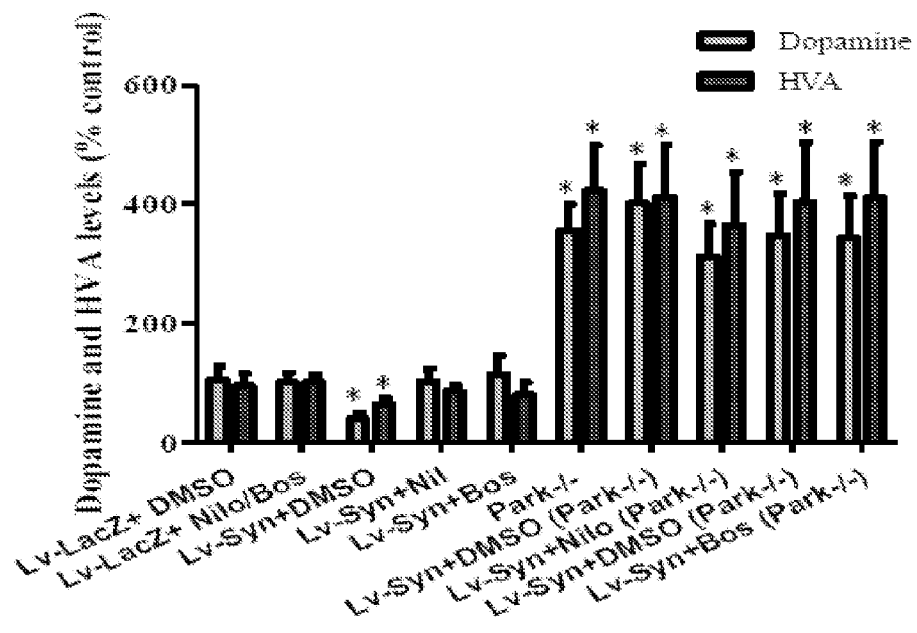
FIG. 15 shows that α-synuclein induced loss of dopamine and homovanillic acid (HVA) levels. Tyrosine kinase inhibition reversed these effects and improved motor performance. Mice were injected stereotaxically (bilaterally) with lentiviral α-synuclein into the substantia nigra for 3 weeks. Then, half the animals were injected with 10 mg/kg Nilotinib or 5 mg/Kg Bosutinib and the other half with DMSO. The effects of α-synuclein expression and tyrosine kinase inhibition on A) dopamine and homovanillic acid (HVA) levels (ELISA) were compared. The effects of treatment on B) motor performance were evaluated using rotarod. An asterisk indicates a significant difference as compared to DMSO. Bars are mean±SD.
Figure 15:
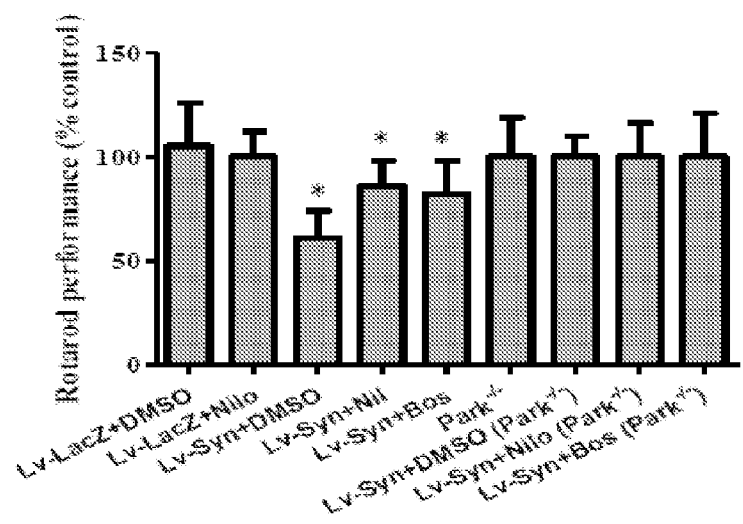

In another study, mice were injected stereotaxically (bilaterally) with lentiviral α-synuclein into the substantia nigra for 3 weeks. Then half the animals were injected with 10 mg/kg Nilotinib or 5 mg/Kg Bosutinib and the other half with DMSO. As shown in FIG. 185, the effects of α-synuclein expression and tyrosine kinase inhibition on dopamine and homovanillic acid (HVA) levels (ELISA) were compared. The effects of treatment on motor performance were evaluated using rotarod (FIG. 15B). This study shows that α-synuclein induced loss of dopamine and homovanillic acid (HVA) levels. Tyrosine kinase inhibition reversed these effects and improved motor performance.

In another study, transgenic A53T mice that express human α-synuclein throughout the brain (excluding substantia nigra) were injected with 10 mg/kg Nilotinib or 5 mg/Kg Bosutinib or DMSO once daily for 3 weeks. The effects of α-synuclein expression and tyrosine kinase inhibition on dopamine and homovanillic acid (HVA) levels (ELISA) were compared. The effects of treatment on motor performance were tested using rotarod. α-synuclein did not induce loss of Dopamine and HVA (due to absence of α-synuclein expression in dopamine producing neurons in these mice. Tyrosine kinase inhibition increased dopamine and HVA. Motor performance also increased.

Figure 16:
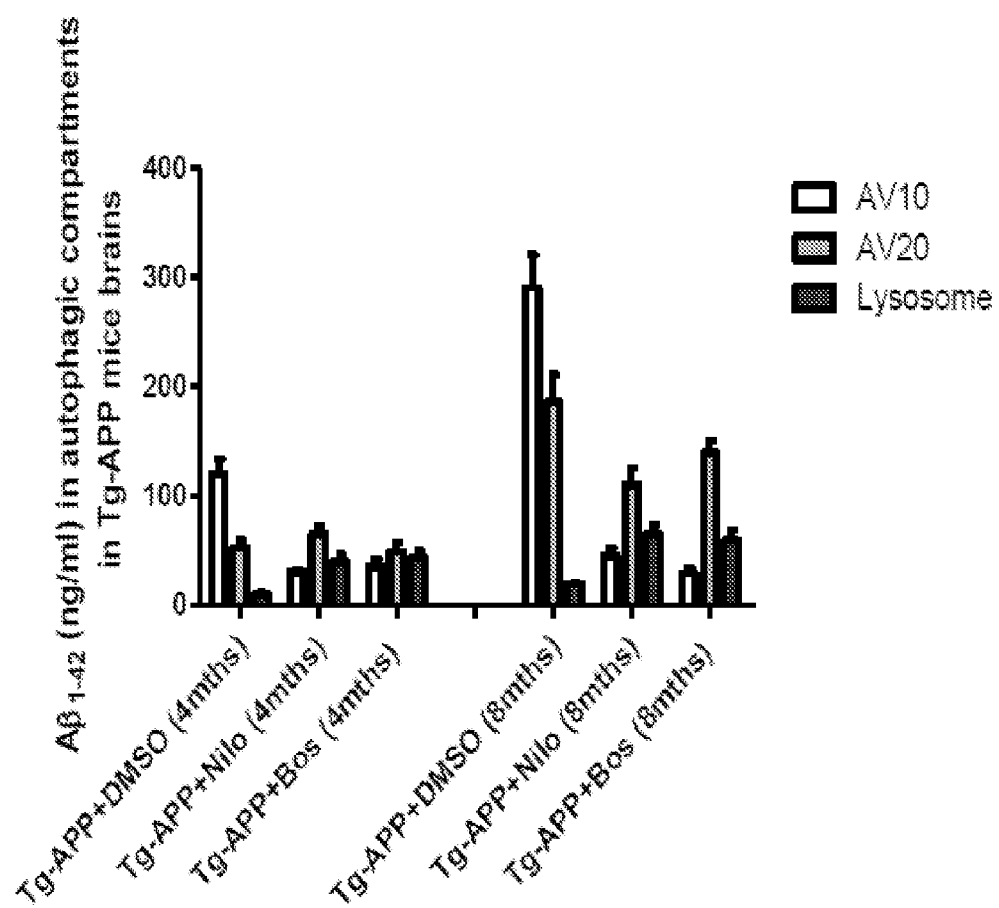
FIG. 16 shows that $A\beta_{1-42}$ accumulates in AV-10 in Tg-APP animals but drug treatment enhances autophagic clearance via deposition of $A\beta_{1-42}$ in AV-20 and lysosome. Histograms show $A\beta_{1-42}$ in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/Kg Bosutinib or DMSO once a day for 3 consecutive weeks. Brain tissues were fractionated to isolate AVs and human specific ELISA was performed to determine protein contents. N=5 animals per treatment.
Figure 17:
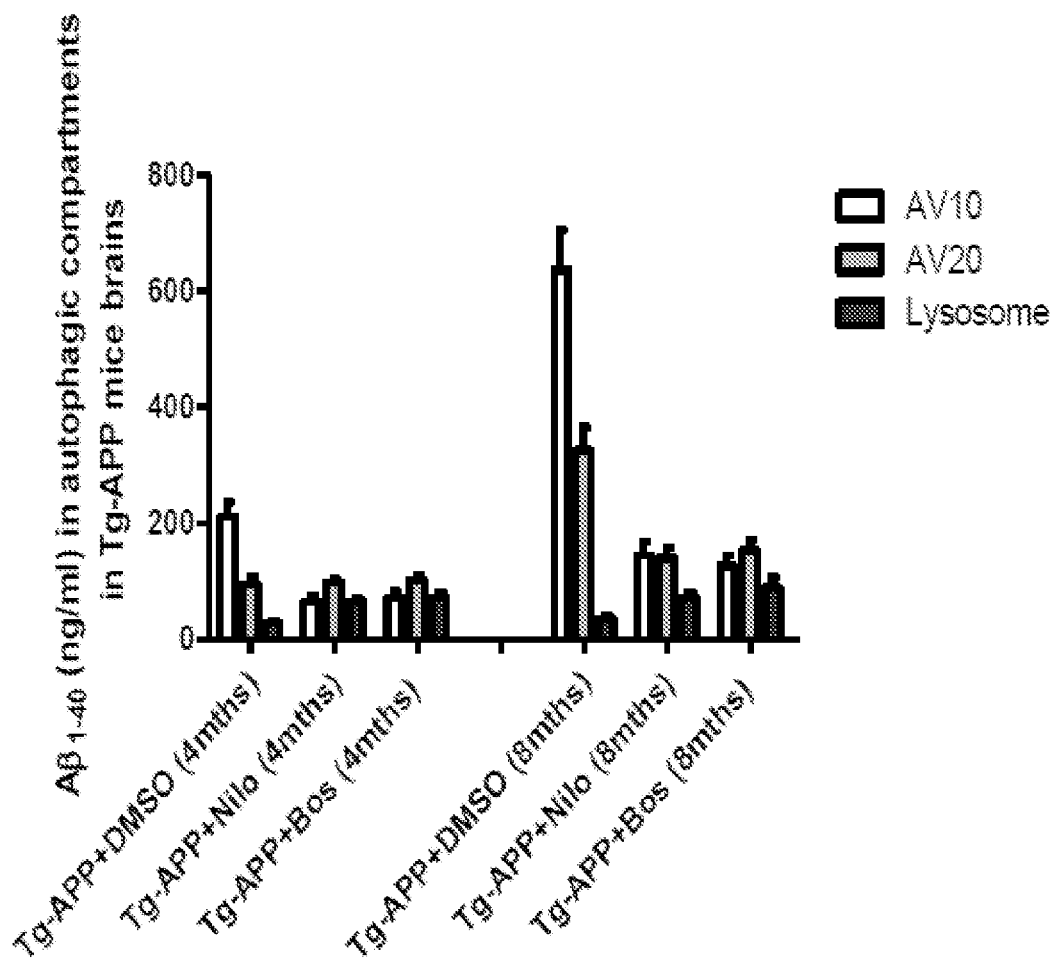
FIG. 17 shows that $A\beta_{1-40}$ accumulates in AV-20 in Tg-APP animals but drug treatment enhances autophagic clearance via deposition of $A\beta_{1-40}$ in AV-20 and lysosome. Histograms show $A\beta_{1-40}$ in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/Kg Bosutinib or DMSO once a day for 3 consecutive weeks. Brain tissues were fractionated to isolate AVs and specific ELISA was performed to determine protein contents. N=5 animals per treatment.
Figure 18:
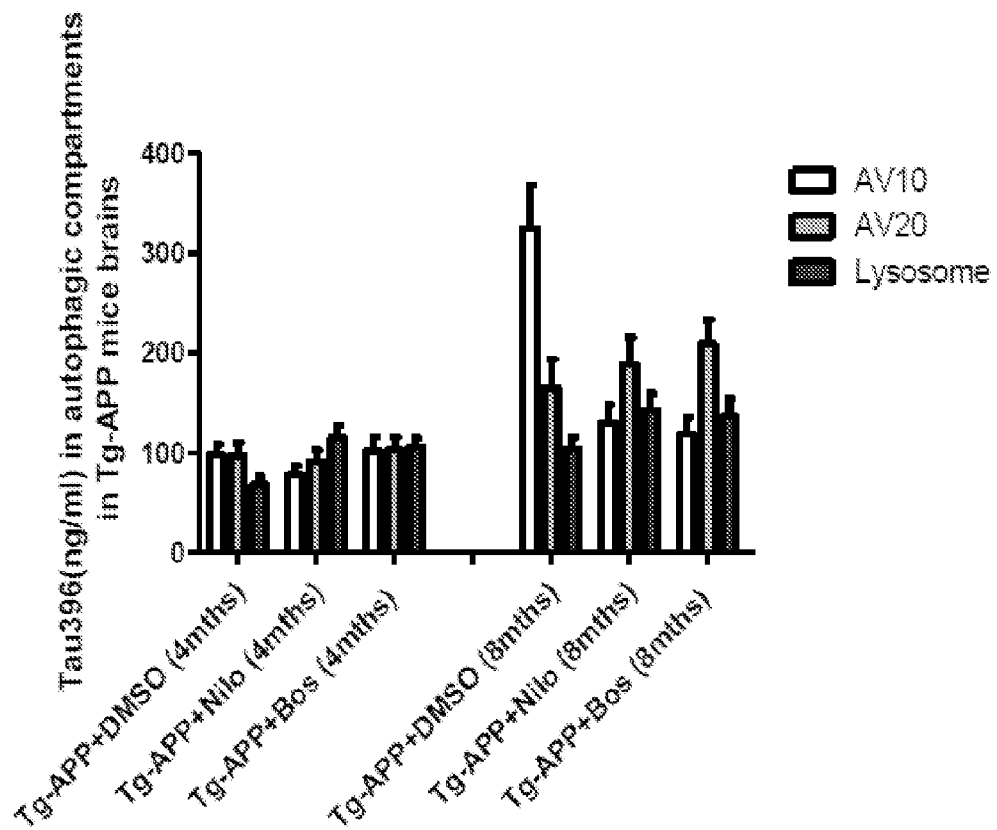
FIG. 18 shows that P-Tau accumulates in AV-10 in Tg-APP animals but drug treatment enhances autophagic clearance via deposition of p-Tau in AV-20 and lysosome, which contains degradative enzymes. Histograms show Tau hyper-phosphorylation (p-Tau) at serine 396 in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/Kg Bosutinib or DMSO once a day for 3 consecutive weeks. Brain tissues were fractionated to isolate AVs and mouse-specific ELISA was performed to determine protein contents. N=5 animals per treatment.
Figure 19:
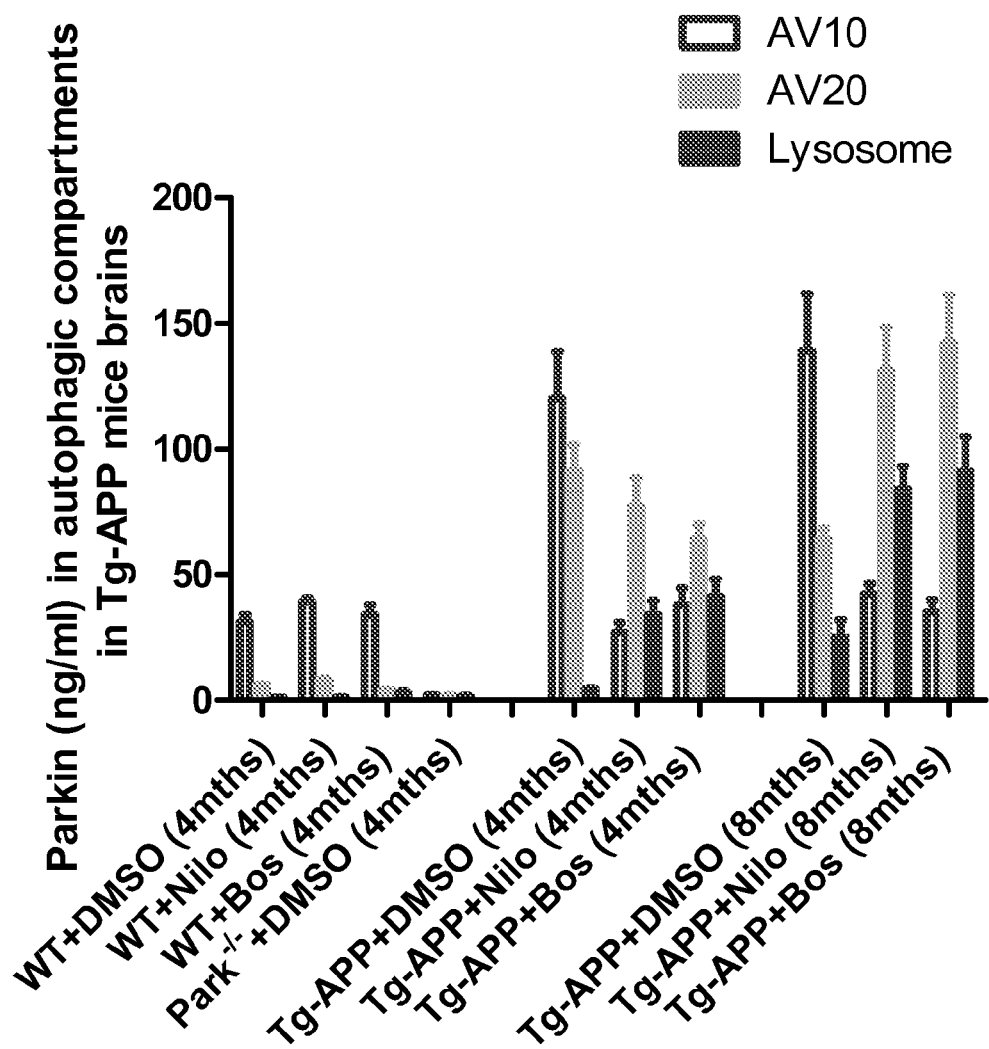
FIG. 19 shows that drug treatment increases parkin activity leading to protein clearance including parkin itself. Histograms show parkin in subcellular fractions, including autophagic vacuole-10 (AV-10; phagophores+autophagosomes), AV-20 (autophagosomes) and lysosomes. Transgenic 3×APP mice were injected IP with 10 mg/kg Nilotinib or 5 mg/kg Bosutinib or DMSO once a day for 3 consecutive weeks. Brain tissues were fractionated to isolate AVs and mouse specific ELISA was performed to determine protein contents. Parkin accumulates in AV-10 in Tg-APP animals but drug treatment enhances autophagic clearance via deposition of parkin in AV-20 and lysosome, which contains degradative enzymes. N=5 animals per treatment.

Studies were also performed to show that $A\beta_{1-42}$ and $A\beta_{1-40}$ accumulate in AV-10 in Tg-APP animals, but drug treatment enhances autophagic clearance via deposition of $A\beta_{1-42}$ or $A\beta_{1-40}$, respectively, in AV-20 and lysosomes (See FIGS. 16 and 17, respectively). Additional studies shows that p-Tau and parkin also accumulate in AV-10 in Tg-APP animals, but drug treatment enhances autophagic clearance via deposition of p-Tau or parkin in AV-20 and lysosomes (See FIGS. 18 and 19, respectively).

Figure 20:
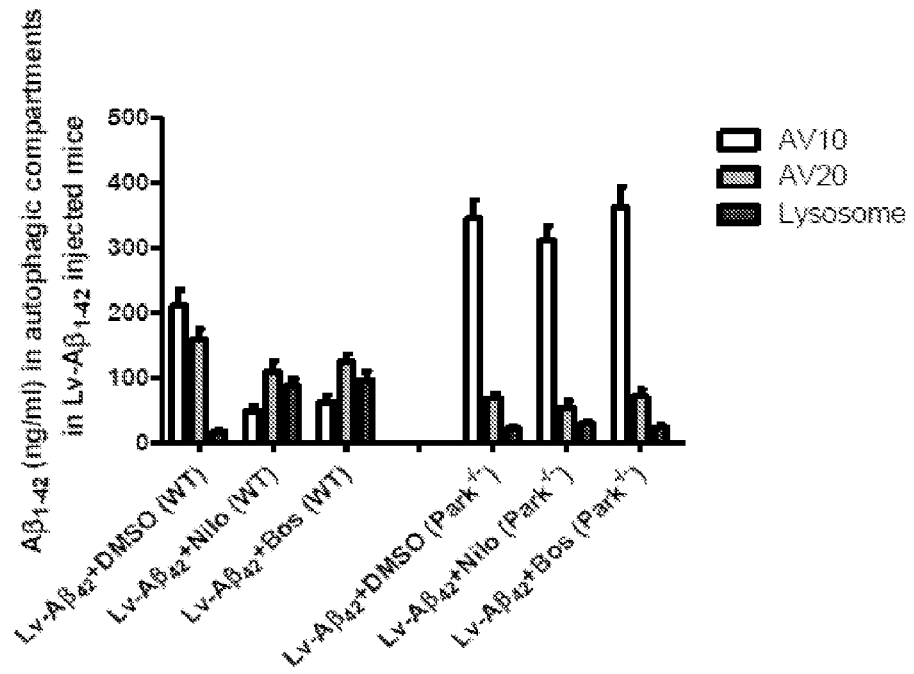
FIG. 20 shows that autophagic clearance is parkin-dependent. Histograms show $A\beta_{1-42}$ in subcellular fractions, including autophagic vacuole-10 (AV-10; phagophores+autophagosomes), AV-20 (autophagosomes) and lysosomes.

In another study, it was shown that $A\beta_{1-42}$ and p-Tau at serine 396 accumulate in the brains of mice injected with lentiviral $A\beta_{1-42}$, but drug treatment enhances autophagic clearance via deposition of $A\beta_{1-42}$ or p-Tau in AV-20 and lysosomes (See FIGS. 20 and 21, respectively). Also shown is that p-Tau and α-synuclein accumulate in the brains of mice injected with lentiviral α-synuclein, but drug treatment enhances autophagic clearance via deposition of p-Tau or α-synuclein in AV-20 and lysosomes (See FIGS. 22 and 23, respectively). Further shown is that α-synuclein and p-Tau accumulate in AV-10 of A53T brains, but drug treatment enhances autophagic clearance via deposition of p-Tau or α-synuclein in AV-20 and lysosomes (See FIGS. 24 and 25, respectively). Parkin also accumulates in the brains of A53T mice, but as shown in FIG. 26, drug treatment enhances autophagic clearance via deposition of parkin in AV-20 and lysosomes. As shown in FIG. 27, tyrosine kinase inhibition increases parkin activity and facilitates autophagic clearance of p-Tau. This process requires Tau stabilization of intact microtubules. Tyrosine kinase activation, p-Tau accumulation and impaired autophagy are recognized in neurodegeneration. Decreased parkin solubility and accumulation with intracellular Aβ and p-Tau in autophagic vacuoles in AD brains occurs, while exogenous parkin facilitates autophagic clearance in animal models.

In another study, wild type or parkin−/− mice were injected with lentiviral Tau±$A\beta_{1-42}$ for 3 weeks and treated IP with 10 mg/kg Nilotinib or DMSO once a day for 3 (additional) consecutive weeks. Brain tissues were fractionated to isolate AVs and human specific ELISA was performed to determine $A\beta_{1-42}$ contents. $A\beta_{1-42}$ accumulates in AV-10 in lentivirus injected brains but drug treatment enhances autophagic clearance via deposition of $A\beta_{1-42}$ in AV-20 and lysosome. It was also observed that autophagic clearance is parkin-dependent. Further, this study shows that Tau expression leads to $A\beta_{1-42}$ accumulation in AV10 and AV20, but not in lysosomes, indicating decreased fusion between autophagosomes and lysosomes.

In another study, wild type or Tau−/− mice were injected with lentiviral $A\beta_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and human specific ELISA was performed to determine protein contents. Results showed that $A\beta_{1-42}$ accumulates in AV-10 in lentivirus injected brains but drug treatment enhances autophagic clearance via deposition of $A\beta_{1-42}$ in AV-20 and lysosomes. Autophagic clearance is less efficient in Tau null animals with $A\beta_{1-42}$ accumulation in AV-10 and AV-20.

In another study, wild type or parkin−/− mice injected with lentiviral human Tau±$A\beta_{1-42}$ for 3 weeks and treated IP with 10 mg/kg Nilotinib or 30 μL DMSO once a day for 3 (additional) consecutive weeks. Brain tissues were fractionated to isolate AVs and mouse specific ELISA was performed to determine protein contents. Results showed that P-Tau at serine 396 accumulates in AV-10 in lentivirus injected brains but drug treatment enhances autophagic clearance via deposition of p-Tau in AV-20 and lysosomes, where it is degraded.

In another study, wild type or parkin−/− mice were injected with lentiviral Tau±Aβ$_{1-42}$ for 3 weeks and treated IP with 10 mg/kg Nilotinib or 5 mg/Kg Bosutinib or DMSO once a day for 3 (additional) consecutive weeks. Brain tissues were fractionated to isolate AVs and human specific ELISA was performed to determine protein contents. Results showed that P-Tau at serine 396 accumulates in AV-10 in lentivirus injected brains, but drug treatment enhances autophagic clearance via deposition of p-Tau in AV-20 and lysosomes, where it is degraded.

FIG. 28 shows A) phosphorylated c-Abl at tyrosine 412 (T412) and B) endogenous parkin expression merged in C) hippocampus of 6 month old C57BL/6 mice treated IP with DMSO daily for 3 weeks. FIG. 28 also shows D) decreased phosphorylated c-Abl at tyrosine 412 (T412) and E) increased endogenous parkin expression merged in F) hippocampus of 6 month old C57BL/6 mice treated IP with 5 mg/kg Bosutinib daily for 3 weeks.

FIG. 29 shows A) parkin and B) Aβ expression merged in C) cortex of 6 months old Tg-APP mice treated with DMSO or 5 mg/kg Bosutinib (D-F) once a day for 3 weeks. Using a different combination of antibodies (see figure G-I show expression of parkin (G) and Aβ (H) in the hippocampus of Tg-APP mice treated DMSO. J-H show the increase in parkin level in animals treated for 3 weeks once a day with Bosutinib (J) along with decreased plaque levels (K and L) in the hippocampus.

FIG. 30 shows plaque Aβ stained with 6E10 antibody and counterstained with DAB in the brain of Tg-APP animals treated IP with DMSO once a day for 3 weeks.

FIG. 31 shows plaque Aβ stained with 6E10 antibody and counterstained with DAB in the brain of Tg-APP animals treated IP with 5 mg/kg Bosutinib once a day for 3 weeks. A decrease in plaque formation in the animals treated with Bosutinib as compared to the animals treated with DMSO was observed.

FIG. 32 shows that Bosutinib decreases α-synuclein levels in transgenic mice expressing A53T throughout the brain. FIGS. 32A-D show human α-synuclein expression in lentiviral LacZ injected (for 3 weeks) substantia nigra with A) DMSO and B) 5 mg/kg Bosutinib once a day for 3 weeks. C and D show human α-synuclein expression in lentiviral α-synuclein injected (for 3 weeks) substantia nigra with C) DMSO and D) or Bosutinib once a day for 3 weeks. FIGS. 32E-H show tyrosine hydroxylase (TH) expression in lentiviral LacZ injected (for 3 weeks) substantia nigra with E) DMSO and F) 5 mg/kg Bosutinib once a day for 3 weeks. G and H show TH expression in lentiviral α-synuclein injected (for 3 weeks) substantia nigra with G) DMSO and H) or Bosutinib once a day for 3 weeks. synuclein decreases TH neurons and Bosutinib rescues these cells. FIGS. 32I-L show human α-synuclein expression in A53T mice in I) Cortex, J) Striatum, K) Brainstem and L) Hippocampus treated with DMSO for 3 weeks. FIGS. 32M-P show human α-synuclein expression in A53T mice in M) cortex, N) striatum, O) brainstem and P) hippocampus treated with 5 mg/kg Bosutinib for 3 weeks.

Performance tests were also done. As shown in FIGS. 33A and B, IP treatment with 5 mg/kg Bosutinib once daily for 3 weeks improved cognitive behavior in mice injected bilaterally with lentiviral Aβ$_{1-42}$ for 3 weeks prior to drug treatment. Bosutinib treated mice found the platform (A) but DMSO treated mice spent more time in NW area, where they were initially placed or the NE or SW area, without effectively finding platform area. Bosutninb improved cognitive performance in a parkin-dependent manner as the parkin−/− mice did not seem to learn much. FIG. 41B shows that Bosutinib treated mice traveled less distance with less speed but entered the platform area more than DMSO treated mice.

Studies also showed that parkin activity was increased in human M17 neuroblastoma cells after treatment with Nilotinib or Bosutinib (FIG. 34A). Treatment with Nilotinib also resulted in increased parkin levels in the brain lysates of wild type mice injected with lentiviral α-synuclein prior to treatment (FIG. 34B).

Western blot analysis of brain lysates from wild type mice treated with Bosutinib revealed that Bosutinib boosts autophagy and degrades ubiquitinated proteins. Western blot analysis of brain lysates from Tg-APP mice treated with 5 mg/kg Bosutinib for 3 additional weeks showed decreased levels of c-Abl, increased parkin and alteration of different molecular markers of autophagy, indicating that Aβ alters normal autophagy and Bosutinib boosts autophagy to clear Aβ$_{1-42}$ (FIG. 35). Western blot analysis of brain lysates from Tg-APP mice treated with Bosutinib showed alterations in the levels of molecular markers of autophagy (FIG. 36). Western blot analysis of brain lysates from Tg-APP mice treated with Bosutinib also showed decreased levels of C-terminal fragments (CTFs) and phosphor-tyrosine (FIG. 37).

Western blot analysis of brain lysates from Tg-APP mice treated with 5 mg/kg Bosutinib once a day for additional weeks showed decreased levels of different Tau isotopes (FIG. 38). Western blot analysis of brain lysates from wild type mice expressing lentiviral Aβ$_{1-42}$ (3 weeks) with and without Bosutinib (5 mg/kg) treatment for 3 additional weeks, showed decreased c-Abl and increased parkin levels with Bosutinib treatment, indicating that Aβ$_{1-42}$ activates c-Abl and Bosutinib activates parkin.

Western blot analysis of brain lysates from wild type mice expressing lentiviral Aβ$_{1-42}$ (3 weeks) with and without Bosutinib (5 mg/kg) treatment for 3 additional weeks showed levels of different molecular markers of autophagy, indicating that Aβ$_{1-42}$ alters normal autophagy and Bosutinib boosts autophagy to clear Aβ$_{1-42}$ (FIG. 39). Western blot analysis of brain lysates from wild type mice expressing lentiviral Aβ$_{1-42}$ (3 weeks) with and without Bosutinib treatment for 3 additional weeks, showed decreased levels of ubiquitin (top blot) and pan phospho-tyrosine (second blot) and SIAH2, indicating that Bosutinib is a broad tyrosine kinase inhibitor (FIG. 40).

Western blot analysis of brain lysates from wild type mice expressing lentiviral Aβ$_{1-42}$ (3 weeks) with and without Bosutinib treatment for 3 additional weeks showed decreased levels of different Tau isotopes (FIG. 41). Western blot analysis of brain lysates from wild type mice expressing lentiviral α-synuclein (3 weeks) with and without Bosutinib treatment for 3 additional weeks was also performed. This blots show increased α-synuclein in lentiviral synuclein injected animals, along with decreased c-Abl levels and phosphorylation, increased parkin levels and markers of autophagy, including P62, HDAC6, LC3 and ATG12 compared to loading controls tubulin and MAP2 (FIG. 42).

Example 2

Parkin Inactivation in Parkinson's Disease

To determine the role of parkin and its association with baseline autophagy in sporadic PD, human postmortem nigrostriatal tissues were analyzed via fractionation to determine protein solubility and the effects of parkin on autophagic clearance in lentiviral gene transfer animal models were investigated. Whether lentiviral expression of α-Synuclein affects autophagy and if parkin activity reverses α-Synuclein effects was investigated. Animal models expressing lentiviral α-Synuclein were studied and it was found that parkin expression decreases α-Synuclein levels in the absence of ubiquitination. Whether parkin expression regulates α-Synuclein clearance via autophagic degradation was studied.

Human Postmortem Brain Tissues.

Human postmortem caudate and midbrain regions from 22 PD patients and 15 age matched control subjects were obtained from John's Hopkins University brain bank. The age, sex, stage of disease and postmortem dissection (PMD) are summarized for each patient in Table 1 and 2. The cause of death is not known. To extract the soluble fraction of proteins, 0.5 g of frozen brain tissues were homogenized in 1×STEN buffer (50 mM Tris (pH 7.6), 150 mM NaCl, 2 mM EDTA, 0.2% NP-40, 0.2% BSA, 20 mM PMSF and protease and phosphatase cocktail inhibitor), centrifuged at 10,000 g for 20 min at 4° C., and the supernatants were collected. All samples were then analyzed by ELISA (see below) or Western blot using 30 μg of protein. To extract the insoluble fraction, the pellet was re-suspended in 4M urea solution and centrifuged at 10,000 g for 15 min, and the supernatant was collected and 30 μg of protein was analyzed by Western blot. Western blots were quantified by densitometry using Quantity One 4.6.3 software (Bio-Rad, Hercules, Calif.). Densitometry was obtained as arbitrary numbers measuring band intensity. Data were analyzed as mean±Standard deviation, using Two-tailed t-test (P<0.02) and ANOVA, Neumann Keuls with multiple comparisons (P<0.05) to compare PD and control groups.

Immunohistochemistry on slides from human patients was performed on 30 μm thick paraffin embedded brain slices de-paraffinized in Xylenes 2×5 minutes and sequential ethanol concentration, blocked for 1 hour in 10% horse serum and incubated overnight with primary antibodies at 4° C. After 3×10 minute washes in 1×PBS, the samples were incubated with the secondary antibodies for 1 hr at RT, washed 3×10 minutes in 1×PBS. Parkin was immunoprobed (1:200) with mouse anti-parkin (PRK8) antibody that recognizes a.a. 399-465 (Signet Labs, Dedham, Mass.) or rabbit polyclonal (1:200) anti-parkin (AB5112) antibody that recognizes a.a. 305-323 (Millipore) and counterstained with DAPI. Map 2 was probed (1:300) with mouse monoclonal antibody (Pierce). Glial Fibrillary Acid Protein (GFAP) was probed (1:200) with mouse (GA5) Mouse mAb #3670 (Cell Signaling) or (1:200) rabbit polyclonal (ab4674) antibody (Abcam). Tyrosine Hydroxylase (TH) was probed (1:100) with rabbit polyclonal (AB152) antibody (Millipore) and counterstained with DAB.

Stereotaxic Injection.

Lentiviral constructs were used to generate the animal models as explained in Burns et al. (*Hum. Mol. Genetics* 18: 3206-3216 (2009); Khandelwal et al. (*Mol. Neurodegener.* 5: 47 (2010) and Herman and Moussa (*Autophagy* 7:919-921 (2011). Stereotaxic surgery was performed to inject the lentiviral constructs into the striatum of 2-month old male Sprague-Dawley rats. N=8 animals were used in each treatment. A total of 116 animals were used in these studies. All procedures were approved by the Georgetown University Animal Care and Use Committee (GUACUC).

Western Blot Analysis.

To extract the soluble protein fraction, brain tissues were homogenized in 1×STEN buffer, centrifuged at 10,000×g for 20 min at 4° C., and the supernatants containing the soluble fraction of proteins were collected. To extract the insoluble fraction the pellet was re-suspended in 4M urea or 30% formic acid and adjusted to pH 7 with 1N NaOH and centrifuged at 10,000×g for 20 min at 4° C., and the supernatant containing the insoluble fraction was collected and analyzed by Western blot. Total parkin was immunoprobed (1:1000) with PRK8 antibody as indicated (Burns et al., 2009) and phospho-parkin was probed (1:1000) with anti-Ser 378 antibodies (Pierce). α-Synuclein was probed with rabbit monoclonal (1:1000) antibody (Santa Cruz). Autophagy antibodies, including beclin-1 (1:1000), autophagy like gene (Atg)-7 (1:1000), Atg12 (1:1000) and LC3-B (1:1000), were used to probe according to autophagy antibody sampler kit 4445 (Cell Signaling, Inc). Histone deacetylase 6 (HDAC6) was probed (1:500) using rabbit polyclonal anti-HDAC6 (Abcam). Rabbit polyclonal anti-SQSTM1/p62 (Cell Signaling Technology) was used (1:500). A rabbit polyclonal (Pierce) anti-LC3 (1:1000) and rabbit polyclonal (Thermo Scientific) anti-actin (1:1000) were used. LAMP-3 was probed (1:500) rabbit polyclonal antibody (Aviva Systems). Rabbit anti-ubiquitin (Santa Cruz Biotechnology) antibody (1:1000) was used. Mitochondrial protein COX-IV was probed (1:1000) with rabbit polyclonal (ab16056) antibody (Abcam) and human poly ADP-ribose polymerase (PARP-1) was probed (1:1500) with monoclonal (MA3-950) antibody (Pierce).

Immunohistochemistry—

These methods were performed on 20 micron-thick 4% paraformaldehyde (PFA) fixed striatal rat brain sections and compared between treatments. Parkin was probed (1:200) with Rabbit polyclonal antibody (Chemicon). Rabbit polyclonal LC3-B (1:100) was used to probe LC3-B (Cell Signaling, Inc). Thioflavin-S and nuclear DAPI staining were performed according to manufacturer's instructions (Sigma). Stereological methods—were applied by a blinded investigator using unbiased stereology analysis (Stereologer, Systems Planning and Analysis, Chester, Md.) to determine the total positive cell counts in 20 cortical fields on at least 10 brain sections (~400 positive cells per animal) as indicated in (Burns et al., 2009, Khandelwal et al., 2010, Herman and Moussa, 2011).

α-Synuclein, Parkin and p-Tau Enzyme-Linked Immunosorbent Assay (ELISA)—

Specific ELISA (Invitrogen) were performed using 50 μl (1 μg/μl) of brain lysates detected with 50 μl primary antibody (3 h) and 100 μl anti-rabbit secondary antibody (30 min) at RT. Parkin levels using specific human ELISA (MYBioSource), and p-Tau and α-Synuclein levels were measured using human specific ELISA (Invitrogen) according to manufacturers' protocols.

Subcellular Fractionation to Isolate Autophagic Vacuoles—

0.5 g of Frozen human or animal brains were homogenized at low speed (Cole-Palmer homogenizer, LabGen 7, 115 Vac) in 1×STEN buffer and centrifuged at 1,000 g for 10 minutes to isolate the supernatant from the pellet. The pellet was re-suspended in 1×STEN buffer and centrifuged once to increase the recovery of lysosomes. The pooled supernatants were then centrifuged at 100,000 rpm for 1 hour at 4° C. to extract the pellet containing autophagic vacuoles (AVs) and lysosomes. The pellet was then re-suspended in 10 ml (0.33 g/ml) 50% Metrizamide and 10 ml in cellulose nitrate tubes. A discontinuous Metrizamide gradient was constructed in layers from bottom to top as follows: 6 ml of pellet suspension, 10 ml of 26%; 5 ml of 24%; 5 ml of 20%; and 5 ml of 10% Metrizamide (Marzella et al., 1982). After centrifugation at 10,000 rpm for 1 hour at 4° C., the fraction floating on the 10% layer (Lysosome) and the fractions banding at the 24%/20% (AV 20) and the 20%/10% (AV10) Metrizamide inter-phases were collected by a syringe and examined.

Transmission Electron Microscopy—

Brain tissue were fixed in (1:4, v:v) 4% paraformaldehyde-picric acid solution and 25% glutaraldehyde overnight, and then washed 3× in 0.1M cacodylate buffer and osmicated in 1% osmium tetroxide/1.5% potassium ferrocyanide for 3 h, followed by another 3× wash in distilled water. Samples were treated with 1% uranyl acetate in maleate buffer for 1 h, washed 3× in maleate buffer (pH 5.2), then exposed to a graded cold ethanol series up to 100% and ending with a propylene oxide treatment. Samples are embedded in pure plastic and incubated at 60° C. for 1-2 days. Blocks are sectioned on a Leica ultracut microtome at 95 nm, picked up onto 100 nm formvar-coated copper grids, and analyzed using a Philips Technai Spirit transmission EM. All sections were acquired and analyzed by a blind investigator.

Results

Decreased Parkin Solubility in Postmortem Striatum of Sporadic PD Patients.

To determine the role of parkin in the brain of sporadic PD patients, human postmortem striatal (caudate) tissues from 12 PD patients and 7 age-matched controls as described in Table 1 were analyzed. ELISA measurement of soluble human parkin revealed a significant ($P<0.05$) decrease (36%) in parkin levels in PD caudate/striatum compared to control (FIG. 43A). Western blot analysis of soluble striatal extracts confirmed the decrease in parkin levels in PD patients compared to control (FIGS. 43B and C, 54%). No differences in parkin levels were detected in PD cortex. Probing with anti-ubiquitin antibody showed a higher smear of ubiquitinated proteins in PD striatum compared to control (FIG. 43B). However, all samples with PMD greater than 16 h showed significantly ($P<0.02$, two-tailed t-test) higher levels of ubiquitin (48%) in both groups and higher parkin levels (25%) with PMD greater than 13 h within the PD group. To further investigate whether the decreased degradation of proteins results in alteration of solubility, the insoluble proteins were extracted in 4M urea. An increase in the level of parkin was detected in the insoluble fraction (FIGS. 43D and E, 82%) in contrast to the soluble extract, which was hardly detected. Parkin phosphorylation at serine 378, which was not detected in the soluble fraction, was observed in the insoluble extract (FIGS. 43D and E, 114%). Additionally, more ubiquitinated proteins (FIG. 43D, 3rd blot) were also detected in the insoluble fraction. The variations among the samples are represented to show variation among individual samples, including soluble, insoluble and phospho-parkin (FIG. 43F). Taken together these data show decreased parkin solubility and increased phosphorylation in PD.

Altered Parkin Expression and Loss of Tyrosine Hydroxylase Neurons in the Nigrostriatum of Sporadic PD Patients.

To determine whether parkin expression is altered in sporadic PD, human postmortem midbrain sections from 10 PD patients and 8 control subjects as identified in Table 2 were examined. To determine the difference in parkin staining between PD and control brains, serial brain sections collected from each case were probed with human anti-parkin antibody (PRK8) that recognizes a.a. 399-495 and counterstained with either GFAP or DAPI. Confocal microscopy was used and diffuse parkin cytosolic staining was observed in the caudate (FIG. 44A) and within GFAP-stained astrocytes of control brain sections (FIG. 44B), and TH staining (FIG. 54C) was also observed in the caudate of a control subject (case 1683). However, intense cytosolic staining in the caudate (FIG. 44D, arrow), and within astrocytes (FIG. 44E), with diminished TH staining (FIG. 44F) were observed in a PD/AD patient (case 2215). To ascertain that parkin or GFAP staining were not due to auto-fluorescence in human slides, the slides were incubated with and without secondary and or primary antibodies and the absence of non-specific antibody binding was determined via confocal microscopy. Parkin expression was further examined in midbrain/SN brain regions. Diffuse parkin cytosolic staining (FIG. 44G) and within GFAP-stained astrocytes (FIG. 44H) with TH staining (FIG. 44I) were observed in serial sections of midbrain/SN of control brain (case 1855). Intense cytosolic parkin staining (FIG. 54J, arrow), and within astrocytes (FIG. 44K), with significantly diminished TH staining (FIG. 44L) were observed in a PD patient (case 2315). Another combination of antibodies using the AB5112 clone that detects parkin at a.a. 305-323 and GFAP antibodies was used to verify of these results. Intense cytosolic parkin staining (FIG. 44M, arrow), and within astrocytes (FIG. 44N), with significantly diminished TH staining (FIG. 44O) were observed in a PD/dementia patient (case 2243). MAP-2 was used as a neuronal marker and co-stained with parkin (DAPI counterstain) and TH. Parkin staining (FIG. 45A) was diffuse within the cytosol and was largely localized to MAP-2 labeled neurons (FIGS. 45B & C) in the midbrain/SN of a control subject (case 1277). TH staining was also detected in serial brain sections (FIG. 45D). However, more intense and less diffuse parkin staining was detected in the cytosol of DAPI stained cells (FIG. 45E) and parkin staining was localized to MAP-2 stained neurons (FIGS. 45F&G), with significantly decreased TH staining (FIG. 45H) in the midbrain/SN of a PD/Dementia patient (case 2267).

Alteration of Baseline Autophagy in Post-Mortem Striatum of PD Patients.

To determine whether the change in parkin solubility is associated with changes of baseline autophagy, the level of some autophagic markers in human PD striatal extracts was examined. The markers of the autophagic cascade were examined, including microtubule-associated light chain protein 3 (LC3). Probing with anti-LC3 antibody suggested an increase in LC3-II levels compared to LC3-I (FIGS. 45I&J, $1^{st}$ blot, 78%, N=12 PD and 7 control), indicating possible conversion and lipidation of LC3. LC3-I is abundant and stable in the brain, the ratio of LC3-II to LC3-I or the amount of LC3-II can be used to monitor the amount of autophagosome. LC3 is expressed as three isoforms in mammalian cells, LC3-A, LC3-B and LC3-C. Because LC3-II itself is degraded by autophagy the amount of LC3 was measured using an antibody specific for the LC3-B isoform. An increase in the level of LC3-B was detected in human striatal extracts from PD patients (N=12) compared to control (N=7) subjects (FIGS. 45I&J, $2^{nd}$ blot, 48%. $P<0.05$, ANOVA, Neumann Keuls). Subcellular fractionation was performed to isolate autophagic vacuoles and lysosomes the levels of α-Synuclein, parkin and p-Tau were measured using quantitative ELISA. First it was determined whether the subcellular fractionation assay successfully extracted autophagosomes from lysosomes in frozen human tissues. Western blot analysis on PD patients brain lysates showed the lysosome-associated membrane glycoprotein 3 (LAMP-3) in the floating fraction containing lysosomes (FIG. 45K, $1^{st}$ blot), while both the AV-10 and AV-20 fractions contained LC3-B (FIG. 45K, $2^{nd}$ blot), suggesting that frozen human brains contain autophagic vacuoles and our fractionation did isolate autophagosomes from lysosomes. Probing for mitochondrial marker cytochrome c oxidase-IV (COX-IV, FIG. 45K, $3^{rd}$ blot) and nuclear marker Poly ADP-ribose polymerase (PARP-1, FIG. 45K, $4^{th}$ blot) was also performed, and markers were detected in all fractions, suggesting that brain samples contained intact organelles. A comprehensive assay that clearly shows mitochondria in autophagosomes or lysosomes must be performed with both IHC co-labeling with LC3-COX-IV (autophagosome) or cathepsin-D-COX-IV (Lysosome) coupled with immuno-EM to determine mitochondrial accumulation in separate autophagic vacuoles. An ELISA was used to measure protein levels in subcellular extracts. The level of α-Synuclein was significantly increased ($P<0.05$, N=12 PD and 7 control) in AV-10 (31%) and AV-20 (64%) compared to control (FIG. 45L, ANOVA, Neumann Keuls), but no α-Synuclein was detected in the lysosomal fraction. Interestingly, ELISA measurement of parkin levels also showed a significant increase in AV-10 (FIG. 45M, 24%) and AV-20 (FIG. 45M, 23%) and a slight non-significant (9%) increase in the lysosome in PD (N=12) compared to control (N=7) subjects. The levels of p-Tau were measured as another protein marker that is occasionally associated with PD pathology. Similarly, no p-Tau was detected in the lysosome but the levels of p-Tau were significantly increased in AV-10 (54%) and AV-20 (64%) compared to control (FIG. 45N, N=12 PD and 7 control). These data show accumulation of un-degraded proteins in autophagosomes in PD.

Parkin Attenuates α-Synuclein-Induced Protein Accumulation in the Striatum.

Because increased parkin insolubility and decreased soluble parkin levels were observed in association with alteration of autophagy in PD striatum, it was sought to over-express parkin and determine whether functional parkin can reverse α-Synuclein effects on autophagic clearance. A gene transfer animal model targeting α-Synuclein expression to the striatum of 2-month old rats was used. Lentiviral parkin led to significant increases (FIG. 46A, 53% by densitometry, N=8, $P<0.05$) in parkin levels and lentiviral α-Synuclein led to significant increases (41%) in α-Synuclein levels. Co-expression of parkin with α-Synuclein attenuated the levels of monomeric α-Synuclein (FIG. 46A) and reduced the level of higher molecular weight proteins back to control (LacZ) 4 weeks post injection (Khandelwal et al., 2010). No changes in total parkin levels were observed in brains injected with lentiviral α-Synuclein (FIG. 46A, $1^{st}$ blot) and no-phosphorylated parkin was detected in rat brains. Independent studies were performed to confirm changes in α-Synuclein levels using quantitative ELISA specific for human α-Synuclein. The levels of human α-Synuclein were significantly increased (FIG. 46B, 54%, N=8) in the striatum of animals injected with lentiviral α-Synuclein compared to LacZ or parkin. Co-injection with lentiviral α-Synuclein and parkin reversed the levels of human α-Synuclein back to control. Lentiviral delivery of parkin into the striatum resulted in a significant increase in parkin when it was expressed alone (FIG. 46C, 44%, N=8) or in the presence of α-Synuclein (53%, N=8).

Changes in rat p-Tau were determined using ELISA. Expression of human α-Synuclein leads to a significant increase (FIG. 46D, 34%, N=8) in p-Tau in the rat striatum, but co-expression of parkin reverses p-Tau back to control. Lentiviral expression of α-Synuclein in the striatum leads to detection of thioflavin-S positive staining (FIG. 46F), compared to lentiviral parkin alone (FIG. 46F). However, co-expression of parkin with α-Synuclein prevents the appearance of thioflavin-S positive staining (FIG. 46G); suggesting that parkin attenuation of α-Synuclein levels can eliminate thioflavin-S positive species in this animal model. To ascertain that thioflavin-S staining is associated with α-Synuclein expression, striatal sections were stained with human α-Synuclein antibody and showed no α-Synuclein staining in sections cut serially with the thioflavin-S sections from lentiviral parkin injected rats (FIG. 46K), compared to an abundant level of α-Synuclein in lentiviral α-Synuclein injected rats, congruent with thioflavin-S staining (FIG. 46L), while parkin co-expression led to disappearance of human α-Synuclein in the rat striatum (FIG. 46M).

Wild Type Functional Parkin, not Mutant T240R, Mediates Clearance of α-Synuclein-Induced Autophagic Vacuoles.

It was sought to determine whether α-Synuclein expression can change normal autophagy, leading to formation of autophagic vacuoles in vivo. EM images of striatal sections showed no vacuoles in lentiviral LacZ injected animals (FIG. 47A) 4 weeks post injection. Lentiviral expression of α-Synuclein led to cytosolic accumulation of vacuoles (FIG. 47B, asterisks), suggesting that α-Synuclein expression alters autophagy in the rat striatum. Co-expression of parkin with α-Synuclein led to formation of autophagic vacuoles containing debris (FIG. 47C). To ascertain whether parkin function mediates clearance of autophagic vacuoles, non-functional T240R parkin was used, which is a mutant form that loses its E3 ubiquitin ligase activity, leading to ARJPD. Co-expression of mutant T240R parkin with α-Synuclein did not prevent the accumulation of cytosolic vacuoles (FIG. 47D, asterisks), suggesting that parkin mediates autophagic clearance via its E3 ubiquitin ligase function.

Levels of human α-Synuclein and p-Tau were measured using quantitative ELISA in subcellular fractions. A significant increase (62%, $P<0.05$, N=5) in the level of α-Synuclein was detected in AV-10 (FIG. 47E) and AV-20 (19%) compared to LacZ injected animals. However, co-expression of parkin eliminated α-Synuclein from AV-10 and significantly increased its levels in AV-20 (45%) and lysosomes (24%) compared to LacZ (FIG. 47E). Co-expression of α-Synuclein with T240R resulted in significantly elevated (51%) levels of α-Synuclein in AV-10, and unlike wild type parkin, failed to show any deposition in AV-20, which is enriched in autophagosomes or lysosomes. Significantly increased levels ($P<0.05$, N=5) of p-Tau were detected in AV-10 in animals injected with α-Synuclein (34%) or α-Synuclein+T240R (39%) compared to LacZ. However, wild type parkin expression led to a significant increase of p-Tau in AV-10 (19%) and lysosome (21%) compared to LacZ, α-Synuclein and α-Synuclein+T240R (FIG. 47F). No parkin as measured by ELISA was detected in subcellular fractions in these animal models, suggesting that parkin accumulation in autophagic vesicles can take place over a protracted time period in PD.

Functional Parkin, not Mutant T240R, Regulates Autophagic Clearance in the Striatum of α-Synuclein Expressing Animals.

To determine the mechanisms by which parkin can mediate clearance of autophagic vacuoles in the rat striatum, molecular markers of the autophagic pathway were examined. WB analysis showed no difference in beclin-1 levels in animals injected with lentiviral LacZ, parkin or α-Synuclein alone (FIG. 48A). A significant increase in beclin-1 levels (54% by densitometry, N=8, P<0.05) was observed when parkin was co-expressed with α-Synuclein, suggesting that parkin responds to α-Synuclein-induced stress. The levels of Atg7 and Atg12 were also significantly increased by 41% and 33%, respectively, in parkin+α-Synuclein injected animals (FIG. 48A) compared to animals injected with LacZ, parkin or α-Synuclein alone. No changes in LC3-B levels were observed between animals injected with lentiviral LacZ or parkin alone (FIG. 48B) but α-Synuclein expression significantly increased (51%) LC3 levels (FIG. 48B), suggesting increased amount of autophagosomes. Co-expression of parkin and α-Synuclein decreased the levels of LC3-B (29% by densitometry, N=8, P<0.05), suggesting degradation of LC3-B-containing autophagic vacuoles. No changes were also observed in HDAC6 levels (FIG. 48B) between animals injected with LacZ, parkin or α-Synuclein alone, but HDAC6 level was significantly increased (37%) levels (FIG. 48B) when animals were co-injected with parkin and α-Synuclein together, suggesting that parkin expression facilitates fusion between autophagosomes and lysosomes. No differences in the levels of molecular markers of autophagy were observed when mutant T240R parkin was injected either alone or with α-Synuclein. These data show that parkin E3 ubiquitin ligase activity may up-regulate protein levels of the beclin-1-dependent autophagic cascade, facilitating autophagic clearance.

The EM and WB data was supplemented with immunohistochemistry to determine the presence of LC3-B. Staining with anti-LC3-B antibody showed no reactivity in the striatum of animals injected with lentiviral parkin (FIG. 48C). Lentiviral expression of α-Synuclein led to an increase in immunoreactivity to LC3-B (FIG. 48D). Stereological counting of LC3-B positive cells revealed a significant increase (FIG. 48G. 43%, P<0.05, N=8) in striata injected with α-Synuclein. Co-injection of lentiviral parkin with α-Synuclein (FIG. 48E) resulted in disappearance of LC3-B from the striatum. To further ascertain that functional E3 ubiquitin ligase parkin mediates autophagic changes, LC3-B antibodies were co-injected with α-Synuclein and mutant T240R parkin (FIG. 48F) in striatal sections and no elimination of LC3-B staining was observed in these animals. Stereological counting of LC3-B stained cells in the striatum co-injected with α-Synuclein and T240R showed a significant increase (37%) in LC3-B reactivity compared to LacZ (FIGS. 48F&G). To further determine whether wild type parkin leads to clearance of ubiquitinated proteins via autophagy we stained with anti-P62 antibody. The levels of P62 were significantly (P<0.05, N=8) increased when α-Synuclein (41% by densitometry relative to actin) was expressed compared to LacZ (FIG. 48F). However, parkin co-expression led to complete disappearance of P62 staining, suggesting autophagic degradation of ubiquitinated proteins.

These studies show decreased parkin solubility in the striatum of sporadic PD patients, independent of early onset disease-causing mutations. In conclusion, decreased parkin solubility can reflect diminished parkin function, which can lead to alteration of baseline autophagy, including parkin, α-Synuclein and p-Tau clearance. Lentiviral expression of α-Synuclein leads to p-Tau and accumulation of autophagic vacuoles. These data demonstrate an association between α-Synuclein and autophagic dysfunction in PD, and indicate a beneficial role for parkin in autophagic clearance. Thus, parkin's role in autophagic clearance can be exploited as a therapeutic strategy in PD.

TABLE 1

Description and clinical diagnosis of human PD patients and control subjects's tissues analyzed by Western blot and ELISA.

| BRC # | FDX | Age | Sex | Race | PMD | FR Area |
|---|---|---|---|---|---|---|
| 399 | Control | 79 | F | W | 24 | Caudate |
| 417 | Control | 80 | F | W | 6 | Caudate |
| 487 | Control | 73 | M | W | 22 | Caudate |
| 515 | Control | 62 | M | W | 19 | Caudate |
| 705 | Control | 73 | M | W | 9 | Caudate |
| 1277 | Control | 80 | F | W | 8 | Caudate |
| 2052 | Control | 79 | M | W | 16 | Caudate |
| 1690 | PD | 76 | M | W | 18 | Caudate |
| 1731 | PD | 77 | M | W | 16 | Caudate |
| 2140 | PD with dementia | 84 | F | W | 11 | Caudate |
| 2067 | PD with dementia, cerebrovas. dis (NC) | 76 | M | W | 19 | Caudate |
| 2019 | PD with dementia, cerebrovas. dis | 83 | M | W | 16.5 | Caudate |
| 1989 | PD with dementia, LBD neocortical | 84 | M | W | 5 | Caudate |
| 2074 | PD, cerebrovascular disease | 85 | F | W | 9 | Caudate |
| 1758 | PD, DLB | 81 | M | W | 11 | Caudate |
| 1948 | PD, DLB | 77 | M | W | 5 | Caudate |
| 1796 | PD, Lewy Body CHG Limbic, porencephalic cyst | 81 | M | W | 8.75 | Caudate |
| 1877 | PD, Lewy Body CHG neocortical | 80 | M | W | 19 | Caudate |
| 1955 | PD, Lewy Body CHG neocortical | 84 | M | B | 13 | Caudate |

TABLE 2

Description and clinical diagnosis of human PD patients and control subjects stained with immonuhistohemistry.

| BRC # | FDX | CERAD | BRAAK | Age | Sex | Race | PMD | FX |
|---|---|---|---|---|---|---|---|---|
| 1062 | Control | | | 58 | M | B | 14 | Hippocampus MB |
| 1252 | Control | | | 70 | M | W | | Hippocampus MB |
| 1277 | Control | | 0 | 80 | F | W | 8 | Caudate, hippocampus, MB |
| 1352 | Control | | | 78 | F | | 14 | Caudate, hippocampus, MB |
| 1615 | Control | | | 72 | M | W | 20 | Caudate |
| 1683 | Control | | 1 | 91 | F | W | 8 | Caudate |
| 1855 | Control | | | 77 | M | W | | Caudate, hippocampus, MB |
| 2201 | Control | 0 | 2 | 85 | F | W | 27 | Caudate, hippocampus, MB |
| 2215 | PD with dementia, AD probable | B | 4 | 88 | M | W | 9 | Caudate, MB |
| 2235 | PD, tauopathy non-AD, cerebrovas. dis (NC) | | | 86 | F | W | 26 | Caudate, MB |
| 2243 | PD with dementia | 0 | 0 | 68 | M | W | 50 | Caudate, MB |
| 2253 | PD, contusion | 0 | 1 | 64 | F | W | 15 | Caudate, MB |
| 2267 | PD with dementia, neocortex | 0 | 1 | 75 | M | W | 22 | Caudate, MB |
| 2290 | PD | A | 2 | 82 | M | W | 53 | Caudate, MB |
| 2292 | PD with dementia, AD probable | B | 4 | 77 | M | W | 8 | Caudate, MB |
| 2312 | PD | 0 | 0 | 56 | M | W | 21 | MB |
| 2315 | PD | 0 | 2 | 84 | M | W | 8.5 | Caudate, MB |
| 2352 | PD with dementia, cerebrovas. dis (NC) | 0 | 2 | 83 | F | W | 163 | Caudate, MB |

Example 3

Parkin Inactivation in Alzheimer's Disease

The role of parkin in post-mortem brain tissues from 21 Alzheimer's disease patients and 15 control subjects was investigated. In order to determine the role of parkin in Aβ clearance, gene transfer animals expressing lentiviral $A\beta_{1-42}$ with and without parkin were generated and autophagic mechanisms were examined.

Materials and Methods

Human Postmortem Brain Tissues.

Human postmortem hippocampal and cortical regions from 21 AD patients and 15 age matched control subjects were obtained from John's Hopkins University brain bank. The age, sex, stage of disease and postmortem dissection (PMD) are summarized for each patient in Table 3 and 4. The cause of death is not known. To extract the soluble fraction of proteins, 0.5 g of frozen brain tissues were homogenized in 1×STEN buffer (50 mM Tris (pH 7.6), 150 mM NaCl, 2 mM EDTA, 0.2% NP-40, 0.2% BSA, 20 mM PMSF and protease cocktail inhibitor), centrifuged at 10,000 g for 20 min at 40C, and the supernatants were collected. All samples were then analyzed by ELISA (see below) or Western blot using 30 μg of protein. To extract the insoluble fraction, the pellet was re-suspended in 4M urea solution and centrifuged at 10,000 g for 15 min, and the supernatant was collected and 30 μg of protein was analyzed by Western blot. Western blots were quantified by densitometry using Quantity One 4.6.3 software (Bio Rad). Densitometry was obtained as arbitrary numbers measuring band intensity. Data were analyzed as mean±Standard deviation, using Two-tailed t-test ($P<0.02$) and ANOVA, Neumann Keuls with multiple comparisons ($P<0.05$) to compare AD and control groups. Insoluble parkin co-localizes with intracellular Aβ.

Immunohistochemistry on slides from human patients was performed on 30 μm thick paraffin embedded brain slices de-paraffinized in Xylenes 2×5 minutes and sequential ethanol concentration, blocked for 1 hour in 10% horse serum and incubated overnight with primary antibodies at 4° C. After 3×10 minute washes in 1×PBS, the samples were incubated with the secondary antibodies for 1 hr at RT, washed 3×10 minutes in 1×PBS. $A\beta_{1-42}$ was probed (1:200) with rabbit polyclonal specific anti-$A\beta_{1-42}$ antibody (Zymed) that recognizes a.a. 1-42, and (1:200) mouse monoclonal antibody (4G8) that recognizes a.a. 17-24 (Covance) and counterstained with DAPI. Parkin was immunoprobed (1:200) with mouse anti-parkin (PRK8) antibody that recognizes a.a. 399-465 (Signet Labs, Dedham, Mass.) and rabbit polyclonal (1:200) anti-parkin (AB5112) antibody that recognizes a.a. 305-622 (Millipore) and counterstained with DAPI. Because human tissues may exhibit a high level of auto-fluorescence, other experiments were performed with the absence of either primary or secondary antibodies to determine the specificity of immunostaining.

Stereotaxic Injection.

Lentiviral constructs were used to generate the animal models as explained in Rebeck et al. (J. Biol. Chem. 285, 7440-7446 (2010)) and the identity of the $A\beta_{1-42}$ species generated was confirmed by mass spectroscopy. Stereotaxic surgery was performed to inject the lentiviral constructs encoding LacZ, parkin or $A\beta_{1-42}$ into the M1 primary motor cortex of 2-month old male Sprague-Dawley rats. All animals were anesthetized (50 mg/kg body weight) with a cocktail of Ketamine and Xylazine (50:8). The stereotaxic coordinates were according to Paxinos and Watson rat brain atlas. Lentiviral stocks were injected through a Micro syringe pump controller (Micro4) using total pump (World Precision Instruments, Inc.) delivery of 6 µl at a rate of 0.2 µl/min. In one side of the brain animals were injected with 1) a lentiviral-LacZ vector at $2\times10^{10}$ multiplicity of infection (m.o.i); 2) with $1\times10^{10}$ m.o.i lentiviral-parkin and $1\times10^{10}$ m.o.i lentiviral-LacZ; 3) $1\times10^{10}$ m.o.i lentiviral-Aβ1-Insoluble parkin co-localizes with intracellular $Aβ_{1-42}$ and $1\times10^{10}$ m.o.i lentiviral-LacZ; or 4) and $1\times10^{10}$ m.o.i lentiviral-$Aβ_{1-42}$ and $1\times10^{10}$ m.o.i lentiviral-parkin. All procedures were approved by the Georgetown University Animal Care and Use Committee (GUACUC). A total of 84 rats were used in these studies.

Western Blot Analysis.

To extract the soluble protein fraction, brain tissues were homogenized in 1×STEN buffer (50 mM Tris (pH 7.6), 150 mM NaCl, 2 mM EDTA, 0.2% NP-40, 0.2% BSA, 20 mM PMSF and protease cocktail inhibitor), centrifuged at 10,000×g for 20 min at 40° C., and the supernatants containing the soluble fraction of proteins were collected. To extract the insoluble fraction the pellet was re-suspended in 4M urea or 30% formic acid and adjusted to pH 7 with 1N NaOH and centrifuged at 10,000×g for 20 min at 40C, and the supernatant containing the insoluble fraction was collected and analyzed by Western blot. The supernatants were analyzed by WB on SDS NuPAGE 4-12% Bis-Tris gel (Invitrogen, Inc.). Protein estimation was performed using Bio-Rad protein assay (Bio-Rad Laboratories Inc., Hercules, Calif.). Total parkin was immunoprobed (1:1000) with PRK8 antibody as indicated [43] and phospho-parkin was probed (1:1000) with anti-Ser 378 antibodies (Pierce). Aβ1-42 was immunoprobed with (1:600) mouse 6E10 antibody (Signet Labs, MA), analyzed alongside a synthetic peptide (AnaSpec, Calif., USA). Rabbit polyclonal antibodies anti-beclin (1:1000), autophagy like gene (Atg)-7 (1:1000), Atg12 (1:1000) and LC3-B (1:1000) were used to probe autophagy proteins using antibody sampler kit 4445 (Cell Signaling, Inc). Histone deacetylase 6 (HDAC6) was probed (1:500) using rabbit polyclonal anti-HDAC6 (Abcam). Rabbit polyclonal anti-SQSTM1/p62 (Cell Signaling Technology) was used (1:500). Lysosomal-associated membrane protein 3 (LAMP-3) was probed (1:500) with rabbit polyclonal antibody (ProteinTech). A rabbit polyclonal (Pierce) anti-LC3 (1:1000) and rabbit polyclonal (Thermo Scientific) anti-actin (1:1000) were used). Rabbit polyclonal (1:1000) Cyclin E (Thermo Scientific), rabbit polyclonal (1:1000) tubulin (Thermo Scientific) and mouse monoclonal (1:500) anti-ubiquitin (Santa Cruz Biotechnology) were used. Map 2 was probed (1:1000) mouse monoclonal antibody (Pierce).

Western blots were quantified by densitometry using Quantity One 4.6.3 software (Bio Rad). Densitometry was obtained as arbitrary numbers measuring band intensity. Data were analyzed as mean±standard deviation, using ANOVA, with Neumann Keuls multiple comparison between treatment groups. A total number of N=8 was used in each treatment.

Immunohistochemistry was performed on 20 micron-thick 4% paraformaldehyde (PFA) fixed cortical brain sections and compared between treatments. $Aβ_{1-42}$ was probed (1:200) with rabbit polyclonal specific anti-$Aβ_{1-42}$ antibody (Zymed). Rabbit polyclonal LC3-B (1:100) was used to probe LC3-B (Cell Signaling, Inc). Thioflavin-S and nuclear DAPI staining were performed according to manufacturer's instructions (Sigma).

Stereological methods were applied by a blinded investigator using unbiased stereology analysis (Stereologer, Systems Planning and Analysis, Chester, Md.) to determine the total positive cell counts in 20 cortical fields on at least 10 brain sections (~400 positive cells per animal) from each animal. These areas were selected across different regions on either side from the point of injection, and all values were averaged to account for the gradient of staining across 2.5 mm radius from the point of injection. An optical fractionator sampling method was used to estimate the total number of positive cells with multi-level sampling design. Cells were counted within the sampling frame determined optically by the fractionator and cells that fell within the counting frame were counted as the nuclei came into view while focusing through the z-axis.

Aβ, Parkin and p-Tau Enzyme-Linked Immunosorbent Assay (ELISA)—

Specific p-Tau, Aβ1-40 and $Aβ_{1-42}$ ELISA (Invitrogen) were performed using 50 µl (1 µg/µl) of brain lysates detected with 50 µl human p-Tau (AT8) or Aβ primary antibody (3 h) and 100 µl anti-rabbit Insoluble parkin co-localizes with intracellular Aβ antibody (30 min) at RT. Extracts were incubated with stabilized Chromogen for 30 minutes at RT and solution was stopped and read at 450 nm, according to manufacturer's protocol. Parkin levels were measured using specific human ELISA (MYBioSource) was measured using human specific ELISA (Invitrogen). All ELISA were performed according to manufacturers' protocols.

Subcellular Fractionation to Isolate Autophagic Vacuoles—

Animal brains were homogenized at low speed (Cole-Palmer homogenizer, LabGen 7, 115 Vac) in 1×STEN buffer and centrifuged at 1,000 g for 10 minutes to isolate the supernatant from the pellet. The pellet was re-suspended in 1×STEN buffer and centrifuged once to increase the recovery of lysosomes. The pooled supernatants were then centrifuged at 100.000 rpm for 1 hour at 40° C. to extract the pellet containing autophagic vacuoles (AVs) and lysosomes. The pellet was then re-suspended in 10 ml (0.33 g/ml) 50% Metrizamide and 10 ml in cellulose nitrate tubes. A discontinuous Metrizamide gradient was constructed in layers from bottom to top as follows: 6 ml of pellet suspension, 10 ml of 26%; 5 ml of 24%; 5 ml of 20%; and 5 ml of 10% Metrizamide. After centrifugation at 100,000 rpm for 1 hour at 40C, the fraction floating on the 10% layer (Lysosome) and the fractions banding at the 24%/20% (AV 20) and the 20%/10% (AV10) Metrizamide inter-phases were collected by a syringe and examined.

Transmission Electron Microscopy—

Brain tissue were fixed in (1:4, v:v) 4% paraformaldehyde-picric acid solution and 25% glutaraldehyde overnight, then washed 3× in 0.1M cacodylate buffer and osmicated in 1% osmium tetroxide/1.5% potassium ferrocyanide for 3 h, followed by another 3× wash in distilled water. Samples were treated with 1% uranyl acetate in maleate buffer for 1 h, washed 3× in maleate buffer (pH 5.2), then exposed to a graded cold ethanol series up to 100% and ending with a propylene oxide treatment. Samples are embedded in pure plastic and incubated at 60° C. for 1-2 days. Blocks are sectioned on a Leica ultracut microtome at 95 nm, picked up onto 100 nm formvar-coated copper grids, and analyzed using a Philips Technai Spirit transmission EM. All images were collected by a blind investigator.

Soluble Parkin is Decreased in Post-Mortem AD Brain Tissues.

To determine whether parkin levels are changed in other regions of AD brain, frozen post-mortem cortical tissues from 12 AD patients and 7 age matched control subjects were examined. The clinical diagnosis and post-mortem dissection (PMD) are summarized in Table 3. No information was provided about the cause of death. Western blot (WB) analysis with anti-parkin antibody (PRK8) revealed a significant decrease (52%, P<0.05) in soluble parkin level in the cortex of AD brain (FIGS. 49A & D). To ascertain that the decrease in parkin level is not due to neuronal loss, an anti-MAP-2 antibody was used as a neuronal marker and loading control (FIG. 49A). Quantitative parkin ELISA showed a significant decrease (46%) in soluble parkin levels (FIG. 49B, P<0.05), suggesting that parkin levels may be reduced in AD. Further analysis using two-tailed t-test (P<0.02) showed no differences within AD or control samples with age, but parkin levels were significantly (P<0.05) reduced (21%) in all samples with PMD greater than 15 hours.

Potential parkin function was investigated via examination of the level of ubiquitinated proteins and possible targets of parkin E3 ubiquitin ligase activity, including tubulin and Cyclin E. The levels of ubiquitinated proteins (FIG. 49C, 1st blot) was increased in WB of soluble AD cortical extracts compared to control subjects, suggesting lack of degradation of ubiquitinated proteins. No significant differences (t-test, P<0.02) were observed within the AD group, but variation was noticeable among control subjects, with older subjects showing smears of ubiquitinated proteins similar to AD (FIG. 49C, 1st blot lane 1 (case#399) and lane 3 (case#1277). Significantly increased levels of tubulin (2nd blot, 63%, FIG. 49D, P<0.05) and Cyclin E (3rd blot, 34%, FIG. 49D) were also observed in AD compared to control subjects. The insoluble protein fraction of human postmortem cortical tissues was then extracted in 4M urea and western blot was performed. Little parkin was detected in the insoluble fraction of control brains, but total parkin was significantly increased (130%, P<0.05) in AD brains, suggesting parkin insolubility (FIGS. 49E & F). We also detected significantly (P<0.05) increased levels (143%) of phosphorylated parkin at serine-378 relative to actin in AD brains but not control subjects (FIG. 49E, 2nd blot and FIG. 49F), suggesting that parkin phosphorylation may be associated with decreased solubility.

Parkin co-localizes with intraneuronal $A\beta_{1-42}$ in the hippocampus and cortex in AD. To investigate whether parkin expression is altered in human AD brains, a mouse monoclonal anti-parkin (PRK8) antibody that recognizes a.a. 399-465 and rabbit polyclonal anti-human $A\beta_{1-42}$ antibody that recognizes a.a. 1-42 were used. Hippocampal staining showed intraneuronal $A\beta_{1-42}$ (FIG. 50A) and parkin (FIG. 50B) in nuclear DAPI-stained neurons in control human subjects, and both parkin and $A\beta_{1-42}$ were detected within the same cells (FIG. 50C). The levels of intraneuronal expression of $A\beta_{1-42}$ were increased in the hippocampus of AD patients (FIG. 50D), without noticeable detection of amyloid plaques. Co-staining showed increased intracellular parkin levels (FIG. 50E) in AD hippocampus compared to control subjects (FIG. 50B), suggesting accumulation of parkin in AD brains. Both intracellular parkin and $A\beta_{1-42}$ were co-localized in hippocampal neurons (FIG. 50F). To ascertain the specificity of these results in human sections alternate rabbit polyclonal anti-parkin (AB5112) antibody that recognizes a.a. 305-622 and mouse monoclonal anti-human $A\beta_{1-42}$ (4G8) antibody that recognizes a.a. 17-42 were used. Hippocampal staining showed intraneuronal $A\beta_{1-42}$ (FIG. 50G) and parkin (FIG. 50H) in nuclear DAPI-stained neurons in AD, and both parkin and $A\beta_{1-42}$ were detected within the same cells (FIG. 50J) without noticeable detection of amyloid plaques.

Other brain regions were examined where extracellular $A\beta$ plaques were detected to ascertain whether parkin co-localizes with intracellular $A\beta_{1-42}$. Staining with anti-$A\beta_{1-42}$ antibody showed plaque formation in the entorhinal cortex as well as intracellular $A\beta_{1-42}$ accumulation (FIG. 51A), suggesting presence of both intracellular and extracellular $A\beta_{1-42}$ in AD cortex. Parkin staining was also observed within nuclear DAPI-stained neurons in the entorhinal cortex (FIG. 51B), but parkin co-localized only with $A\beta_{1-42}$ containing neurons and not with extracellular $A\beta_{1-42}$ plaques (FIG. 51C, arrows). Further analysis of the neocortex also resulted in detection of intracellular accumulation and plaque $A\beta_{1-42}$ (FIG. 51D) in AD, as well as intracellular parkin expression (FIG. 51E). Similarly, parkin and $A\beta_{1-42}$ were co-localized (FIG. 51F, arrows) intracellularly in AD cortex. An alternate combination of antibodies was used (as above) and plaque formation was detected in the cortex as well as intracellular $A\beta_{1-42}$ accumulation (FIG. 51G), suggesting presence of both intracellular and extracellular $A\beta_{1-42}$ in AD cortex. Parkin staining within nuclear DAPI-stained neurons in AD cortex was also observed (FIG. 51H), but parkin co-localized only with $A\beta_{1-42}$ containing neurons and not with extracellular $A\beta_{1-42}$ plaques (FIG. 51I, arrows).

Accumulation of Parkin, $A\beta$ and p-Tau in Autophagosomes in AD Brain.

To determine whether parkin co-staining with intracellular $A\beta_{1-42}$ is associated with autophagic activities in AD, anti-microtubule-associated light chain protein 3 (LC3) antibodies were used as probles and sub-cellular fractionation was performed to measure the levels of amyloid proteins in autophagic organelles using quantitative ELISA. Probing with anti-LC3 antibody suggested a significant increase in LC3-II compared to LC3-I (28%) levels (FIG. 52A, 1st blot & FIG. 52B), indicating possible lipidation of LC3. The amount of LC3 compared to actin was measured using an antibody specific for the LC3-B isoform. A significant increase (33%, P<0.05) in the level of LC3-B was detected in human cortical extracts from AD patients compared to control subjects (FIG. 52A, 2nd blot & FIG. 52B).

To ascertain that sub-cellular fractionation leads to isolation of autophagic vacuoles, WB was performed with lysosomal marker using anti-LAMP-3 antibody that showed lysosomal fraction in the top layer of Metrazimide gradient (FIG. 52C, top blot), and anti-LC3B (2nd blot), which detected autophagosomes in both the 10% (AV-10) and 20% (AV-20) gradient fractions. The levels of $A\beta$ and p-Tau were measured using quantitative ELISA in these fractions. A significant increase (89%, P<0.05) in the level of $A\beta_{1-42}$ was detected in AV-10 (FIG. 52D) and AV-20 (78%), which are enriched in autophagosomes in AD compared to control. Similarly, a significant increase (110%, P<0.05) in the level of $A\beta1-40$ was detected in AV-10 (FIG. 52E) and AV-20 (89%) in AD compared to control. No $A\beta$ was detected in the lysosomal fraction. The levels of p-Tau were measured as another protein marker associated with AD. No p-Tau was detected in the lysosome but the levels of p-Tau (AT8) were significantly increased in AV-10 (81%) and AV-20 (140%) compared to control (FIG. 52F). Because AV-20 is enriched in autophagosomes, these data show accumulation of un-degraded proteins in autophagosomes in AD. Surprisingly, the level of parkin was significantly increased (P<0.05) in AV-10 (64%) and AV-20 (52%) compared to control (FIG. 52G), but not in the lysosomal fraction, suggesting that accumulated parkin co-localizes with $A\beta$ and p-Tau in autophagic compartments.

Lentiviral $A\beta_{1-42}$ induces p-Tau and amyloidogenic protein and exogenous parkin reverses these effects. Because parkin insolubility and co-localization was detected with intraneuronal $A\beta_{1-42}$ in AD brain, lentiviral gene transfer was used to co-express $A\beta_{1-42}$ and parkin in the rat cortex and the effects of these proteins on autophagy were investigated. It was observed that lentiviral delivery led to an increase (50% by densitometry, N=8) of parkin expression (FIG. 53A, 1st blot) and $A\beta_{1-42}$ clearance 2 weeks post-injection of lentiviral parkin together with $A\beta_{1-42}$ (FIG. 53A, 2nd blot). No changes in total parkin levels were observed in brains injected with lentiviral $A\beta_{1-42}$ (FIG. 53A, 1st blot), and no phospho-parkin was detected in the insoluble 4M urea or 30% formic acid fractions. To determine parkin levels, quantitative ELISA was performed for human parkin in cortical lysates. Human parkin was significantly increased in parkin (34%, N=8) or parkin+$A\beta_{1-42}$ (38%) injected animals (FIG. 53B) compared to LacZ or $A\beta_{1-42}$ alone. Independent studies were then performed to determine the effects of parkin activity on $A\beta_{1-42}$ levels in the cortex, using human specific $A\beta_{1-42}$ ELISA. A significant increase (FIG. 53C, 7.8-fold, N=8, P<0.05, ANOVA, Neumann Keuls with multiple comparison) in the level of $A\beta_{1-42}$ was observed 2 weeks post-injection with lentiviral $A\beta_{1-42}$ into the cortex. Co-expression of parkin significantly decreased (6-fold) $A\beta_{1-42}$ levels, but $A\beta_{1-42}$ remained significantly higher (89%) compared to parkin or LacZ injected animals (FIG. 53E).

The effects of parkin on amyloidogenic proteins in animals expressing $A\beta_{1-42}$ were then determined. ELISA was performed and a significant increase in rat p-Tau (AT8) was observed in the cortex at 4 weeks but not 2 weeks post-injection (FIG. 53D). Thioflavin-S staining was performed to examine whether lentiviral $A\beta_{1-42}$ and p-Tau accumulation lead to formation of amyloidogenic proteins. Cortical brain sections showed thioflavin-S positive staining in $A\beta_{1-42}$-expressing animals (FIG. 53H) compared to lentiviral LacZ injected controls (FIG. 53E). Co-expression of parkin with $A\beta_{1-42}$ eliminated thioflavin-S positive staining in the cortex 4 weeks post-injection (FIG. 53G). These data show that parkin counteracts $A\beta_{1-42}$ induced amyloidogenic proteins.

Parkin Mediates Clearance of Autophagic Vacuoles Containing p-Tau and $A\beta_{1-42}$—

Whether parkin expression can mediate the clearance of $A\beta_{1-42}$-induced accumulation of autophagic vacuoles was determined. Electron microscopy scanning of cortical sections showed no accumulation of Insoluble parkin co-localizes with intracellular Aβ vacuoles in the cytosol of lentiviral LacZ (FIG. 54A) or lentiviral parkin (FIG. 54B) injected animals. Lentiviral expression of $A\beta_{1-42}$ led to cytosolic accumulation of autophagic vacuoles (FIG. 54C, arrows), suggesting induction of autophagy 2-week post-injection with lentiviral $A\beta_{1-42}$. Co-expression of lentiviral parkin with lentiviral $A\beta_{1-42}$ led to formation of double membrane vacuoles containing debris (FIG. 54D). These data suggest that parkin leads to autophagic clearance of lentiviral $A\beta_{1-42}$-induced vacuoles. Sub-cellular fractionation was performed and levels of $A\beta_{1-42}$ and p-Tau were measured using quantitative ELISA in these fractions. A significant increase (61%, P<0.05, N=5) in the level of $A\beta_{1-42}$ was detected in AV-10 (FIG. 54E) compared to LacZ, parkin or parkin+$A\beta_{1-42}$ injected animals, indicating that $A\beta_{1-42}$ alters normal autophagy, leading to accumulation of autophagosomes. However, co-expression of parkin led to clearance of $A\beta_{1-42}$ from AV-10 and significantly increased $A\beta_{1-42}$ levels in AV-20 (42%) and lysosomes (35%) compared to LacZ and parkin alone (FIG. 54E). Because $A\beta_{1-42}$ expression induced p-Tau at 4 weeks post-injection, levels of p-Tau (AT8) were also measured. Animals injected with $A\beta_{1-42}$ had a significant increase (31%) in p-Tau levels in AV-10 compared to LacZ, parkin and parkin-$A\beta_{1-42}$ (FIG. 54F). However, parkin+$A\beta_{1-42}$ expression led to clearance from AV-10 and significantly increased p-Tau levels in AV-20 (18%) and lysosomes (20%).

Parkin Regulates Autophagosome Clearance in $A\beta_{1-42}$-Expressing Animals.

To determine the mechanisms by which parkin can mediate clearance of autophagic vacuoles, molecular markers of the autophagic pathway, leading to autophagosomal clearance were examined. WB analysis showed no difference in beclin levels in animals injected with lentiviral LacZ, parkin or $A\beta_{1-42}$ (FIG. 55A). However, a significant increase in beclin levels (48% by densitometry, N=8, P<0.05) were detected when parkin was co-expressed with $A\beta_{1-42}$, suggesting that parkin responds to $A\beta_{1-42}$-induced stress. The levels of autophagy-related genes (Atgs) including Atg7 and Atg12 were also increased by 34% and 29%, respectively, in parkin+$A\beta_{1-42}$ injected animals (FIG. 55A) compared to animals injected with LacZ, parkin or $A\beta_{1-42}$ alone. Other markers of the autophagic cascade LC3 were examined. No changes in LC3-B levels were detected in animals injected with lentiviral LacZ or parkin alone (FIG. 55B). Lentiviral $A\beta_{1-42}$ expression lead to a significant increase (32%, N=8, P<0.05) in LC3-B levels, but parkin co-expression reversed the increase in LC3-B (FIG. 55B). A significant increase in histone deacetylase 6 (HADC6) levels (44%) were observed in animals injected with lentiviral parkin+$A\beta_{1-42}$ (FIG. 55B) compared to all other conditions. These data suggest that parkin responds to $A\beta_{1-42}$ stress via up-regulation of molecular markers of autophagy.

The EM and WB data was supplemented with immunohistochemistry to evaluate the appearance of LC3-B staining. Staining with anti-LC3-B antibody showed no reactivity in the cortex of animals injected with LacZ (FIG. 55C) or parkin (FIG. 55D). However, lentiviral injection of $A\beta_{1-42}$ increased LC3-B staining (FIG. 55E), in agreement with WB data. Co-injection of lentiviral parkin with $A\beta_{1-42}$ (FIG. 55F) led to disappearance of LC3-B staining Stereological counting of LC3-B positive cells revealed a significant increase (FIG. 55G. 52%, P<0.05, N=8) in cortices co-injected with $A\beta_{1-42}$ compared to other treatments, indicating that parkin activity regulates autophagosome clearance in $A\beta_{1-42}$ expressing animals. To further determine whether parkin leads to clearance of ubiquitinated proteins via autophagy anti-P62 antibody was used as a probe. The levels of P62 were significantly (P<0.05, N=8) increased when $A\beta_{1-42}$ (21% by densitometry relative to actin) was expressed compared to LacZ (FIG. 55F). However, parkin co-expression led to complete disappearance of P62 staining, suggesting autophagic degradation of ubiquitinated proteins.

These studies provide the first evidence of parkin inactivity and decreased solubility in AD. The present data show that parkin is inactivated and accumulates with $A\beta_{1-42}$ and p-Tau in autophagosomes in AD. This novel finding shows that decreased parkin E3 ubiquitin ligase activity can result in lack of autophagic clearance leading to accumulation of the autophagic vacuoles observed in AD brains. The gene transfer animal studies provide evidence that lentiviral $A\beta_{1-42}$ could inhibit autophagosome maturation similar to AD. In conclusion, these data demonstrate an association between parkin inactivation and co-localization with intraneuronal $A\beta_{1-42}$ with autophagic dysfunction, indicating a beneficial role for parkin in autophagic clearance. Parkin inactivation could lead to decreased autophagic clearance and accumulation of un-degraded amyloidogenic proteins in autophagosomes. Lentiviral expression of $A\beta_{1-42}$ leads to p-Tau and accumulation of autophagic vacuoles via inhibition of autophagosome maturation and/or impairment of transport of autophagic organelles. Parkin E3 ubiquitin ligase activity enhances autophagic flux and amyloid clearance, possibly through increased autophagosome maturation and recognition with lysosomes. Parkin's role in autophagic clearance could be exploited as a therapeutic strategy in neurodegenerative diseases.

TABLE 3

Summary and clinical diagnoses of AD patients and control subjects used for biochemistry studies.

| BRC # | FDX | Age | Sex | Race | PMD | FR Area |
|---|---|---|---|---|---|---|
| 399 | Control | 79 | F | W | 24 | Motor |
| 417 | Control | 80 | F | W | 6 | Motor |
| 487 | Control | 73 | M | W | 22 | Motor |
| 515 | Control | 62 | M | W | 19 | Motor |
| 705 | Control | 73 | M | W | 9 | Motor |
| 1277 | Control | 80 | F | W | 8 | Motor |
| 2052 | Control | 79 | M | W | 16 | Motor |
| 1390 | AD | 75 | M | | 12 | Motor |
| 1336 | AD | 82 | M | W | 10 | Motor |
| 1652 | AD | 85 | M | W | 18 | Motor |
| 1657 | AD | 82 | M | W | 15 | Motor |
| 1697 | AD/Infarcts | 86 | M | | 6 | Motor |
| 1671 | AD | 77 | M | W | | Motor |
| 1801 | AD | 75 | M | | 15 | Motor |
| 1870 | AD | 85 | M | W | 3.5 | Motor |
| 1997 | AD | 85 | M | W | 5.5 | Motor |
| 2070 | AD | 82 | M | W | 9 | Motor |
| 2076 | AD | 84 | F | W | 16 | Motor |
| 2078 | AD, cerebrovas. dis (NC) | 80 | M | | 16 | Motor |

TABLE 4

Summary and clinical diagnoses of AD patients and control subjects used for immuno-histochemistry studies.

| BRC # | FDX | CERAD | BRAAK | Age | Sex | Race | PMD | FX |
|---|---|---|---|---|---|---|---|---|
| 1062 | Control | | | 58 | M | B | 14 | Hippocampus, MB |
| 1252 | Control | | | 70 | M | W | | Hippocampus, MB |
| 1277 | Control | | 0 | 80 | F | W | 8 | Caudate, hippocampus, MB |
| 1352 | Control | | | 78 | F | | 14 | Caudate, hippocampus, MB |
| 1615 | Control | | | 72 | M | W | 20 | Caudate |
| 1683 | Control | | 1 | 91 | F | W | 8 | Caudate |
| 1855 | Control | | | 77 | M | W | | Caudate, hippocampus, MB |
| 2201 | Control | 0 | 2 | 85 | F | W | 27 | Caudate, hippocampus, MB |
| 1774 | AD | C | 6 | 87 | F | W | 17.5 | Hippocampus |
| 1778 | AD | C | 6 | 80 | F | W | 6.5 | Hippocampus, MB |
| 1782 | AD | | | 86 | M | W | 19.5 | Hippocampus, MB |
| 1788 | AD | C | | 62 | F | W | 36.5 | Hippocampus |
| 1833 | AD | | | 79 | F | W | 4.5 | Entorhinal/Hippo |
| 1851 | AD | | | 86 | F | | | Entorhinal/Hippo |
| 1854 | AD | C | 6 | 89 | M | W | 9.5 | Hippocampus |
| 1861 | AD | | | 85 | M | W | 29 | Hippocampus |
| 2291 | AD | B | 4 | 77 | M | W | 8 | Neocrotex |

Example 4

Parkinson's disease is a movement disorder characterized by death of dopaminergic (DA) substantia nigra (SN) neurons and brain accumulation of α-Synuclein. The tyrosine kinase c-Abl is activated in neurodegeneration. Lentiviral expression of α-Synuclein leads to c-Abl activation (phosphorylation) and c-Abl expression increases α-Synuclein levels in mouse SN, in agreement with c-Abl activation in PD brains. Lentiviral α-Synuclein induces accumulation of autophagosomes, and boosting autophagy with the c-Abl inhibitor Nilotinib increases autophagic clearance. Nilotinib is used for adult leukemia treatment and it enters the brain within FDA approved doses, leading to autophagic degradation of α-Synuclein and limitation of cell death, including SN neurons. Nilotinib enhances motor behavior in lentiviral PD models, increases DA levels and induces hyper-activity in transgenic A53T mice. These data show that Nilotinib can be a therapeutic strategy to degrade α-Synuclein in PD and other Synucleinopathies.

Stereotaxic Injection.

Six months old C57BL/6 mice were stereotaxically injected with 1×104 m.o.i lentiviral c-Abl, α-Synuclein (or LacZ control) bilaterally into the SN using co-ordinates: lateral: 1.5 mm, ventral: 4.1 mm and horizontal: −3.64. Viral stocks were injected through a microsyringe pump controller (Micro4) using total pump (World Precision Instruments, Inc.) delivery of 2 μl at a rate of 0.2 μl/min as previously described (54-56). All animal experiments will be conducted in full compliance with the recommendations of Georgetown University Animal Care and Use Committee (GUAUC).

Nilotinib Treatment.

Three weeks post-injection with the lentivirus, half the animals were IP treated daily with 10 mg/Kg Nilotinib dissolved in DMSO and the other half received DMSO treatments (3 μl total) for an additional 3 weeks. Half of 6-8 months old A53T transgenic mice were IP treated daily with 10 mg/Kg Nilotinib and the other half DMSO.

WB Analysis.

The nigrostriatal region was isolated from α-Synuclein or c-Abl expressing mice and compared with LacZ or total brain extracts from A53T mice. Tissues were homogenized in 1×STEN buffer (50 mM Tris (pH 7.6), 150 mM NaCl, 2 mM EDTA, 0.2% NP-40, 0.2% BSA, 20 mM PMSF and protease cocktail inhibitor), centrifuged at 10,000×g for 20 min at 40C and the supernatant containing the soluble protein fraction was collected. The supernatant was analyzed by WB on SDS NuPAGE Bis-Tris gel (Invitrogen). α-Synuclein was probed with (1:1000) mouse anti-α-Synuclein antibody (BD Transduction Laboratories, USA) or (1:1500) human antibodies (ThermoScientific). Total c-Abl was probed with (1:500) rabbit polyclonal antibody (Thermo Fisher) and p-c-Abl (Tyr-214) with (1:500) rabbit polyclonal antibody (Millipore). β-actin was probed with (1:1000) with polyclonal antibody (Cell Signaling Technology, Beverly, Mass., USA). Autophagy antibodies, including beclin-1

(1:1000), Atg5 (1:1000), Atg12 (1:1000) were used to probe according to autophagy antibody sampler kit 4445 (Cell Signaling, Inc). A rabbit polyclonal (Pierce) anti-LC3 (1:1000) and rabbit polyclonal (Thermo Scientific) anti-actin (1:1000) were used). Rabbit polyclonal (1:1000) tubulin (Thermo Scientific) was used. Map 2 was probed (1:1000) mouse monoclonal antibody (Pierce). Rabbit polyclonal anti-SQSTM1/p62 (Cell Signaling Technology) was used (1:500). WBs were quantified by densitometry using Quantity One 4.6.3 software (Bio Rad).

IHC of Brain Sections.

Animals were deeply anesthetized with a mixture of Xylazine and Ketamine (1:8), washed with 1× saline for 1 min and then perfused with 4% paraformaldehyde (PFA) for 15-20 min. Brains were quickly dissected out and immediately stored in 4% PFA for 24 h at 40C, and then transferred to 30% sucrose at 40C for 48 h. Tyrosine Hydroxylase (TH) was probed (1:100) with rabbit polyclonal (AB152) antibody (Millipore) and human α-Synuclein was probed (1:100) with mouse monoclonal antibodies (Thermo Scientific) and DAB counterstained.

Stereological Methods.

These were applied by a blinded investigator using unbiased stereology analysis (Stereologer, Systems Planning and Analysis, Chester, Md.) to determine the total positive cell counts in 20 cortical fields on at least 10 brain sections (~400 positive cells per animal) from each animal.

Cell Culture and Transfection.

Human neuroblastoma M17 cells were grown in 24 well dishes (Falcon) as previously described (57, 58). Transient transfection was performed with 3 μg α-Synuclein, or c-Abl or beclin-1 shRNA cDNA (Open Biosystems), or 3 μg LacZ cDNA for 24 hr. Cells were treated with 10 μM Nilotinib for 24 hr. Cells were harvested 48 hr after transfection. Cells were harvested one time with STEN buffer and centrifuged at 10,000×g for 20 min at 4° C., and the supernatant was collected.

Human α-Synuclein Enzyme-Linked Immunosorbent Assay (ELISA)

These were performed using 50 μl (1 μg/μl) of brain lysates (in STEN buffer) detected with 50 μl primary antibody (3 h) and 100 μl anti-rabbit secondary antibody (30 min) at RT. α-Synuclein levels were measured using human specific ELISA (Invitrogen) according to manufacturers' protocols.

Caspase-3 Fluorometric Activity Assay—

To measure caspase-3 activity in the animal models, we used EnzChek® caspase-3 assay kit #1 (Invitrogen) on cortical extracts and Z-DEVD-AMC substrate and the absorbance was read according to manufacturer's protocol.

ELISA Dopamine and HVA.

Total brain or mesencephalon were collected and fresh 50 μl (1 μg/μl) brain lysates (in STEN buffer) were detected with 50 μl primary antibody (1 h) and 100 μl anti-rabbit secondary antibody (30 min) at RT according to manufacturer's protocols (Abnova, Cat# BOLD01090J00011) for DA and (Eagle Biosciences, Cat# HVA34-K01) for HVA.

Transmission EM.

Brain tissues are fixed in (1:4, v:v) 4% PFA-picric acid solution and 25% glutaraldehyde overnight, then washed 3× in 0.1 M cacodylate buffer and osmicated in 1% osmium tetroxide/1.5% potassium ferrocyanide for 3 h, followed by another 3× wash in distilled water. Samples will be treated with 1% uranyl acetate in maleate buffer for 1 h, washed 3× in maleate buffer (pH 5.2), then exposed to a graded cold ethanol series up to 100% and ending with a propylene oxide treatment. Samples are embedded in pure plastic and incubated at 60° C. for 1-2 days. Blocks are sectioned on a Leica ultracut microtome at 95 nm, picked up onto 100 nm formvar-coated copper grids and analyzed using a Philips Technai Spirit transmission EM. For immuno-EM studies, sections with be incubated overnight with the primary antibodies and Gold impregnated for EM analysis.

MALDI-TOF Mass Spec.

Brain extracts are freeze dried (in DMSO) and re-suspended in acetonitrile. Nilotinib quantification will carried out on a 4800 MALDI-TOF-TOF Analyzer (Applied Biosystems, CA, USA) in reflector-positive mode and then validated in MS/MS mode as previously described (54, 59). Detected fragment masses will be identified in SWISS-PROT databases using MASCOT.

Rotarod Tests.

Mice were placed on an accelerating rotarod (Columbus Instruments) equipped with individual timers for each mouse. Mice were trained to stay on the rod at a constant 5 rpm rotation for at least 2 minutes, then the speed was gradually increased by 0.2 rpm/min and the latency to fall was measured. All values were converted to % control.

c-Abl Activation is Associated with Accumulation of α-Synuclein.

To examine the relationship between c-Abl and α-Synuclein, male C57BL/6 mice were stereotaxically injected with $1×10^4$ m.o.i lentiviral c-Abl, or α-Synuclein (or LacZ) bilaterally into the SN. Lentiviral α-Synuclein expression for 6 weeks (FIG. 56A, 1st blot, 42% over LacZ level, N=9) led to an increase in total c-Abl (110%) and tyrosine 412 (T412) phosphorylated (82%) c-Abl (FIG. 56A, p<0.05, N=9) compared to actin, indicating c-Abl activation. Human post-mortem PD striatal extracts also showed an increase in total (220%) and T412 (150%) c-Abl (FIGS. 56B&C, N=9) compared to control subjects (N=7, p<0.02, two-tailed t-test). Conversely, lentiviral expression of c-Abl in the mouse SN for 6 weeks led to an increase (132%) in total c-Abl (FIG. 56D, p<0.05, N=9) and T412 phosphorylation (71%) compared to actin and resulted in increased levels of monomeric (51%) and high molecular weight (30%) α-Synuclein, further confirming the relationship between c-Abl and α-Synuclein accumulation.

Nilotinib is a second-generation c-Abl tyrosine kinase inhibitor (TKI) formerly known as AMN107 (35-37). Mass spectroscopy analysis revealed that intraperotenial (IP) injection of 10 or 20 mg/kg Nilotinib into wild type mice (N=5/time point), led to detection of up to 30 ng Nilotinib per mg brain tissue 3-4 hr after injection (FIG. 56E). The level of Nilotinib decreased to 3.4 ng/mg 7-8 hr post-injection, indicating that Nilotinib enters the brain and is washed out within a few hours. Caspase-3 activity was then evaluated as a measure of cell death 3 weeks post-injection with lentiviral α-Synuclein followed by 3 weeks treatment with either DMSO or Nilotinib (total 6 weeks). Daily IP injection of 10 mg/kg Nilotinib or DMSO (30 μl) for 6 weeks did not result in any difference in caspase-3 activity in LacZ injected mice (FIG. 56F, N=32), but lentiviral α-Synuclein expression increased caspase-3 activity (FIG. 56F, 740%, p<0.05, N=14) and Nilotinib reversed this increase to 140% of LacZ levels (p<0.05, N=14). Similarly, daily IP injection of 10 mg/kg Nilotinib or DMSO (30 μl) for 3 weeks into 7-8 months old transgenic model that harbors the A53T mutation of α-Synuclein, showed an increase in caspase-3 activity (FIG. 56G, 670%, 5 p<0.05, N=15) and Nilotinib reversed this increase to 101% of wild type age-matched controls with and without Nilotinib (N=64).

c-Abl Inhibition Via Nilotinib Promotes Autophagic Degradation of α-Synuclein.

All animals were treated daily with IP injection of 10 mg/kg Nilotinib or DMSO (A53T mice) for 3 weeks and lentiviral models were Nilotinib (or DMSO) treated 3 weeks post-injection with lentiviral α-Synuclein or LacZ. Western blot (WB) showed significant decrease in total c-Abl (78%) and T412 phosphorylated (52%) c-Abl compared to tubulin in mesencephalon neurons in lentiviral α-Synuclein mice treated daily with 10 mg/Kg Nilotinib compared to DMSO. Human α-Synuclein levels increased to 202 ng/ml in lentiviral α-Synuclein mice treated with DMSO, and Nilotinib reversed this increase to 31 ng/ml compared to LacZ with and without Nilotinib. Nilotinib treatment resulted in decreased levels of monomeric (42%) and high molecular weight α-Synuclein compared to actin level. An increase in several molecular markers of autophagy including beclin-1 (62%), Atg-5 (43%) and Atg-12 (58%) were observed compared to actin. Further analysis of autophagic markers showed significant decreases in P62 (69%) and LC3-II compared to both LC3-I (39%) and MAP-2 (41%) with Nilotinib treatment, suggesting autophagic clearance of α-Synuclein. Similarly, daily IP injection of Nilotinib for 3 weeks into 7-8 months A53T mice, which do not express α-Synuclein in the SN, showed significant decrease in total c-Abl (64%) and T412 phosphorylated (70%) c-Abl compared to MAP-2 in total brain extracts compared to DMSO treated mice. An increase in the level of total (109%) and T412 (76%) c-Abl were observed in A53T mice treated with DMSO compared to age-matched controls. A significant increase in LC3-II level was observed in A53T+DMSO mice compared to control and LC3-II completely disappeared in A53T mice treated with Nilotinib, suggesting autophagic clearance. Human α-Synuclein levels were increased to 785 ng/ml in A53T mice treated with DMSO, and Nilotinib reversed this increase to 467 ng/ml compared to control. Nilotinib treatment resulted in decreased levels of monomeric (41%) and high molecular weight human α-Synuclein compared to actin level. No differences in beclin-1 and Atg5 levels were observed between A53T+DMSO mice and wild type control, but an increase in Atg12 (24%) was noted compared to actin. However, Nilotinib increased beclin-1 (69%) and Atg-5 (29%) compared to DMSO treatment in A53T mice.

To further determine whether autophagy mediates α-Synuclein clearance, human M17 neuroblastoma cells were transfected with 3 μg lacZ, α-Synuclein or shRNA beclin-1 for 24 hr and then treated with 10 μM Nilotinib for additional 24 hr. An increase in α-Synuclein (264 ng/ml) was observed in α-Synuclein transfected cells compared to LacZ (FIG. 57H, p<0.05, N=12) treated with 1 μl DMSO. Nilotinib reversed α-Synuclein to 35 ng/ml (p<0.05) but blocking beclin-1 expression with shRNA attenuated Nilotinib clearance of α-Synuclein (150 ng/ml) compared to DMSO (251 ng/ml), suggesting autophagic involvement in α-Synuclein clearance.

Nilotinib clears α-Synuclein and protects SN Tyrosine hydroxylase (TH) neurons. Immunohistochemical staining of 20 μm thick brain sections showed human α-Synuclein expression in mice injected with lentiviral α-Synuclein into the SN and treated with DMSO (FIG. 57B) compared to LacZ+Nilotinib (or DMSO) mice (FIG. 57A, N=12) and Nilotinib led to 84% (by stereology) decrease of human α-Synuclein (FIG. 57C, p<0.05, N=12) in SN neurons. A significant decrease in TH+ neurons (89% by stereology) was observed in lentiviral α-Synuclein+DMSO (FIGS. 57E&H) compared to LacZ+Nilotinib (FIGS. 57D&G) mice, and Nilotinib treatment of α-Synuclein expressing mice reversed TH+ neuron loss back to 82% (FIGS. 57F&I, by stereology) of LacZ level (p<0.05, N=12). Stereological counting showed a similar decrease (72%) of Nissl counter-stained TH+ cells in α-Synuclein+DMSO (FIG. 57K) compared to LacZ (FIG. 57J) and 64% of α-Synuclein+Nilotinib (FIG. 57L, p<0.05, N=12), suggesting that α-Synuclein causes cell death and not down-regulation of TH. Transmission electron microscopy of SN neurons showed accumulation of cytosolic debris (FIG. 58A) and autophagic vacuoles (AV) in Lentiviral α-Synuclein expressing mice with DMSO treatment. Accumulation of cytosolic AVs containing debris was observed in these animals (FIGS. 58C&E), suggesting autophagosome accumulation, consistent with increased LC3-II by WB. Nilotinib treatment led to appearance of larger AVs that seemed to be derived from fusion of multiple autophagic compartments (FIGS. 58B, D &F).

Nilotinib Attenuates α-Synuclein Levels in A53T Mice.

Immunohistochemical staining of 20 μm 7 thick brain sections showed abundant expression of human α-Synuclein in the striatum of 6-8 months old transgenic A53T mice treated with DMSO (FIG. 59A), brainstem (FIG. 59B), cortex (FIG. 59C) and Hippocampus (FIG. 59D). No α-Synuclein staining was detected in SN of A53T mice. Daily IP injection of Nilotinib for 3 weeks led to striatal decrease (72%) of human α-Synuclein (FIG. 59E), completely eliminated α-Synuclein from brainstem (FIG. 59F), and reduced cortical (FIG. 59G, 71%) and hippocampal (FIG. 59H, 81%) α-Synuclein (p<0.05, N=7) in transgenic A53T mice.

Nilotinib Increases DA Level and Improves Motor Performance.

To evaluate α-Synuclein and Nilotinib effects on DA metabolism, DA and its metabolite Homovanilic acid (HVA) were measured using ELISA. A significant decrease (p<0.05, N=8) in DA (62%) and HVA (36%) were observed in brain mesencephalon extracts of lentiviral α-Synuclein+DMSO compared to LacZ mice with and without Nilotinib. However, Nilotinib injection significantly (P<0.05, N=8) reversed DA and HVA loss back to control lacZ levels Lentiviral α-Synuclein expression in SN decreased rotarod motor performance to 39% of LacZ controls with and without Nilotinib, but Nilotinib treatment of α-Synuclein mice reversed motor performance to 86% of LacZ level, suggesting that reversal of DA levels leads to improved motor performance. No loss of DA or HVA were observed in transgenic A53T mice treated with DMSO compared to age-matched control with and without Nilotinib, but Nilotinib dramatically increased both DA (174%) and HVA (50%) levels in A53T mice. No noticeable differences of rotarod performance were observed between 6-8 months old A53T mice treated with DMSO and wild type controls. However, Nilotinib increased rotarod motor performance (45%) above control levels, suggesting hyperactivity in A53T mice.

Example 5

The tyrosine kinase c-Abl is activated in neurodegenerative disorders, including Alzheimer's disease (AD). Nilotinib is a c-Abl inhibitor approved by the U.S. Food and Drug Administration (FDA) for treatment of adult leukemia. These studies show that Nilotinib-mediated parkin activation stimulated the autophagic clearance pathway, leading to amyloid degradation and cognitive improvement in a parkin-dependent manner. Nilotinib failed to clear autophagic vacuoles and amyloid proteins in parkin−/− mice, despite an increase in beclin-1 levels, whereas beclin-1 knockdown attenuated Aβ clearance, underscoring an indispensable role for endogenous parkin in autophagy. These data showed that Nilotinib-mediated c-Abl inhibition is a therapeutic strategy to rescue cells from intraneuronal amyloid toxicity and prevent both plaque deposition and progression from mild cognitive impairment to AD.

Human Postmortem Brain Tissues.

Human postmortem samples were obtained from John's Hopkins University brain bank. Patients' description and sample preparation are summarized in Example 1. Data were analyzed as mean±Standard deviation, using Two-tailed t-test (P<0.05).

Stereotaxic Injection.

Lentiviral constructs encoding LacZ, or $A\beta_{1-42}$ were stereotaxically injected 1×106 multiplicity of infection (m.o.i) bilaterally into the CA1 hippocampus of 1 year old C57BL/6 or parkin−/−. A Total of 6 µl lentiviral stocks were delivered at a rate of 0.2 µl/min and. All procedures were approved by the Georgetown University Animal Care and Use Committee (GUACUC).

Nilotinib Treatment.

Nilotinib was dissolved in DMSO and a total volume of 30 µl were intra-peroteneally (IP) injected once a day for 3 weeks. Half the animals received DMSO and the other half received Nilotinib in DMSO.

Western Blot Analysis.

Brain tissues were homogenized in 1×STEN buffer, centrifuged at 10,000×g for 20 min at 40C, and the supernatants containing the soluble fraction of proteins were collected. The pellet was re-suspended in either 4M urea or 30% formic acid and adjusted to pH 7 with 1N NaOH and centrifuged at 10,000×g for 20 min at 4° C., and the supernatant containing the insoluble fraction was collected. Total parkin was immunoprobed (1:1000) with PRK8 antibody. Rabbit polyclonal antibodies anti-beclin-1 (1:1000), autophagy like gene (Atg)-5 (1:1000), Atg12 (1:1000) and LC3-B (1:1000) were used to probe autophagy proteins using antibody sampler kit 4445 (Cell Signaling, Inc). A rabbit polyclonal (Pierce) anti-LC3 (1:1000) and rabbit polyclonal (Thermo Scientific) anti-actin (1:1000) were used. Rabbit polyclonal (1:1000) tubulin (Thermo Scientific) and mouse monoclonal (1:500) anti-ubiquitin (Santa Cruz Biotechnology) were used. Map 2 was probed (1:1000) mouse monoclonal antibody (Pierce).

Immunohistochemistry.

Immunohistochemistry was performed on 20 micron-thick 4% paraformaldehyde (PFA) fixed cortical brain sections. Aβ1-42 was probed (1:200) with rabbit polyclonal specific anti-Aβ1-42 antibody (Zymed) that recognizes a.a. 1-42, and (1:200) mouse monoclonal antibody (4G8) that recognizes amino acid 17-24 (Covance) and counterstained with DAPI. Parkin was immunoprobed (1:200) with mouse anti-parkin (PRK8) antibody that recognizes amino acid 399-465 (Signet Labs, Dedham, Mass.) and rabbit polyclonal (1:200) anti-parkin (AB5112) antibody that recognizes amino acid 305-622 (Millipore) and counterstained with DAPI. Mouse monoclonal (6E10) antibody (1:100) with DAB were used (Covance) and thioflavin-S was performed according to manufacturer's instructions (Sigma).

Stereological Methods.

Stereological methods were applied by a blinded investigator using unbiased stereology analysis (Stereologer, Systems Planning and Analysis, Chester, Md.) as described in (20,36).

ELISA.

Aβ and p-Tau enzyme-linked immunosorbent assay (ELISA) using specific p-Tau, Aβ1-40 and $A\beta_{1-42}$ ELISA and caspase-3 activity were performed according to manufacturer's protocol.

Transmission Electron Microscopy.

Brain tissue were fixed in (1:4, v:v) 4% paraformaldehyde-picric acid solution and 25% glutaraldehyde and analyzed by a blind investigator as described in (20,36).

Cell Culture and Transfection.

Human neuroblastoma M17 or rat B35 cells were grown in 24 well dishes (Falcon). Transient transfection was performed with 3 µg $A\beta_{1-42}$ cDNA, or 3 µg LacZ cDNA for 24 hr. Cells were treated with 10 µM Nilotinib for 24 hr. Cells were harvested 48 hr after transfection. Cells were harvested one time with STEN buffer and centrifuged at 10,000×g for 20 min at 4° C., and the supernatant was collected.

Parkin ELISA.

ELISA was performed on brain soluble brain lysates (in STEN buffer) or insoluble brain lysates (4M urea) using mouse specific parkin kit (MYBioSource) in 50 µl (1 µg/µl) of brain lysates detected with 50 µl primary parkin antibody (3 h) and 100 µl anti-rabbit antibody (30 min) at RT. Extracts were incubated with stabilized Chromogen for 30 minutes at RT and solution was stopped and read at 450 nm, according to manufacturer's protocol.

Parkin E3 Ubiquitin Ligase Activity.

To determine the activity of parkin E3 ligase activity, E3LITE Customizable Ubiquitin Ligase Kit (Life Sensors, UC#101), which measures the mechanisms of E1-E2-E3 activity in the presence of different ubiquitin chains was used. To measure parkin activity in the presence or absence of substrates, parkin was immunoprecipitated (1:100) with PRK8 antibodies. UbcH7 was used as an E2 that provides maximum activity with parkin E3 ligase and added E1 and E2 in the presence of recombinant ubiquitin, including wild type or no lysine mutant (K0), or K48 or K63 to determine the lysine-linked type of ubiquitin. E3 was added as IP parkin to an ELISA microplate that captures poly-ubiquitin chains formed in the E3-dependent reaction, which was initiated with ATP at room temperature for 60 minutes. Controls included, E1-E2-E3 and a poly-ubiquitin chain control in addition to E1, E2 and $A\beta_{1-42}$ without parkin and assay buffer for background reading. The plates were washed 3 times and incubated with streptavidin-HRP for 5 minutes and were read on a chemiluminecense plate reader.

20S Proteasome Activity Assay.

Brain extracts 100 µg were incubated with 250 µM of the fluorescent 20S proteasome specific substrate Succinyl-LLVY-AMC at 37° C. for 2 h. The medium was discarded and proteasome activity was measured in tissue homogenates.

Morris Water Maze.

All animals were pre-trained (trials) to swim for 90 seconds in a water maze containing a platform submerged in water (invisible) for 4 consecutive days once a day. The pretraining trials "teach" the swimming animals that to "escape", they must find the hidden platform, and stay on it. The water maze "test" was performed on day 5, (40), when the platform was removed and mice have to swin and find it, thus assessing acquisition and retention. All parameters, including distance travelled to reach platform, speed to get to the platform, latency or time spent on platform, and platform entry were digitally recorded on a computer and analyzed by a blind investigator.

Novel Object Recognition (NOR).

Mice were placed individually in a 22×32×30 cm testing chamber for a 5 min habituation interval and returned to their home cages. Thirty minutes later mice were placed in the testing chamber for 10 min with two identical objects (acquisition session), then returned to their home cages and 90 later placed back in the testing chamber in the presence with one of the original objects and one novel object of the same size but of a different color and shape (recognition session). Sessions were video recorded. Time spent exploring the objects were scored by blind observer. The recognition index was calculated as (time exploring one of the objects/time exploring both objects)×100 for acquisition session, and (time exploring new object/time exploring both familiar and novel objects)×100 for the recognition session. Statistical calculations to estimate differences between sessions were performed with a pairwise t-test.

Nilotinib Activates Parkin and Induces Autophagic Clearance in a Beclin-1-Dependent Manner.

To test Nilotinib effects on autophagic mechanisms, human M17 or rat B35 neuroblastoma cells were transfected with 3 µg of human cDNA A$\beta_{1-42}$ (or LacZ) for 24 hr, and then treated these cells with several concentrations (1 nM, 100 nM, 1 µM and 10 µM) of Nilotinib for 24 hr. No cell death (by MTT, 3-(4,5-Dimethylthiazol-2-yl)-2,5-diphenyltetrazolium bromide) was detected in LacZ cells treated with DMSO or Nilotinib (FIG. 60A). Cells expressing A$\beta_{1-42}$ had a significant level of cell death (62%, p<0.05, N=12) that was reversed to 83% of control level by Nilotinib (FIG. 60A, N=12), suggesting protective effects for Nilotinib against A$\beta_{1-42}$ toxicity. Parkin levels were measured via ELISA using parkin−/− brain extracts as a specificity control (FIG. 66A). A non-significant increase (17%) in parkin was observed with 10 µM Nilotinib but a significant increase (24%, FIG. 78A, N=12, p<0.05) was reached in extracts treated with A$\beta_{1-42}$+Nilotinib, suggesting that parkin increases in response to A$\beta_{1-42}$ stress. To determine whether parkin increase is associated with proteasome activity, the Chymotrypsin-like assay was used with the 20S proteasome inhibitor lactacystin as a specificity control (FIG. 60B). Nilotinib did not affect proteasome activity in LacZ cells (FIG. 60B). Proteasome activity was increased (43%, p<0.05, N=12) in A$\beta_{1-42}$ cells, an effect that was reversed by treatment with Nilotinib. Soluble (STEN buffer), insoluble (30% formic acid) and cell culture medium levels of A$\beta_{1-42}$ were measured after Nilotinib treatment. The level of secreted A$\beta_{1-42}$ was (6-fold) higher than LacZ cells; and Nilotinib decreased this by 24% (FIG. 60C, p<0.05, N=12). Nilotinib completely reversed the 2-fold increase in soluble and 3.5-fold increase in insoluble A$\beta_{1-42}$.

Lentiviral Parkin Injected into AD Mice Increases Beclin-1 Levels and Autophagic Clearance of A$\beta$.

Blocking beclin-1 expression using shRNA (FIG. 60D, top blot) resulted in a significant increase (FIG. 60D, 28%, N=12) in Nilotinib-induced parkin. A$\beta_{1-42}$ levels were unaffected in the media with Nilotinib treatment compared to A$\beta_{1-42}$ expressing cells, and were significantly higher than A$\beta_{1-42}$+Nilotinib (FIG. 60C). Soluble and insoluble A$\beta_{1-42}$ were partially (42% and 21%, respectively) decreased compared to A$\beta_{1-42}$ transfected cells, but remained 2-fold higher compared to A$\beta_{1-42}$+Nilotinib (FIG. 60C, p<0.05, N=12), indicating that beclin-1 is required for complete A$\beta_{1-42}$ clearance. Secreted A$\beta_{1-42}$ (media) may have accumulated in the first 24 hr after transfection, prior to Nilotinib treatment. To verify whether autophagy is involved in A$\beta_{1-42}$ clearance, LC3 (Light Chain Protein-3) levels (FIG. 60D) were examined and LC3-II with expression of A$\beta_{1-42}$ alone, or with shRNA beclin-1+Nilotinib (N=12) was detected, indicating autophagosome formation, but LC3-II completely disappeared with Nilotinib, suggesting autophagic clearance (FIG. 60D). To determine Nilotinib effects on parkin function, parkin (E3) was immunoprecipitated and E1, E2 (UbcH7) was added and either wild type ubiquitin containing all seven lysines or the no-lysine mutant ubiquitin (K0).

Nilotinib (24 hr) significantly increased parkin self poly-ubiquitination compared to DMSO and specificity controls (FIG. 60E, 170%, N=5, P<0.05), including recombinant E1-E2-E3 (positive) or K0 (negative) (FIG. 60E), suggesting that Nilotinib increases parkin E3 ubiquitin ligase activity.

Nilotinib Crosses the Blood Brain Barrier.

To determine whether Nilotinib crosses the blood brain barrier 2-month old C57BL/6 mice were intraperoteneally (IP) injected with 10 mg/kg, 20 mg/kg or 50 mg/kg Nilotinib (304 in DMSO) and the animals were sacrificed 4-6 hr after injection. Mass spectroscopy analysis of total brain lysates showed up to 30 ng/ml Nilotinib in the brain with 10 mg/kg. Nilotinib treatment (N=35) daily for 9 consecutive days significantly decreased (44%) total c-Abl levels and T412 (50%), suggesting c-Abl inhibition. This treatment with 10 mg/kg Nilotinib decreased pan-tyrosine phosphorylation, increased (29%, p<0.05, N=35) parkin and decreased ubiquitinated protein smear.

To determine Nilotinib effects on neuronal death, 1×10$^6$ m.o.i lentiviral A$\beta_{1-42}$ was stereotaxicaly injected bilaterally into the hippocampus of 1 year old C57BL/6 (wild type) or parkin−/− mice and 3 weeks later 10 mg/kg as injected once a day for 3 additional weeks. No differences in caspase-3 activation were observed between DMSO and Nilotinib treated wild type mice (FIG. 60F, N=64); however, a significant increase (165%) in caspase-3 activation was observed in lentiviral A$\beta_{1-42}$ age-matched mice (FIG. 60F, p<0.05, N=35), while Nilotinib significantly reversed (45% above control) the effects of A$\beta_{1-42}$. Similarly, no differences in caspase-3 activation were observed between DMSO and Nilotinib treated parkin−/− mice (FIG. 60F, N=16), but a significant increase was observed in lentiviral A$\beta_{1-42}$ mice with (165%) or without (180%) Nilotinib (P<0.05, N=19), suggesting that Nilotinib depends on parkin to protect against A$\beta_{1-42}$.

Nilotinib Clearance of Brain Amyloid is Associated with Parkin Activation.

To determine whether Nilotinib affects AP level in vivo, 8-12 months old AD transgenic mice which express neuronally derived human APP gene, 770 isoform, containing the Swedish K670N/M671L, Dutch E693Q and Iowa D694N mutations (Tg-APP) under the control of the mouse thymus cell antigen 1, theta, Thy1, promoter were treated (10 mg/kg IP injection) for 3 weeks. These mice expressed significantly higher levels of soluble (156 ng/ml) and insoluble (173 ng/ml) A$\beta_{1-42}$ compared to 1-year old control with and without Nilotinib (FIG. 61A, p<0.05, N=9) while Nilotinib greatly reduced soluble A$\beta_{1-42}$ (35 ng/ml, which remained significantly higher than control) and reversed the increase in insoluble A$\beta_{1-42}$. Significant increases in soluble (281 ng/ml) and insoluble (250 ng/ml) A$\beta$1-40 were also detected in Tg-APP mice compared to 1-year old control (FIG. 61B, p<0.05, N=9), and were reversed by Nilotinib. p-Tau was also increased at ser 396 (109 ng/ml) and AT8 (288 ng/ml) compared to 1-year old control (FIG. 61C, p<0.05, N=9). Nilotinib significantly reduced but did not completely reverse these increases.

Nilotinib Abrogates Alteration of Parkin Solubility in AD Mice.

To determine whether parkin level is affected in AD models, the level of parkin was measured in Tg-APP mice in both the soluble (STEN) and insoluble (4M urea) fractions. Brain lysates from parkin−/− mice were used as specificity controls. No changes in soluble or insoluble parkin were detected in control mice with and without Nilotinib (FIG. 61D, N=9). However, Nilotinib significantly increased the level of soluble parkin from 64 ng/ml in Tg-APP+DMSO to 119 ng/ml (FIG. 61D, N=11, p<0.05) while it significantly decreased insoluble parkin level from 54 ng/ml to 31 ng/ml in Nilotinib treated mice (FIG. 61D, p<0.05, N=11). These data suggest increased levels of insoluble parkin in Tg-APP. Western blot revealed increased levels of total (51%) and T412 c-Abl (64%) in Tg-APP compared to control (FIG. 61E, p<0.05, N=11), while Nilotinib again reversed these increases (FIG. 61E, p<0.05, N=11). c-Abl inhibition with Nilotinib reduced the level of CTFs (44%, p<0.05, N=11) relative to MAP-2.

c-Abl Activation is Associated with Decreased Parkin Level in Post-Mortem AD Cortex.

Whether c-Abl is altered in human post-mortem AD cortex was examined (N=12 AD and 7 control). Significantly increased levels (90%) of total (FIG. 61F) and T412 (184%) c-Abl were detected in AD brains (FIG. 61F). The ratio of p-cAbl over total c-Abl (FIG. 61G) was also increased (102%). In contrast, parkin was decreased (70%) in AD cortex (FIGS. 61F&G) compared to actin. Parkin insolubility may be associated with loss of E3 ligase function, so it was determined whether endogenous parkin can mediate $A\beta_{1-42}$ clearance. Significant increases (p<0.05, N=12) in soluble (180 ng/ml) and insoluble (209 ng/ml) $A\beta_{1-42}$ were observed in wild type lentiviral $A\beta_{1-42}$ mice (FIG. 61H), but Nilotinib completely reversed $A\beta_{1-42}$ back to control level. Lentiviral $A\beta_{1-42}$ in parkin−/− mice (FIG. 61H) significantly increased soluble (241 ng/ml) and insoluble (246 ng/ml) $A\beta_{1-42}$ compared to lentiviral $A\beta_{1-42}$ in wild type mice (N=12). Interestingly, Nilotinib failed to clear soluble (297 ng/ml) and insoluble (274 mg/ml) $A\beta_{1-42}$ in parkin−/− mice, suggesting that endogenous parkin is required for $A\beta_{1-42}$ clearance. Similarly, Nilotinib decreased p-Tau ser 396 (FIG. 61I) in wild type mice (68 ng/ml) compared to $A\beta_{1-42}$ expression (124 ng/ml) while p-Tau was increased (264 ng/ml) in parkin−/− mice and Nilotinib did not lower p-Tau (189 ng/ml) level (FIG. 61I, p<0.05, N=11).

Nilotinib Promotes Autophagic Clearance of Amyloid in a Parkin-Dependent Manner.

Western blot (WB) of total brain lysates in 1 year old wild type mice injected with lentiviral $A\beta_{1-42}$ showed a significant decrease in total (55%) and T412 (45%) c-Abl following daily treatment with 10 mg/kg Nilotinib for 3 weeks (FIG. 62A, p<0.05, N=9). A significant decrease (38%) in LC3-B and disappearance of LC3-II (which indicates autophagosome accumulation) were observed in Nilotinib compared to DMSO treated mice (FIG. 62A, p<0.05, N=9). No changes in the neuronal marker MAP-2 (loading control) were detected. A significant increase in parkin level (62%) was associated with a similar increase in beclin-1 (53%) and other molecular markers of autophagy, including Atg5 (34%) and Atg12 (41%) relative to tubulin (FIG. 62B, p<0.05, N=9), consistent with the hypothesis that c-Abl inhibition may mediate autophagic clearance via increased parkin activity. Nilotinib treatment of $A\beta_{1-42}$ mice also increased parkin, decreased autophagic markers LC3-B and LC3-II (FIG. 62C, p<0.05, N=12), and increased beclin-1 (53%) and Atg5 (62%) compared to DMSO (p<0.05). Total Tau was unaffected in Tg-APP mice between DMSO and Nilotinib groups (FIG. 62D, N=12). A significant decrease in AT8 (71%), AT180 (34%) and Ser 396 (64%) with no change in p-Tau Ser 262 compared to actin (FIG. 62D, P<0.05) were observed in Nilotinib treated $A\beta_{1-42}$ mice.

Nilotinib effects also were examined in lentiviral $A\beta_{1-42}$ treated parkin−/− and wild type mice (FIGS. 62E&F). Interestingly, parkin−/− mice had significantly higher levels of autophagic markers, including beclin-1 (FIG. 62E, 120%, N=9) compared to control. Nilotinib did not clear LC3-II in parkin−/− mice and no difference was observed in LC3-A between parkin−/− and control mice (FIG. 62E). Significant increases in Atg12 (FIG. 62F, 64%) and Atg5 (FIG. 62F, 74%) were observed in parkin−/− compared to control and the levels of these markers also were not changed in response to Nilotinib. These data indicate that despite the compensatory increase in autophagic markers, Nilotinib cannot clear autophagosomes in parkin−/− mice, further suggesting that parkin is essential for autophagosome maturation.

Nilotinib Increases Parkin Level and Decreases Plaque Load in Tg-APP Mice.

Staining of 20 µm brain sections shows plaque formation within various brain regions in Tg-APP mice treated with DMSO (FIG. 63A-D representing different animals), though plaque staining disappeared in the Nilotinib group after 3-week treatment (FIG. 63E-H). These results were confirmed by thioflavin-S staining (FIG. 67). Higher magnification shows endogenous parkin associated with Tg-APP (FIG. 63I) and plaque deposition (FIGS. 63I &K) in the hippocampus. Nilotinib increases endogenous parkin (FIG. 63L) and results in plaque disappearance (FIGS. 63M&N). Using different parkin antibodies to show parkin (FIG. 63O) and plaque (FIGS. 63P&Q), Nilotinib increased parkin levels (FIG. 63R) and dissolved plaques (FIGS. 63S&T). To determine whether parkin targets intracellular Aβ to decrease extracellular plaque load, lentiviral injection was used to show intracellular $A\beta_{1-42}$ within the hippocampus (FIG. 63U, inset higher magnification) and Nilotinib clearance of intracellular $A\beta_{1-42}$ (FIG. 63V, inset is higher magnification). Lentiviral injection into the hippocampus led to intracellular $A\beta_{1-42}$ expression throughout the cortex (FIG. 63W, inset higher magnification) and, again, Nilotinib eliminated $A\beta_{1-42}$ accumulation (FIG. 63X, inset higher magnification). Lower magnification images show formation of plaques in $A\beta_{1-42}$ expressing mice 6 weeks post-injection (FIG. 64A-C). Nilotinib (daily for 3 weeks) eliminates plaque formation in $A\beta_1$-42 wild type mice (FIG. 64D-F). $A\beta_{1-42}$ expression in parkin−/− mice showed more plaque formation (FIGS. 64G-I) and Nilotinib did not reduce plaque load in these mice (FIG. 64J-L). Quantification of plaque size using Image J to delineate boundaries around individual plaques (N=15-25 plaques, 2 plaques per animal) (FIG. 68A-D) showed an average plaque size around 48 µm (FIGS. 68A&I, N=12) in $A\beta_{1-42}$ wild type mice, while Nilotinib reduced plaque size to 5 µm (FIGS. 68B&I, p<0.05). In contrast, plaque size was larger in parkin−/− mice (FIGS. 68C&I, 85 µm, N=6), and Nilotinib did not reduce plaque size (FIGS. 68D&I, 79 µm). Stereological counting of Aβ-42 positive cells showed significantly reduced (N=5200 cells) staining in Nilotinib treated (FIGS. 68F&J) compared to DMSO treated $A\beta_{1-42}$ expressing wild type mice (FIGS. 68E&J, p<0.05). However, parkin−/− mice had significantly fewer $A\beta_{1-42}$ positive cells (FIGS. 68G&J, N=14566) and Nilotinib did not alter intracellular staining (FIGS. 68H&J, N=13250), raising the possibility that endogenous parkin can modify intracellular $A\beta_{1-42}$, leading to intraneuronal degradation, thus limiting its secretion.

Parkin Mediates K63-Linked Ubiquitination of $A\beta_{1-42}$.

To determine whether parkin mediates any specific poly-ubiquitin linkages of $A\beta_{1-42}$ that would facilitate its degradation, parkin was immunoprecipitated and synthetic $A\beta_{1-42}$ was used as a substrate. A cocktail of recombinant E1-E2-E3 and poly-ubiquitin chains were used as positive controls (FIG. 68K). No activity was detected with lysine null ubiquitin (K0), and parkin activity was not significantly altered with K48 ubiquitin mutant. However, poly-ubiquitin signals were significantly increased (89%) in the presence of A$\beta_{1-42}$ compared to parkin alone (FIG. 68K, p<0.05, N=6) with K63 ubiquitin, suggesting that parkin promotes K63-linked poly-ubiquitination of A$\beta_{1-42}$. Poly-ubiquitin signals were also significantly higher with wild type ubiquitin in the presence of A$\beta_{1-42}$ (43%).

Impairment of Autophagic Clearance in the Absence of Parkin.

Transmission electron microscopy revealed (N=6 animals per treatment) autophagic defects in lentiviral A$\beta_{1-42}$ expressing mice, manifested in hippocampal appearance of dystrophic neurons (FIG. 64M), accumulation of undigested vacuoles in the cortex (FIG. 64N) and enlargement of hippocampal lysosomes (FIG. 64O), suggesting deficits in proteolytic degradation. Nilotinib reversed these effects in the hippocampus (FIGS. 64P&R), where no dystrophic neurons or lysosomal enlargement were detected, and contributed to cortical clearance of vacuoles (FIG. 64Q). In contrast, Nilotinib failed to eliminate dystrophic neurons in the hippocampus of parkin−/− mice (FIGS. 64S&V), and was unable to clear vacuoles in cortex and hippocampus (FIG. 64T-X).

Nilotinib Improves Cognitive Performance in a Parkin-Dependent Manner.

Figure 65A:
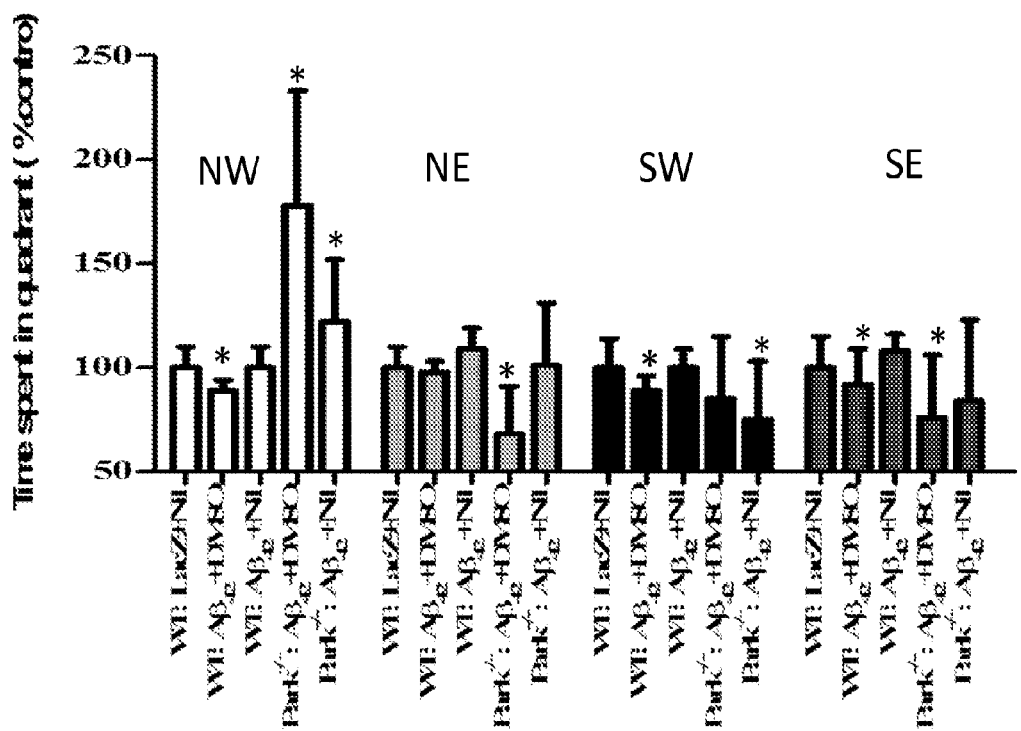
Figure 65B:
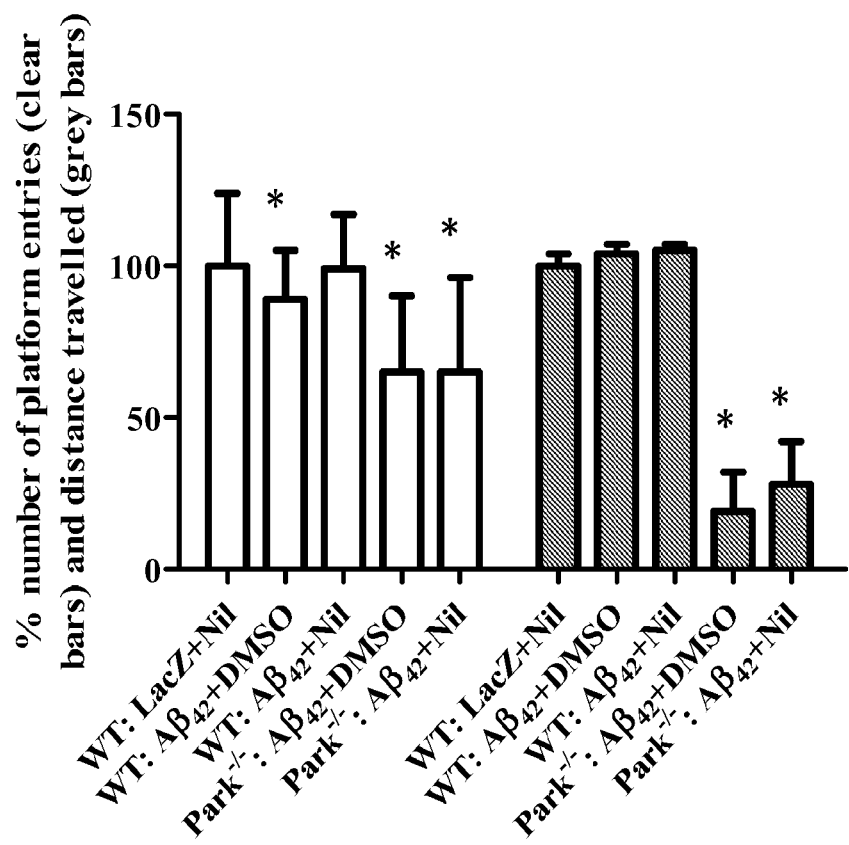
Figure 65C:
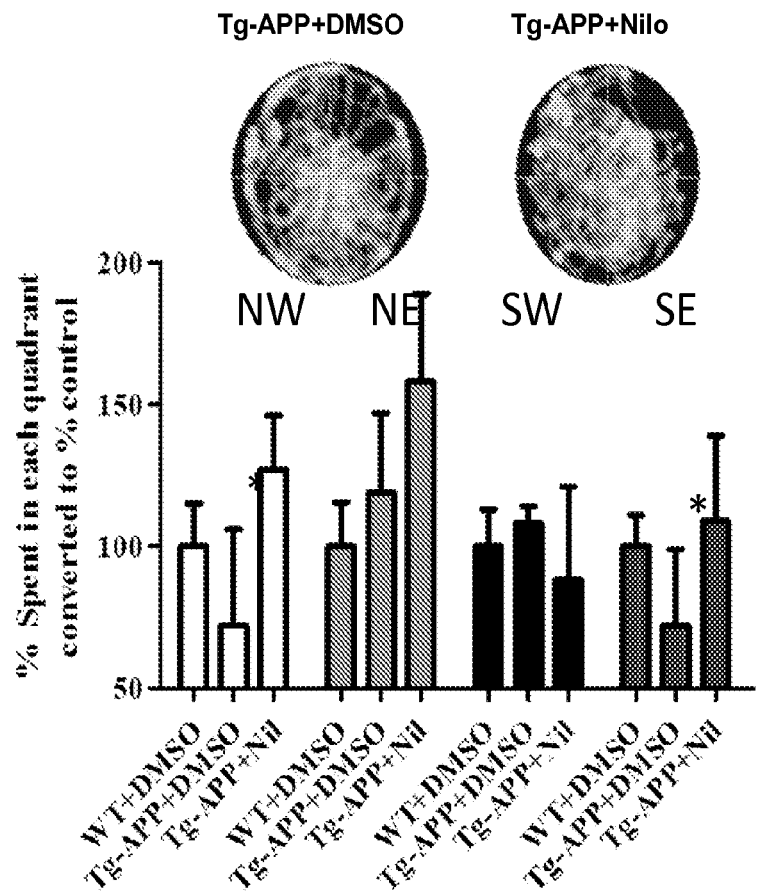
Figure 65D:
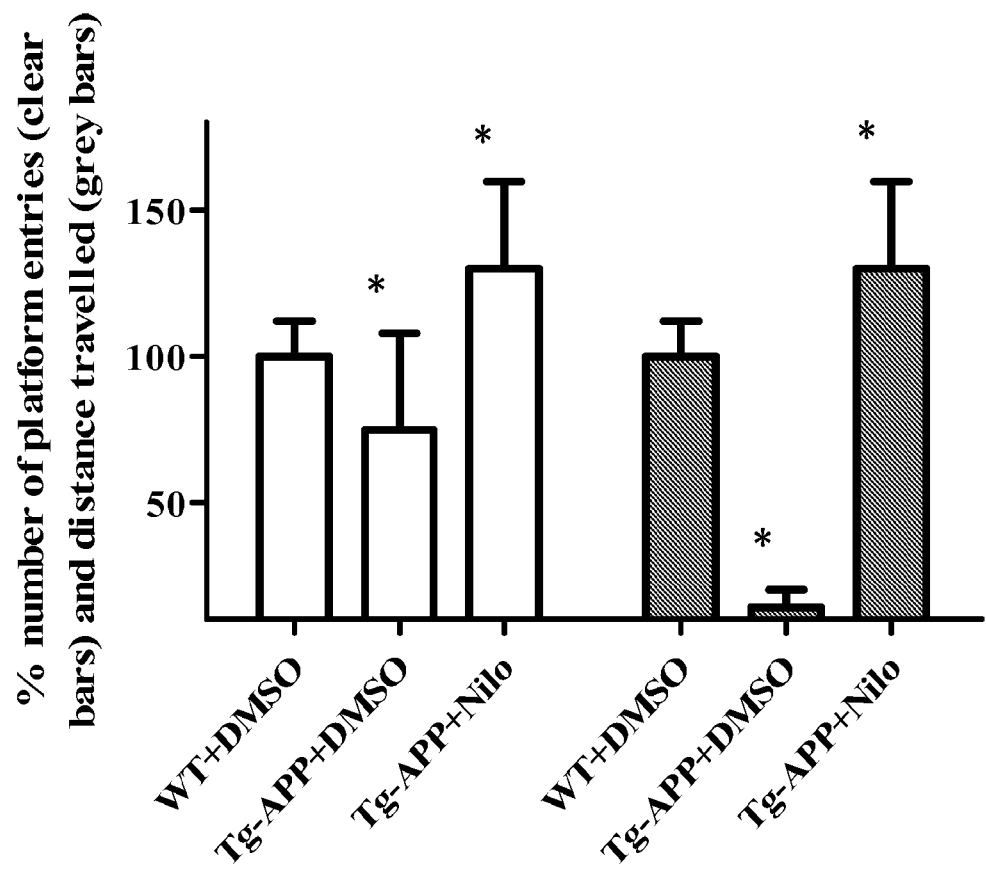
Figure 65E:
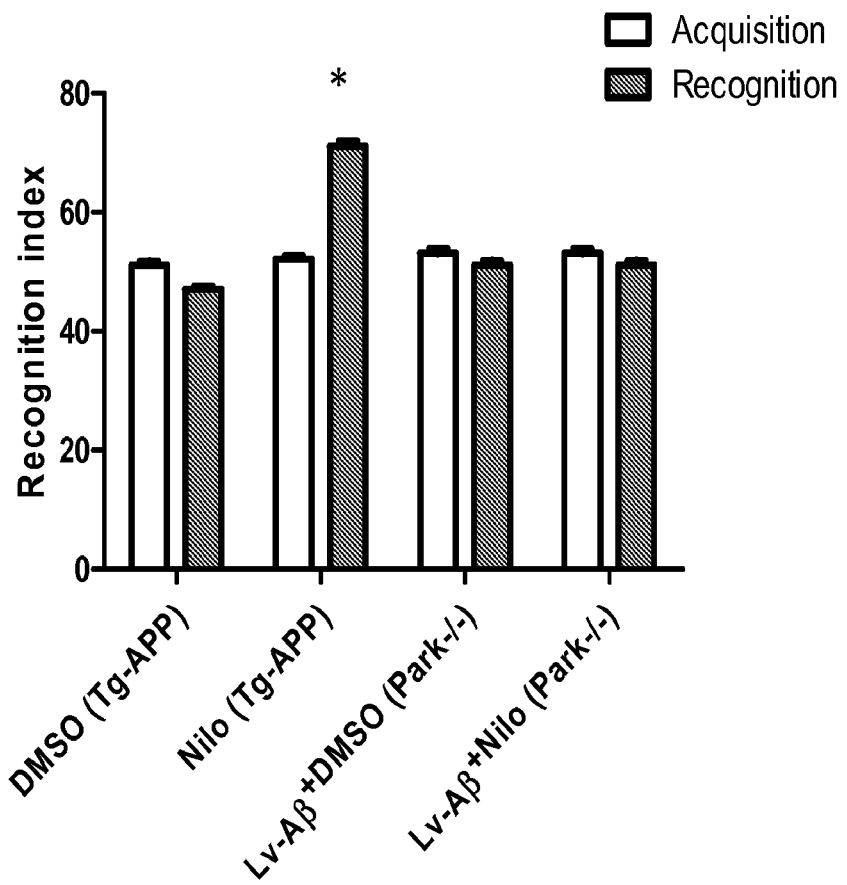

The Morris water maze test was performed after 4 days of training trials in which the platform was placed in the SE corner and mice were initially placed in the NW corner of the pool. A$\beta_{1-42}$-injected (+DMSO) mice remained longer (24%) in the NW quadrant compared to control (LacZ+Nilo) (FIG. 65A, N=14), while Nilotinib reversed time (in seconds) spent in NW back to the level observed in control mice. A$\beta_{1-42}$ parkin−/− mice (N=7) with and without Nilotinib remained significantly more in the NW quadrant (FIG. 65A). A$\beta_{1-42}$ expressing wild type and parkin−/− spent significantly less time in SE (FIG. 65A, 47%, p<0.05) compared to control, but Nilotinib significantly improved time spent in SE in wild type but not parkin−/− compared to control (26%) and DMSO (61%). A heat map for each group showed that controls learned quickly to find (SE) platform area, and A$\beta_{1-42}$ (DMSO) animals spent more time roaming, while Nilotinib improved platform search. In contrast, parkin−/−±Nilotinib wandered aimlessly in the maze. A$\beta_{1-42}$ animals entered the SE (platform entry, clear bars) less (FIG. 77B, 37%) than control, but Nilotinib reversed the number of entries back to control, while parkin−/− entered significantly less (34%, P<0.05, N=7), suggesting that Nilotinib enhanced memory in a parkin-dependent manner. However, the distance travelled (FIG. 77B, back bars) by A$\beta_{1-42}$ parkin−/−±Nilotinib was significantly decreased (80% and 75%, respectively) compared to control and wild type (P<0.05).

These experiments were repeated in 1 year old Tg-APP mice and age-matched control (C57BL/6). Tg-APP (+DMSO) mice remained less (24%) in NW (FIG. 77C, 28%, N=12) and spent significantly less time in SE (FIG. 77C, 28%, p<0.05). Nilotinib treatment (10 mg/kg daily for 3 weeks) significantly reversed time spent in SE back to control level. A heat map for each group shows that Tg-APP did better in finding the platform with Nilotinib (FIG. 77C), and Tg-APP+Nilotinib entered SE (platform entry, clear bars) significantly more times than did control mice (FIG. 77D, 30% higher than control), while Tg-APP+DMSO did significantly worse than control (FIG. 77D, 25%). The distance traveled (FIG. 77D, black bars) was also significantly reduced in DMSO (86%) compared to Nilotinib treated Tg-APP mice, which had values 30% above control levels (FIG. 77D, P<0.05, N=12). Novel object recognition was also tested and showed that Tg-APP+Nilotinib performed significantly better at finding new objects (FIG. 77E, 31%, p<0.001, N=17) than DMSO mice, while A$\beta_{1-42}$ parkin−/− mice did not learn with or without Nilotinib (FIG. 77E, N=5).

Example 6

These studies shows that parkin ubiquitinates TDP-43 and facilitates its cytosolic accumulation through a multi-protein complex with HDAC6.

Experimental Procedures.

Stereotaxic Injection—

Stereotaxic surgery was performed to inject the lentiviral (Lv) constructs encoding either LacZ, parkin and/or TDP-43 into the primary motor cortex of two-month-old male Sprague-Dawley rats weighing between 170-220 g. Animals were injected into left side of the motor cortex with 2×10$^9$ m.o.i Lv-LacZ and into the right side with 1×10$^9$ m.o.i Lv-parkin+1×10$^9$ m.o.i Lv-LacZ; or 1×10$^9$ m.o.i Lv-TDP-43+1×10$^9$ m.o.i Lv-LacZ; or 1×10$^9$ m.o.i Lv-parkin+1×10$^9$ m.o.i Lv-TDP-43. All animals were sacrificed two weeks post-injection and the left cortex was compared to the right cortex. A total of 8 animals of each treatment (32 animals) were used for WB, ELISA and immuno-precipitation and 8 animals of each treatment (32 animals) for immunohistochemistry. A total N=64 animals were used. Transgenic hemizygous mice harboring human TDP-43 with the A315T mutation under the control of prion promoter and C57BL6/J mice controls were used. The colony was obtained from Jackson Laboratory Repository (JAX Stock No. 010700) and displayed a lifespan considerably shorter than previous reports, with almost 90% of all pups, including males and females manifesting motor symptoms around 21-30 days. Hemizygous mice were bred via mating of hemizygous with non-carrier wild type C57BL/6, and upon genotyping, half were identified as transgenic and the other half was non-transgenic control. All mice used are F1 generation from direct mating between hemizygous and C57BL/6 mice. These studies were approved and conducted according to Georgetown University Animal Care and Use Committee (GUACAC).

Cell Culture and Transfection.

Human neuroblastoma M17 cells (seeding density 2×10$^5$ cells) were grown in 24 well dishes (Falcon) to 70% confluence in Dulbecco's Modified Eagle Medium (DMEM; Invitrogen) plus 10% (v/v) heat-inactivated fetal bovine serum (Invitrogen), penicillin/streptomycin, and 2 mM L-glutamine at 37° C. and 5% CO2, washed twice in phosphate-buffered saline (PBS). Transient transfection was performed with 3 µg parkin cDNA or 3 µg TDP-43 cDNA, or 3 µg LacZ cDNA. Cells were treated with 5 µM tubacin for 24 hours and DAPI stained in 12 well dishes. Cells were harvested 24 hours after transfection. Transfection was performed in DMEM without serum using Lipofectamine 2000 (Invitrogen) according to the manufacturer's protocol. Cells were harvested one time with lysis buffer (20 mM Tris (pH 7.5), 150 mM NaCl, 1 mM ethylenediaminetetraacetic acid, 1 mM ethyleneglycoltetraacetic acid (EGTA), 1% Triton X-100, 2.5 mM sodium pyrophosphate, 1 mM β-glycerophosphate, 1 mM sodium orthovanadate, 1 µg/ml leupeptin, and 0.1 mM PMSF) and centrifuged at 10,000×g for 20 min at 4° C., and the supernatant was collected. Western blot was performed on NuPAGE 4-12% Bis-Tris gel (Invitrogen). Protein estimation was performed using the microscale BioRad protein assay (BioRad Laboratories Inc, Hercules, Calif., USA).

Western Blot Analysis—

The cortex was dissected out and homogenized in 1×STEN buffer (50 mM Tris (pH 7.6), 150 mM NaCl, 2 mM EDTA, 0.2% NP-40, 0.2% BSA, 20 mM PMSF and protease cocktail inhibitor). The pellet was then re-suspended in 4M urea and homogenized and centrifuged at 5.000 g and the supernatant containing the insoluble protein fraction was collected. Total TDP-43 was probed either with (1:1000) mouse monoclonal (2E2-D3) antibody generated against N-terminal 261 amino acids of the full length protein (Abnova) or (1:1000) Rabbit polyclonal (ALS10) antibody (ProteinTech, Cat#10782-2-AP). Rabbit polyclonal anti-ubiquitin (Chemicon International) was used (1:1000), and rabbit polyclonal anti-parkin (Millipore) antibody was used (1:1000) for WB. Rabbit polyclonal anti-actin (Thermo Scientific) was used (1:1000). Rabbit polyclonal anti-SQSTM1/p62 (Cell Signaling Technology) was used (1:500). Rabbit monoclonal (1:1000) HDAC6 (Cell Signaling Technology) was used. SIAH2 was probed (1:400) with mouse monoclonal antibody (Novus Biologicals) and HIF-1a with (1:1000) mouse monoclonal antibody (Novus Biologicals). Immuno-precipitation was performed on a total of 100 mg protein with (1:100) rabbit polyclonal TDP-43 antibody (ProteinTech), or rabbit monoclonal (1:100) parkin antibody (Invitrogen) and then compared with the input samples. Western blots were quantified by densitometry using Quantity One 4.6.3 software (Bio Rad). Densitometry was obtained as arbitrary numbers measuring band intensity. Data were analyzed as mean±St.Dev, using ANOVA, with Neumann Keuls multiple comparison between treatment groups.

Parkin Enzyme-Linked Immunosorbent Assay (ELISA)—was performed on brain soluble brain lysates (in STEN buffer) or insoluble brain lysates (4M urea) using mouse specific parkin kit (MYBioSource) in 50 μl (1 μg/μl) of brain lysates detected with 50 μl primary antibody (3 h) and 100 μl anti-rabbit antibody (30 min) at RT. Extracts were incubated with stabilized Chromogen for 30 minutes at RT and solution was stopped and read at 450 nm, according to manufacturer's protocol.

Parkin E3 Ubiquitin Ligase Activity.

To determine the activity of parkin E3 ligase activity E3LITE Customizable Ubiquitin Ligase Kit (Life Sensors, UC#101), which measures the mechanisms of E1-E2-E3 activity in the presence of different ubiquitin chain, was used. To measure parkin activity in the presence or absence of substrates, parkin (1:100) was immunoprecipitated with PRK8 antibodies and TDP-43 (1:100) was immunoprecipitated with human TDP-43 (Abnova) from 100 mg TDP43-Tg brain lysates. UbcH7 was used as an E2 that provides maximum activity with parkin E3 ligase and added E1 and E2 in the presence of recombinant ubiquitin, including wild type containing all seven possible surface lysines, no lysine mutant (K0), or K48 or K63 to determine the lysine-linked type of ubiquitin. E3 was added as IP parkin or recombinant parkin (Novus Biologicals) to an ELISA microplate that captures polyubiquitin chains formed in the E3-dependent reaction, which was initiated with ATP at room temperature for 60 minutes. Also included were an E1-E2-E3 and a polyubiquitin chain control in addition to E1, E2 and TDP-43 without parkin and assay buffer for background reading. The plates were washed 3 times and incubated with detection reagent and streptavidin-HRP for 5 minutes and the polyubiquitin chains generated by E1-E2-E3 machinery were read on a chemiluminecense plate reader.

Immunoprecipitation and Ubiquitination Assay.

Either TDP-43 or parkin were separately immunoprecipitated in 100 μl (100 μg of proteins) 1×STEN buffer using (1:100) human specific anti-TDP-43 monoclonal antibody (Abnova) or (1:100) anti-parkin mouse monoclonal antibody (PRK8; Signet Labs; Dedham, Mass.), respectively. Following immunoprecipitation, 300 ng of each substrate protein (parkin and TDP-43) were mixed in the presence of 1 μg recombinant human ubiquitin (Boston Biochem, MA), 100 mm ATP, 1 μg recombinant UbcH7 (Boston Biochem), 40 ng E1 recombinant enzyme (Boston Biochem) and incubated at 37° C. in an incubator for 20 min. The reaction was heat inactivated by boiling for 5 min and the substrates were analyzed by western blot.

Immunohistology—

Immunohistochemistry was performed on 20 μm-thick sections of brain or cervical spinal cord. TDP-43 was probed (1:200) with rabbit polyclonal (ALS10) antibody (ProteinTech, Cat#10782-2-AP). Rabbit polyclonal anti-ubiquitin (Chemicon International) was used (1:100), and mouse monoclonal anti-parkin (Millipore) antibody was used (1:200) for immunohistochemistry. Toluidine blue and DAPI staining were performed according to manufacturer's instructions (Sigma). Counting of Toluidine blue staining of centric axons within 10 random fields of each slide was performed by a blind investigator in N=8 animals of each treatment. All staining experiments were scored by a blind investigator to the treatments.

20S Proteasome Activity Assay—

Brain extracts 100 μg were incubated with 250 μM of the fluorescent 20S proteasome specific substrate Succinyl-LLVY-AMC at 37° C. for 2 h. The medium was discarded and homogenates were lysed in 50 mM HEPES, pH 7.5, 5 mM EDTA, 150 mM NaCl and 1% Triton X-100, containing 2 mM ATP. The fluoropore 7-Amino-4-methylcoumarin (AMC), which is released after cleavage from the labeled substrate Succinyl-LLVY-AMC (Chemicon International, Inc.), is detected and free AMC fluorescence is quantified using a 380/460 nm filter set in a fluorometer (absorption at 351 nm and emission at 430 nm). Non-proteasomal side reactivity was measured by adding lactacystin as a specific proteasome inhibitor to the reaction mix and subtracted these values from total for an accurate measure of specific proteasome activity.

qRT-PCR in Neuronal Tissues.

qRT-PCR was performed on Real-time OCR system (Applied Biosystems) with Fast SYBR-Green PCR master Mix (Applied Biosystems) in triplicate from reverse transcribed cDNA from control un-injected, or lentiviral LacZ, parkin, TDP-43 and TDP-43+parkin injected rat cortical brain tissues. These experiments were repeated in human neuroblastoma M17 cells and A315T-Tg compared to non-transgenic C57BL/6 controls. Human wild-type parkin forward primer CCA TGA TAG TGT TTG TCA GGT TC and a reverse primer GTT GTA CTT TCT CTT CTG CGT AGT GT were used. Gene expression values were normalized using GADPH levels.

Results

TDP-43 Inhibits Proteasome Activity and Alters Parkin Protein Levels.

To determine the effects of TDP-43 on parkin in transgenic animals, the A315T mutant TDP-43 transgenic mice (TDP43-Tg), which were reported to have aggregates of ubiquitinated proteins in layer 5 pyramidal neurons in frontal cortex, as well as spinal motor neurons, without cytoplasmic TDP-43, was used. This model is relevant to these studies because it shows nuclear TDP-43 driven pathology, independent of cytoplasmic TDP-43 inclusions. Western blot analysis showed accumulation of full length and TDP-43 fragments (~35 kDA) as well as higher molecular weight species with human TDP-43 antibody (FIG. 69A, 1st blot) compared to non-transgenic controls, suggesting TDP-43 pathology. Further analysis of the soluble brain lysate (STEN extract) showed increased parkin levels by Western blot (FIG. 69A, 2nd blot, 82%, P<0.05, N=8) and appearance of a lower molecular weight band, perhaps indicating parkin cleavage. Increased levels of ubiquitin smears (FIG. 69A, 3rd blot) were also observed using anti-ubiquitin antibodies, suggesting accumulation of ubiquitinated proteins. It was determined whether parkin solubility was altered in TDP43-Tg mice. The protein pellet was resuspended after STEN extraction in 4M urea to detect the insoluble fraction and we detected a significant increase (FIG. 69B, 95% by densitometry, P<0.05, N=8) in insoluble parkin in 1-month old TDP43-Tg mice compared to control (FIGS. 69B&C, P<0.05, N=8), suggesting that TDP-43 aggregates are associated with altered parkin solubility. The ratio of soluble over insoluble parkin was not significantly changed (FIG. 69C, P<0.05), suggesting that TDP-43 accumulation increases soluble and insoluble parkin levels. Probing for TDP-43 in 4M urea extracts was also performed and increased levels of insoluble TDP-43 (FIG. 69B, 2nd blot) were detected in TDP43-Tg compared to control. To verify the changes in parkin level observed by WB, quantitative parkin ELISA was performed to determine the levels of both soluble (STEN extract) and insoluble (4M urea) parkin, using brain extracts from parkin$^{-/-}$ mice as control for ELISA specificity (FIG. 69D, N=8). A significant increase in both soluble (46%, P<0.05) and insoluble (64%) parkin was detected in TDP43-Tg mice compared to control level (FIG. 69D, P<0.05, N=8), further suggesting an increase in parkin level and insolubility in TDP43-Tg mice.

The seven in absentia homolog (SIAH) protein is another E3 ligase involved in ubiquitination and proteasomal degradation of specific proteins. SIAH is rapidly degraded via the proteasome. SIAH2 was used as an E3 ligase control to determine whether TDP-43 decreases parkin solubility, leading to alteration of its E3 ligase function independent of other E3 ligases. Western blot analysis showed a significant increase (215%) in soluble SIAH2 levels (FIGS. 69E&F, P<0.05, N=8) in TDP43-Tg mice compared to control, indicating lack of degradation of SIAH2 perhaps due to proteasomal impairment. However, SIAH2 was not detected in the insoluble fraction. A lower molecular weight band was also observed at 17 kDa (FIG. 69E) in transgenic mice, suggesting possible cleavage of SIAH2 dimeric structure. Further examination of the level of SIAH2 target molecule HIF-1α showed a significant increase (76%, P<0.05) in protein level (FIGS. 69E&F), suggesting lack of proteasomal degradation.

To ascertain the effect of TDP-43 on parkin level and proteasome activity wild type TDP-43, (FIG. 69G, 1st blot) was expressed in the presence or absence of parkin (FIG. 69G, 2nd blot) in human M17 neuroblastoma cells. Expression of TDP-43 alone led to appearance of endogenous parkin protein (FIG. 69G, 2nd blot), suggesting that TDP-43 regulates parkin mRNA to induce protein expression. Co-expression of exogenous parkin and TDP-43 led to a slight decrease in TDP-43 levels (FIG. 69G, 1st blot) and a noticeable decrease in ubiquitinated proteins (FIG. 69G, 3rd blot) compared to TDP-43 alone. SIAH2 was difficult to detect in control M17 cells (FIG. 69G, 4th blot), but accumulated when TDP-43 was expressed despite the increase in endogenous parkin, however, exogenous parkin co-expression with TDP-43 led to disappearance of SIAH2 (FIG. 69G, 4th blot). The effects of parkin expression alone (FIG. 69G, 2nd blot) were further compared to LacZ on TDP-43 and SIAH2 levels. No differences were observed between control (FIG. 69F), LacZ and parkin transfected M17 cells (FIG. 69H) on endogenous TDP-43 expression level (FIG. 69H, 1st blot). A higher level of ubiquitinated protein smears were observed with parkin expression (FIG. 69H, 3$^{rd}$ blot), consistent with parkin role as an E3 ubiquitin ligase, but the level of SIAH2 was significantly decreased (FIG. 69H, 4th blot, 74%, P<0.05) compared to actin control. To determine whether SIAH2 accumulation is due to decreased E3 ligase activity or proteasomal function, we measured proteasome activity (FIG. 69I) and found that TDP-43 significantly decreased (66%) proteasome activity (P<0.05, N=12), while parkin co-expression significantly reversed proteasome activity to 74% of control or parkin levels, but remained significantly less (26%) than control. These data show that TDP-43 increases parkin expression levels, while proteasomal inhibition leads to decreased degradation of proteins, including the rapidly degrading SIAH2.

Lentiviral Expression of TDP-43 in Rat Motor Cortex Results in Increased Protein Levels in Preganglionic Cervical Spinal Cord Inter-Neurons.

Wild type TDP-43 was expressed using lentiviral gene delivery into the motor cortex of 2-month old Sprague Dawley rats. Immunohistochemistry using rabbit polyclonal antibody that recognizes human and rat TDP-43 (ALS10, ProteinTech) showed increased TDP-43 protein levels and cytosolic accumulation 2 weeks post-injection (FIG. 70B) compared to LacZ injected contralateral (FIG. 70A) hemisphere. To ascertain specificity of gene expression, human specific (hTDP-43) mouse monoclonal antibody that recognizes a.a. 1-261 (Abcam) was used and positive human TDP-43 staining was observed within 4 mm radius in 38% (by stereology, N=8) of cortical neurons (FIG. 70D) compared to LacZ injected (FIG. 82C) hemisphere. Further examination of cervical spinal cord revealed 13% increase in immunoreactivity to hTDP-43 (FIG. 70F) and increased reactivity to TDP-43 antibody (FIG. 70G) in preganglionic inter-neurons, which were morphologically identified in the contralateral side of TDP-43 injected motor cortex (FIG. 70E) compared to the contralateral spinal cord injected with LacZ (FIGS. 70H&I), suggesting that hTDP-43 expression in the motor cortex leads to increased protein levels in the contralateral spinal cord. Furthermore, stereological counting revealed 46% (by stereology, N=8) increase in the levels of hTDP-43 (FIG. 70J) and increased immunoreactivity to TDP-43 antibody (FIG. 70K) in the dorso-cortical spinal tract (DCST) of cervical spinal cord contralateral to cortical TDP-43 expression compared to LacZ injected side (FIGS. 70L&M). Toluidine blue staining and quantification by a blind investigator of centric axons within 10 random fields of each slide showed increased number (18%, N=8) of axons (FIG. 70N, arrows) in enlarged circles, suggesting axonal degeneration compared to the contralateral DCST (FIG. 70O). Some centric axons were detected in all treatments.

Lentiviral Parkin Expression Increases Cytosolic Co-Localization of TDP-43 with Ubiquitin.

Because TDP-43 is detected in ubiquitinated forms within the cytosol in human disease, it was sought to determine whether ubiquitination is beneficial or detrimental to TDP-43 using parkin as a ubiquitous E3-ubiquitin ligase in the human brain. TDP-43 was co-expressed with parkin and animals were sacrificed 2 weeks post-injection. Staining of 20 μm thick brain sections showed endogenous parkin expression (FIG. 71A) and TDP-43 (FIG. 71B), which was predominantly localized to DAPI stained nuclei (FIG. 71C) in LacZ-injected rat motor cortex. Staining with anti-ubiquitin antibodies (FIG. 71D) in rats expressing TDP-43 in the motor cortex (FIG. 71E) did not result in any noticeable co-localization between TDP-43 and ubiquitin (FIG. 71F). Stereological counting showed 38% increase in hTDP-43 stained cells (FIG. 71D). However, cytosolic TDP-43 was observed in cortical neurons expressing TDP-43 (FIG. 71F) compared to nuclear TDP-43 in LacZ injected animals (FIG. 71C). We expressed parkin in the rat motor cortex (FIG. 71G) together with TDP-43 (FIG. 71H) and observed cytosolic co-localization of parkin and TDP-43 (FIG. 71I, 35% by stereology). We further stained with anti-ubiquitin antibodies and observed increased levels of ubiquitin (FIG. 71J, 35% by stereology) in animals injected with parkin and TDP-43 (FIG. 71K). Interestingly, enhanced ubiquitin signals co-localized with TDP-43 in the cytosol, suggesting that ubiquitination may result in cytosolic sequestration of TDP-43. To determine whether exogenous parkin expression affects endogenous TDP-43 protein localization, we stained with parkin (FIG. 71M, 28% by stereology) and TDP-43 (FIG. 71N) antibodies, but we did not observe any changes in the pattern of TDP-43 staining (FIG. 71O).

Parkin Promotes K48 and K63-Linked Ubiquitin to TDP-43.

To demonstrate whether parkin mediates TDP-43 ubiquitination immuno-precipitation was performed to show ubiquitinated TDP-43 in the presence of parkin expression. Western blot analysis of the input showed that increased exogenous parkin (FIG. 72A, 1st blot, N=8, P<0.05, 42%) in the rat motor cortex, increases the levels of ubiquitinated proteins (FIG. 72A, 2nd blot). Densitometry analysis of TDP-43 blots (FIG. 72A, 3rd blot) showed a significant increase (48%, N=8) in TDP-43 levels in brains injected with lentiviral TDP-43 (consistent with our previous work compared to LacZ or parkin injected brains. However, co-injection of TDP-43 and parkin did not result in any significant changes in TDP-43 levels (P<0.05, N=8), suggesting that parkin mediates TPD-43 ubiquitination, which may not lead to protein degradation. A non-functional parkin mutant (T240R, threonine to arginine mutation), which was co-expressed with TDP-43 (FIG. 72A, top blot) was also used and no changes in ubiquitinated proteins (FIG. 72A, 2nd blot) or TDP-43 levels (FIG. 72A, 3rd blot) were detected. TDP-43 was immune-precipitated and probed with ubiquitin (FIG. 72A, 4th blot) to ascertain that high molecular weight species are ubiquitinated TDP-43 proteins and not some protein aggregates. An increase in protein smear was observed when TDP-43 was co-injected with parkin, compared to TDP-43, parkin or LacZ alone, suggesting increased TDP-43 ubiquitination in the presence of wild type parkin. However, no differences were observed in the levels of ubiquitinated proteins (FIG. 72A, 4th blot) when TDP-43 was immuno-precipitated with or without expression of T240R mutant parkin, suggesting that functional parkin mediates TDP-43 ubiquitination.

To determine whether TDP-43 affects parkin E3 ubiquitin ligase activity, parkin (FIG. 72B, left blot) and TDP-43 (FIG. 4B, right blot) were immune-precipitated and an enzyme activity assay was performed. Positive controls with E1-E2-E3 or poly-ubiquitin chains or recombinant parkin (Novus Biologicals) were used to measure E3 ubiquitin ligase activity and poly-ubiquitin chain readings (FIG. 72C). No parkin activity was detected with the lysine null (K0) ubiquitin, but either mutant K48 or K63-linked ubiquitin showed an increase in parkin E3 ubiquitin ligase activity compared to control K0 (FIG. 72C, N=4). Parkin activity with K63 ubiquitin was significantly higher (83%, P<0.05, N=4) than K48-linked ubiquitin, suggesting that parkin undergoes K48 and K63-linked auto-ubiquitination. Parkin was also ubiquitinated using wild type ubiquitin, which contains all 7 lysine residues. To determine whether parkin activity is altered in the presence of TDP-43, both parkin and TDP-43 were added to the enzyme mix. As expected no activity was detected with lysine null ubiquitin (K0), but parkin activity was significantly increased compared to parkin alone (FIG. 72C, P<0.05, N=8) with K48 (154%) and K63 (156%) ubiquitin, indicating that parkin activity is even higher in the presence of a substrate. Parkin also showed a significantly higher level of activity with wild type ubiquitin in the presence of TDP-43 (279%) compared to parkin alone.

To ascertain that parkin mediates ubiquitination of TDP-43, parkin and TDP-43 were immunoprecipitated separately and in vitro ubiquitination assays were performed. Incubation of both parkin and TDP-43 in the presence of either wild type (FIG. 72D, 2nd lane) or K48 (7th lane) or K63 (8th lane) ubiquitin (FIG. 72D, N=3), showed a protein smear upon WB analysis with TDP-43 antibodies compared to lysine null (K0) ubiquitin (6th lane), or in the absence of E1 or E2 or both (all other lanes, suggesting that parkin mediates K48 and K63-linked ubiquitination of TDP-43. Additionally, parkin incubation in the presence of either wild type (FIG. 72E, 2nd lane) or K48 (7th lane) or K63 (8th lane) ubiquitin (FIG. 72E, N=3), showed a protein smear upon WB analysis with parkin antibodies compared to lysine null (K0) ubiquitin (6th lane), or in the absence of E1 or E2 or both (all other lanes, suggesting that parkin undergoes K48 and K63-linked auto-ubiquitination.

The activity of the 20S proteasome (FIG. 72F), which was significantly decreased (31%, P<0.05) when TDP-43 was expressed alone (N=8, P<0.05), but co-expression of parkin significantly reversed proteasome activity (48%, P<0.05) compared to TDP-43 alone, was measured. However, proteasome activity in parkin expressing cortex remained significantly higher than LacZ (73%, P<0.05) and parkin+TDP-43 (31%, P<0.05) injected animals, indicating that parkin activity partially reverses proteasome activity.

Parkin Forms a Multi-Protein Complex with HDAC6 to Mediate TDP-43 Translocation from Nucleus to Cytosol.

Lack of degradation of ubiquitinated TDP-43 and cytosolic accumulation of parkin, TDP-43 and ubiquitin in gene transfer animals led to examination of possible mechanisms to translocate TDP-43 to the cytosol. Western blot analysis showed a significant increase (41%, P<0.05) in HDAC6 levels when TDP-43 was expressed compared to LacZ or parkin injected animals (FIGS. 72G&H, 1st blot, P<0.05, N=8). However, further increases in HDAC6 levels (FIGS. 72G&H, 112%, P<0.05) were detected when parkin was co-expressed with TDP-43, suggesting possible interaction between these proteins. Examination of molecular markers of autophagy showed a significant increase in P62 (28%, P<0.05) when parkin was co-expressed with TDP43 (FIGS. 72G&H, 2nd blot) compared to all other treatments, suggesting accumulation of ubiquitinated proteins. No changes in other markers of autophagy (LC3, beclin, Atgs) or appearance of autophagic vacuoles by EM were seen. Human TDP-43 was immunoprecipitated from transgenic mice and TDP-43 was verified at 46 kDa using hTDP-43 antibody (FIG. 73A, 1st & 2nd blots). Stripping and re-probing with parkin antibody showed a slightly higher band around 50 kDa, suggesting presence of parkin protein (FIG. 73A, 3rd blot). Further stripping and probing with HDAC6 antibody (FIG. 73A, 4th blot) showed a higher molecular weight band around 120 kDa, indicating a multi-protein complex between parkin, TDP43 and HDAC6. A reserve experiment was performed via parkin immuno-precipitation and verification of human TDP-43 presence (FIG. 73B, 1st & 2nd blot). Stripping and probing with parkin antibody showed parkin band in both transgenic and non-transgenic control mice (FIG. 73B, 3rd blot), indicating that parkin was successfully immuno-precipitated. A higher molecular weight band representative of HDAC6 (FIG. 73B, 4th blot) was detected in transgenic but not control mice, further suggesting multi-protein complex formation between TDP43, parkin and HDAC6.

To ascertain that both parkin and HDAC6 are required for TDP-43 translocation, GFP-tagged TDP-43 was expressed in M17 neuroblastoma cells in the presence of wild type or loss-of-function mutant (T240R) parkin, and treated with 5 µM selective HDAC6 inhibitor for 24 hours. GFP expression was predominantly observed within DAPI-stained nuclei in live M17 cells (FIG. 73C, insert is higher magnification), however parkin co-expression led to significant GFP fluorescence within the cytoplasm (FIGS. 73D&E) and neuronal processes (FIG. 73D, insert shows higher magnification of GFP fluorescence). Treatment with the HDAC6 inhibitor, tubacin, did not lead to GFP fluorescence in the cytosol in the presence (FIG. 73F) or absence (FIG. 73G) of parkin. Loss of parkin E3 ubiquitin ligase function (T240R) did not lead to TDP-43 accumulation in the cytosol (FIG. 73H), suggesting that the E3 ubiquitin ligase function of parkin and HDAC6 activity are required to facilitate TDP-43 accumulation within the cytosol.

To verify whether TDP-43 expression increases parkin mRNA levels, performed qRT-PCR was performed in samples isolated from rat cortex, human M17 cells and TDP43-Tg mice. Park2 mRNA levels in M17 cells expressing parkin was significantly higher (FIGS. 73I&J, 55%, P<0.05, N=4) than LacZ, but similar to TDP-43 injected brains (61%, P<0.05). Parkin co-expression with TDP-43 showed significantly higher levels of park2 mRNA (FIG. 73J, 74%, P<0.05, N=4) compared to parkin alone. Similarly, Park2 mRNA levels in rat brains expressing parkin was significantly higher (FIGS. 73K&L, 41%, P<0.05, N=4) than LacZ animals, as well as TDP-43 injected brains (21%, P<0.05). However, parkin co-expression with TDP-43 showed significantly higher levels of park2 mRNA (FIG. 73J, 84%, P<0.05, N=4) compared to all other treatments. Therefore, park2 mRNA levels between TDP43-Tg and non-transgenic control littermates were compared. A significant increase (FIGS. 73M&N, 114%, N=4, P<0.05) in park2 mRNA was observed in TDP43-Tg brains injected compared to C57BL/6 controls, showing that parkin is a transcriptional target for TDP-43.

Example 7

Parkin Plays an Essential Role in Motor Neuron Survival Via Modulation of Nuclear TDP-43 Transport to the Synapse E3 ubiquitin ligase Parkin is important in neurodegeneration. Parkin promotes specific ubiquitination of TAR-DNA binding protein (TDP)-43, and could mediate its transport via complex formation with histone deacetylase 6 (HDAC6). In healthy neurons, TDP-43 is predominantly nuclear and could be transported to the synapse for generation of synaptic proteins. As shown in FIG. 74, 1). Parkin could ubiquitinate TDP-43 and translocate it from the nucleus to the cytosol; 2). Parkin-HDAC6 complex is required for axoplasmic TDP-43 transport to the synapse; and 3). TDP-43 availability at the synapse modulates expression of synaptic proteins that maintain glutamate metabolism.

Long motor neurons, which degenerate in Amyotrophic Lateral Sclerosis (ALS), could depend on axonal TDP-43 transport to distant synapses, thus increasing their vulnerability to TDP-43 localization. In neurodegeneration, including ALS and Frontotemporal Dementia (FTD-TDP), wild type and mutated TDP-43 aggregate, and neurons bearing TDP-43 aggregates express less parkin. Data provided herein show that parkin alters TDP-43 localization, reverses TDP-43-induced alteration in glutamate levels and improves motor performance. TDP-43 binds to mRNAs that code for proteins involved in synaptic function, including synaptotagmin and vesicular glutamate transporters. Glutamate transport is defective in ALS, due to loss of glutamate transporters that facilitate conversion of synaptic glutamate into glutamine. Thus, nuclear TDP-43 translocation and axoplasmic transport to the synapse could be particularly important for motor neurons.

Parkin-mediated TDP-43 localization to the synapse could affect synaptic proteins that maintain glutamate metabolism. Thus, parkin could play an essential role in motor neuron survival via modulation of nuclear TDP-43 transport to the synapse.

The following data support these conclusions. FIG. 75 shows the distribution of GFP-tagged TDP-43 in M17 cells transfected with 3 mg cDNA for 24 hrs and then treated with Nilotinib (10 mM) or Bosutinib (5 mM) and HDAC6 inhibitor Tubacin (5 mM) for additional 24 hrs. Inserts (B&D) represent higher magnification images showing translocation of GFP-tagged TDP-43 from nucleus (A) into the cytosol (B&D, and inserts), while tubacin impairs translocation (C&E).

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating an α-Synucleinopathy in a subject, comprising:
   selecting a subject with an α-Synucleinopathy or at risk for an α-Synucleinopathy; and
   systemically administering to the subject an effective amount of nilotinib, wherein the nilotinib is administered to the subject at a dosage of about 5 mg/kg or less.

2. The method of claim 1, wherein the effective amount of nilotinib promotes Parkin activity.

3. The method of claim 1, wherein the nilotinib is administered daily.

4. The method of claim 1, further comprising administering a second therapeutic agent to the subject.

5. A method of inhibiting toxic protein aggregation in a neuron of a subject with an α-Synucleinopathy, comprising contacting the neuron in the subject with an effective amount of nilotinib, wherein the neuron is contacted with nilotinib by systemically administering nilotinib to the subject at a dosage of about 5 mg/kg or less.

6. The method of claim 5, wherein the protein is selected from the group consisting of alpha-synuclein, and insoluble Parkin.

7. A method of rescuing a neuron from neurodegeneration associated with an α-Synucleinopathy in a subject comprising contacting the neuron in the subject with an effective amount of, nilotinib, wherein the neuron is contacted with the nilotinib by systemically administering a nilotinib to the subject at a dosage of about 5 mg/kg or less.

8. The method of claim 1, further comprising determining that the subject has a decreased level of parkin activity relative to a control prior to administering to the subject an effective amount of nilotinib.

* * * * *